United States Patent
Nukada et al.

(10) Patent No.: US 8,748,070 B2
(45) Date of Patent: Jun. 10, 2014

(54) THIOL GROUP-CONTAINING CHARGE TRANSPORTING MATERIAL, THIOL GROUP-CONTAINING CHARGE TRANSPORTING MATERIAL-DISSOLVING SOLUTION, PHOTOELECTRIC CONVERSION DEVICE, ELECTROPHOTOGRAPHIC PHOTORECEPTOR, IMAGE FORMING APPARATUS, AND PROCESS CARTRIDGE

(75) Inventors: Katsumi Nukada, Kanagawa (JP); Kenya Sonobe, Tokyo (JP); Wataru Yamada, Kanagawa (JP); Takatsugu Doi, Kanagawa (JP); Tsuyoshi Miyamoto, Kanagawa (JP); Yuko Iwadate, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 131 days.

(21) Appl. No.: 13/218,013

(22) Filed: Aug. 25, 2011

(65) Prior Publication Data
US 2012/0196215 A1 Aug. 2, 2012

(30) Foreign Application Priority Data

Jan. 28, 2011 (JP) ................................ 2011-016704
Jan. 28, 2011 (JP) ................................ 2011-016963

(51) Int. Cl.
| | |
|---|---|
| *G03G 5/07* | (2006.01) |
| *G03G 5/06* | (2006.01) |
| *C07C 323/52* | (2006.01) |
| *C07C 323/12* | (2006.01) |
| *C07C 323/29* | (2006.01) |
| *G03G 15/00* | (2006.01) |

(52) U.S. Cl.
CPC ............ *G03G 15/751* (2013.01); *G03G 5/0614* (2013.01); *G03G 5/0609* (2013.01); *C07C 323/52* (2013.01); *C07C 323/12* (2013.01); *C07C 323/29* (2013.01); *G03G 5/0607* (2013.01); *G03G 5/062* (2013.01)
USPC ......... 430/58.7; 430/58.75; 560/48; 560/147; 560/433; 528/321; 399/159

(58) Field of Classification Search
USPC ................ 430/58.7, 58.75; 560/48, 147, 433; 528/321; 399/159
See application file for complete search history.

(56) References Cited

U.S. PATENT DOCUMENTS

| | | | |
|---|---|---|---|
| 4,539,507 A | 9/1985 | VanSlyke et al. | |
| 4,764,625 A | 8/1988 | Turner et al. | |

(Continued)

FOREIGN PATENT DOCUMENTS

| | | |
|---|---|---|
| JP | A-59-194393 | 11/1984 |
| JP | A-01-245087 | 9/1989 |

(Continued)

OTHER PUBLICATIONS

Tang, et al., "Electroluminescence of doped organic thin films," Journal of Applied Physics, vol. 65, No. 9, pp. 3610-3616, May 1989.

(Continued)

*Primary Examiner* — Peter Vajda
(74) *Attorney, Agent, or Firm* — Oliff PLC

(57) ABSTRACT

Provided is a thiol group-containing charge transporting material represented by the following general formula (1):

$$F-[(G)_{a1}-(X)_{a2}-Y-SH]_b \quad (1)$$

wherein F represents an organic group derived from a charge transporting compound, G represents a divalent organic group having 1 to 5 carbon atoms, X represents a group selected from a —CO—O— group, an —O—CO— group, and an —O— group, Y represents a divalent organic group having 1 to 5 carbon atoms, a1 and a2 each independently represent 0 or 1, and b represents an integer of 1 or more and 6 or less.

14 Claims, 12 Drawing Sheets

(56) References Cited

U.S. PATENT DOCUMENTS

| | | | |
|---|---|---|---|
| 4,923,774 | A | 5/1990 | Van der Auweraer et al. |
| 4,950,950 | A | 8/1990 | Perry et al. |
| 5,298,617 | A | 3/1994 | Nukada et al. |
| 2009/0004583 | A1* | 1/2009 | Nukada et al. ............... 430/58.5 |

FOREIGN PATENT DOCUMENTS

| | | |
|---|---|---|
| JP | A-02-222484 | 9/1990 |
| JP | A-02-247278 | 10/1990 |
| JP | A-04-129271 | 4/1992 |
| JP | A-04-133065 | 5/1992 |
| JP | A-04-175395 | 6/1992 |
| JP | A-04-189873 | 7/1992 |
| JP | A-04-264189 | 9/1992 |
| JP | A-04-290851 | 10/1992 |
| JP | A-04-304466 | 10/1992 |
| JP | A-04-308688 | 10/1992 |
| JP | A-04-335087 | 11/1992 |
| JP | A-04-364153 | 12/1992 |
| JP | A-05-025473 | 2/1993 |
| JP | A-05-040360 | 2/1993 |
| JP | A-05-070773 | 3/1993 |
| JP | A-05-098181 | 4/1993 |
| JP | A-05-140472 | 6/1993 |
| JP | A-05-140473 | 6/1993 |
| JP | A-05-198377 | 8/1993 |
| JP | A-05-202135 | 8/1993 |
| JP | A-05-216249 | 8/1993 |
| JP | A-05-234681 | 9/1993 |
| JP | A-05-239455 | 9/1993 |
| JP | A-05-263007 | 10/1993 |
| JP | A-05-279591 | 10/1993 |
| JP | A-05-310949 | 11/1993 |
| JP | A-05-320634 | 12/1993 |
| JP | A-05-323630 | 12/1993 |
| JP | A-05-331459 | 12/1993 |
| JP | A-06-001972 | 1/1994 |
| JP | A-06-025659 | 2/1994 |
| JP | A-06-049079 | 2/1994 |
| JP | A-06-256428 | 9/1994 |
| JP | A-06-322362 | 11/1994 |
| JP | A-07-053953 | 2/1995 |
| JP | A-07-138562 | 5/1995 |
| JP | A-07-252474 | 10/1995 |
| JP | A-08-176293 | 7/1996 |
| JP | A-08-208820 | 8/1996 |
| JP | A-08-315983 | 11/1996 |
| JP | A-09-012630 | 1/1997 |
| JP | A-10-074586 | 3/1998 |
| JP | A-11-052603 | 2/1999 |
| JP | A-2000-206715 | 7/2000 |
| JP | A-2000-264961 | 9/2000 |
| JP | A-2000-310870 | 11/2000 |
| JP | A-2001-166510 | 6/2001 |
| JP | A-2004-021136 | 1/2004 |
| JP | A-2004-078147 | 3/2004 |
| JP | A-2005-002291 | 1/2005 |
| JP | A-2005-055818 | 3/2005 |
| JP | A-2005-070648 | 3/2005 |
| JP | A-2005-070649 | 3/2005 |
| JP | A-2005-181992 | 7/2005 |
| JP | A-2006-126327 | 5/2006 |
| JP | A-2006-184803 | 7/2006 |
| JP | A-2007-011005 | 1/2007 |
| JP | A-2007-322483 | 12/2007 |
| WO | WO 97/33193 A2 | 9/1997 |

OTHER PUBLICATIONS

Adachi, et al., "Organic electroluminescent device having a hole conductor as an emitting layer," Applied Physics Letters, vol. 55, No. 15, pp. 1489-1491, Oct. 1989.

Hung, et al., "Enhanced electron injection in organic electroluminescence devices using an Al/LiF electrode," Applied Physics Letters, vol. 70, No. 2. pp. 152-154, Jan. 1997.

Wakimoto et al., "Organic EL Cells Using Alkaline Metal Compounds as Hectron Injection Materials," IEEE Transactions on Electron Devices, vol. 44, No. 8, pp. 1245-1248, Aug. 1997.

* cited by examiner

THIOL GROUP-CONTAINING CHARGE TRANSPORTING MATERIAL, THIOL GROUP-CONTAINING CHARGE TRANSPORTING MATERIAL-DISSOLVING SOLUTION, PHOTOELECTRIC CONVERSION DEVICE, ELECTROPHOTOGRAPHIC PHOTORECEPTOR, IMAGE FORMING APPARATUS, AND PROCESS CARTRIDGE

CROSS-REFERENCE TO RELATED APPLICATIONS

This application is based on and claims priority under 35 USC 119 from Japanese Patent Applications Nos. 2011-016704 and 2011-016963 both filed on Jan. 28, 2011.

BACKGROUND (i) Technical Field

The present invention relates to a thiol group-containing charge transporting material, a thiol group-containing charge transporting material-dissolving solution, a photoelectric conversion device, an electrophotographic photoreceptor, an image forming apparatus, and a process cartridge.

(ii) Related Art

Recently, electronic devices such as an electrophotographic photoreceptor, an organic EL device, an organic transistor, an organic solar cell, and the like, each of which uses an organic compound, have been actively developed.

In particular, it is known that a crosslinked structure is effective in terms of heat resistance and strength. There is further disclosed a film formed by subjecting a mixture of a monomer having a carbon-carbon double bond, a charge transfer material having a carbon-carbon double bond, and a binder resin to the energy of heat or light to allow the carbon-carbon double bond of the monomer and the carbon-carbon double bond of the charge transfer material to undergo a reaction.

SUMMARY

According to an aspect of the invention, there is provided a thiol group-containing charge transporting material represented by the following general formula (1):

$$F\text{-}[(G)_{a1}\text{-}(X)_{a2}\text{—}Y\text{—}SH]_b \quad (1)$$

wherein F represents an organic group derived from a charge transporting compound, G represents a divalent organic group having 1 to 5 carbon atoms, X represents a group selected from a —CO—O— group, an —O—CO— group, and an —O— group, Y represents a divalent organic group having 1 to 5 carbon atoms, a1 and a2 each independently represent 0 or 1, and b represents an integer of 1 or more and 6 or less.

BRIEF DESCRIPTION OF THE DRAWINGS

Exemplary embodiments of the present invention will be described in detail based on the following figures, wherein.

DETAILED DESCRIPTION

Figure 1:
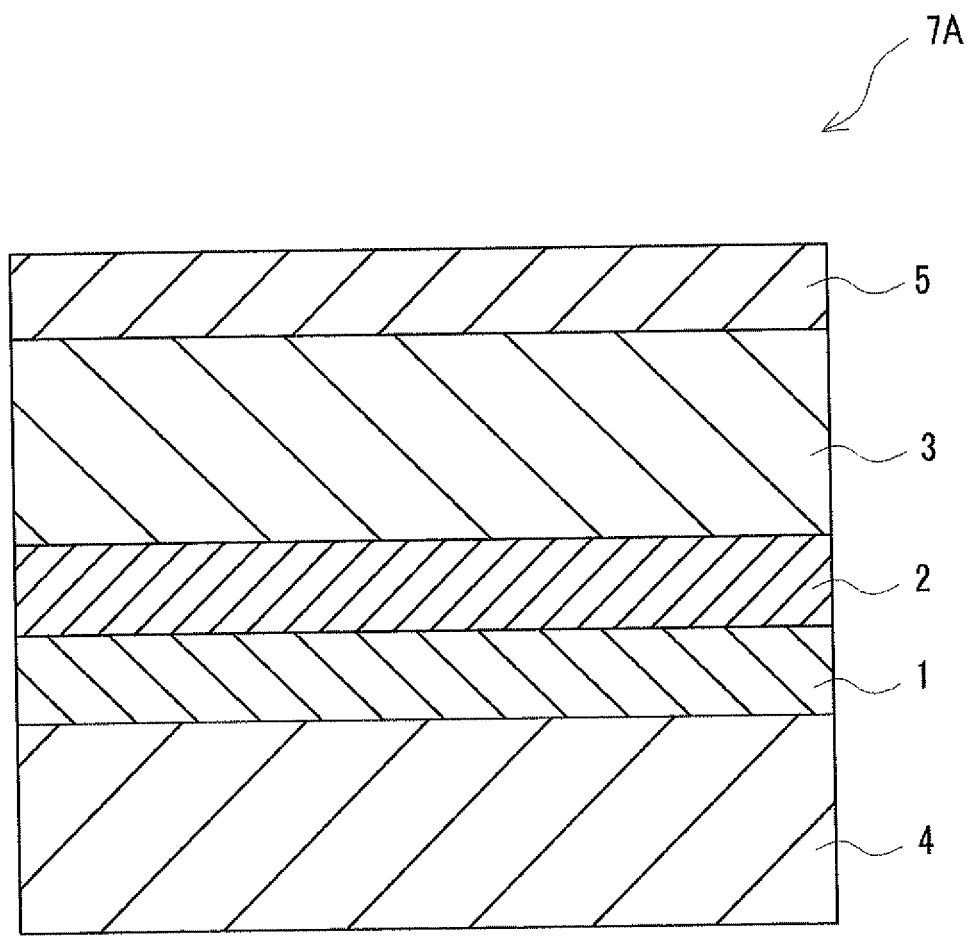
FIG. 1 is a schematic partial cross-sectional view showing an example of the layer configuration of the electrophotographic photoreceptor according to the present exemplary embodiment.

Hereinbelow, the exemplary embodiments of the present invention will be described in detail.

<Thiol Group-Containing Charge Transporting Material>

The novel thiol group-containing charge transporting material of the present exemplary embodiment is represented by the following general formula (1):

$$F\text{-}[(G)_{a1}\text{-}(X)_{a2}\text{—}Y\text{—}SH]_b \quad (1)$$

(in the general formula (1), F represents an organic group derived from a charge transporting compound, G represents a divalent organic group having 1 to 5 carbon atoms, X represents a group selected from —CO—O—, —O—CO—, and —O—, Y represents a divalent organic group having 1 to 5 carbon atoms, a1 and a2 each independently represent 0 or 1, and b represents an integer of 1 or more and 6 or less).

Preferable examples of G include organic groups having a combination of a substituted or unsubstituted alkylene group having 1 to 5 carbon atoms (including straight-chained, branch-chained, and cyclic ones) or a substituted or unsubstituted alkylene group having 1 to 5 carbon atoms with —O—. Among these, an organic group having a combination of a straight-chained and unsubstituted alkylene group having 1 to 5 carbon atoms or a straight-chained and unsubstituted alkylene group having 1 to 5 carbon atoms with —O— is more preferable.

More specific preferable examples of G include —CH$_2$—, —C$_2$H$_4$—, —C$_3$H$_6$—, —C$_4$H$_8$—, —C$_5$H$_{10}$—, —O—C$_2$H$_4$—O—, —CH$_2$—O—C$_2$H$_4$—O—, and the like.

Preferable examples of Y include a substituted or unsubstituted alkylene group having 1 to 5 carbon atoms (including straight-chained, branch-chained, and cyclic ones), a substituted or unsubstituted alkenyl group having 1 to 5 carbon atoms, and the like. Further, examples of the substituent include an —SH group, a halogen atom, an alkyl group, an alkoxy group, and the like, and among these, an —SH group is particularly preferable.

Among these, a straight-chained or branch-chained alkylene group which is substituted with —CH$_3$ or an —SH group, or unsubstituted, and has 1 to 5 carbon atoms is more preferable.

More specific preferable examples of Y include —CH$_2$—, —C$_2$H$_4$—, —CH(CH$_3$)—CH$_2$—, —CH(CH$_3$)—, —CH$_2$—CH(SH)—CH$_2$—, —CH$_2$—CH(CH$_2$—SH)—, and the like.

F represents a structure having a charge transporting property, and specifically, a phthalocyanine-based compound, a porphyrin-based compound, an azobenzene-based compound, a triarylamine-based compound, a bendizine-based compound, an arylalkane-based compound, an aryl-substituted ethylene-based compound, a stilbene-based compound, an anthracene-based compound, a hydrazone-based compound, a quinone-based compound, a fluorenone-based compound, or the like is used.

Among these, one having an arylamine skeleton is preferable since it has a charge transporting property, and in particular, among the thiol group-containing charge transporting materials represented by the general formula (1), those represented by the following general formula (2) are particularly preferable.

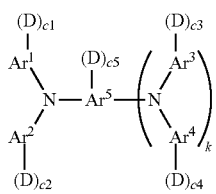

(2)

In the general formula (2), D represents a binding group represented by -(G)$_{a1}$-(X)$_{a2}$—Y—SH, Ar$^1$ to Ar$^4$ each independently represent a substituted or unsubstituted aryl group, Ar$^5$ represents a substituted or unsubstituted aryl group or a substituted or unsubstituted arylene group, G represents a divalent organic group having 1 to 5 carbon atoms, X represents a group selected from —CO—O—, —O—CO—, and —O—, Y represents a divalent organic group having 1 to 5 carbon atoms, and a1 and a2 each independently represent 0 or 1. One or more and four or less of Ar$^1$ to Ar$^5$ have a bond which is capable of binding to a binding group represented by -(G)$_{a1}$-(X)$_{a2}$—Y—SH, c1 to c5 each independently represent an integer of 0 or more and 2 or less, and k represents 0 or 1.

In the general formula (2), Ar$^1$, Ar$^2$, Ar$^3$, and Ar$^4$ each independently represent a substituted or unsubstituted aryl group, and Ar$^1$, Ar$^2$, Ar$^3$, and Ar$^4$ may be the same as or different from each other.

Here, examples of the substituent in the substituted aryl group include, in addition to -D (that is, a binding group represented by -(G)$_{a1}$-(X)$_{a2}$—Y—SH), an alkyl group having 1 to 4 carbon atoms, an alkoxy group having 1 to 4 carbon atoms, an aryl group having 6 to 10 carbon atoms, and the like. Further, these alkyl group, alkoxy group, and aryl group may be either substituted or unsubstituted.

The thiol group-containing charge transporting material according to the present exemplary embodiment is preferably represented by the following general formula (1)':

(1)'

(in the general formula (1)', F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less).

It is presumed that since the thiol group-containing charge transporting material represented by the general formula (1)' has —SH as a polar group and a relatively small number of polar groups interfering with carrier transportation such as —OH, —NH—, and the like, a film formed by using the same has inhibition of formation of a trap capturing the charge, and thus, accumulation of residual potential is inhibited.

In addition, usually, with a film obtained by crosslinking a polyfunctional charge transporting material, as immobilization proceeds, the residual strain in the film increases, but with the thiol group-containing charge transporting material represented by the general formula (1)', for the purpose of crosslinking the charge transporting components through a thioester group having a high degree of motion freedom, the residual strain in the film is inhibited and thus the structural trap is not easily generated, which is presumed to lead to excellent electrical characteristics.

As a result, while obtaining excellent electrical characteristics, the thickness of the film formed can further increase.

Furthermore, in the case where for the purpose of increasing the strength of the film formed, a charge transporting material is additionally mixed with a polyfunctional acrylic monomer to form a film, the compatibility of the two components in usual charge transporting materials is low, and accordingly, an increase in the amount of the polyfunctional acrylic monomer to be added is limited. However, it is presumed that since the thiol group-containing charge transporting material represented by the general formula (1)' has an ester structure which is similar to that of the polyfunctional acrylic monomer, and the compatibility between the two components is excellent, crosslinking is conducted without a phase separation with the polyfunctional acrylic monomer, and thus, a film having both electrical characteristics and strength is obtained.

Moreover, by forming a film using the thiol group-containing charge transporting material represented by the general formula (1)', crystallization is inhibited, and accordingly, a thin film having inhibition of irregularities in the thickness is easily obtained which is presumed to lead to excellent electrical characteristics.

Furthermore, by providing a crosslinked structure, a film having further higher heat resistance and solvent resistance is obtained, and thus, a performance stable over a long period of time can be obtained.

The novel thiol group-containing charge transporting material of the present exemplary embodiment is preferably represented by the following general formula (1)'.

(1)'

(in the general formula (1)', F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less).

Preferable examples of G include organic groups having a combination of a substituted or unsubstituted alkylene group having 1 to 5 carbon atoms (including straight-chained, branch-chained, and cyclic ones), a substituted or unsubstituted alkenylene group having 1 to 5 carbon atoms, an organic group having a combination of a substituted or unsubstituted alkylene group having 1 to 5 carbon atoms with —O—, or an organic group having a combination of a substituted or unsubstituted alkenylene group having 1 to 5 carbon atoms with —O—. Among these, a straight-chained and unsubstituted alkylene group having 1 to 5 carbon atoms or an organic group having a combination of a straight-chained and unsubstituted alkylene group having 1 to 5 carbon atoms with —O— is more preferable.

Furthermore, examples of the substituent include a halogen atom, an alkyl group, an alkoxy group, and the like.

More specific preferable examples of G include —$CH_2$—, —$C_2H_4$—, —$C_3H_6$—, —$C_4H_8$—, —$C_5H_{10}$—, —O—$C_2H_4$—O—, —$CH_2$—O—$C_2H_4$—O—, —CH=CH—$CH_2$—, —O—$C_2H_2$—O—, —$CH_2$—O—$C_2H_2$—O—, and the like, and among these, —$CH_2$—, —$C_2H_4$—, —$C_3H_6$—, —$C_4H_8$—, —$C_5H_{10}$—, —O—$C_2H_4$—O—, and —$CH_2$—O—$C_2H_4$—O— are particularly preferable.

Preferable examples of Y include a substituted or unsubstituted alkylene group having 1 to 5 carbon atoms (including straight-chained, branch-chained, and cyclic ones), a substituted or unsubstituted alkenylene group having 1 to 5 carbon atoms, and the like. Further, examples of the substituent include a —SH group, a halogen atom, an alkyl group, an alkoxy group, and the like, and among these, an —SH group is particularly preferable.

Among these, a straight-chained or branch-chained alkylene group which is substituted with an —SH group, or unsubstituted, and has 1 to 5 carbon atoms is more preferable.

More specific preferable examples of Y include —$CH_2$—, —$C_2H_4$—, —CH($CH_3$)—$CH_2$—, —CH($CH_3$)—, —$CH_2$—CH(SH)—$CH_2$—, —$CH_2$—CH($CH_2$—SH)—, and the like.

F represents a structure having a charge transporting property, and specifically, a phthalocyanine-based compound, a porphyrin-based compound, an azobenzene-based compound, a triarylamine-based compound, a bendizine-based compound, an arylalkane-based compound, an aryl-substituted ethylene-based compound, a stilbene-based compound, an anthracene-based compound, a hydrazone-based compound, a quinone-based compound, a fluorenone-based compound, or the like is used.

Among these, one having an arylamine skeleton is preferable since it has a charge transporting property, and in particular, among the thiol group-containing charge transporting materials represented by the general formula (1)', those represented by the following general formula (2)' are particularly preferable.

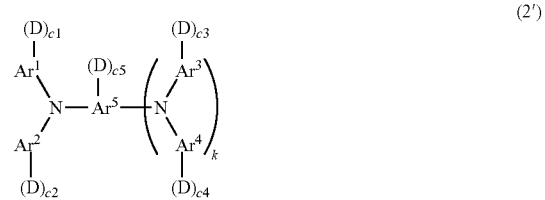

In the general formula (2)', D represents a binding group represented by -$(G)_a$-X—Y—SH, $Ar^1$ to $Ar^4$ each independently represent a substituted or unsubstituted aryl group, $Ar^5$ represents a substituted or unsubstituted aryl group or a substituted or unsubstituted arylene group, G represents a divalent organic group having 1 to 5 carbon atoms, X represents a —CO—O— group or an —O—CO— group, Y represents a divalent organic group having 1 to 5 carbon atoms, and a represents 0 or 1. One or more and four or less of $Ar^1$ to $Ar^5$ have a bond which is capable of binding to a binding group represented by -$(G)_a$-X—Y—SH, c1 to c5 each independently represent an integer of 0 or more and 2 or less, and k represents 0 or 1.

In the general formula (2)', $Ar^1$, $Ar^2$, $Ar^3$, and $Ar^4$ each independently represent a substituted or unsubstituted aryl group, and $Ar^1$, $Ar^2$, $Ar^3$, and $Ar^4$ may be the same as or different from each other.

Here, examples of the substituent in the substituted aryl group include, in addition to -D (that is, a binding group represented by -$(G)_a$-X—Y—SH), an alkyl group having 1 to 4 carbon atoms, an alkoxy group having 1 to 4 carbon atoms, an aryl group having 6 to 10 carbon atoms, and the like. Further, these alkyl group, alkoxy group, and aryl group may be either substituted or unsubstituted.

$Ar^1$, $Ar^2$, $Ar^3$, and $Ar^4$ are preferably any one of the following formulae (1) to (7). Further, the following formulae (1) to (7) represent "-$(D)_C$", which generally denotes "-$(D)_{C1}$" to "-$(D)_{C4}$" that can be substituted with each of $Ar^1$, $Ar^2$, $Ar^3$, and $Ar^4$.

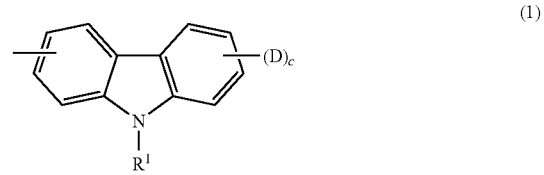

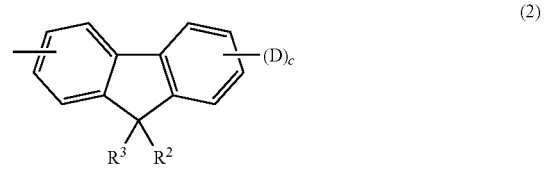

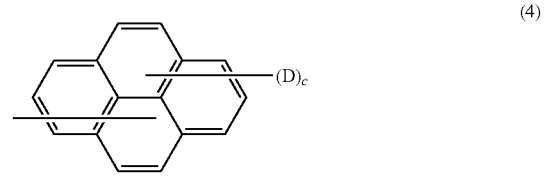

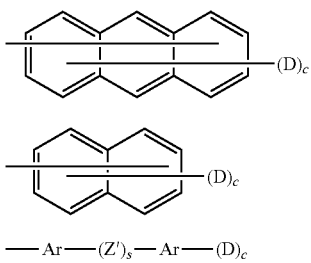
(5)

(6)

—Ar—(Z')$_s$—Ar—(D)$_c$ (7)

In the formulae (1) to (7), $R^1$ represents one selected from the group consisting of a hydrogen atom, an alkyl group having 1 to 4 carbon atoms, a phenyl group substituted with an alkyl group having 1 to 4 carbon atoms or an alkoxy group having 1 to 4 carbon atoms, an unsubstituted phenyl group, and an aralkyl group having 7 to 10 carbon atoms, $R^2$, $R^3$, and $R^4$ each independently represent one selected from the group consisting of a hydrogen atom, an alkyl group having 1 to 4 carbon atoms, an alkoxy group having 1 to 4 carbon atoms, a phenyl group substituted with an alkoxy group having 1 to 4 carbon atoms, an unsubstituted phenyl group, an aralkyl group having 7 to 10 carbon atoms, and a halogen atom, Ar represents a substituted or unsubstituted arylene group, D represents a binding group represented by -(G)$_{a1}$-(X)$_{a2}$—Y—SH, c represents 0, 1, or 2, s represents 0 or 1, t represents an integer of 0 or more and 3 or less, and Z' represents a divalent organic linking group.

Here, Ar in the formula (7) is preferably represented by the following structural formula (8) or (9).

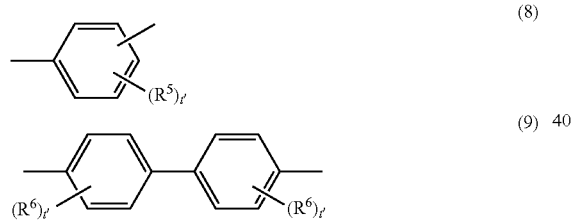
(8)

(9)

In the formulae (8) and (9), $R^5$ and $R^6$ each independently represent one selected from the group consisting of a hydrogen atom, an alkyl group having 1 to 4 carbon atoms, an alkoxy group having 1 to 4 carbon atoms, a phenyl group substituted with an alkoxy group having 1 to 4 carbon atoms, an unsubstituted phenyl group, an aralkyl group having 7 to 10 carbon atoms, and a halogen atom, and each t' represents an integer of 0 or more and 3 or less.

Furthermore, in the formula (7), Z' is preferably represented by any one of the following formulae (10) to (17). Further, each s represents 0 or 1.

—(CH$_2$)$_q$— (10)

—(CH$_2$CH$_2$O)$_r$— (11)

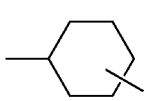
(12)

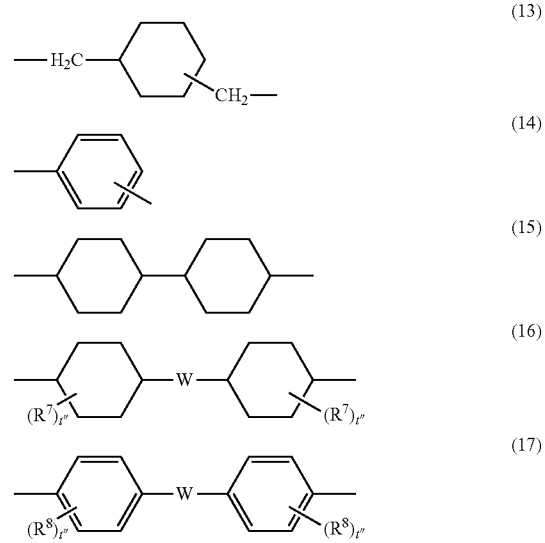

In the formulae (10) to (17), $R^7$ and $R^8$ each independently represent one selected from the group consisting of a hydrogen atom, an alkyl group having 1 to 4 carbon atoms, an alkoxy group having 1 to 4 carbon atoms or a phenyl group substituted with an alkoxy group having 1 to 4 carbon atoms, an unsubstituted phenyl group, an aralkyl group having 7 to 10 carbon atoms, and a halogen atom, W represents a divalent group, q and r each independently represent an integer of 1 or more and 10 or less, and each t'' represents an integer of 0 or more and 3 or less.

W in the formula (16) to (17) is preferably any one of divalent groups represented by the following formulae (18) to (26). However, in the formula (25), u represents an integer of 0 or more and 3 or less.

—CH$_2$— (18)

—C(CH$_3$)$_2$— (19)

—O— (20)

—S— (21)

—C(CF$_3$)$_2$— (22)

—Si(CH$_3$)$_2$— (23)

(24)

(25)

(26)

Furthermore, in the general formula (2), $Ar^5$ is a substituted or unsubstituted aryl group when k is 0, and examples of the aryl group include the aryl groups exemplified in the explanation of $Ar^1$ to $Ar^4$. Further, when k is 1, $Ar^5$ is a substituted or unsubstituted arylene group, and examples of the arylene group include arylene groups formed by removal of a hydrogen atom from the aryl groups exemplified in the explanation of $Ar^1$ to $Ar^4$.

In -D (that is, a binding group represented by $-(G)_{a1}-(X)_2-Y-SH$) in the general formula (2), examples of G and Y include each of the groups exemplified in the explanation of the general formula (1).

In the general formula (2), c1 to c5 each independently represent 0, 1, or 2, and the total number of D's is 1 or more. From the viewpoint of increasing the strength of the cured film obtained, and thus, inhibiting the decrease in the image quality after repeated use, the total number of D's is preferably 2 or more, and still more preferably 4 or more.

Here, specific examples of thiol group-containing charge transporting material represented by the general formula (1) are shown below, but are not limited thereto. Further, in the following tables showing examples of the compound represented by the general formula (1), the linking part between $F-(G)_{a1}-$ and $-(X)_{a2}-$ is denoted as "*" and the linking part between $-(X)_{a2}-$ and $-Y-SH$ is denoted as "#". However, in the case of a2=0, "*" and "#" are directly linked.

| Compound | $F-(G)_{a1}-$ | a1 |
|---|---|---|
| (1) | 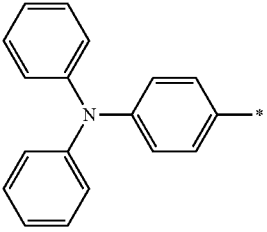 | 0 |
| (2) | 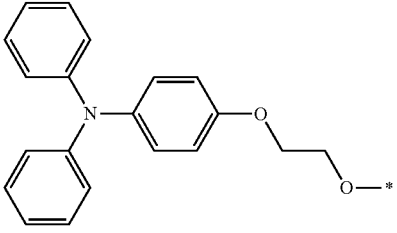 | 1 |
| (3) | 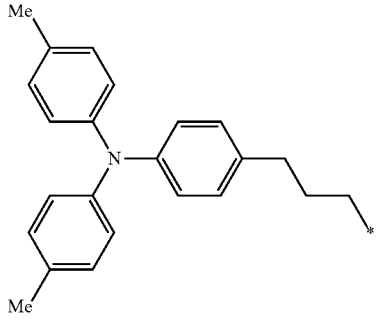 | 1 |
| (4) | 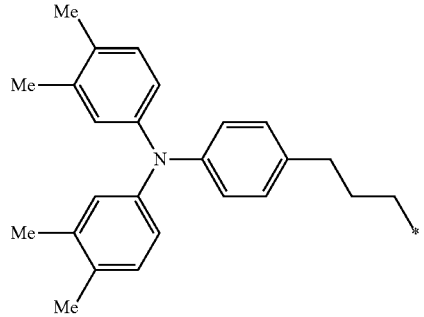 | 1 |

-continued
(5) 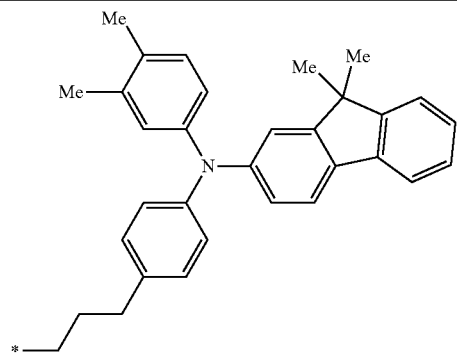 1
(6) 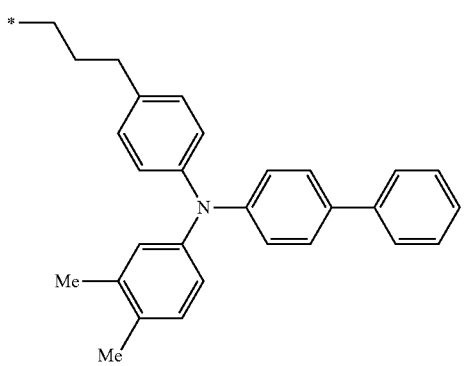 1
(7) 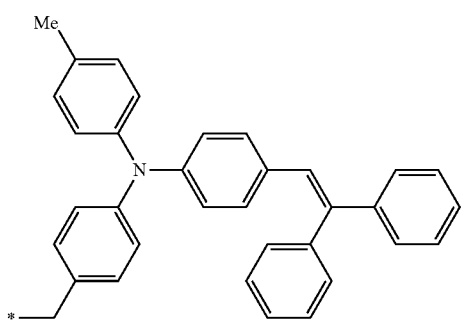 1
(8) 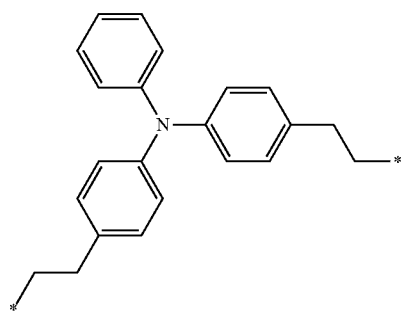 1

-continued
(9)
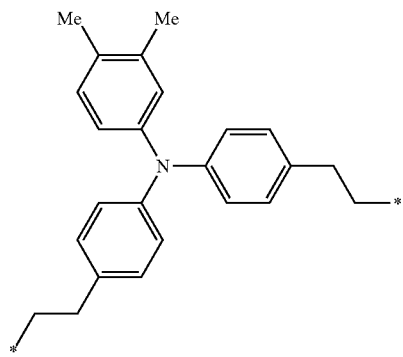
1
(10)
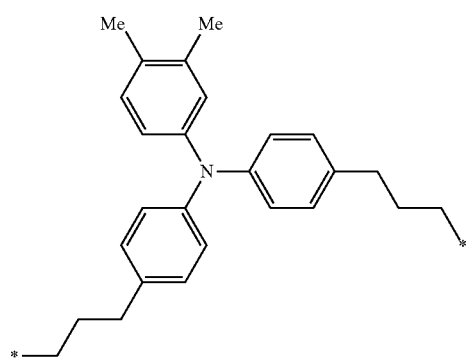
1
(11)
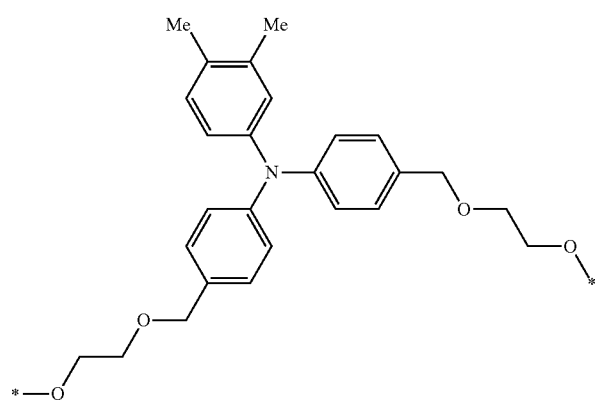
1
(12)
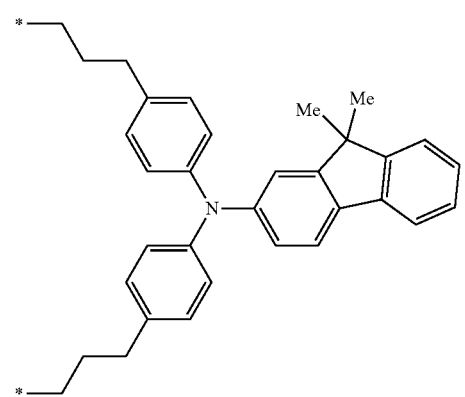
1

-continued
(13)
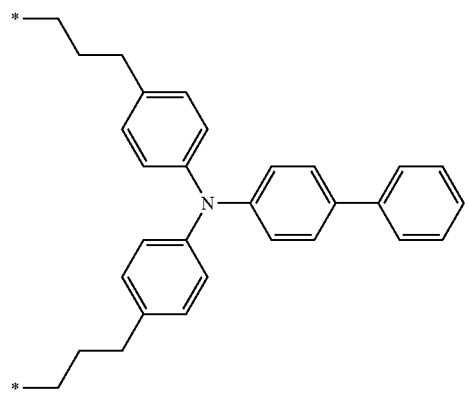
1
(14)
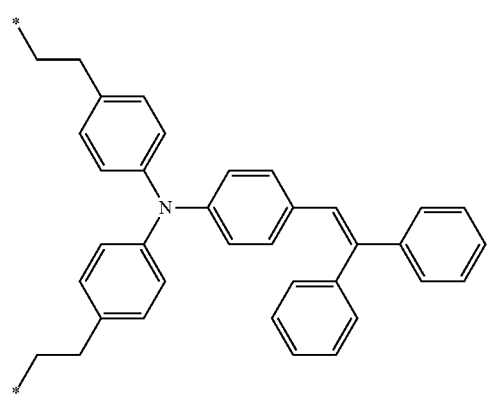
1
(15)
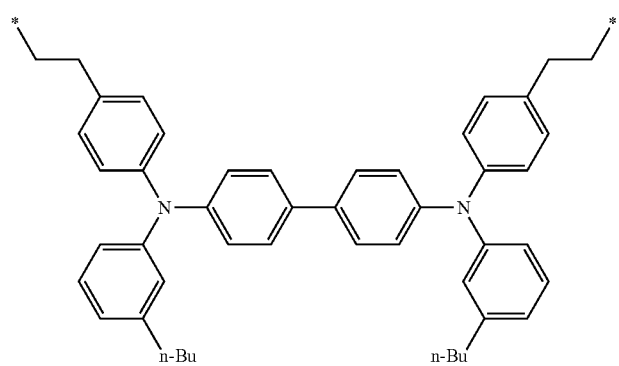
1
(16)
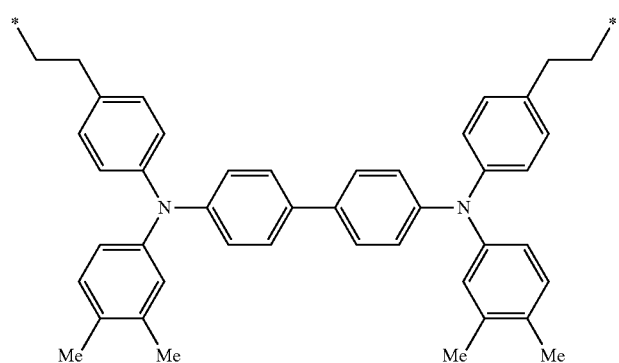
1

-continued
(17)
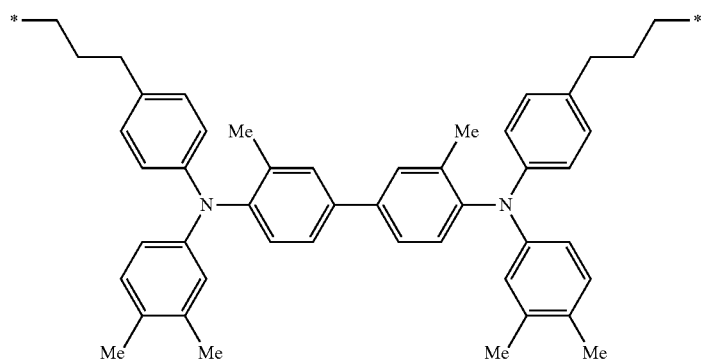
1
(18)
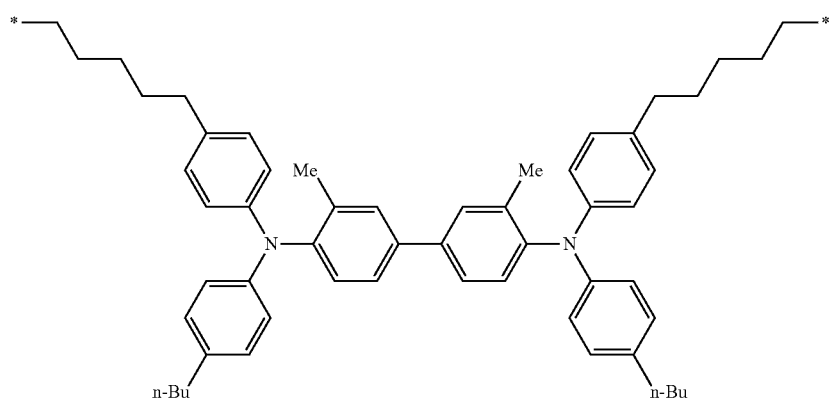
1
(19)
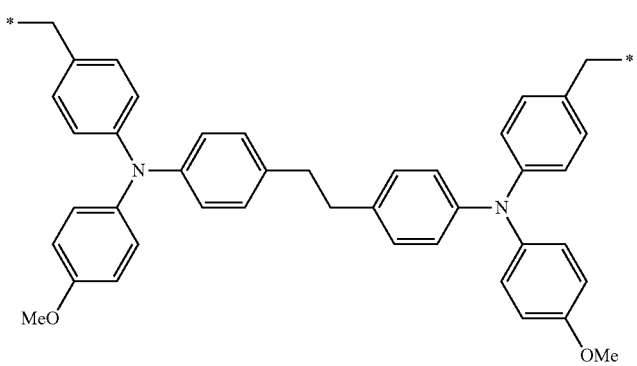
1
(20)
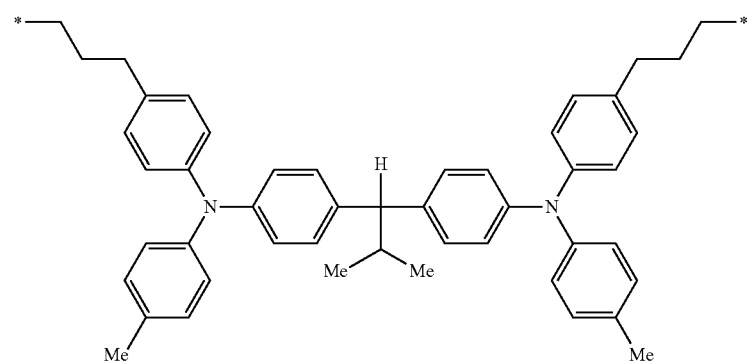
1

-continued
(21)
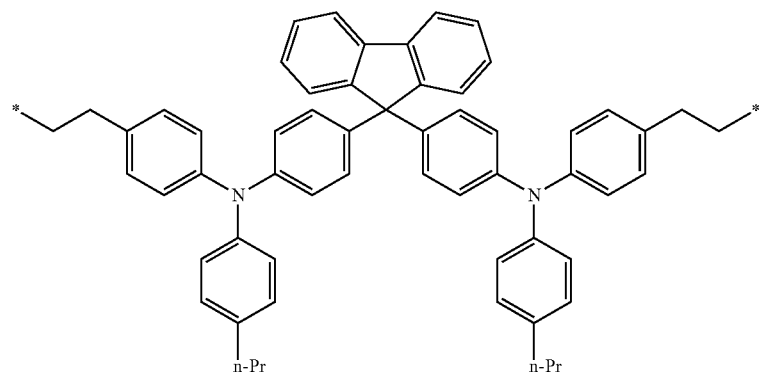
(22)
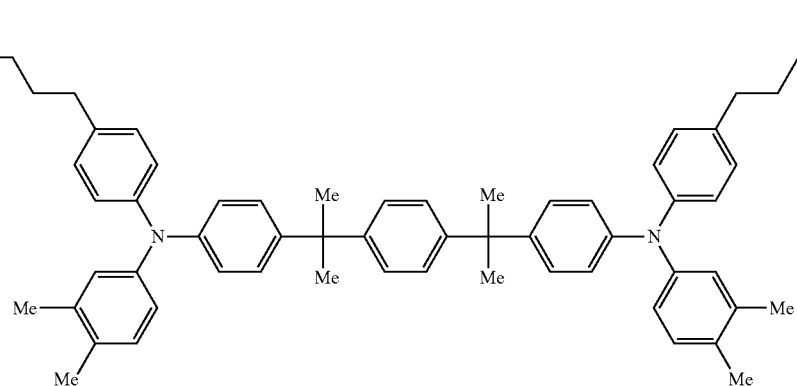
(23)
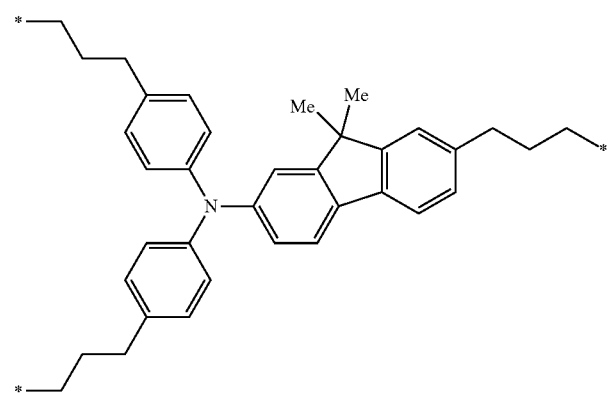
(24)
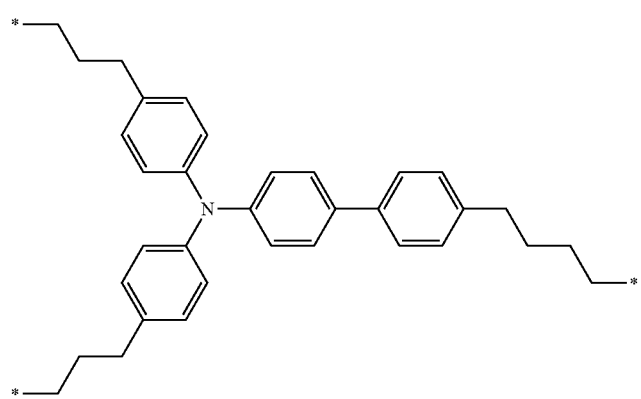

-continued
(25)
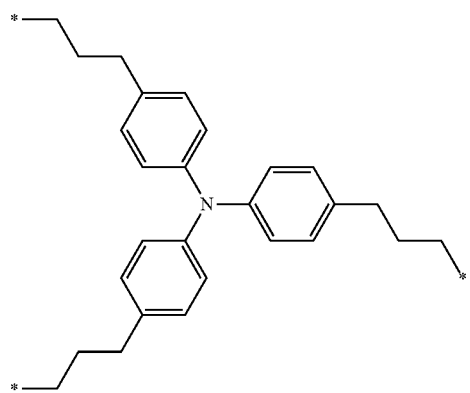
1
(26)
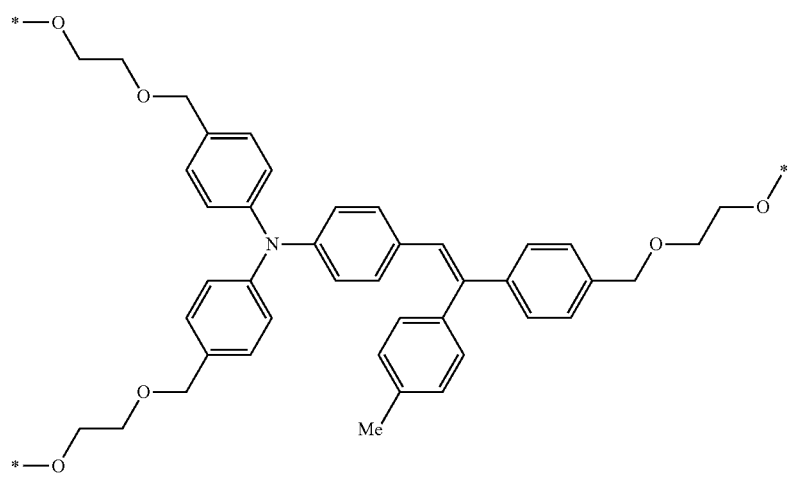
1
(27)
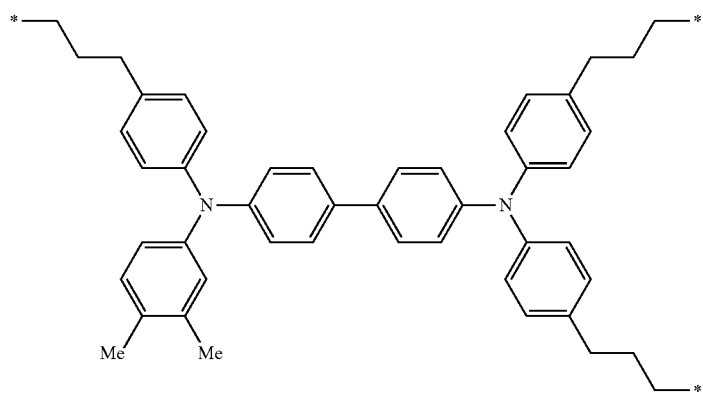
1

-continued
(28)
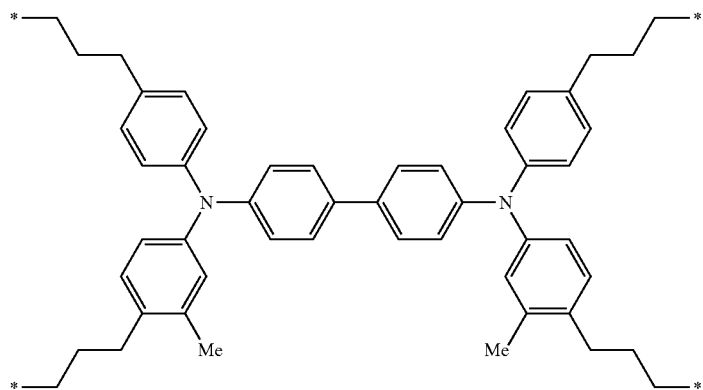
1
(29)
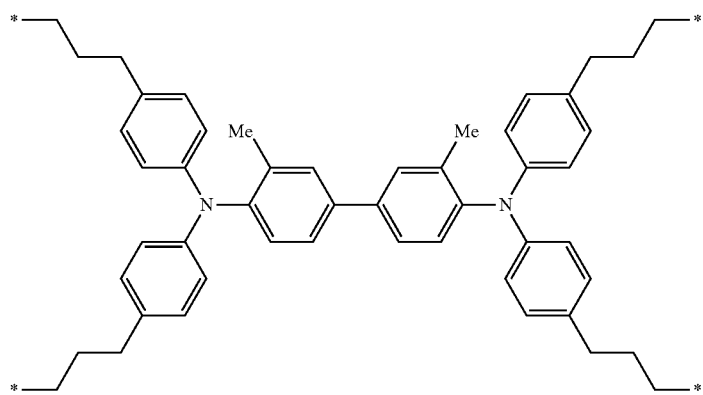
1
(30)
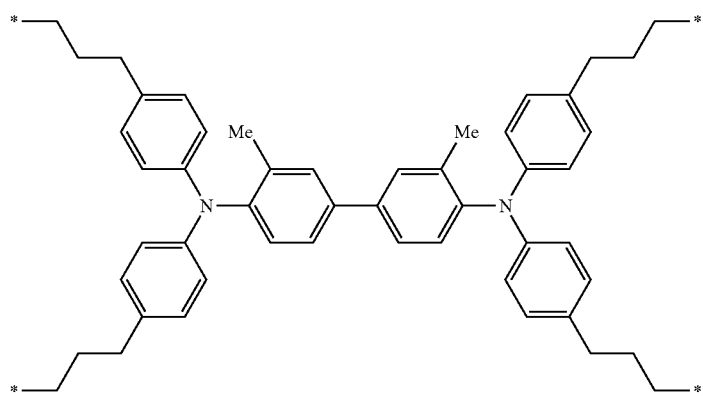
1
(31)
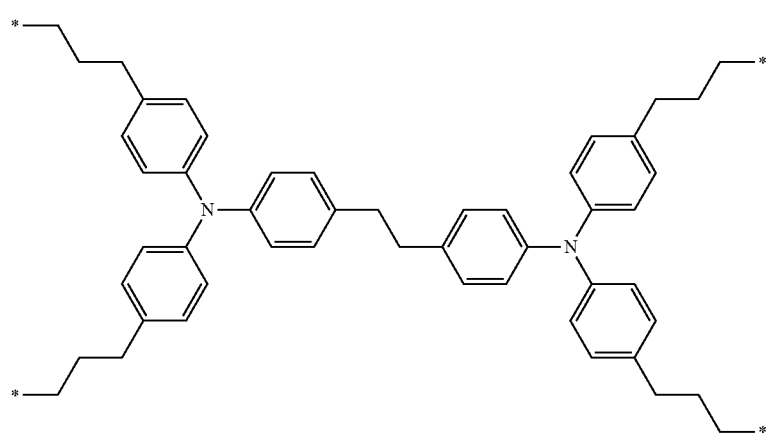
1

(32)
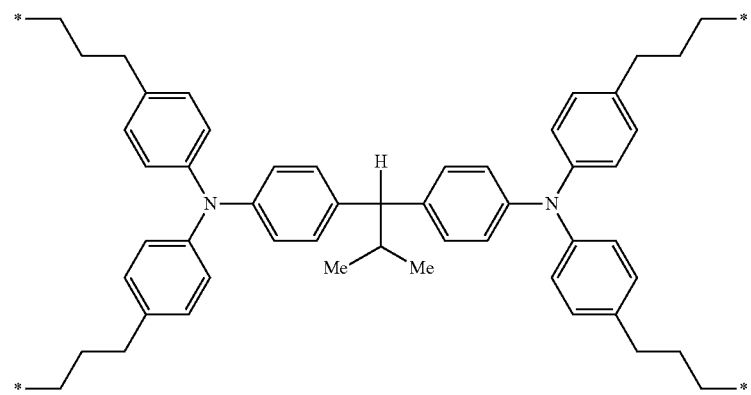
(33)
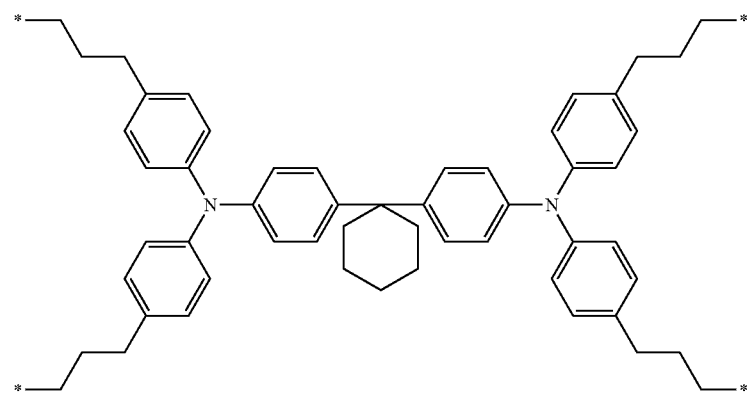
(34)
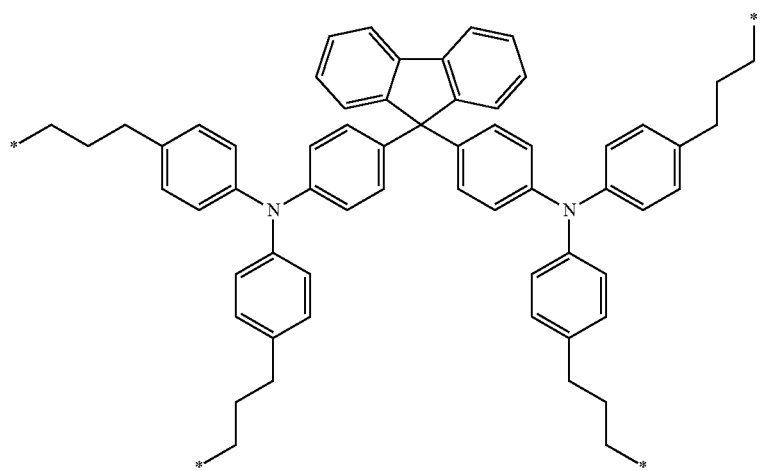

-continued
| | | |
|---|---|---|
| (35) | 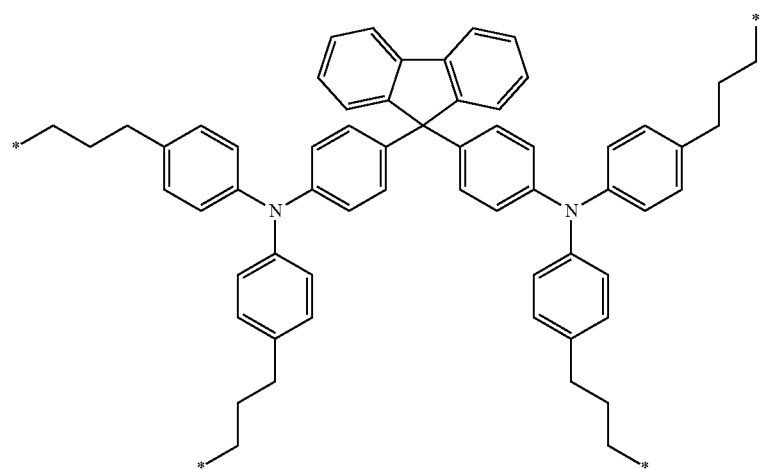 | 1 |
| (36) | 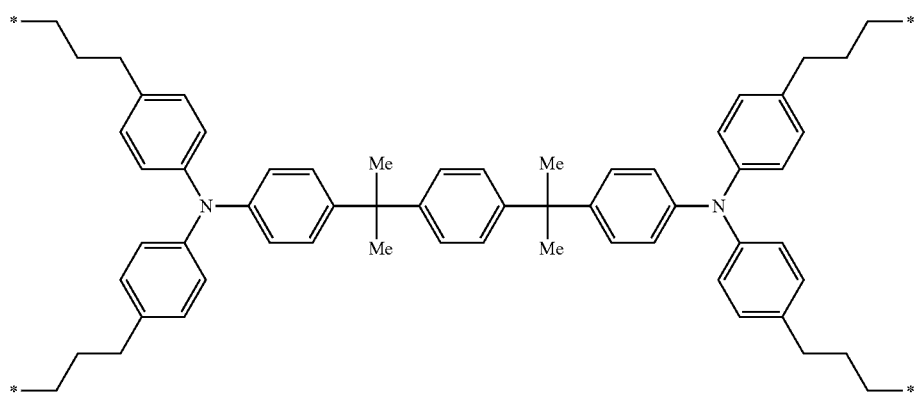 | 1 |
| (37) | 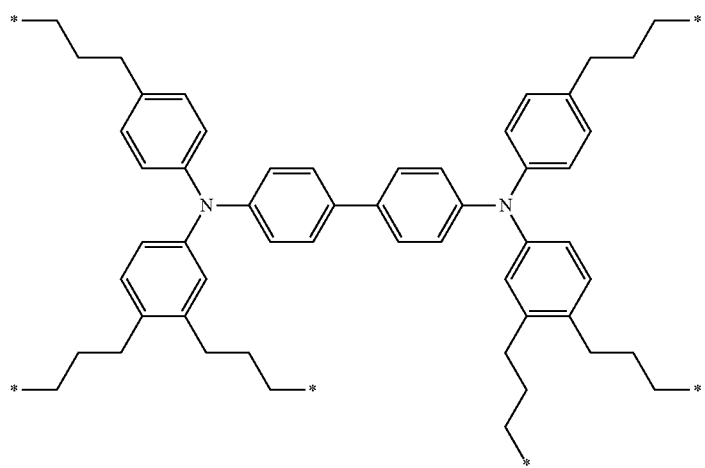 | 1 |
| (38) | 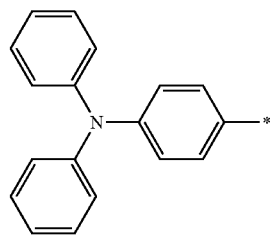 | 0 |

(39) 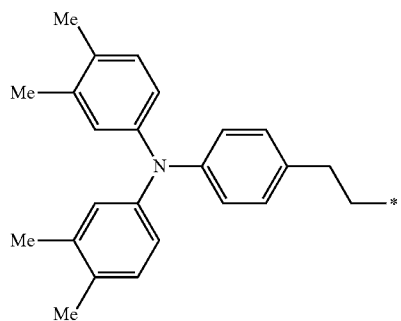 1
(40) 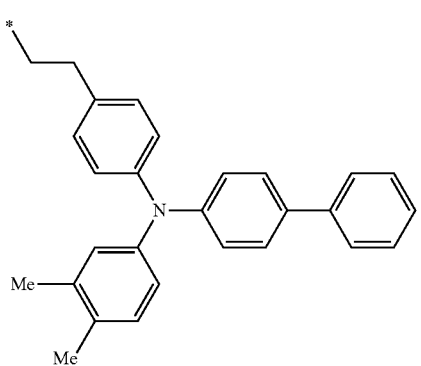 1
(41) 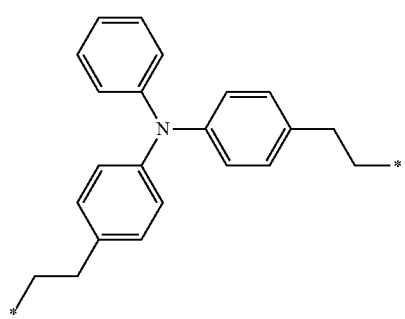 1
(42) 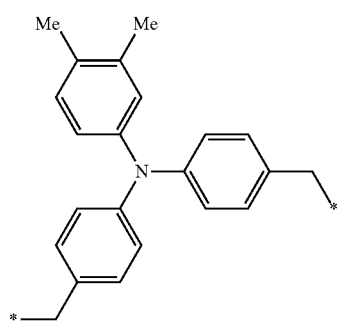 1

-continued
(43) 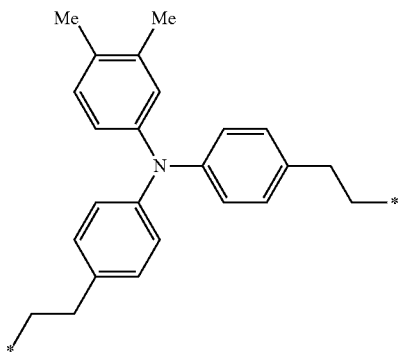 1
(44) 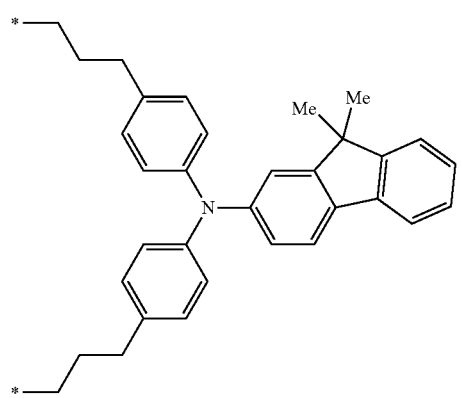 1
(45) 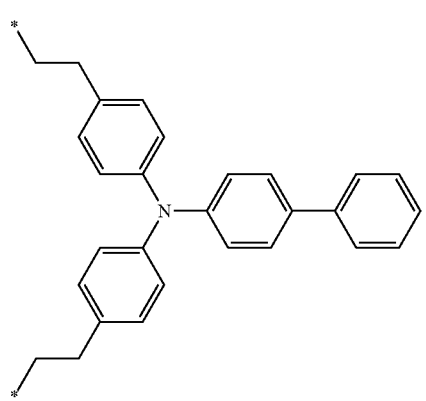 1
(46) 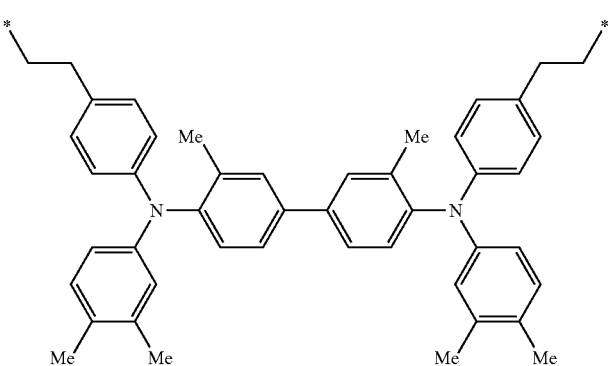 1

(47) 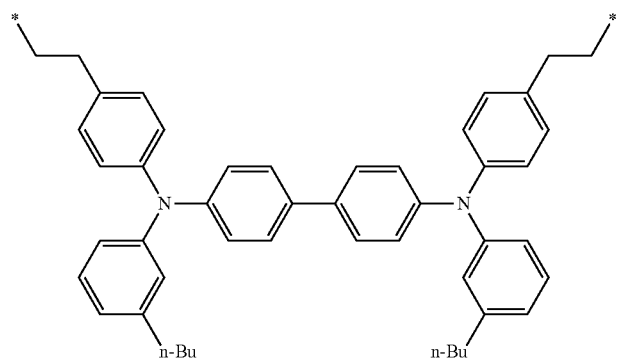 1
(48) 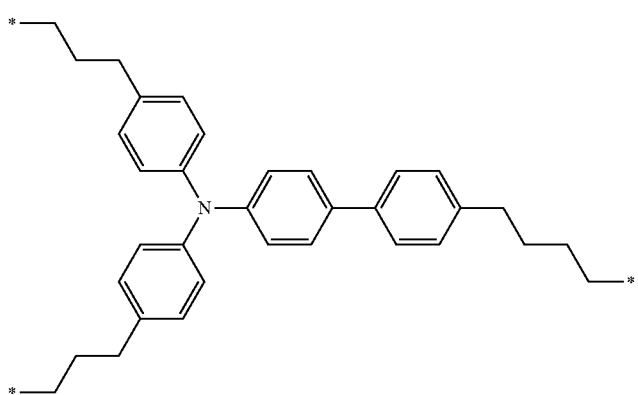 1
(49) 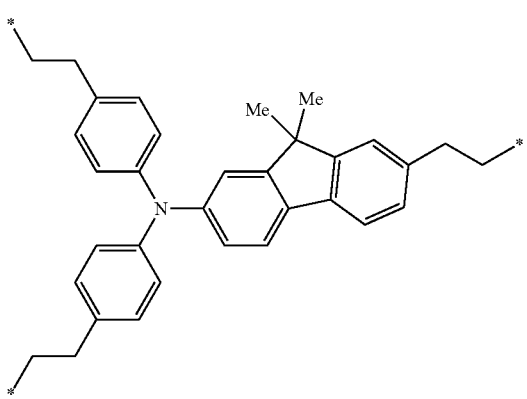 1
(50) 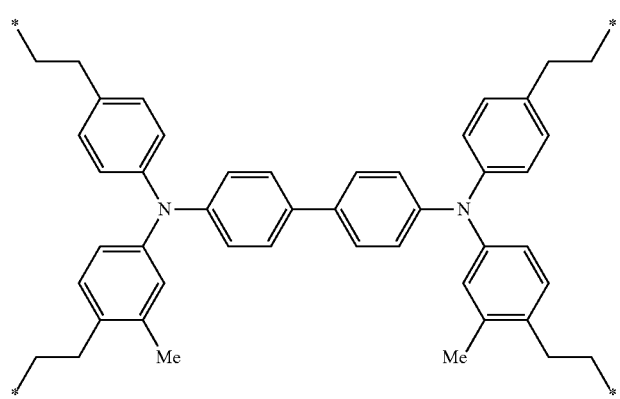 1

(51)
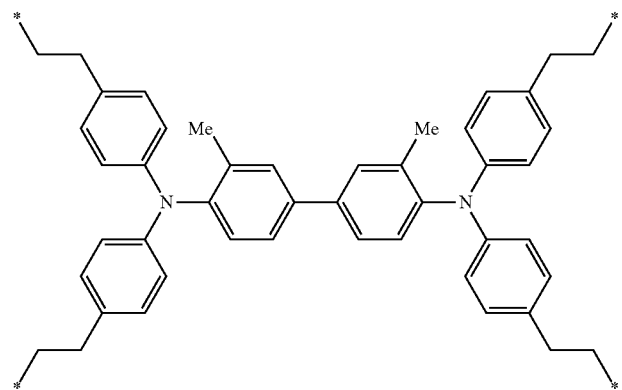
(52)
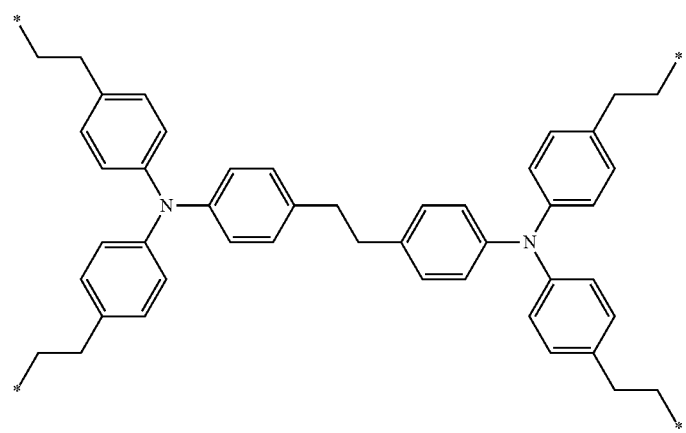
(53)
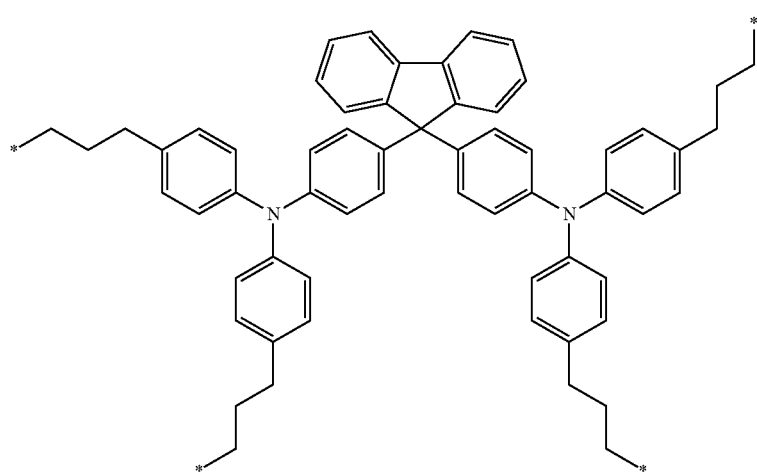

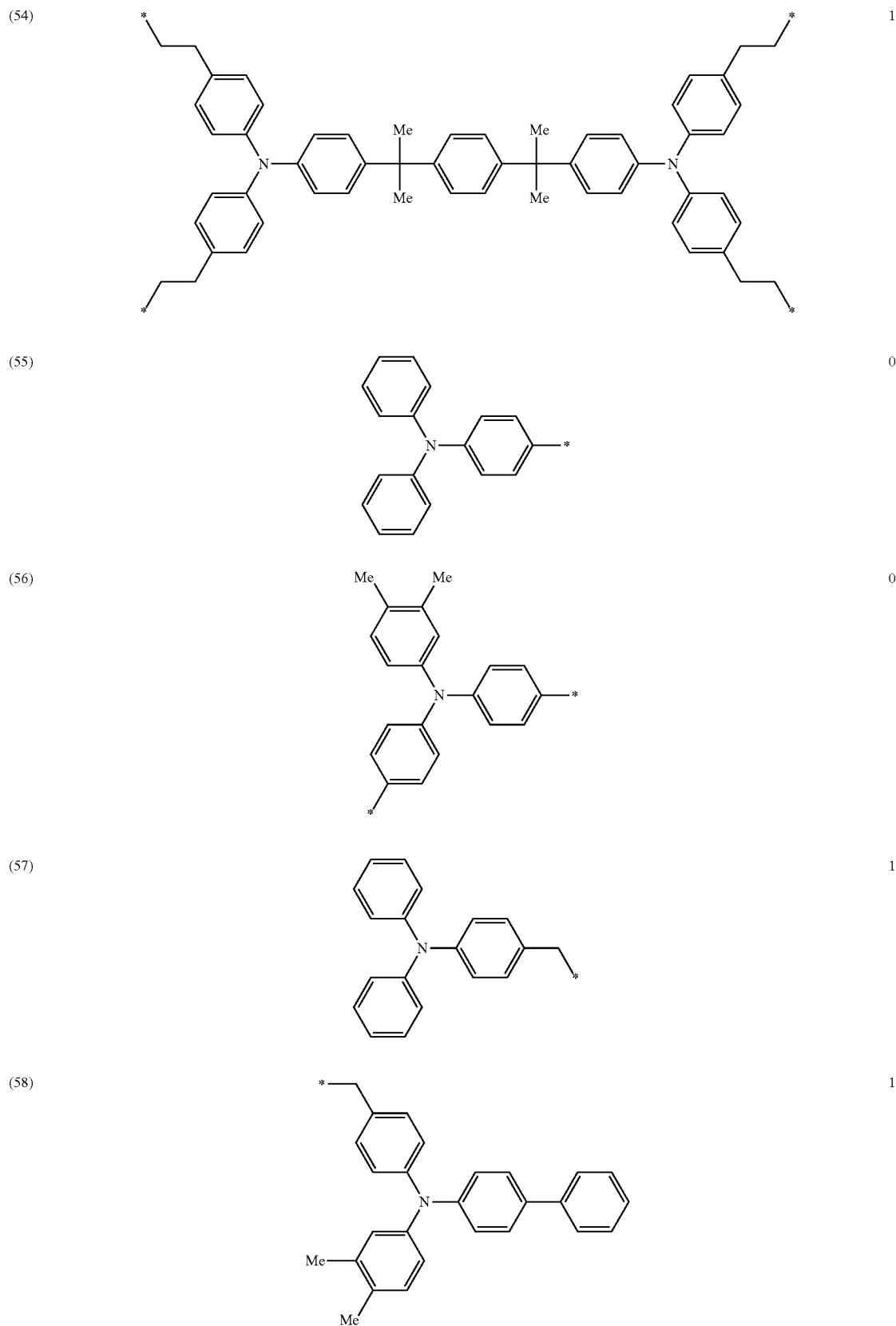

(59) 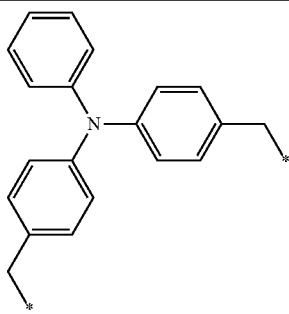 1
(60) 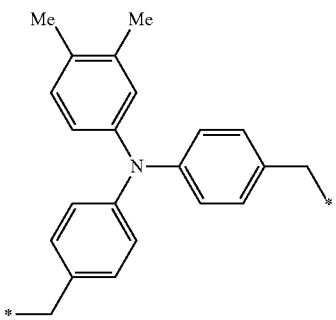 1
(61) 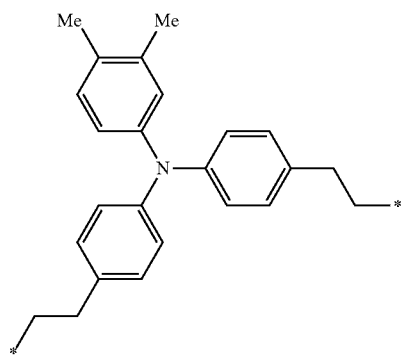 1
(62) 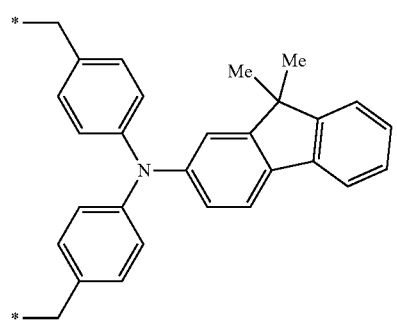 1
(63) 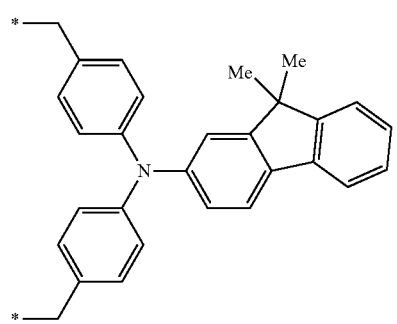 1

(64) 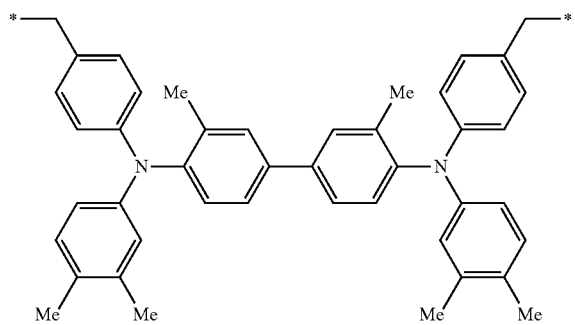 1
(65) 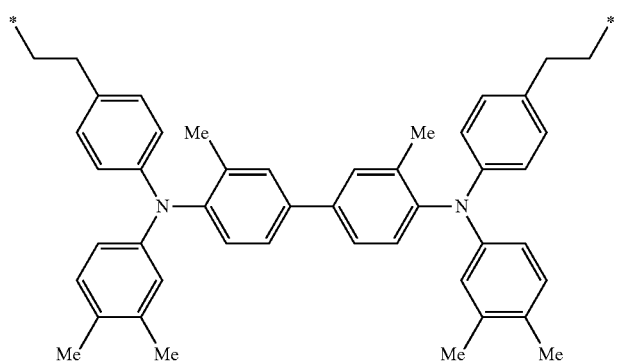 1
(66) 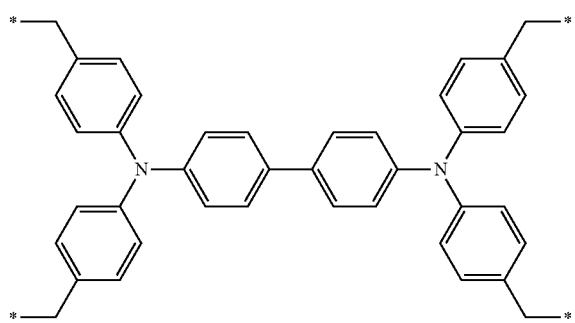 1
(67) 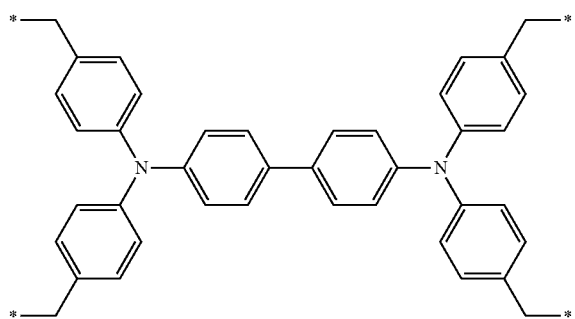 1

-continued
(68) 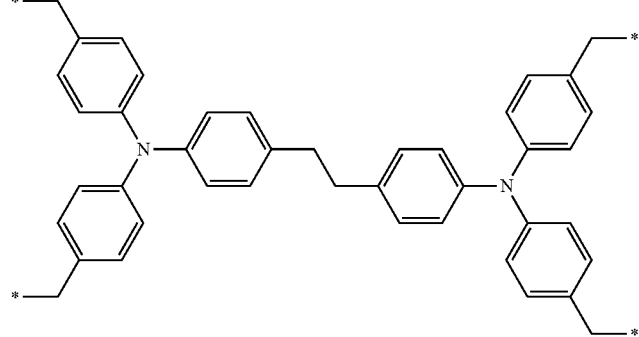 1
(69) 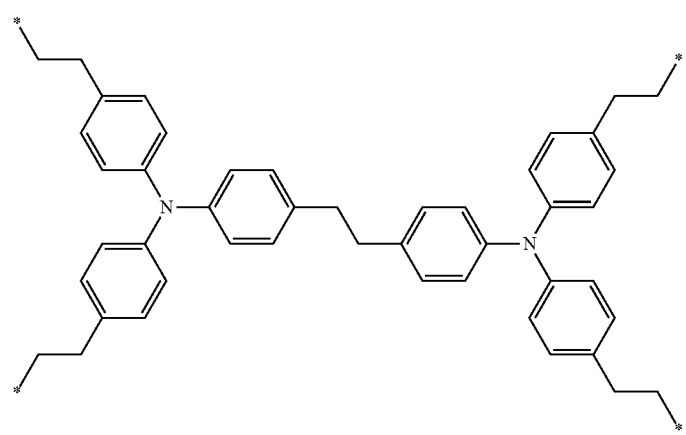 1
(70) 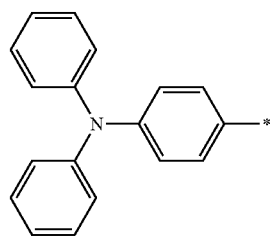 0
(71) 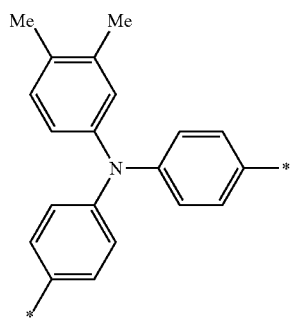 0

-continued
(72) 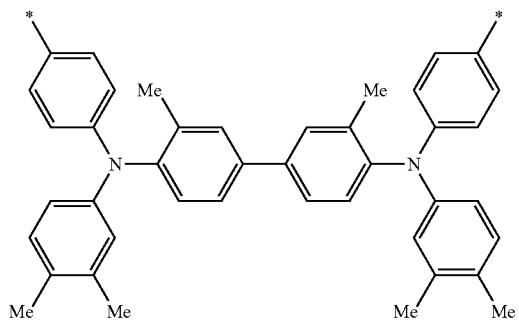 0
(73) 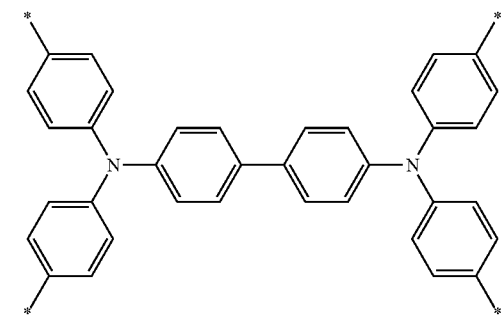 0
(74) 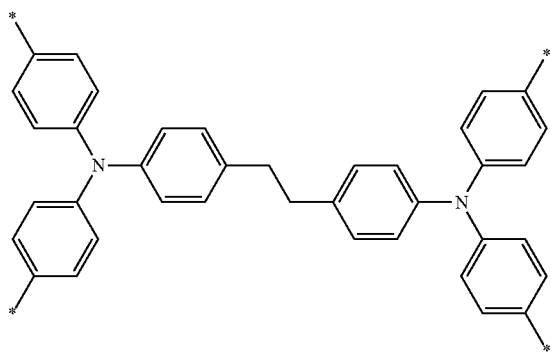 0
| Compound | —(X)$_{a2}$— | a2 | —Y—SH | b |
|---|---|---|---|---|
| (1) | *—O—C(=O)—# | 1 | #—CH$_2$—SH | 1 |
| (2) | *—O—C(=O)—# | 1 | #—CH(Me)—CH$_2$—SH | 1 |
| (3) | *—O—C(=O)—# | 1 | #—CH(Me)—SH | 1 |
| (4) | *—O—C(=O)—# | 1 | #—CH$_2$CH$_2$—SH | 1 |
| (5) | *—O—C(=O)—# | 1 | #—CH(Me)—SH | 1 |
| (6) | *—O—C(=O)—# | 1 | #—CH$_2$CH$_2$—SH | 1 |

-continued

| | | | | |
|---|---|---|---|---|
| (7) | *—O—C(=O)—# | 1 | CH(SH)(Me) with # | 1 |
| (8) | *—O—C(=O)—# | 1 | CH(SH)(Me) with # | 2 |
| (9) | *—O—C(=O)—# | 1 | #—CH2CH2—SH | 2 |
| (10) | *—O—C(=O)—# | 1 | #—CH2CH2—SH | 2 |
| (11) | *—O—C(=O)—# | 1 | #—CH(Me)CH2—SH | 2 |
| (12) | *—O—C(=O)—# | 1 | CH(SH)(Me) with # | 2 |
| (13) | *—O—C(=O)—# | 1 | #—CH2CH2—SH | 2 |
| (14) | *—O—C(=O)—# | 1 | CH(SH)(Me) with # | 2 |
| (15) | *—O—C(=O)—# | 1 | CH(SH)(Me) with # | 2 |
| (16) | *—O—C(=O)—# | 1 | #—CH(Me)CH2—SH | 2 |
| (17) | *—O—C(=O)—# | 1 | #—CH2CH2—SH | 2 |
| (18) | *—O—C(=O)—# | 1 | #—CH(Me)CH2—SH | 2 |
| (19) | *—O—C(=O)—# | 1 | #—CH(Me)CH2—SH | 2 |
| (20) | *—O—C(=O)—# | 1 | #—CH(Me)CH2—SH | 2 |
| (21) | *—O—C(=O)—# | 1 | CH(SH)(Me) with # | 2 |
| (22) | *—O—C(=O)—# | 1 | CH(SH)(Me) with # | 2 |

-continued

| | | | | |
|---|---|---|---|---|
| (23) | *—O—C(=O)—# | 1 | Me-CH(#)-CH2-SH | 3 |
| (24) | *—O—C(=O)—# | 1 | Me-CH(#)-CH2-SH | 3 |
| (25) | *—O—C(=O)—# | 1 | #-CH(SH)-Me | 3 |
| (26) | *—O—C(=O)—# | 1 | Me-CH(#)-CH2-SH | 3 |
| (27) | *—O—C(=O)—# | 1 | Me-CH(#)-CH2-SH | 3 |
| (28) | *—O—C(=O)—# | 1 | #-CH2-CH2-SH | 4 |
| (29) | *—O—C(=O)—# | 1 | #-CH2-CH2-SH | 4 |
| (30) | *—O—C(=O)—# | 1 | #-CH(Me)-SH | 4 |
| (31) | *—O—C(=O)—# | 1 | #-CH2-CH2-SH | 4 |
| (32) | *—O—C(=O)—# | 1 | #-CH(Me)-SH | 4 |
| (33) | *—O—C(=O)—# | 1 | #-CH(Me)-SH | 4 |
| (34) | *—O—C(=O)—# | 1 | #-CH2-CH2-SH | 4 |
| (35) | *—O—C(=O)—# | 1 | Me-CH(#)-CH2-SH | 4 |
| (36) | *—O—C(=O)—# | 1 | #-CH(Me)-SH | 4 |
| (37) | *—O—C(=O)—# | 1 | Me-CH(#)-CH2-SH | 6 |
| (38) | *—C(=O)—O—# | 1 | #-CH2-CH2-SH | 1 |
| (39) | *—C(=O)—O—# | 1 | #-CH2-CH2-SH | 1 |

-continued

| | | | | | |
|---|---|---|---|---|---|
| (40) | *—C(=O)—O—# | 1 | #—CH2—CH(SH)—CH2—SH | 1 |
| (41) | *—C(=O)—O—# | 1 | #—CH2—CH(SH)—CH2—SH | 2 |
| (42) | *—C(=O)—O—# | 1 | #—CH2—CH(SH)—CH2—SH | 2 |
| (43) | *—C(=O)—O—# | 1 | #—CH2—CH(SH)—CH2—SH | 2 |
| (44) | *—C(=O)—O—# | 1 | #—CH2—CH2—CH2—SH | 2 |
| (45) | *—C(=O)—O—# | 1 | #—CH2—CH(SH)—CH2—SH | 2 |
| (46) | *—C(=O)—O—# | 1 | #—CH2—CH(SH)—CH2—SH | 2 |
| (47) | *—C(=O)—O—# | 1 | #—CH2—CH(SH)—CH2—SH | 2 |
| (48) | *—C(=O)—O—# | 1 | #—CH2—CH2—CH2—SH | 3 |
| (49) | *—C(=O)—O—# | 1 | #—CH2—CH2—CH2—SH | 3 |
| (50) | *—C(=O)—O—# | 1 | #—CH2—CH2—CH2—SH | 4 |
| (51) | *—C(=O)—O—# | 1 | #—CH2—CH(SH)—CH2—SH | 4 |
| (52) | *—C(=O)—O—# | 1 | #—CH2—CH2—CH2—SH | 4 |
| (53) | *—C(=O)—O—# | 1 | #—CH2—CH(SH)—CH2—SH | 4 |
| (54) | *—C(=O)—O—# | 1 | #—CH2—CH(SH)—CH2—SH | 4 |
| (55) | *—O—# | 1 | #—CH2—CH2—CH2—SH | 1 |
| (56) | *—O—# | 1 | #—CH2—CH2—CH2—SH | 2 |
| (57) | *—O—# | 1 | #—CH2—CH(SH)—CH2—SH | 1 |

-continued

| | | | | |
|---|---|---|---|---|
| (58) | *—O—# | 1 | #-CH2-CH(SH)-CH2-SH | 1 |
| (59) | *—O—# | 1 | #-CH2-CH(SH)-CH2-SH | 2 |
| (60) | *—O—# | 1 | #-CH2-CH2-SH | 2 |
| (61) | *—O—# | 1 | #-CH2-CH2-SH | 2 |
| (62) | *—O—# | 1 | #-CH2-CH2-SH | 2 |
| (63) | *—O—# | 1 | #-CH2-CH(SH)-CH2-SH | 2 |
| (64) | *—O—# | 1 | #-CH2-CH(SH)-CH2-SH | 2 |
| (65) | *—O—# | 1 | #-CH2-CH2-SH | 2 |
| (66) | *—O—# | 1 | #-CH2-CH2-SH | 4 |
| (67) | *—O—# | 1 | #-CH2-CH(SH)-CH2-SH | 4 |
| (68) | *—O—# | 1 | #-CH2-CH2-SH | 4 |
| (69) | *—O—# | 1 | #-CH2-CH(SH)-CH2-SH | 4 |
| (70) | — | 0 | #-CH2-CH2-SH | 1 |
| (71) | — | 0 | #-CH2-CH2-SH | 2 |
| (72) | — | 0 | #-CH2-SH | 2 |
| (73) | — | 0 | #-CH2-CH2-SH | 4 |
| (74) | — | 0 | #-CH2-CH2-SH | 4 |

Next, the synthesis methods will be explained.

The thiol group-containing charge transporting materials represented by the general formula (1) and the general formula (1)' are synthesized by an ordinary esterification reaction.

For example, they are synthesized by a method in which an ester group-containing arylamine compound is subjected to an esterification reaction with a thiol-containing alcohol, a method in which an ester group-containing arylamine compound is made into a free carboxylic acid by hydrolysis and then esterified into chlorides, bromides, iodides, or the like of a thiol-containing alcohol or a thiol-containing hydrocarbon, or other methods. Further, they are also synthesized by a method in which an ester group-containing arylamine compound is reduced to an alcohol corresponding to lithium aluminum hydride, sodium borohydride, or the like, and then reacted with a thiol-containing carboxylic acid compound.

Furthermore, the thiol group-containing charge transporting materials are synthesized by esterification of an alcohol represented by the following general formula (3), a carboxylic acid represented by the following general formula (4), a carboxylic acid represented by the following general formula (5), or an alcohol represented by the following general formula (6), using an acid catalyst such as sulfuric acid, p-toluenesulfonic acid, and the like. Further, a corresponding carboxylic acid chloride may be used instead of the carboxylic acid.

$$F\text{-}[(G)_{a1}\text{-}OH]_b \quad (3)$$

$$HOOC\text{—}Y\text{—}SH \quad (4)$$

$$F\text{-}[(G)_{a1}\text{-}COOH]_b \quad (5)$$

$$HO\text{—}Y\text{—}SH \quad (6)$$

(wherein F represents an organic group derived from a charge transporting compound, G represents a divalent organic group having 1 to 5 carbon atoms, Y represents a divalent organic group having 1 to 5 carbon atoms, which may have an —SH group as a substituent, a1 represents 0 or 1, and b represents an integer of 1 to 6).

Furthermore, a compound in which X is an ether bond is synthesized from an alcohol represented by the following general formula (7), an alcohol represented by the following general formula (8) or a halide, an alcohol represented by the following general formula (9) or a halide, and an alcohol represented by the following general formula (10).

$$F\text{-}[(G)_{a1}\text{-}OH)]_b \quad (7)$$

$$J\text{-}Y\text{—}SH \quad (8)$$

$$F\text{-}[(G)_{a1}\text{-}J]_b \quad (9)$$

$$HO\text{—}Y\text{—}SH \quad (10)$$

(wherein F represents an organic group derived from a charge transporting compound, G represents a divalent organic group having 1 to 5 carbon atoms, Y represents a divalent organic group having 1 to 5 carbon atoms, which may have an —SH group as a substituent, a1 represents 0 or 1, b represents an integer of 1 to 6, and J represents a hydroxyl group, or chlorine, bromine, or iodine).

The esterification is carried out by heating using an excess amount of a thiol-containing alcohol and an organic metal compound such as titanium, tin, zinc, and the like as described in, for example, Experimental Chemistry Lecture Course, $4^{th}$ Ed., Vol. 28, P. 217, or the like.

The thiol-containing alcohol is desirably added to the ester group of an arylamine compound in an amount of 1 equivalent or more, preferably 1.2 equivalents or more, and more preferably 1.5 equivalents or more.

Inorganic acids such as sulfuric acid, phosphoric acid, and the like, titanium alkoxide, acetate or carbonate of calcium, cobalt, or the like, or oxides of zinc or lead may be added as a catalyst. The catalyst is desirably used in an amount of 1/10000 part by weight or more and 1 part by weight or less, and preferably 1/1000 part by weight or more and ½ part by weight or less, based on 1 part by weight of the arylamine compound.

The reaction is preferably carried out at a reaction temperature of 100° C. or higher and 300° C. or lower, and more preferably carried out at a boiling point of the leaving alcohol or higher.

As an ester group of the arylamine compound, an ester of a low-boiling point alcohol such as methanol, ethanol, and the like is preferable for the purpose of promoting the esterification reaction.

The reaction is preferably carried out in inert gas such as nitrogen, argon, and the like, and further, the reaction may be carried out using a high-boiling point solvent such as p-cymene, 1-chloronaphthalene, and the like.

The arylamine compound carboxylic acid is obtained by subjecting an ester group of an arylamine compound to hydrolysis using a basic catalyst such as NaOH, $K_2CO_3$, and the like, or an acidic catalyst such as phosphoric acid, sulfuric acid, and the like as described in, for example, Experimental Chemistry Lecture Course, $4^{th}$ Ed., Vol. 20, P. 51, or the like.

Here, as the solvent, various ones may be used, but an alcohol-based solvent such as methanol, ethanol, ethylene glycol, and the like, or a mixture thereof with water is preferably used. Further, in the case of a low solubility, methylene chloride, chloroform, toluene, dimethylsulfoxide, ether, tetrahydrofuran, or the like may be added.

The amount of the solvent is not particularly limited, but is preferably 1 part by weight or more and 100 parts by weight or less, and preferably 2 parts by weight or more and 50 parts by weight or less, based on 1 part by weight of an ester group-containing arylamine compound.

The reaction temperature is set to a temperature of room temperature (20° C.) or higher and the boiling point of the solvent or lower, and in view of the reaction rate, it is preferably 50° C. or higher.

The amount of the catalyst is not particularly limited, but is preferably 0.001 part by weight or more and 1 part by weight or less, and more preferably 0.01 part by weight or more and 0.5 part by weight or less, based on 1 part by weight of an ester group-containing arylamine compound.

In the case where after the hydrolysis reaction, the hydrolysis is carried out with a basic catalyst, the obtained salt is neutralized with an acid such as hydrochloric acid and the like, and thus released. Further, the product may be used after sufficiently washing with water and then drying, and if necessary, recrystallizing with a suitable solvent such as methanol, ethanol, toluene, ethyl acetate, acetone, and the like, and then drying.

The thiol-containing alcohol is desirably added in an amount of 1 equivalent or more, preferably 1.2 equivalents or more, and still more preferably 1.5 equivalents or more, based on the arylamine compound carboxylic acid.

Dehydration and esterification are carried out using an inorganic acid such as sulfuric acid, phosphoric acid, and the like, or an organic acid such as p-toluenesulfonic acid and the like as a catalyst so as to perform synthesis. The catalyst is desirably used in an amount of 1/10000 part by weight or more and 1 part by weight or less, and preferably 1/1000 part by weight or more and ½ part by weight or less, based on 1 part by weight of the arylamine compound.

The reaction is preferably carried out using a solvent which can be azeotroped with water, in order to remove water produced during the polymerization. Toluene, chlorobenzene, 1-chloronaphthalene, and the like are effective, and are desirably used in an amount in the range of 1 part by weight or more and 100 parts by weight or less, preferably 2 parts by weight or more and 50 parts by weight or less, based on 1 part by weight of the arylamine compound.

The reaction temperature is arbitrarily determined, but for the purpose of removing water produced during the polymerization, the reaction is preferably carried out at the boiling point of the solvent. After completion of the reaction, the reaction liquid is poured into water, extracted with a solvent such as toluene, hexane, ethyl acetate, and the like, and if necessary, purification may be carried out using an adsorbent such as activated carbon, silica gel, porous alumina, activated white clay, and the like.

Furthermore, 1 equivalent or more and 5 equivalents or less, and preferably 1.1 equivalents or more and 3 equivalents or less, based on the acid group of the arylamine compound carboxylic acid, of a thiol-containing hydrocarbon having a halogen atom such as Cl, Br, I, and the like is reacted with a base such as pyridine, piperidine, triethylamine, dimethylaminopyridine, trimethylamine, DBU, sodium hydride, sodium hydroxide, potassium hydroxide, and the like, in an organic solvent, such as an aprotic polar solvent such as N-methylpyrrolidone, dimethyl sulfoxide, N,N-dimethylformamide, and the like, a ketone-based solvent such as acetone, methyl ethyl ketone, and the like, and an ether-based solvent such as diethyl ether, tetrahydrofuran, and the like to perform synthesis.

The base is desirably used in an amount of 1 equivalent or more and 3 equivalents or less, and preferably 1 equivalent or more and 2 equivalents or less, based on the carboxylic acid. The aprotic organic solvent used is desirably used in an amount of 1 part by weight or more and 50 parts by weight or less, and preferably 1.5 parts by weight or more and 30 parts by weight or less, based on the carboxylic acid derivative.

The reaction temperature is arbitrarily determined within a range of 0° C. or higher and the boiling point of the solvent or lower, but is preferably 0° C. or higher and 150° C. or lower. After completion of the reaction, the reaction liquid is poured into water, extracted with a solvent such as toluene, hexane, ethyl acetate, and the like, and if necessary, purification may be carried out using an adsorbent such as activated carbon, silica gel, porous alumina, activated white clay, and the like.

Furthermore, the ester group of the arylamine compound may be reduced to a corresponding alcohol using aluminum lithium hydride, sodium borohydride, and the like as described in, for example, Experimental Chemistry Lecture, $4^{th}$ Ed., Vol. 20, P. 10, or the like, and esterified with a thiol-containing carboxylic acid to perform synthesis.

<Thiol Group-Containing Charge Transporting Material-Dissolving Solution>

The dissolving solution for the thiol group-containing charge transporting material according to the present exemplary embodiment is formed by dissolving the thiol group-containing charge transporting material represented by the general formula (1) or (1)' in a solvent.

As the solvent, an aromatic solvent such as toluene, xylene, a ketone-based solvent such as methyl ethyl ketone, methyl isobutyl ketone, cyclohexanone, and the like, an ester-based solvent such as ethyl acetate, butyl acetate, and the like, an ether-based solvent such as tetrahydrofuran, dioxane, and the like, a cellosolve-based solvent such as ethylene glycol monomethyl ether and the like, and an alcohol-based solvent such as isopropyl alcohol, butanol, and the like is used singly or in mixture.

Furthermore, a method for dissolving the thiol group-containing charge transporting material represented by the general formula (1) or (1)' in the solvent may be a usual method, such as that of stirring and mixing with the solvent at 10° C. to 150° C., and preferably 15° C. to 120° C., or of stirring with ultrasonic wave irradiation, or the like.

The dissolving solution for the thiol group-containing charge transporting material according to the present exemplary embodiment is used in, for example, film formation in a photoelectric conversion device (an organic EL device, an electrophotographic photoreceptor, and the like), or formation of a solar cell, an organic transistor, or the like.

<Photoelectric Conversion Device>

Next, the photoelectric conversion device will be described.

The thiol group-containing charge transporting material according to the present exemplary embodiment may be used to form a film as a vapor deposited film, but a dissolving solution in which the thiol group-containing charge transporting material is dissolved may be used to form a film. Moreover, this film may contain a polymer in which the thiol group-containing charge transporting material is polymerized.

In addition, a film in which the thiol group-containing charge transporting material is dispersed as molecules in a resin such as a polycarbonate resin, a polyarylate resin, a polyester resin, and the like is excellent in practical use, and a cured film formed by mixing with a monomer, oligomer, or polymer having a double bond and curing is most preferably used.

<Electrophotographic Photoreceptor>

The electrophotographic photoreceptor according to the present exemplary embodiment (which may be sometimes simply referred to as a "photoreceptor") has a conductive substrate, and a photosensitive layer containing a polymer formed by polymerization of at least one kind of the thiol group-containing charge transporting material represented by the following general formula (I) and at least one kind of the compound having an unsaturated bond (which may be sometimes simply referred to as a "specific polymer"), on the conductive substrate.

$$F\text{-}[(G)_{a1}\text{-}(X)_{a2}\text{—}Y\text{—}SH]_b \qquad (I)$$

(in the general formula (I), F represents an organic group derived from a charge transporting compound, G represents a divalent organic group having 1 to 5 carbon atoms, X represents a group selected from —CO—O—, —O—CO—, and —O—, Y represents a divalent organic group having 1 to 5 carbon atoms, which may have an —SH group as a substituent, a1 and a2 each independently represent 0 or 1, and b represents an integer of 1 or more and 6 or less).

It is presumed that since the thiol group-containing charge transporting material represented by the general formula (I) has an —SH group as a polar group, but has the low electronegativity of a sulfur atom, as a result, unlike —OH, —NH—, and the like, the effect of interfering with the carrier transportation is relatively small. Therefore, with a film formed using the same, formation of a trap that captures the charge is inhibited, accumulation of the residual potential is inhibited, and thus, the potential stability is excellent.

In addition, usually, with a film obtained by crosslinking a polyfunctional charge transporting material, as immobilization proceeds, the residual strain in the film increases, but with the thiol group-containing charge transporting material represented by the general formula (I), for the purpose of crosslinking the charge transporting components through a thioester group having a high degree of motion freedom, the residual strain in the film is inhibited and thus the structural trap is not easily generated, which is presumed to lead to excellent electrical characteristics.

As a result, while obtaining excellent electrical characteristics, the thickness of the film formed can further increase.

Furthermore, in the case where for the purpose of increasing the strength of the film formed, a charge transporting material is additionally mixed with a polyfunctional acrylic monomer to form a film, the compatibility of the two components in usual charge transporting materials is low, and accordingly, an increase in the amount of the polyfunctional acrylic monomer to be added is limited. However, it is presumed that since the thiol group-containing charge transporting material represented by the general formula (I) has an ester structure which is similar to that of the polyfunctional acrylic monomer, and the compatibility between the two components is excellent, crosslinking is conducted without a phase separation with the polyfunctional acrylic monomer, and thus, a film having both electrical characteristics and strength is obtained.

Accordingly, by using the thiol group-containing charge transporting material represented by the general formula (I), a photosensitive layer having both electrical characteristics and strength is formed. Particularly, a case in which a thicker film has a thickness of 10 μm or more can be attained. Further, a layer including a polymer formed by polymerization of at least one kind of the thiol group-containing charge transporting material represented by the general formula (I) and at least one kind of the compound having an unsaturated bond (specific polymer) is a surface layer constituting the outermost surface in the photoreceptor according to the present exemplary embodiment, and formation of the thicker film above inhibits decrease in the image quality after the repeated use. In the case of having a high-strength surface layer, the lifespan of the photoreceptor is determined to be a point of time when the surface layer is worn out. Thus, formation of a thicker film is effective for providing a longer lifespan to the photoreceptor.

Further, in order to form an image, the photoreceptor is charged by discharging and used, but at that time, due to electrical stress or stress from discharge gas such as ozone and the like, the surface material of the photoreceptor is deteriorated, and as a result, ionic materials such as ammonium nitrate called a discharge product is easily adsorbed. As a result, particularly, under high humidity, the moisture is adsorbed and the surface resistivity of the photoreceptor is lowered. Thus, in the formed image, latent image blurring occurs, and as a result, image degradation easily occurs. In order to inhibit this, a method in which a member to be cleaned that is in contact with the photoreceptor is provided, and abrasion with the member to be cleaned suitably abrades the surface layer to remove the discharge products and inhibit the latent image blurring, is effective. In addition, since the abrasion amount is greatly affected by the charging type and the cleaning type in the image formation, the shape of the toner used, and the like, it is highly dependent on the image forming systems. As a result, it is important to adjust the strength of the surface layer of the photoreceptor thereto.

In this regard, in the electrophotographic photoreceptor according to the present exemplary embodiment, the ratio of the crosslinking components of the thiol group-containing charge transporting material represented by the general formula (I) and the like and the structures of the reactive monomers of the thiol group-containing charge transporting material represented by the general formula (I) and the like can be chosen to form a surface layer having a strength optimal to the system.

Furthermore, by using the thiol group-containing charge transporting material represented by the general formula (I) itself as a polyfunctional charge transporting monomer, strength can be provided for the photosensitive layer without lowering the concentration of the charge transporting component.

Among the thiol group-containing charge transporting materials represented by the general formula (I), one having an arylamine skeleton is preferable since it has a high charge transporting property, and those represented by the following general formula (II) are particularly preferable.

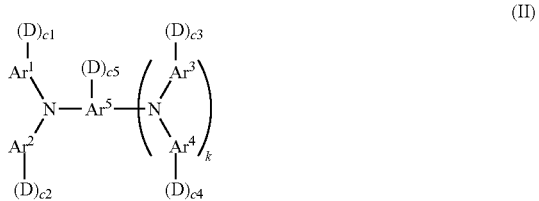

In the general formula (II), D represents a binding group represented by $-(G)_{a1}-(X)_{a2}-Y-SH$, $Ar^1$ to $Ar^4$ each independently represent a substituted or unsubstituted aryl group, $Ar^5$ represents a substituted or unsubstituted aryl group or a substituted or unsubstituted arylene group, G represents a divalent organic group having 1 to 5 carbon atoms, X represents a group selected from $-CO-O-$, $-O-CO-$, and $-O-$, Y represents a divalent organic group having 1 to 5 carbon atoms, which may have an $-SH$ group as a substituent, and a1 and a2 each independently represent 0 or 1. One or more and four or less of $Ar^1$ to $Ar^5$ have a bond which is capable of binding to a binding group represented by $-(G)_{a1}-(X)_{a2}-Y-SH$, c1 to c5 each independently represent an integer of 0 or more and 2 or less, and k represents 0 or 1.

—Compound Having Unsaturated Bond—

Next, the compound having an unsaturated bond will be described. The compounds having no charge transporting component include the following.

Examples of the monofunctional monomer include isobutyl acrylate, tert-butyl acrylate, isooctyl acrylate, lauryl acrylate, stearyl acrylate, isobornyl acrylate, cyclohexyl acrylate, 2-methoxyethyl acrylate, methoxytriethylene glycol acrylate, 2-ethoxyethyl acrylate, tetrahydrofurfuryl acrylate, benzyl acrylate, ethyl carbitol acrylate, phenoxyethyl acrylate, 2-hydroxyacrylate, 2-hydroxypropyl acrylate, 4-hydroxybutyl acrylate, methoxypolyethylene glycol acrylate, methoxypolyethylene glycol methacrylate, phenoxypolyethylene glycol acrylate, phenoxypolyethylene glycol methacrylate, hydroxyethyl o-phenylphenol acrylate, o-phenylphenol glycidyl ether acrylate, styrene, and the like.

Examples of the difunctional monomer include diethylene glycol di(meth)acrylate, polyethylene glycol di(meth)acrylate, polypropylene glycol di(meth)acrylate, neopentyl glycol di(meth)acrylate, 1,6-hexanediol di(meth)acrylate, divinylbenzene, diallyl phthalate, and the like.

Examples of the trifunctional monomer include trimethylolpropane tri(meth)acrylate, pentaerythritol tri(meth)acrylate, aliphatic tri(meth)acrylate, trivinyl cyclohexane, and the like.

Examples of the tetrafunctional monomer include pentaerythritol tetra(meth)acrylate, ditrimethylolpropane tetra(meth)acrylate, aliphatic tetra(meth)acrylate, and the like.

Examples of the penta- or higher functional monomer include dipentaerythritol penta(meth)acrylate, dipentaerythritol hexa(meth)acrylate, and the like, as well as (meth)acrylates having a polyester skeleton, a urethane skeleton or a phosphazene skeleton.

Furthermore, examples of the reactive polymer include those disclosed in, for example, JP-A-5-216249, JP-A-5-323630, JP-A-11-52603, JP-A-2000-264961, JP-A-2005-2291, and the like.

In the case where a compound has an unsaturated bond, which has no charge transporting component, it is used singly or in a mixture of two or more kinds thereof. The compound having an unsaturated bond, which has no charge transporting component is used to form an outermost surface layer of the electrophotographic photoreceptor; it is used in an amount of preferably 60% by weight or less, more preferably 55% by weight or less, and still more preferably 50% by weight or less, based on the total solid content of the composition used for the surface layer.

Next, the compound having an unsaturated bond, which further has a charge transporting skeleton (monomers, oligomers, and polymers) will be described.

(I) Compound Having Chain Polymerizable Functional Group and Charge Transporting Skeleton in the Same Molecule The chain polymerizable functional group in the compound having a chain polymerizable functional group and a charge transporting skeleton in the same molecule is not particularly limited as long as it is a functional group that is capable of radical polymerization, and it is, for example, a functional group having at least carbon double bonds. Specific examples thereof include a group containing at least one selected from a vinyl group, a vinyl ether group, a vinyl thioether group, a styryl group, an acryloyl group, a methacryloyl group, and derivatives thereof, and the like. Among these, in terms of high reactivity, the chain polymerizable functional group is preferably a group containing at least one selected from a vinyl group, a styryl group, an acryloyl group, a methacryloyl group, and derivatives thereof.

Further, the charge transporting skeleton in the (I) compound having a chain polymerizable functional group and a charge transporting skeleton in the same molecule is not particularly limited as long as it has a structure known in electrophotographic photoreceptors, and it is, for example, a skeleton derived from a nitrogen-containing hole transporting compound such as a triarylamine-based compound, a benzidine-based compound, a hydrazone-based compound, and the like. Examples thereof include structures having conjugation with nitrogen atoms. Among these, a triarylamine skeleton is preferable.

Here, as the (I) compound having a chain polymerizable functional group and a charge transporting skeleton in the same molecule, a compound represented by the following general formula (A) may be mentioned as a preferable example in terms of an excellent charge transporting property as well as excellent chain polymerizability.

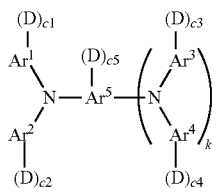

(A)

In the general formula (A), $Ar^1$ to $Ar^4$ each independently represent a substituted or unsubstituted aryl group, $Ar^5$ represents a substituted or unsubstituted aryl group or a substituted or unsubstituted arylene group, D represents a group having a functional group having a carbon double bond, c1 to c5 each independently represent 0, 1, or 2, k represents 0 or 1, and the total number of D's is 1 or more (preferably 2 or more).

Here, the compound represented by the general formula (A) may be the compound in which D represents a group having at least one group (particularly, a group having the group at an end) selected from an acryloyl group, a methacryloyl group, a vinyl phenyl group, an allyl group, a vinyl group, a vinyl ether group, an allyl vinyl ether group, and derivatives thereof.

In addition, the compound represented by the general formula (A) may be the compound in which D represents $—(CH_2)_d—(O—CH_2—CH_2)_e—O—CO—C(R')=CH_2$ (wherein R' represents a hydrogen atom or a methyl group, d represents an integer of 1 or more and 5 or less, and e represents 0 or 1).

In the general formula (A), $Ar^1$ to $Ar^4$ each independently represent a substituted or unsubstituted aryl group. $Ar^1$ to $Ar^4$ may be the same as or different from each other.

Here, examples of the substituent in the substituted aryl group include, in addition to the group represented by D, an alkyl group having 1 to 4 carbon atoms, an alkoxy group having 1 to 4 carbon atoms, a substituted or unsubstituted aryl group having 6 to 10 carbon atoms, and the like.

Specific examples of $Ar^1$ to $Ar^4$ may any one of the following formula (1) to (7). Further, the following formulae (1) to (7) represent "$-(D)_C$", which generally denotes "$-(D)_{C1}$" to "$-(D)_{C4}$" that can be substituted with each of $Ar^1$ to $Ar^4$.

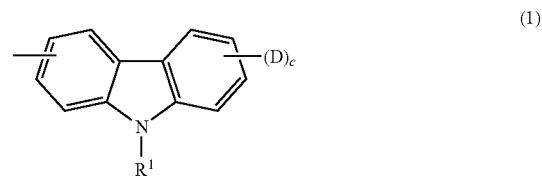

(1)

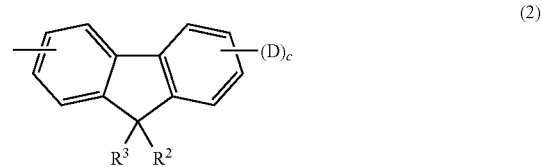

(2)

(3)

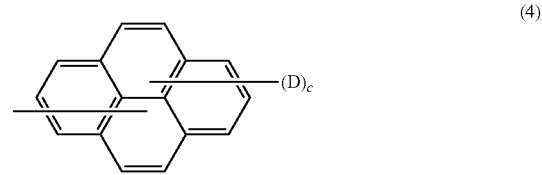

(4)

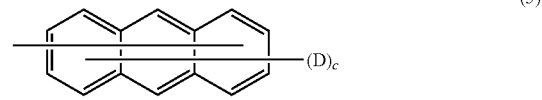

(5)

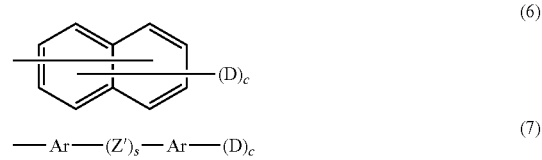

(6)

(7)

In the formula (1) to (7), $R^1$ represents at least one selected from a hydrogen atom, an alkyl group having 1 to 4 carbon atoms, an alkyl group having 1 to 4 carbon atoms or a phenyl group substituted with an alkoxy group having 1 to 4 carbon atoms, an unsubstituted phenyl group, and an aralkyl group having 7 to 10 carbon atoms. $R^2$ to $R^4$ each independently represent at least one selected from a hydrogen atom, an alkyl group having 1 to 4 carbon atoms, an alkoxy group having 1 to 4 carbon atoms, a phenyl group substituted with an alkoxy group having 1 to 4 carbon atoms, an unsubstituted phenyl group, an aralkyl group having 7 to 10 carbon atoms, and a halogen atom. Ar represents a substituted or unsubstituted arylene group, D represents the same group as D in the general formula (A), c represents 1 or 2, s represents 0 or 1, and t represents an integer of 0 or more and 3 or less.

Here, Ar in the formula (7) is represented by the following structural formula (8) or (9).

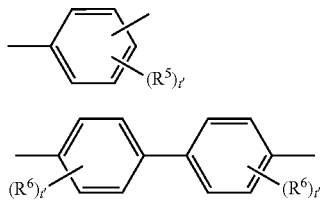

In the formula (8) and (9), $R^5$ and $R^6$ each independently represent one selected from the group consisting of a hydrogen atom, an alkyl group having 1 to 4 carbon atoms, an alkoxy group having 1 to 4 carbon atoms, a phenyl group substituted with an alkoxy group having 1 to 4 carbon atoms, an unsubstituted phenyl group, an aralkyl group having 7 to 10 carbon atoms, and a halogen atom, and t' represents an integer of 0 or more and 3 or less.

Furthermore, in the formula (7), Z' represents a divalent organic linking group, but is represented by any one of the following formulae (10) to (17). Further, s represents 0 or 1.

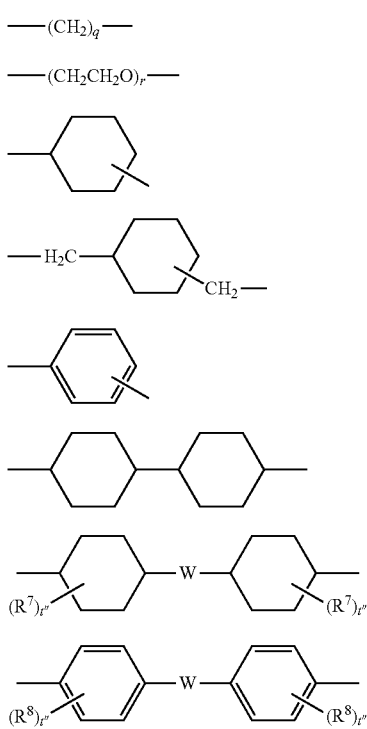

In the formulae (10) to (17), $R^7$ and $R^8$ each independently represent one selected from the group consisting of a hydrogen atom, an alkyl group having 1 to 4 carbon atoms, an alkoxy group having 1 to 4 carbon atoms, a phenyl group substituted with an alkoxy group having 1 to 4 carbon atoms, an unsubstituted phenyl group, an aralkyl group having 7 to 10 carbon atoms, and a halogen atom, W represents a divalent group, q and r each independently represent an integer of 1 or more and 10 or less, and t" represents an integer of 0 or more and 3 or less.

W in the formulae (16) to (17) may be any one of the divalent groups of the following formulae (18) to (26). However, in the formula (25), u represents an integer of 0 or more and 3 or less.

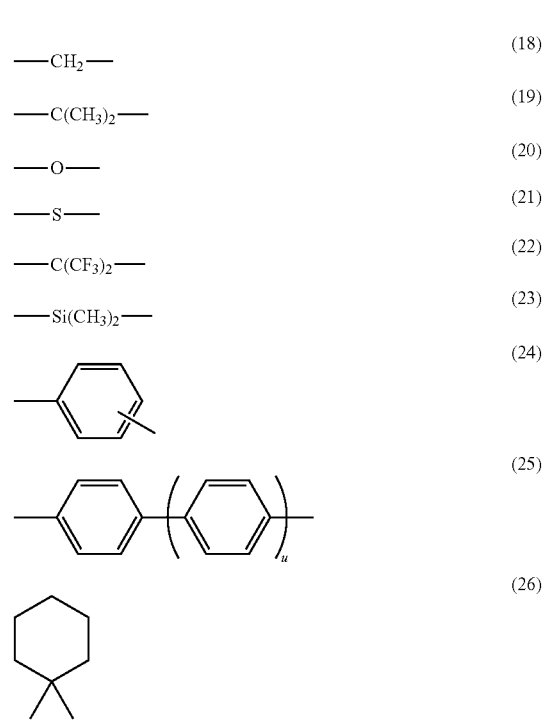

Furthermore, in the general formula (A), $Ar^5$ is a substituted or unsubstituted aryl group when k is 0, and examples of the aryl group include those listed as an aryl group exemplified in the explanation of $Ar^1$ to $Ar^4$. Further, $Ar^5$ is a substituted or unsubstituted arylene group when k is 1, and examples of the arylene group include those listed as an arylene obtained by removing one hydrogen atom at a desired position from the aryl group exemplified in the explanation of $Ar^1$ to $Ar^4$.

Hereinbelow, specific examples of the compound represented by the general formula (A) (compound of (I)) are shown. Further, the compound represented by the general formula (A) is not limited thereto.

First, specific examples of the compound having one reactive functional group having a carbon double bond are shown, but are not limited thereto.

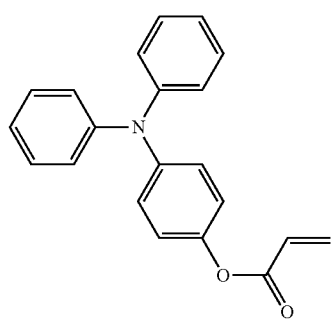

i-1 i-2
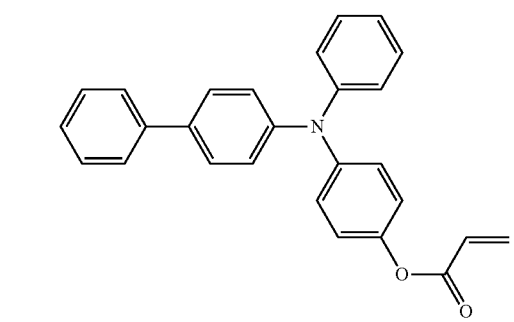
i-3
i-4
i-5
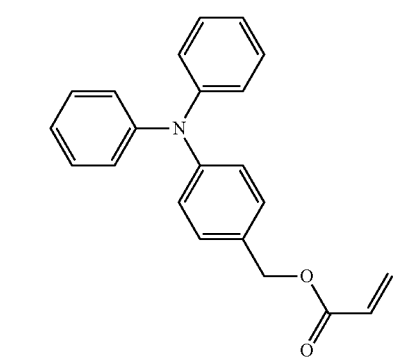
i-6
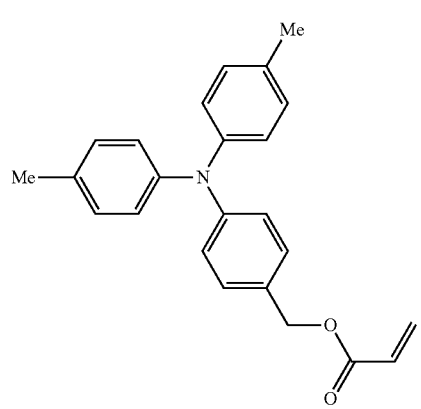
i-7
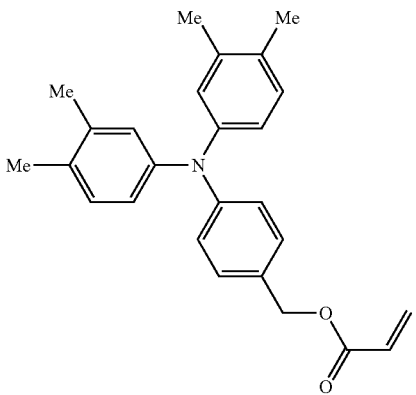
i-8
i-9
i-10
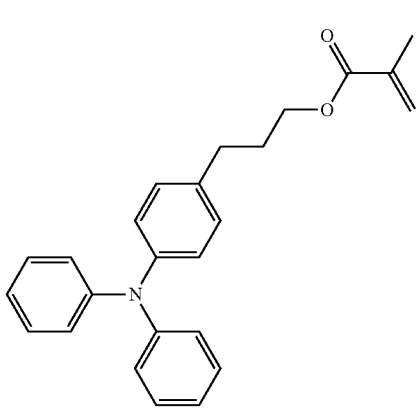

-continued
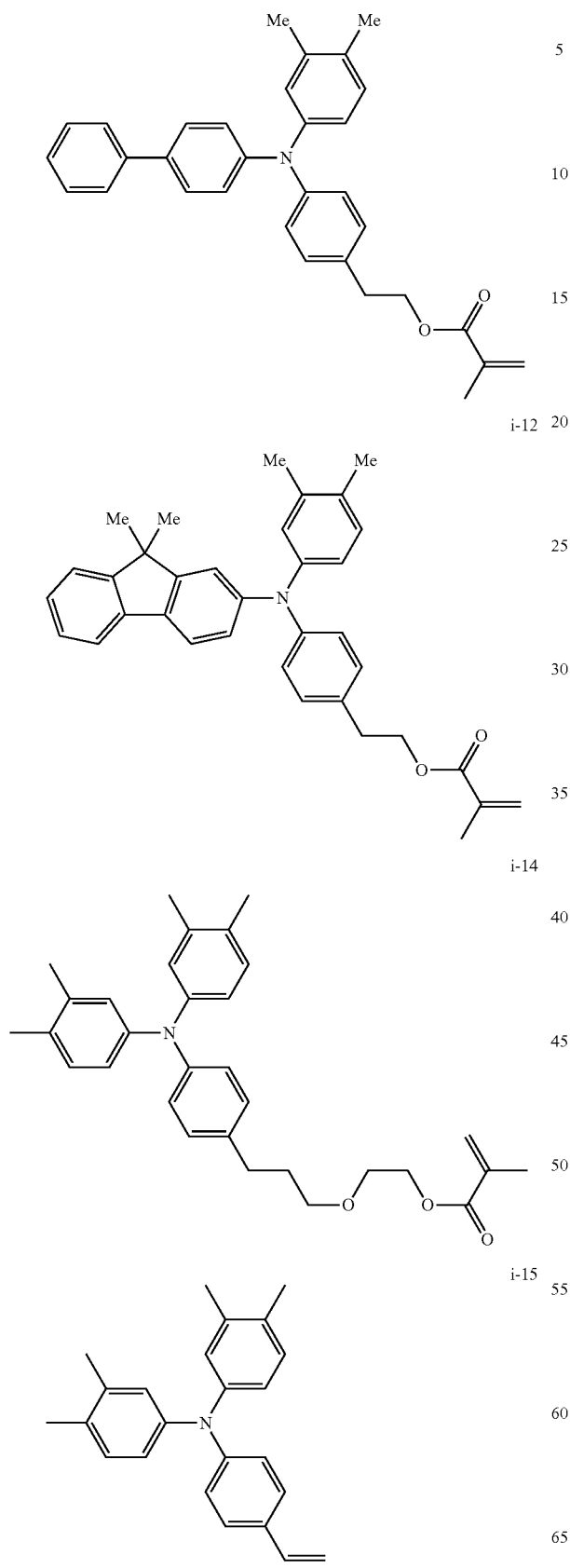
i-11
i-12
i-14
i-15
-continued
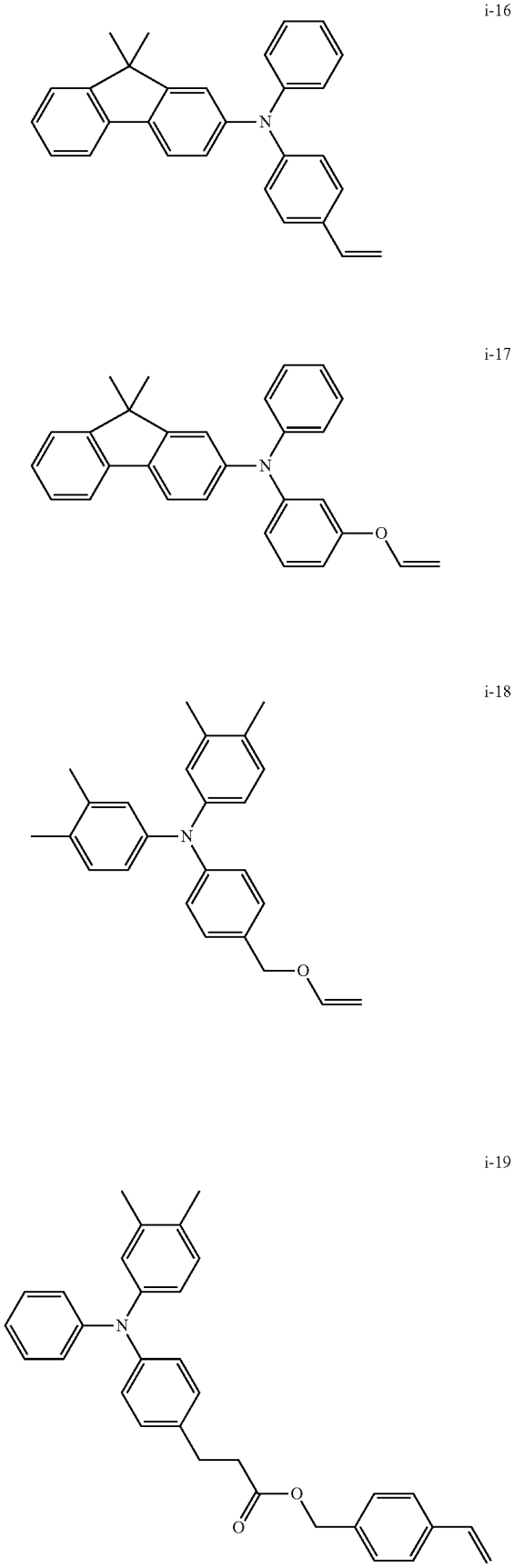
i-16
i-17
i-18
i-19 i-20
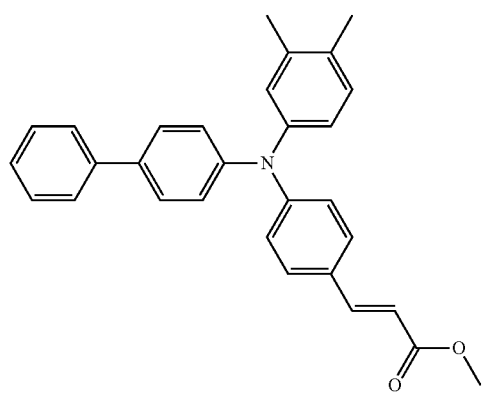
i-21
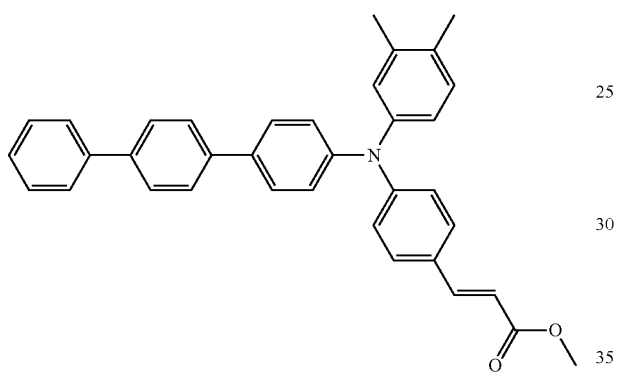
i-22
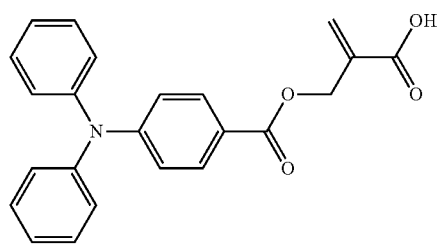
i-23
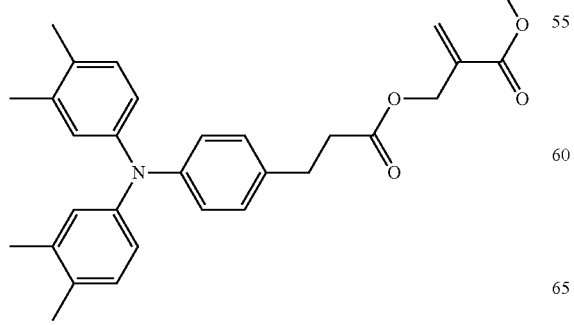
i-24
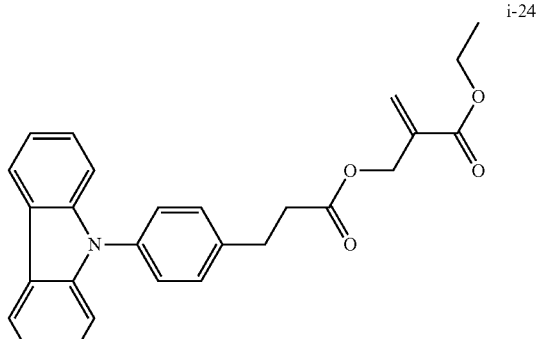
i-25
i-26
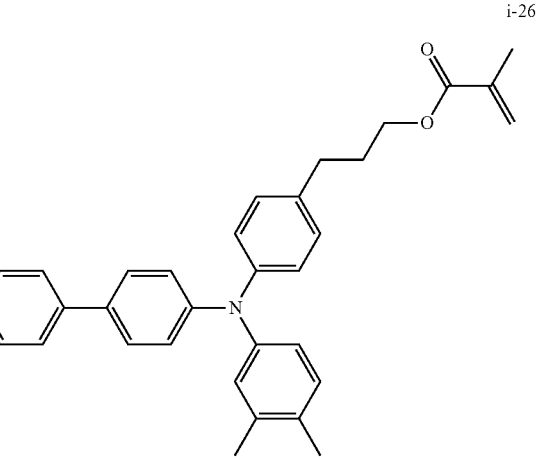
Next, specific examples of the compound having two reactive functional groups having a carbon double bond are shown, but are not limited thereto.

71　　　　　　　　　　　　　　72
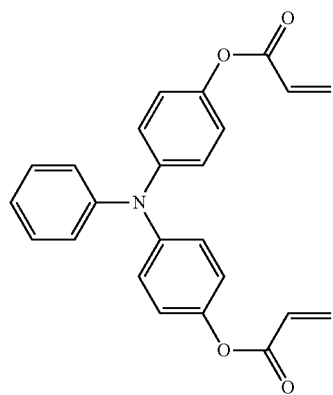
ii-1
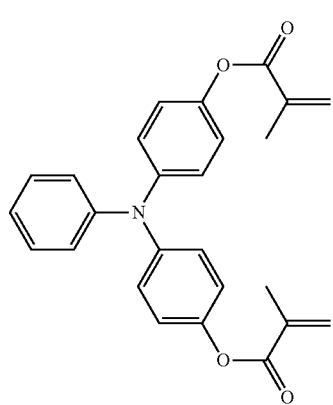
ii-2
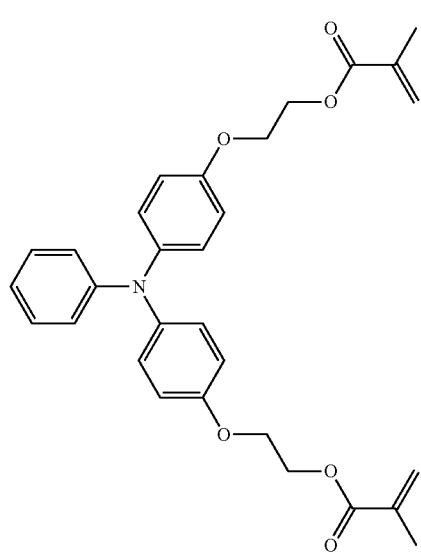
ii-3
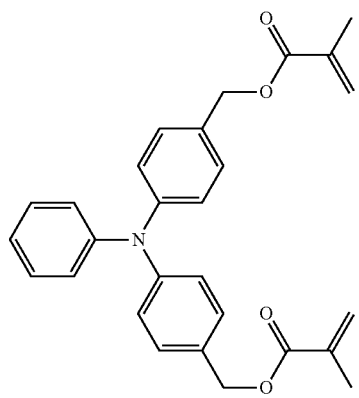
ii-4
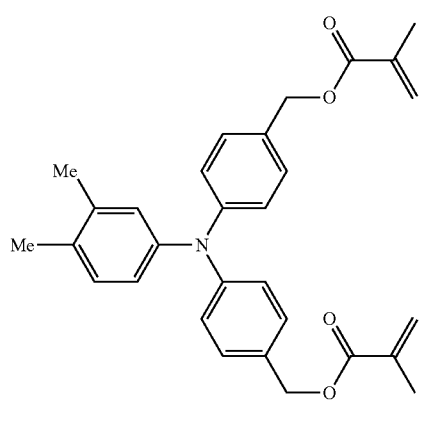
ii-5
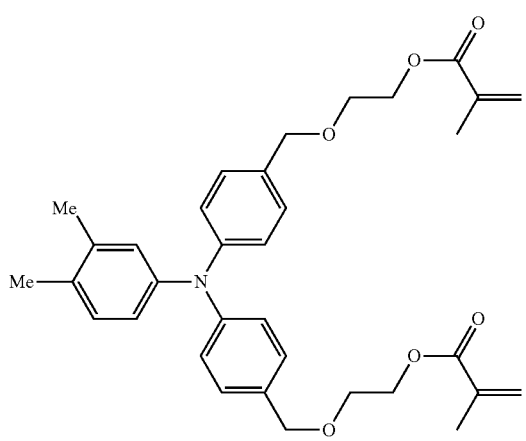
ii-6

-continued
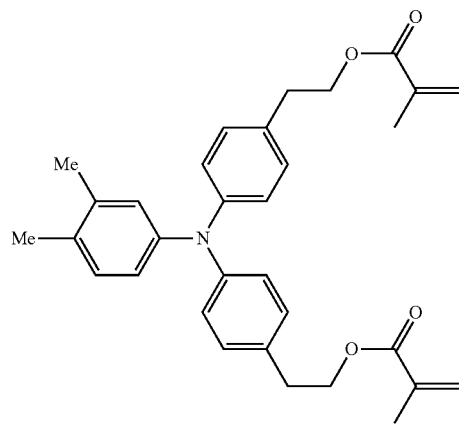
ii-7
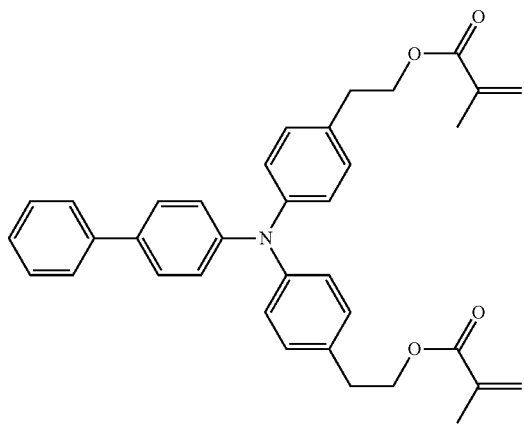
ii-8
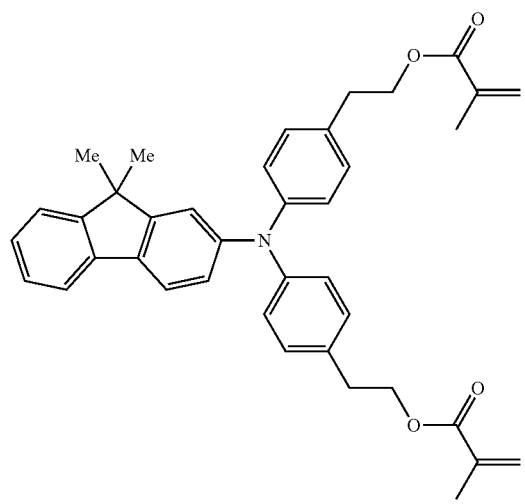
ii-9
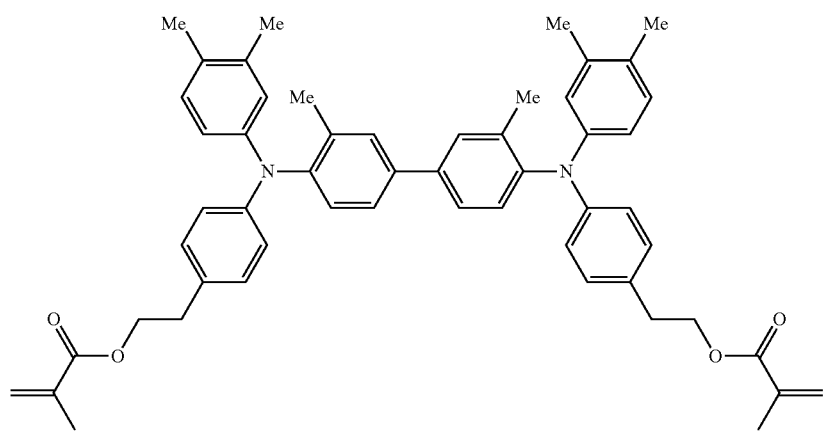
ii-10

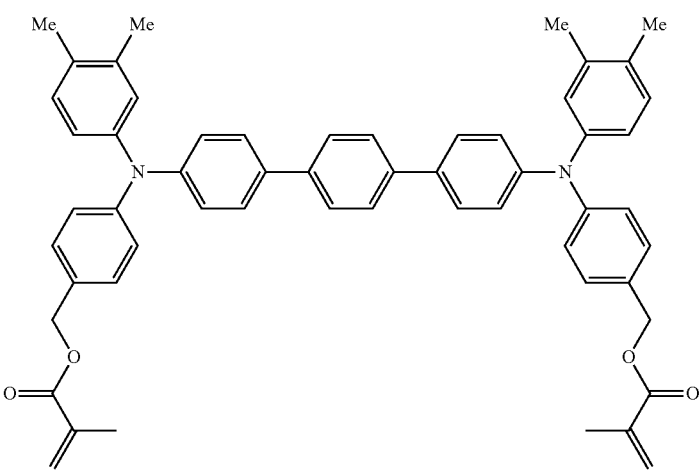
ii-11
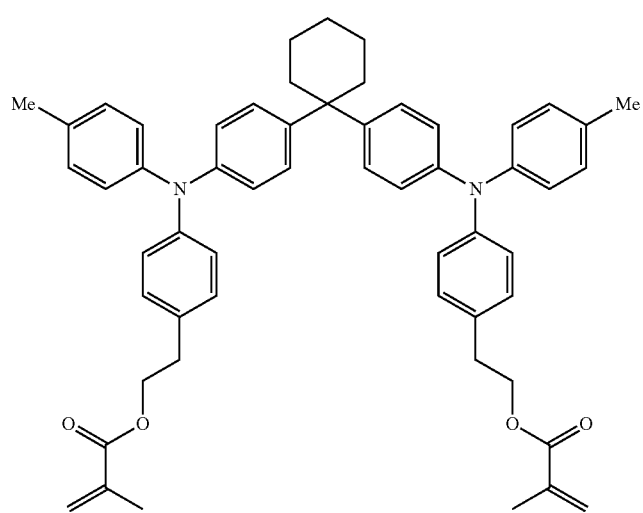
ii-12
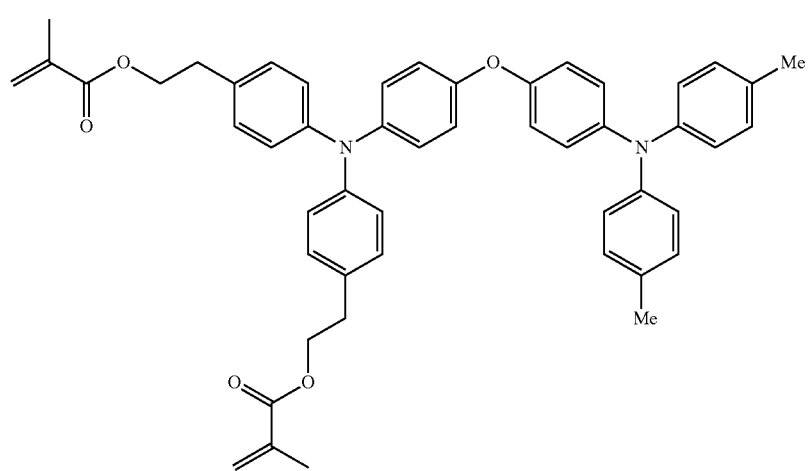
ii-13

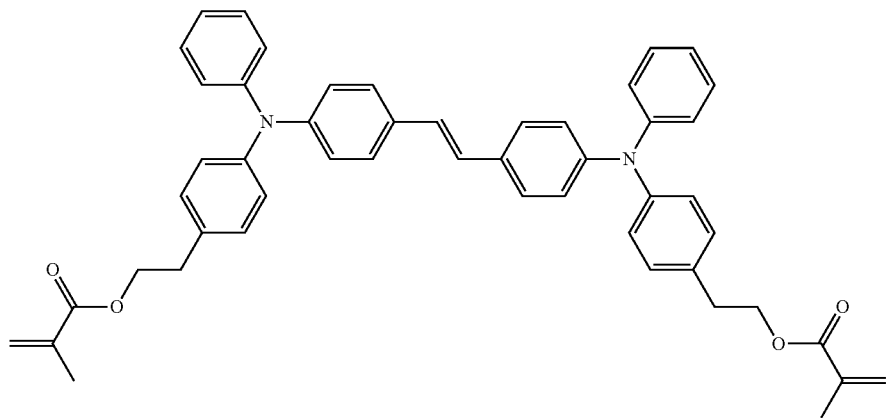
ii-14
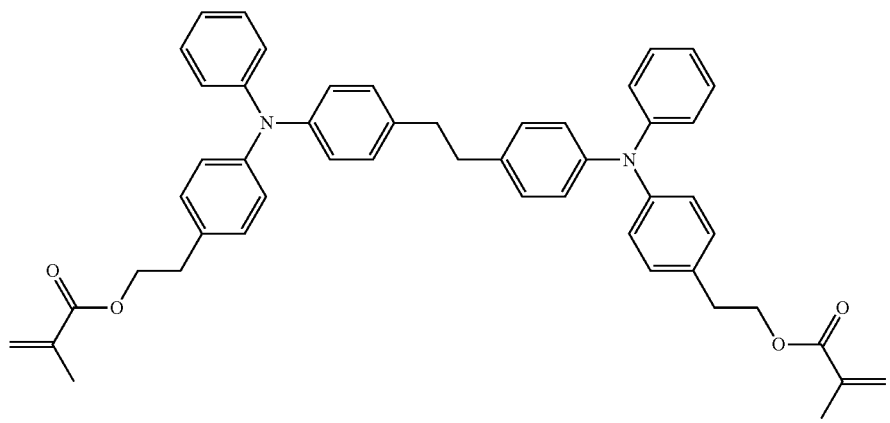
ii-15
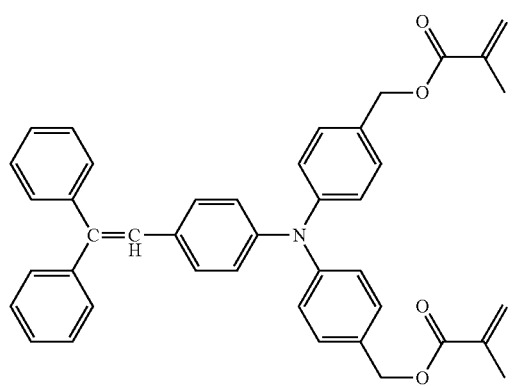
ii-16
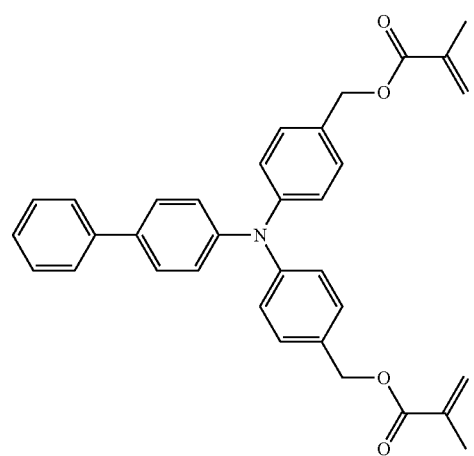
ii-17

-continued
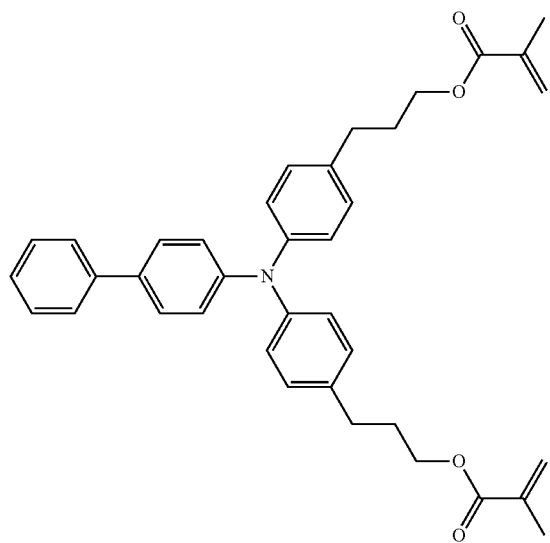
ii-18
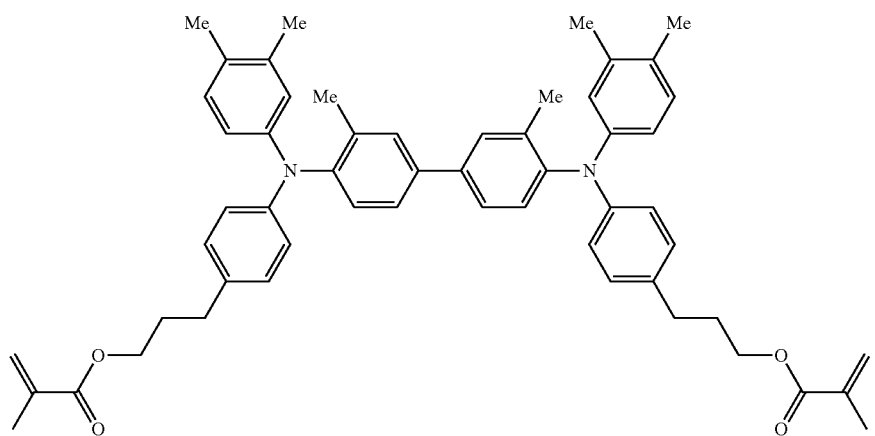
ii-19
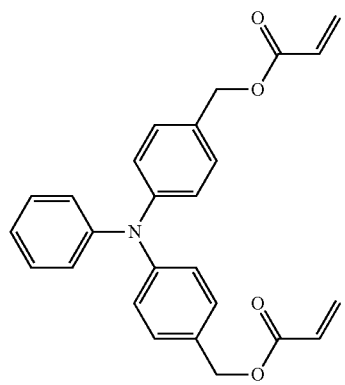
ii-20
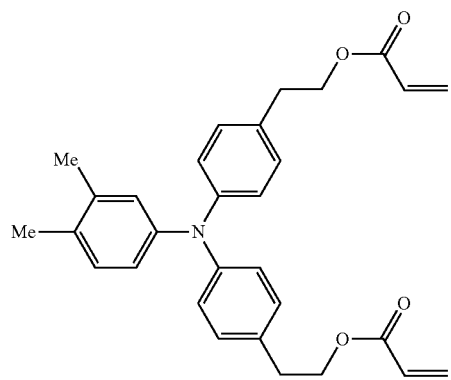
ii-21 ii-22
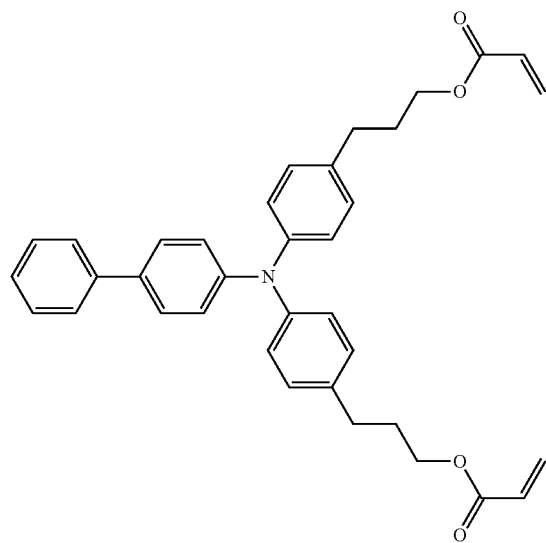
ii-23
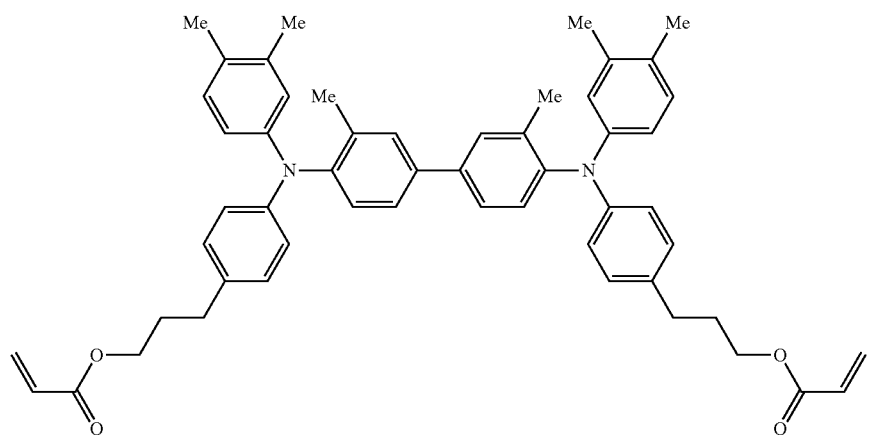
ii-24
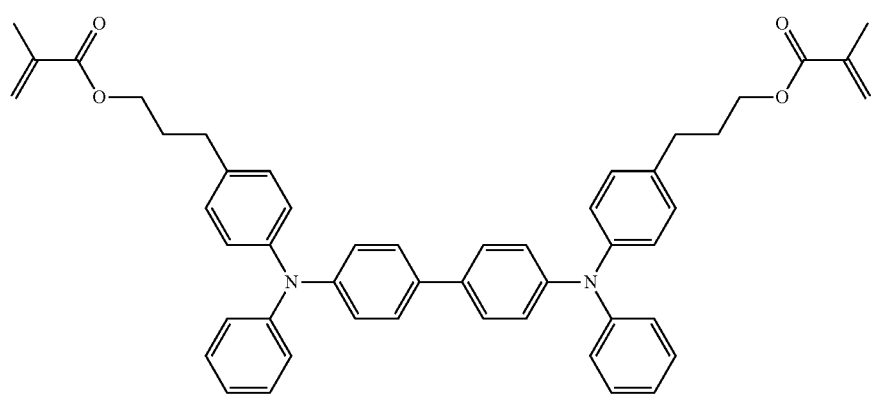

ii-25
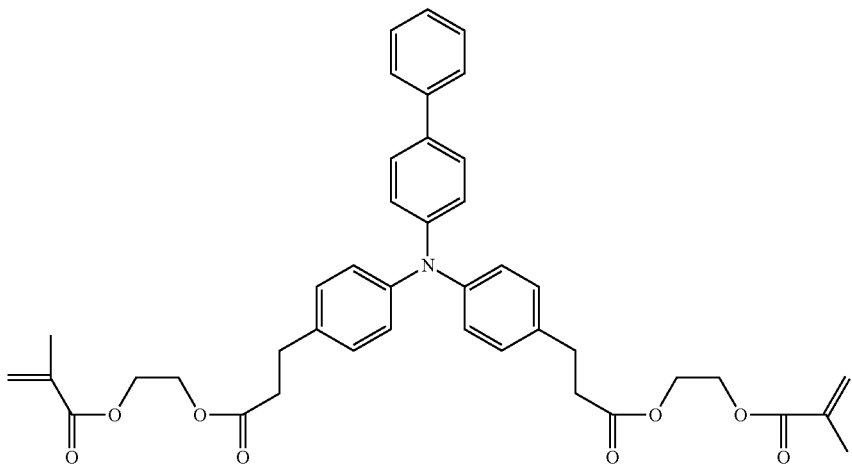
ii-26
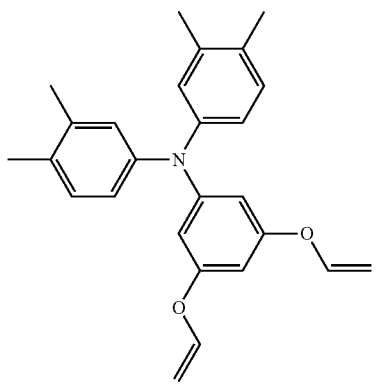
ii-27
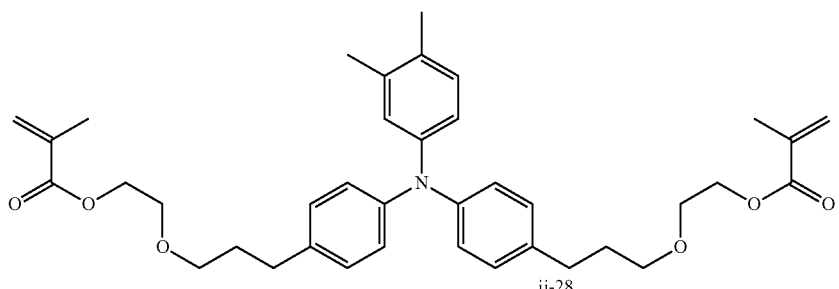
ii-28  ii-29
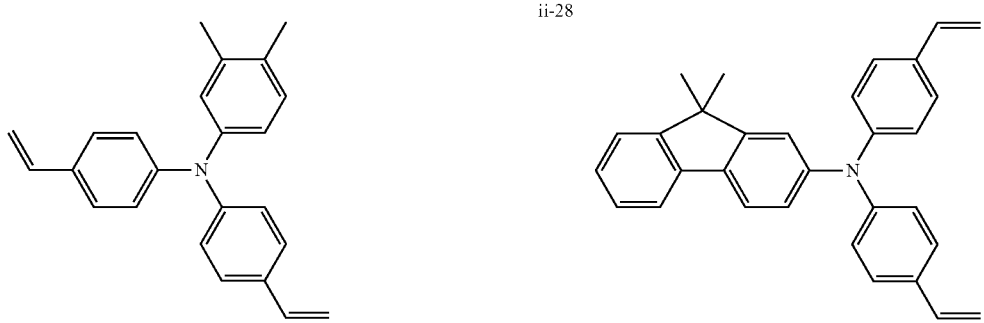

-continued
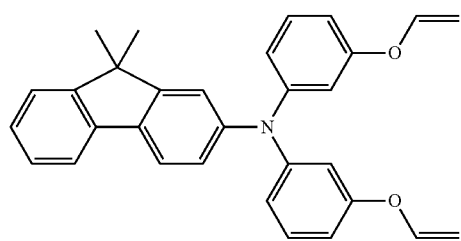
ii-30
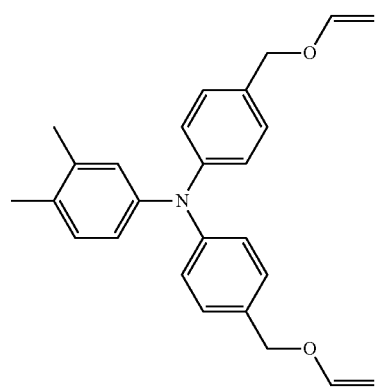
ii-31
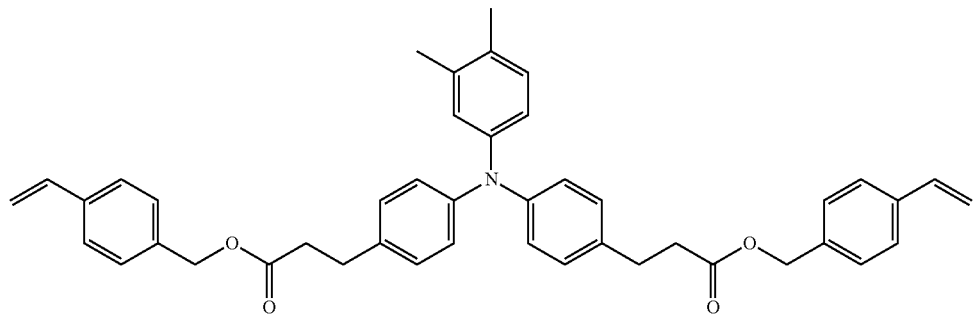
ii-32
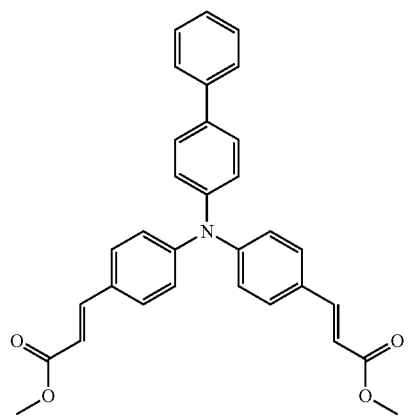
ii-33
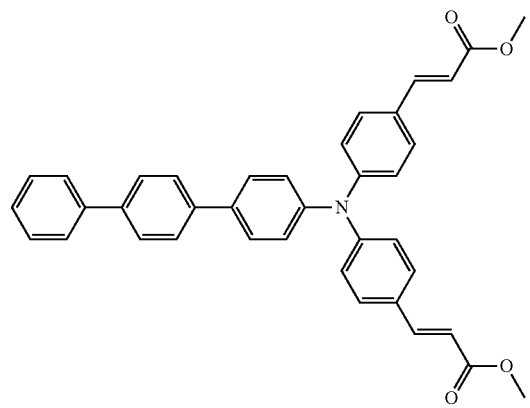
ii-34
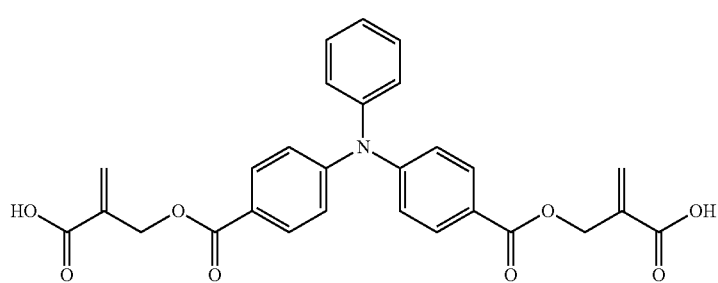
ii-35 ii-36
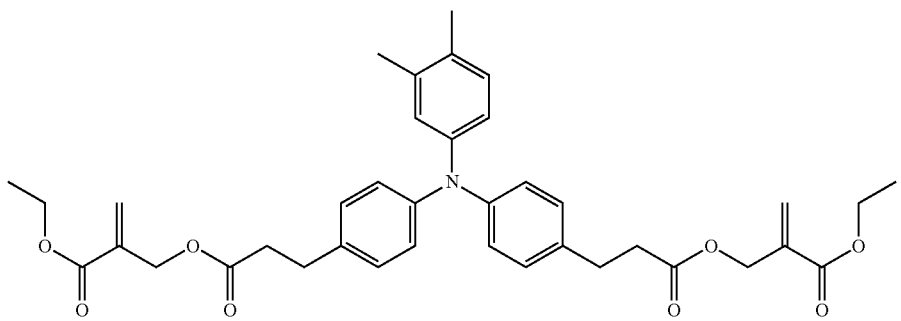
ii-37
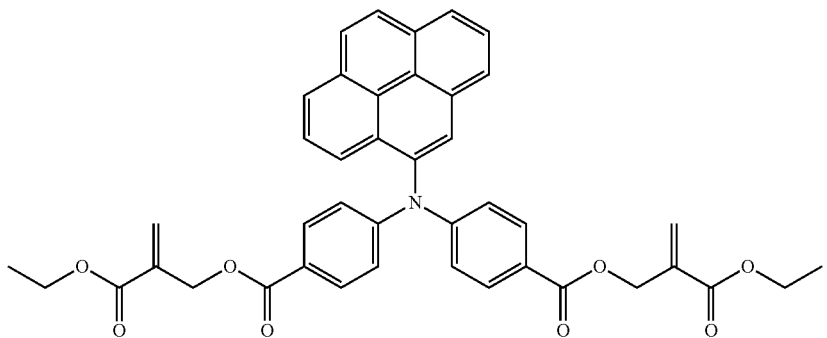
ii-38
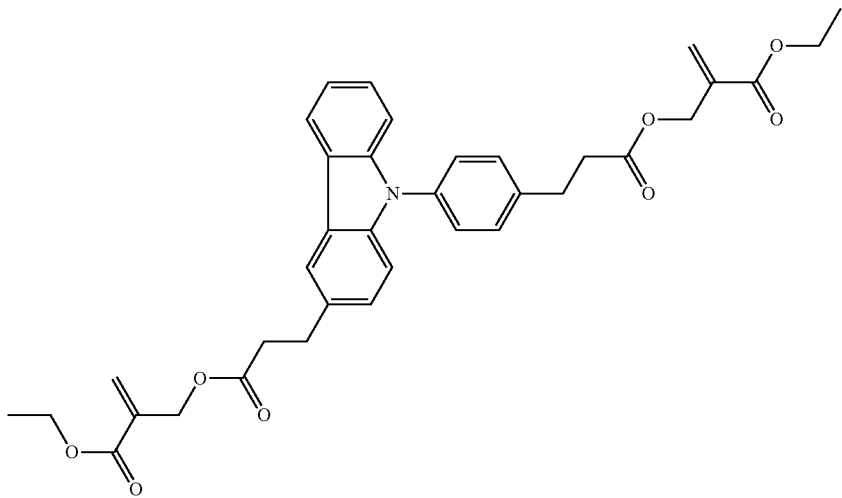
ii-39
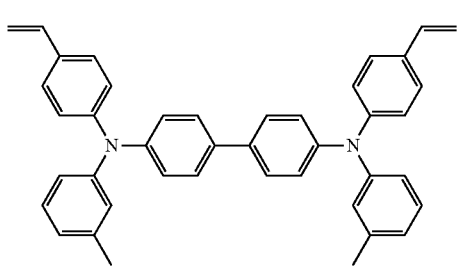
ii-40
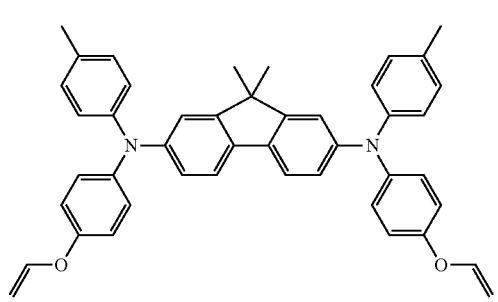

ii-41
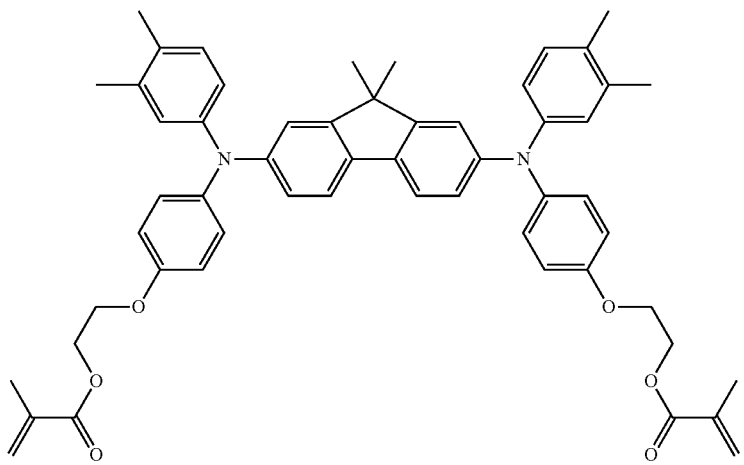
ii-42
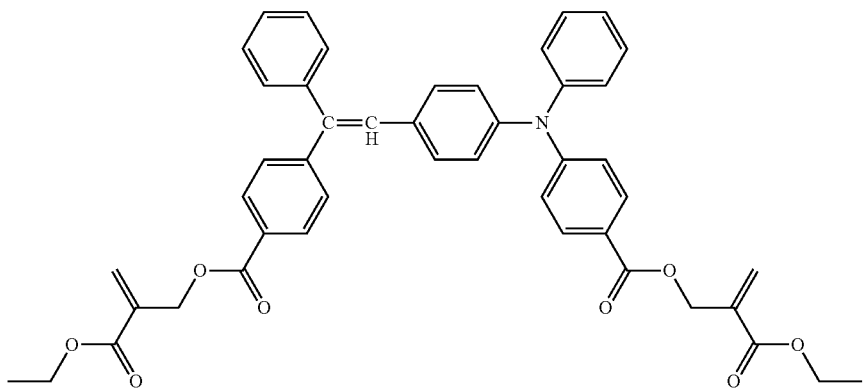
ii-43
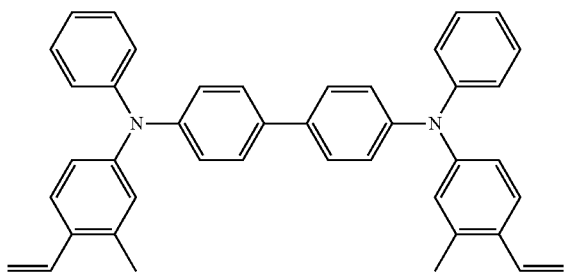
ii-44
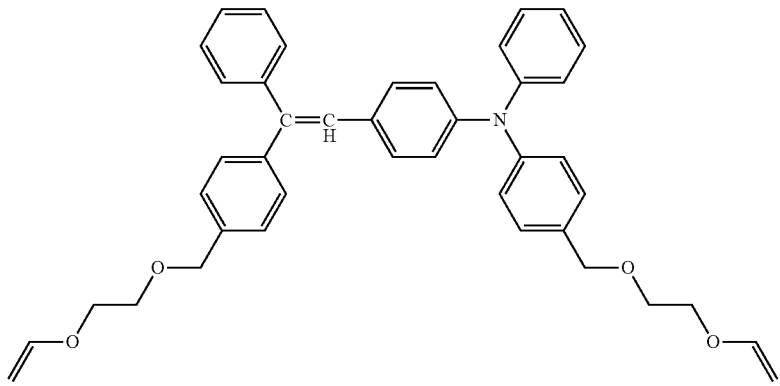

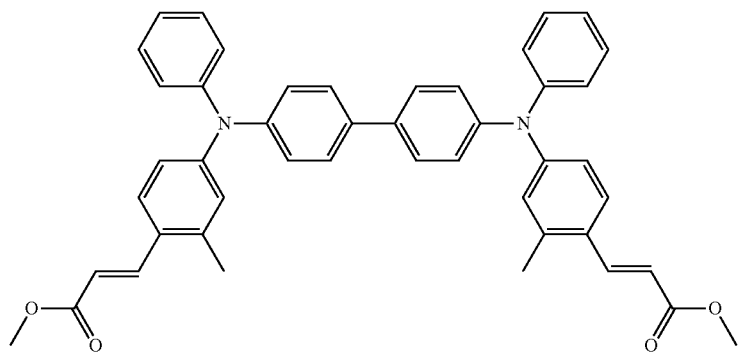
ii-45
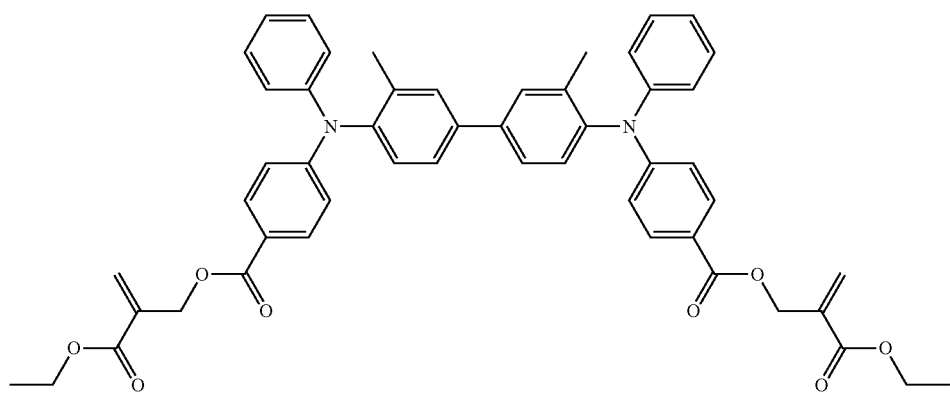
ii-46
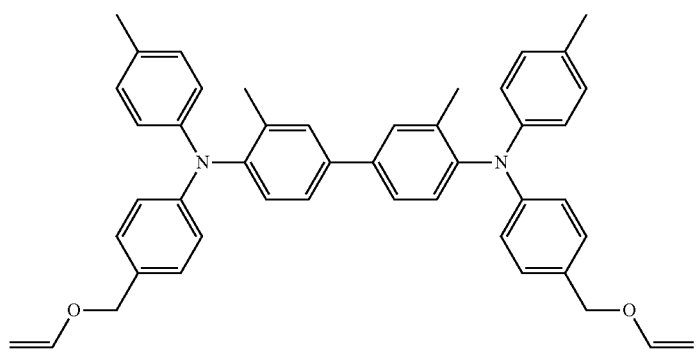
ii-47
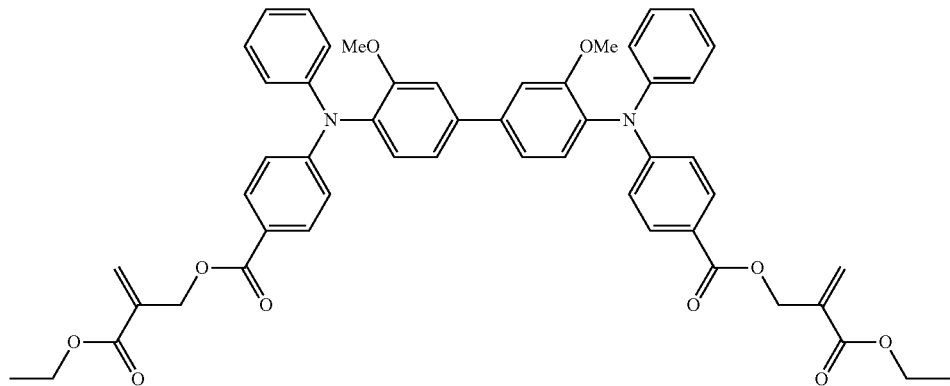
ii-48 ii-49
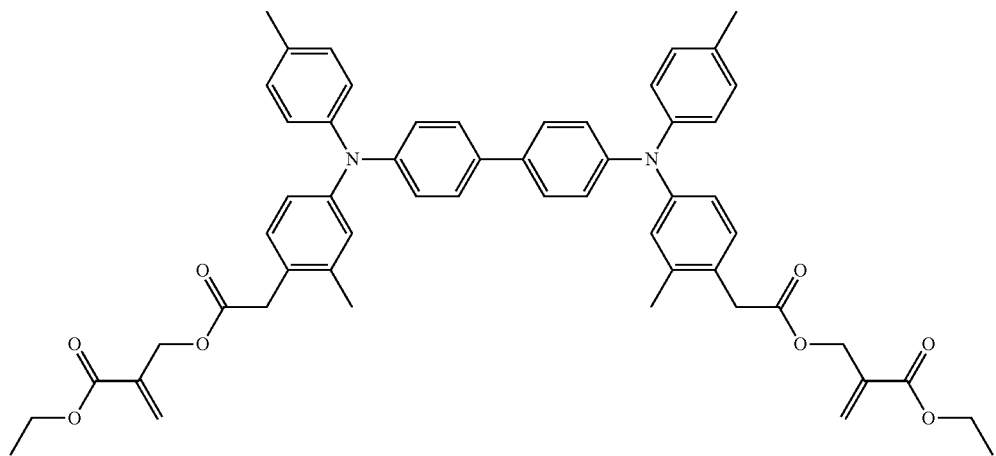
ii-50
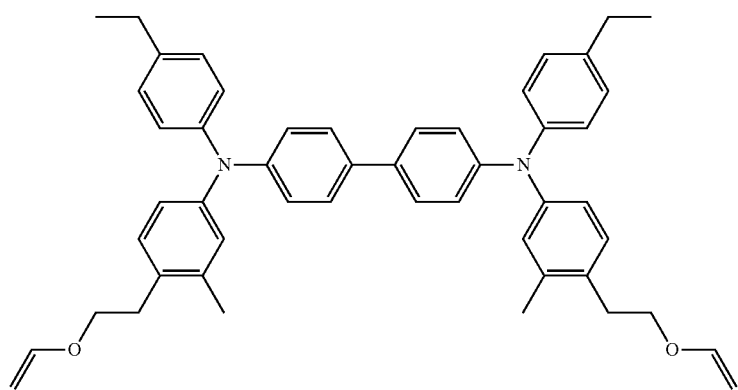
ii-51
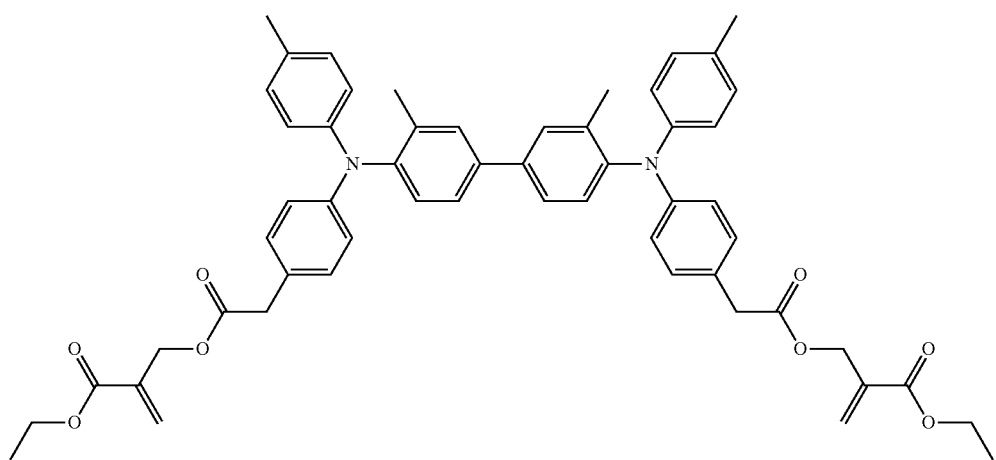

-continued
ii-52
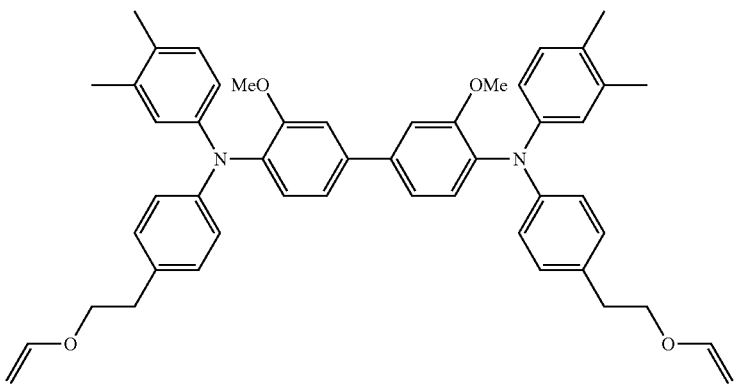
ii-53
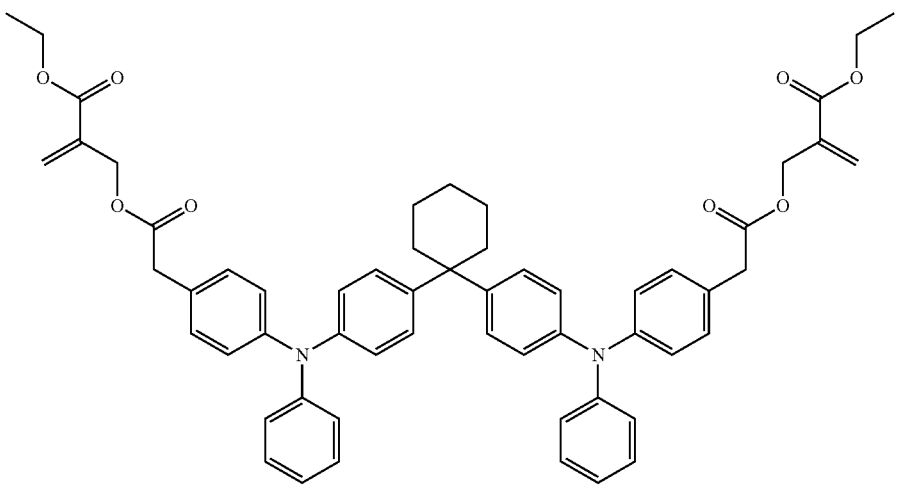
ii-54
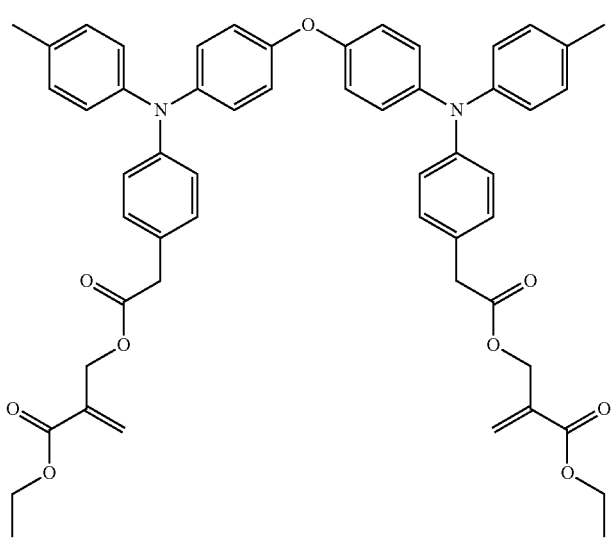

-continued
ii-55
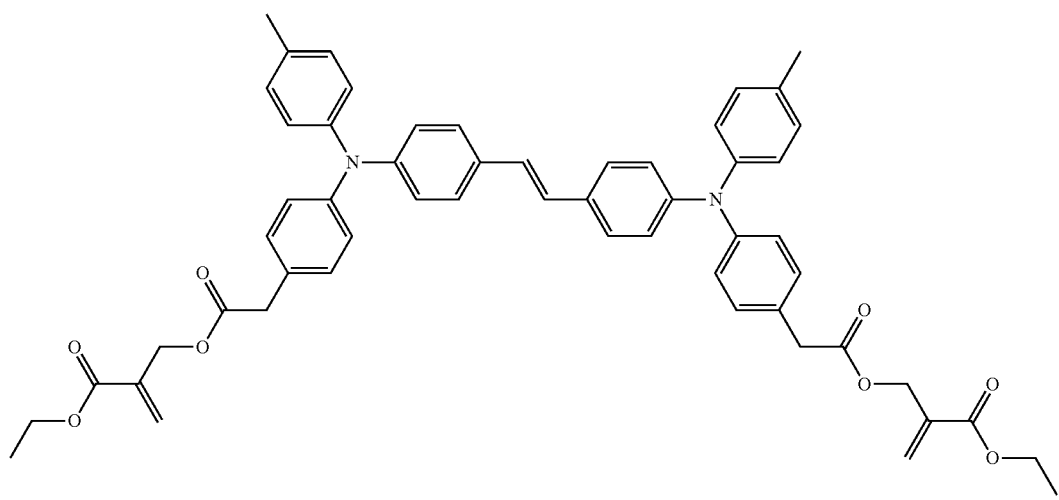
ii-56
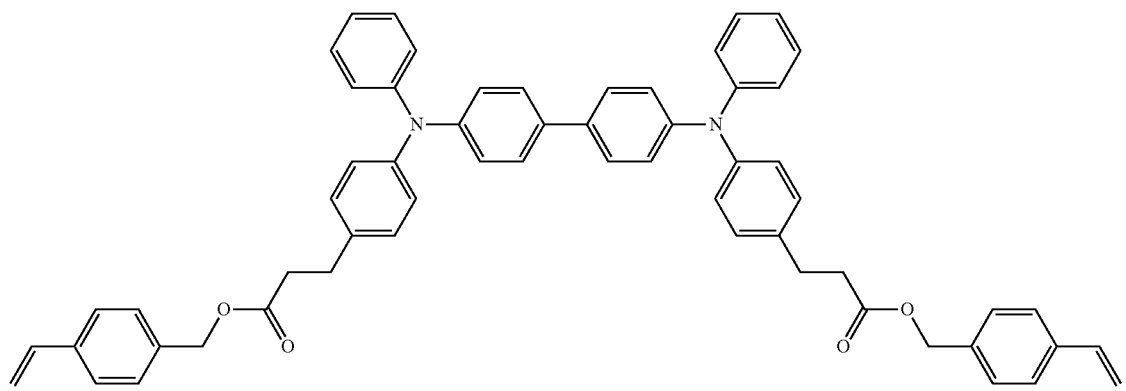
ii-57
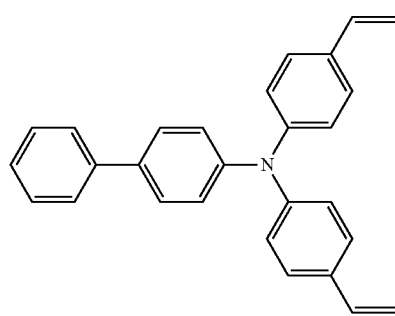
ii-58
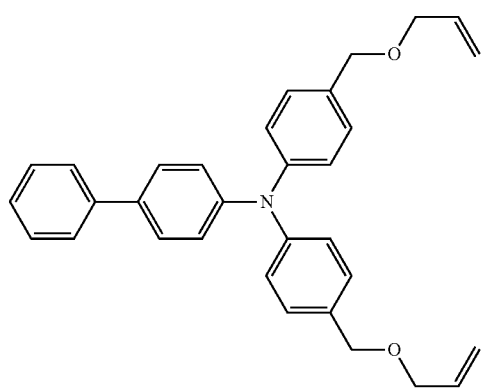

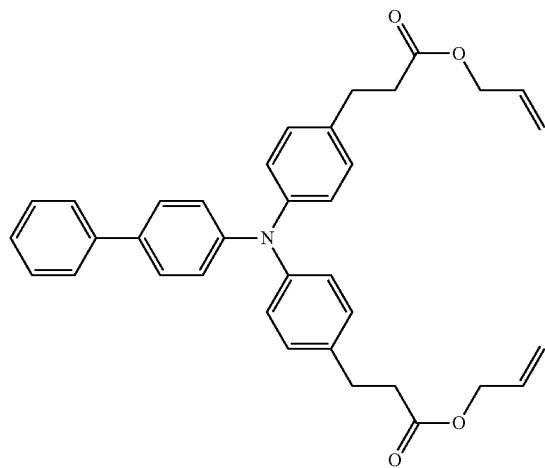
ii-59
Next, specific examples of the compound having three reactive functional groups having a carbon double bond are shown, but are not limited thereto.
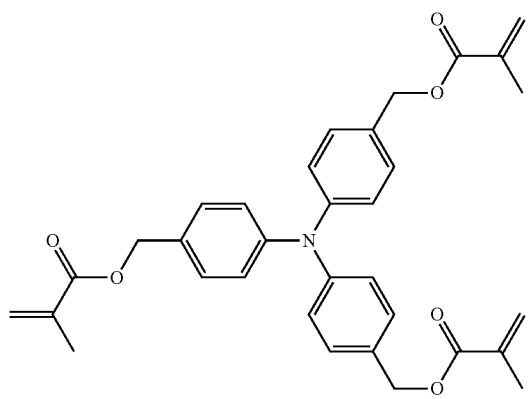
iii-1
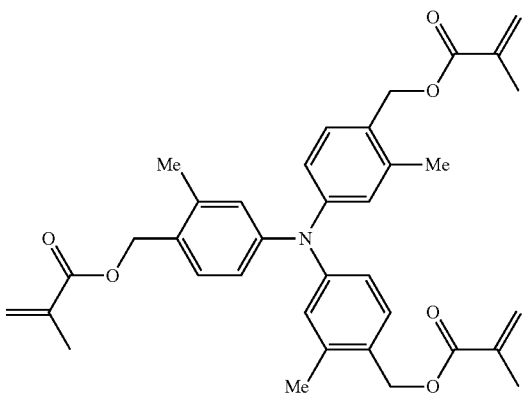
iii-2
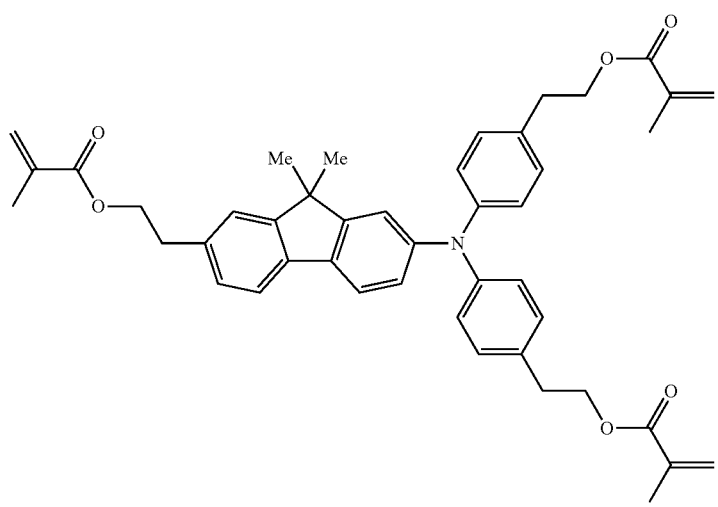
iii-3 iii-4
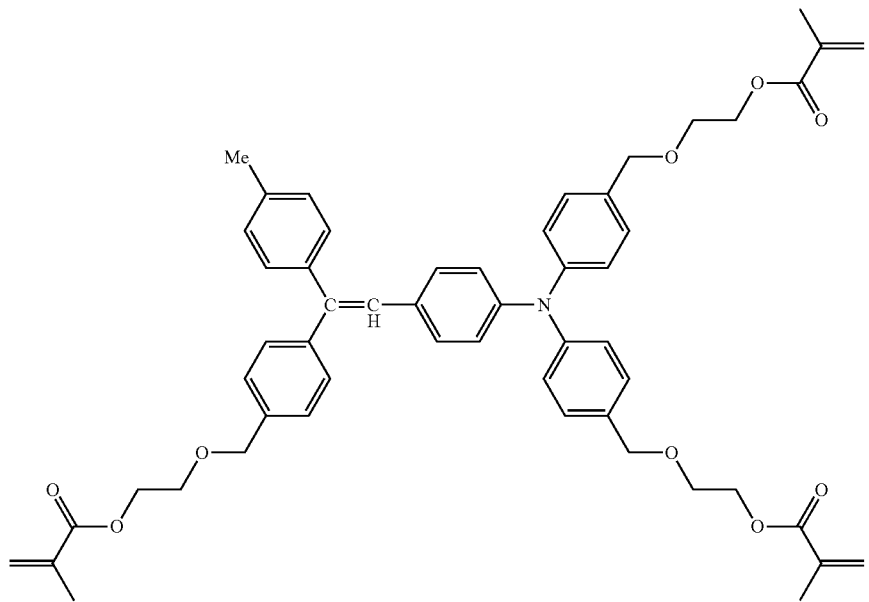
iii-5
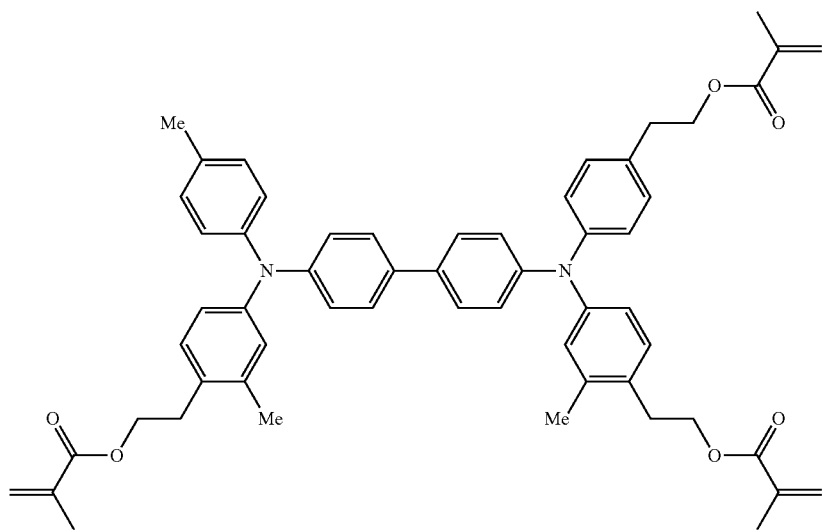
iii-6
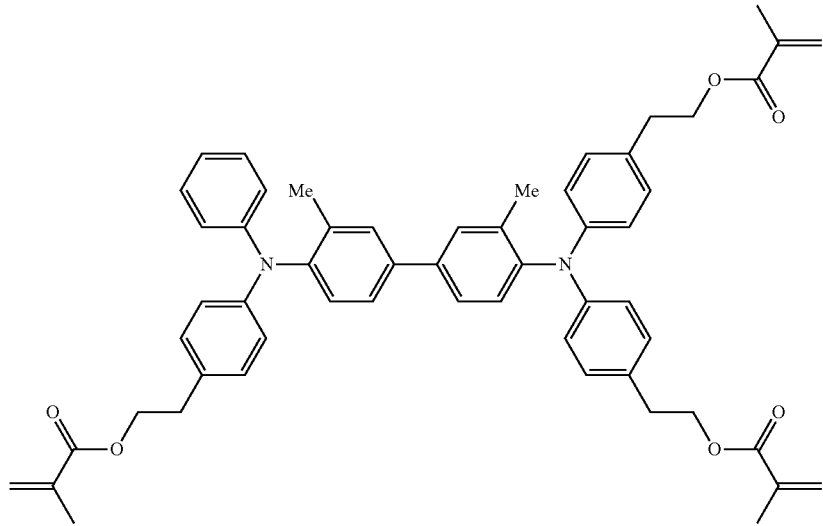

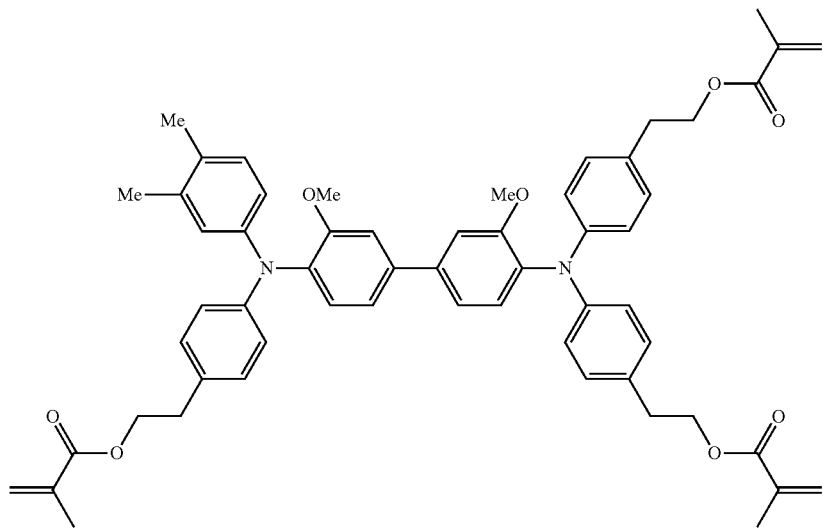
iii-7
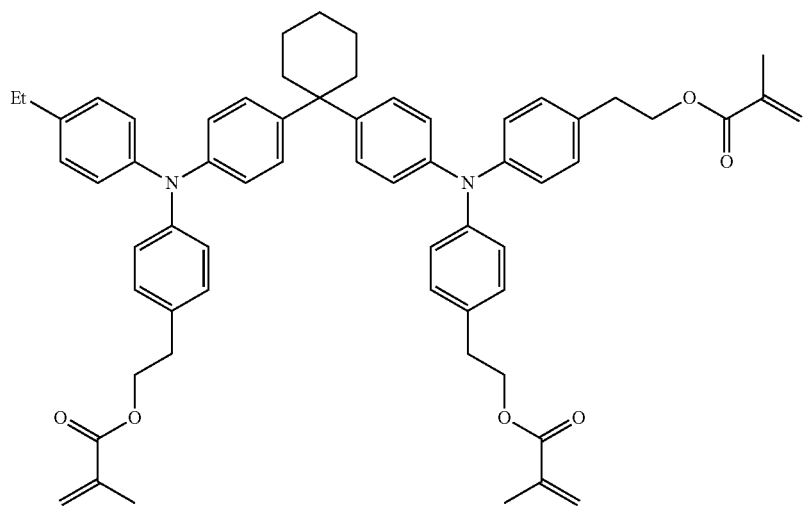
iii-8
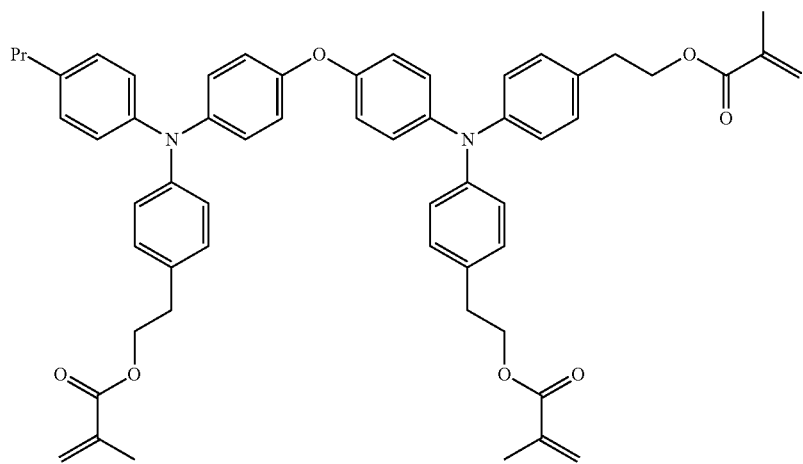
iii-9 iii-10
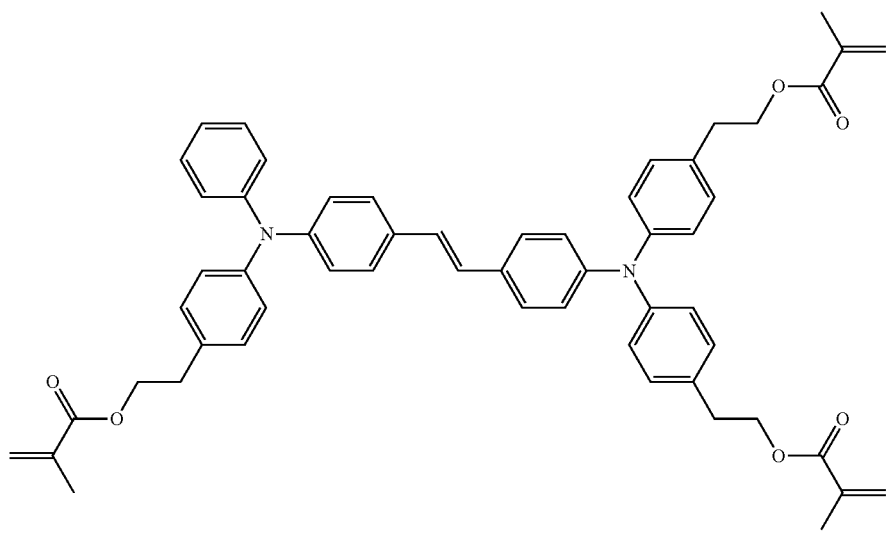
iii-11
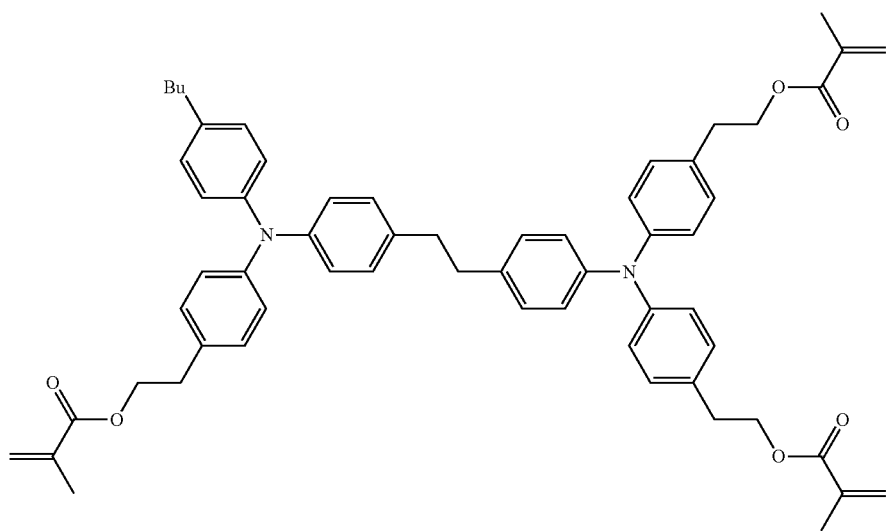
iii-12 iii-13
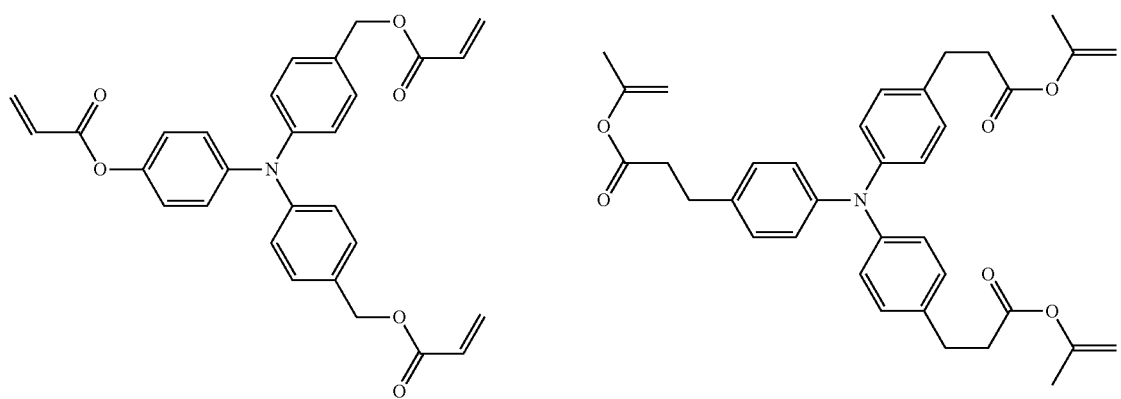

-continued
107
iii-14
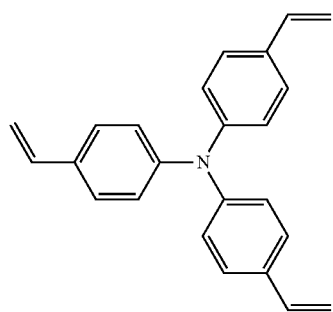
108
iii-15
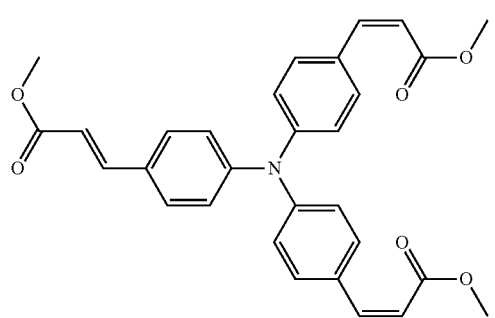
iii-16
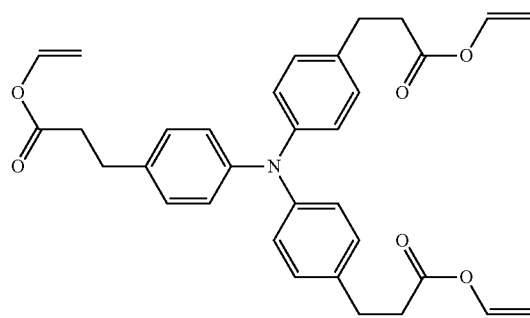
iii-17
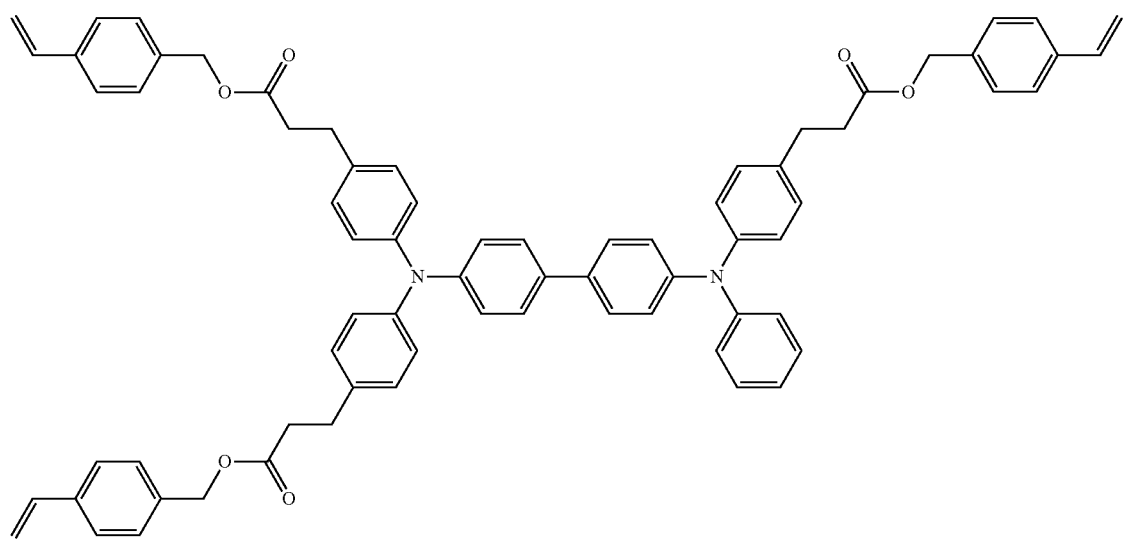

iii-18
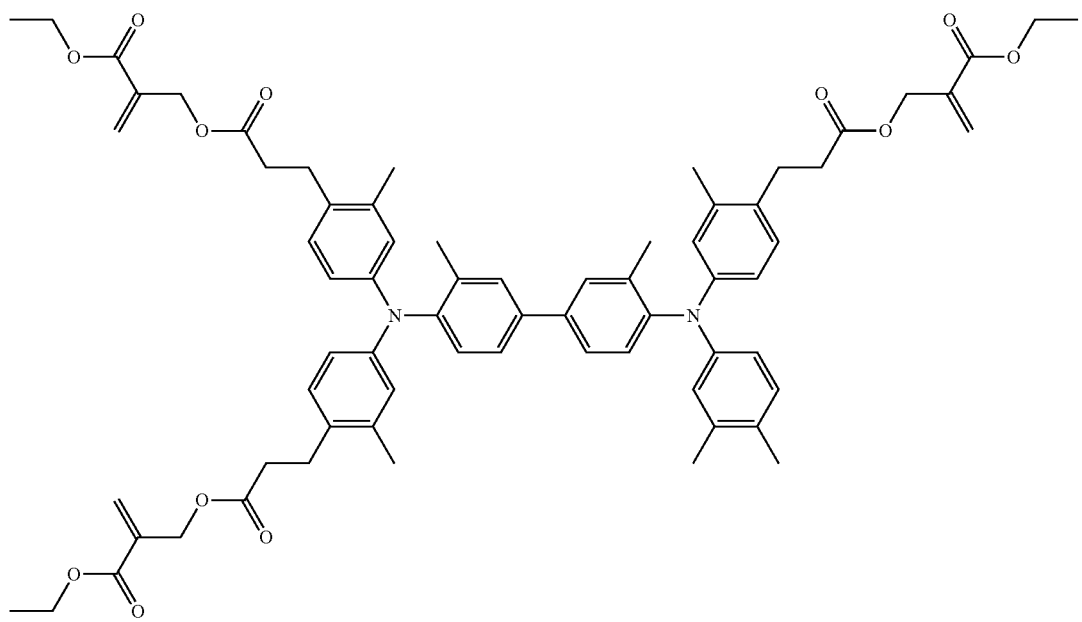
iii-19
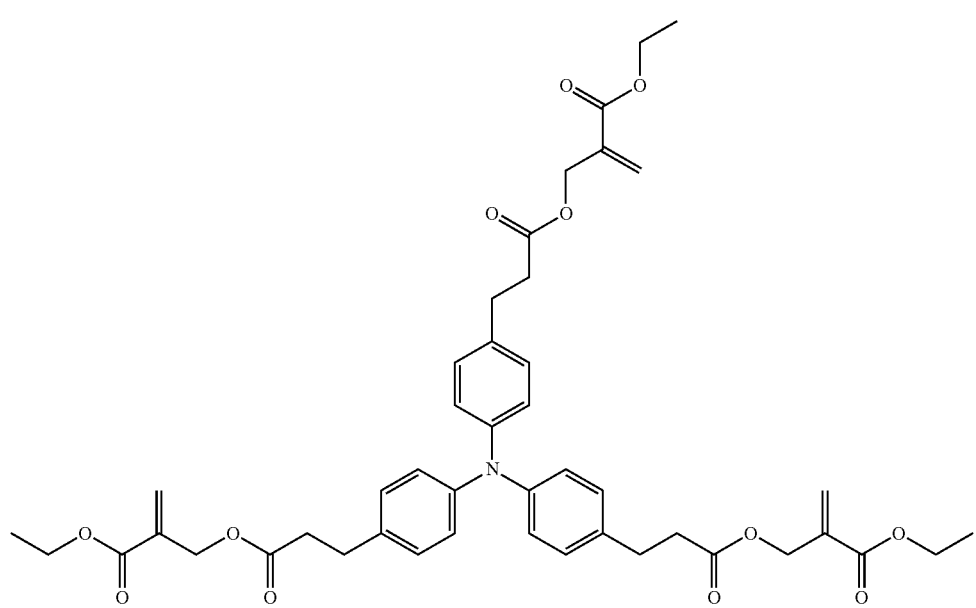

Next, specific examples of the compound having four to six reactive functional groups having a carbon double bond are shown, but are not limited thereto.
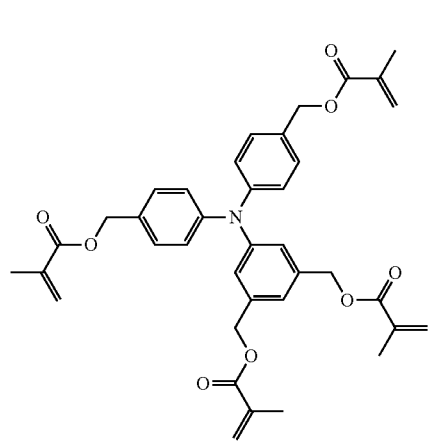
iv-1
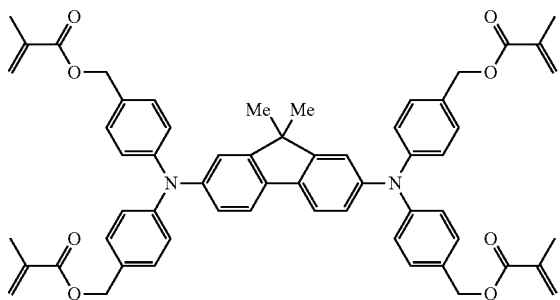
iv-2
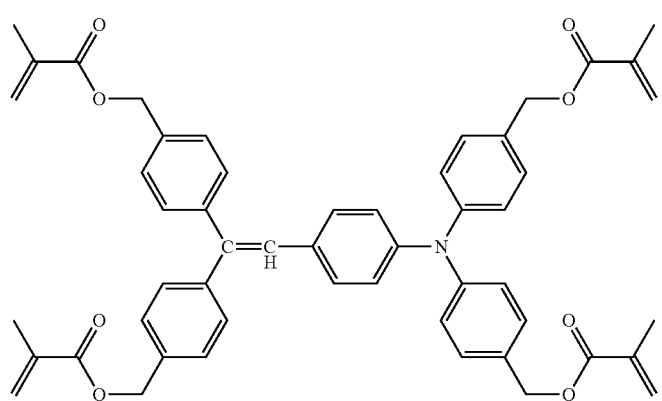
iv-3
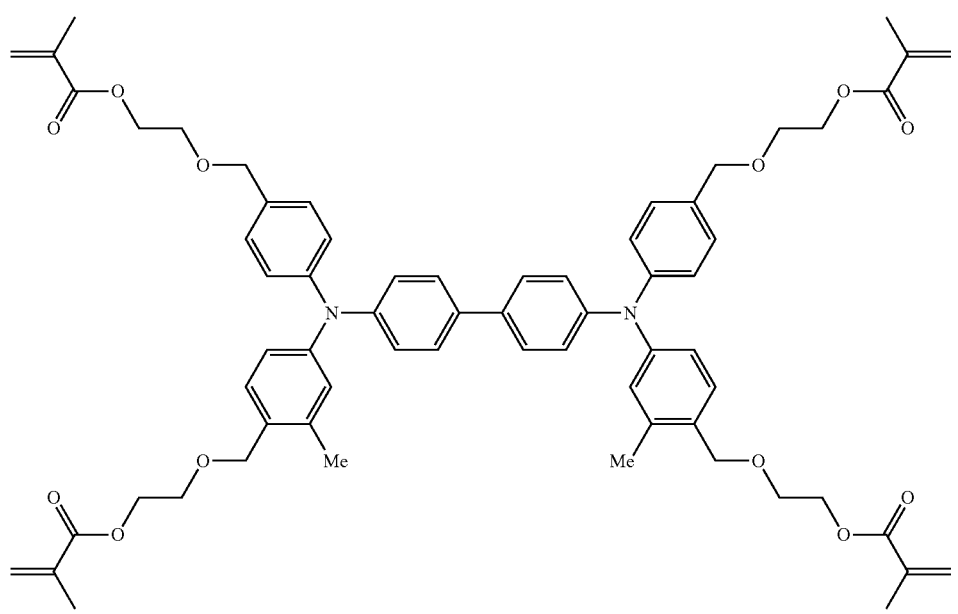
iv-4

-continued
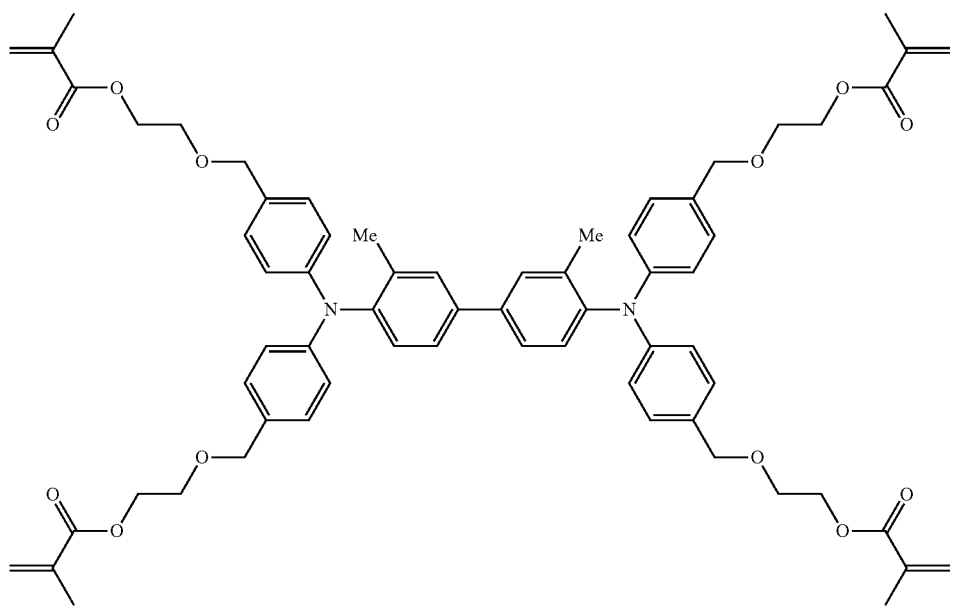
iv-5
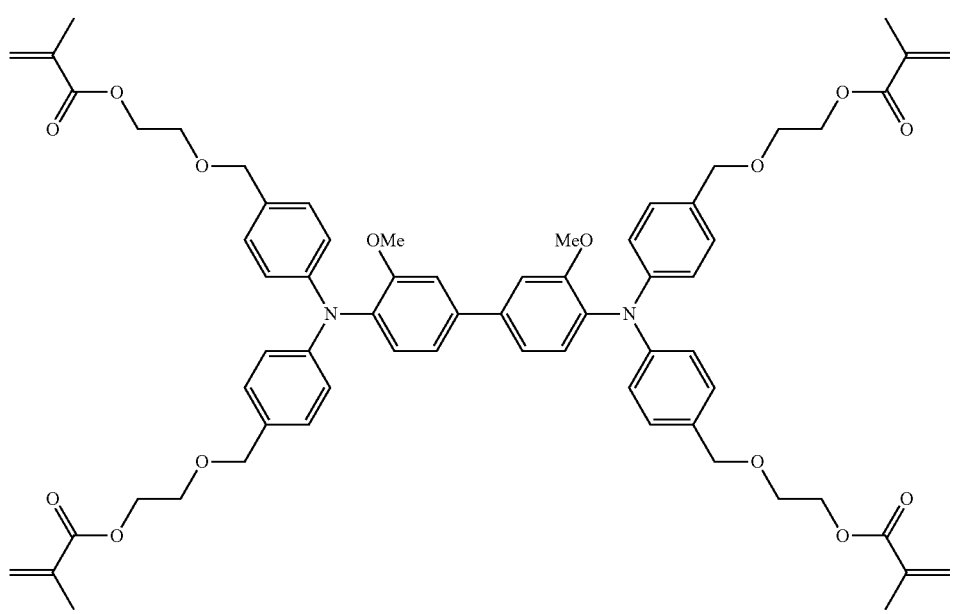
iv-6

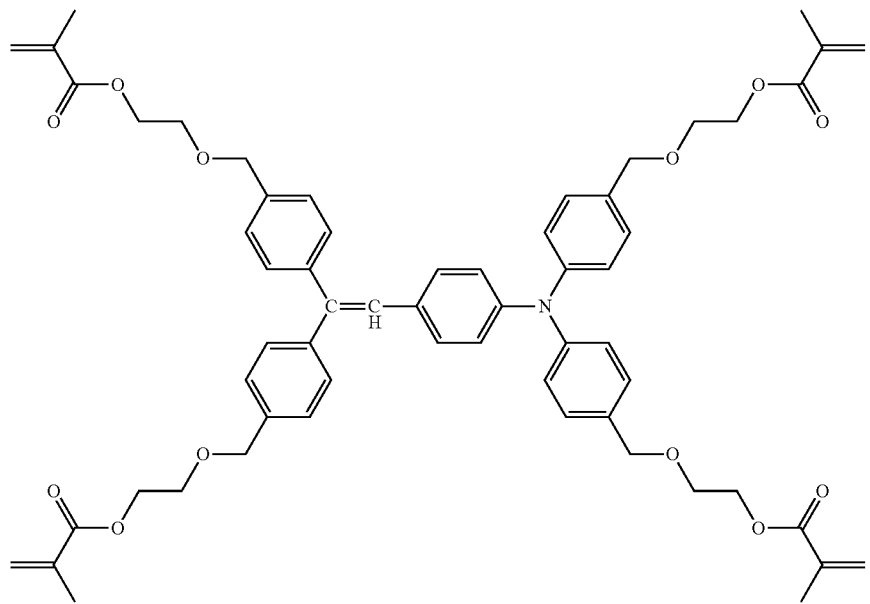
iv-7
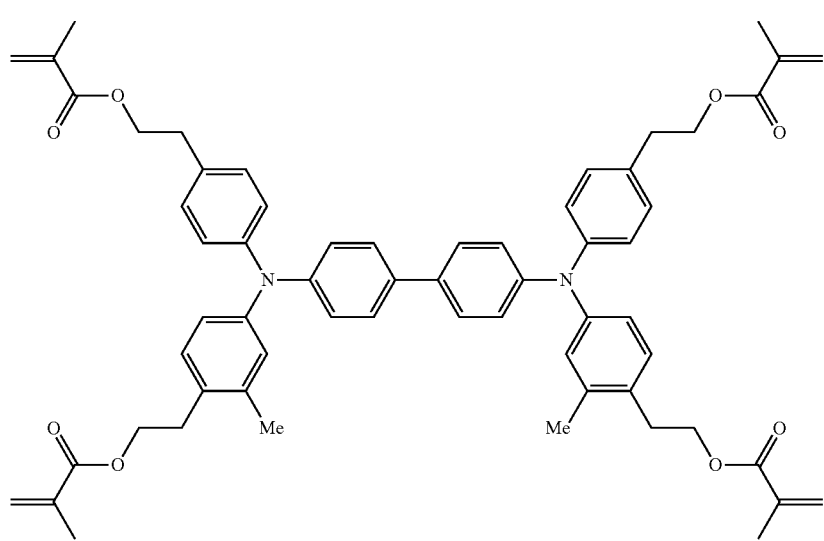
iv-8
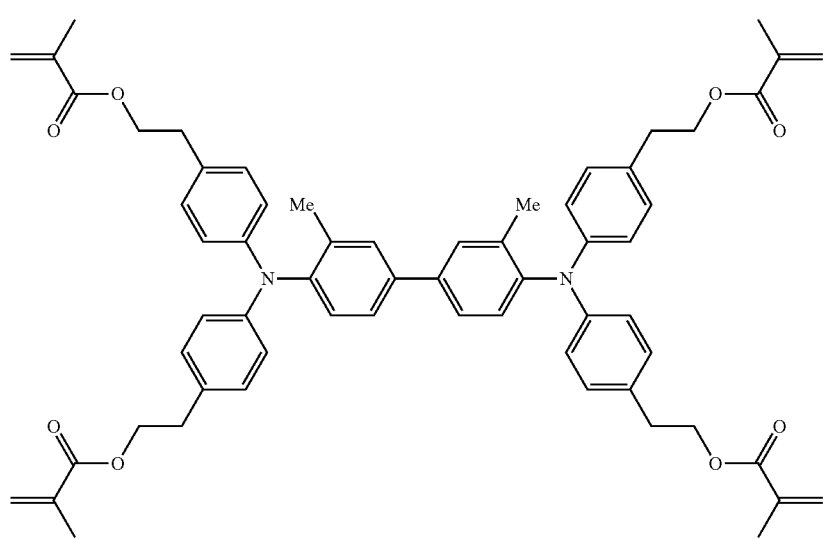
iv-9 iv-10
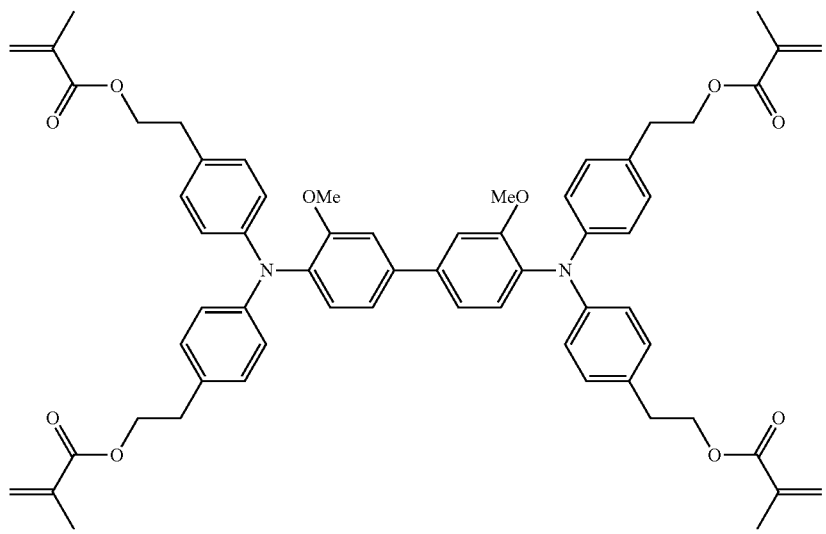
iv-11
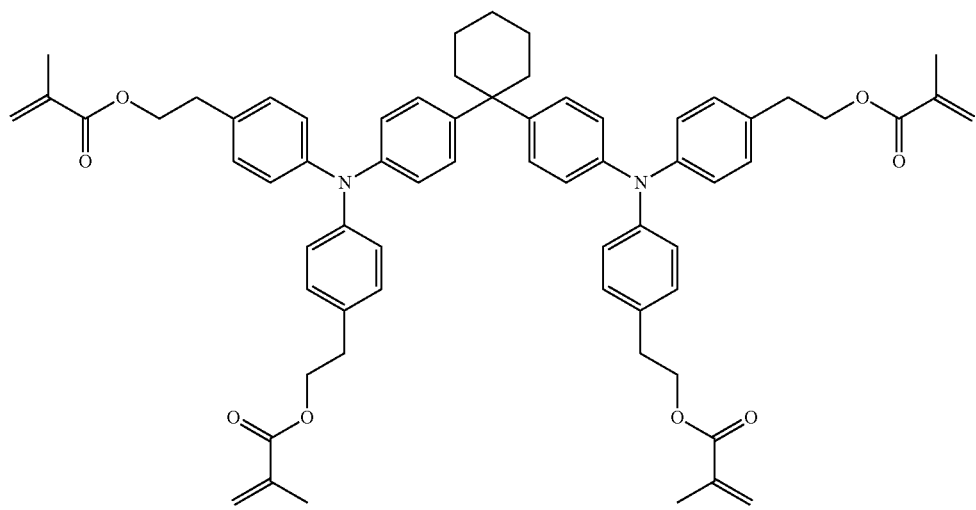
iv-12
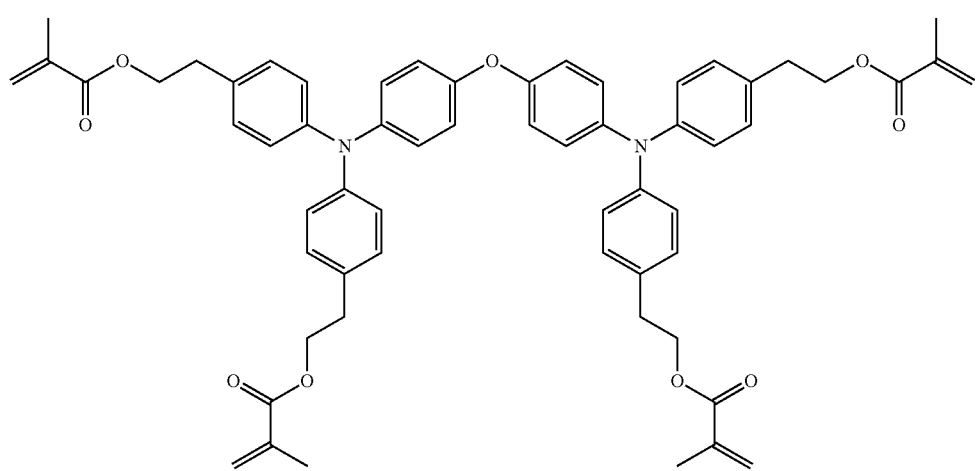

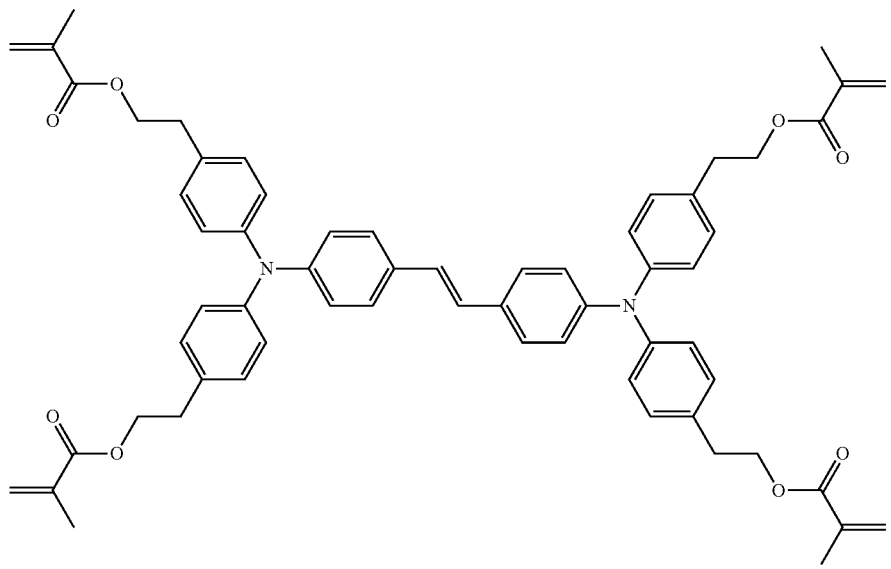
iv-13
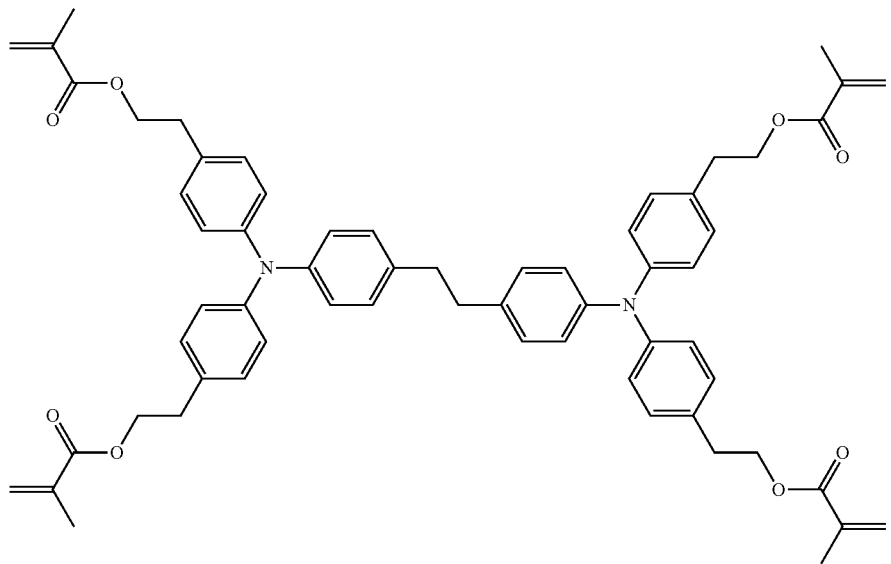
iv-14
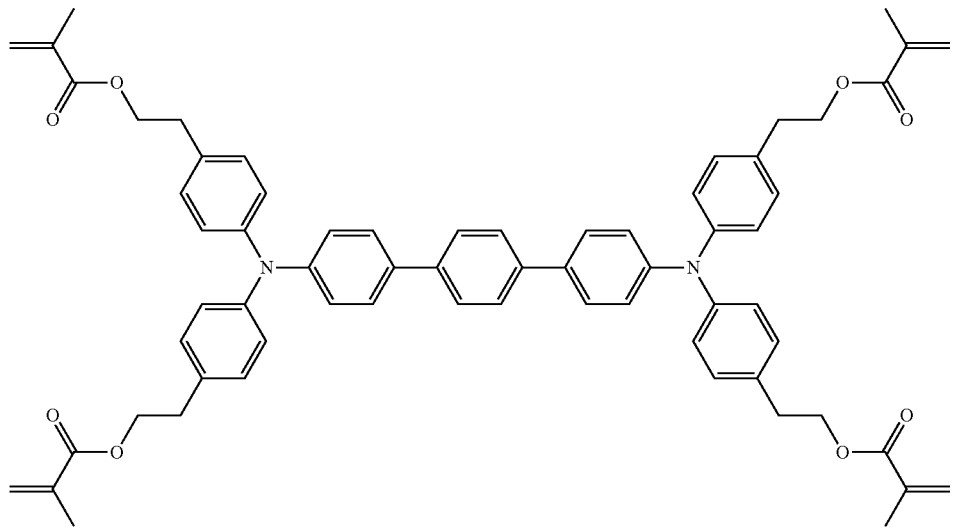
iv-15

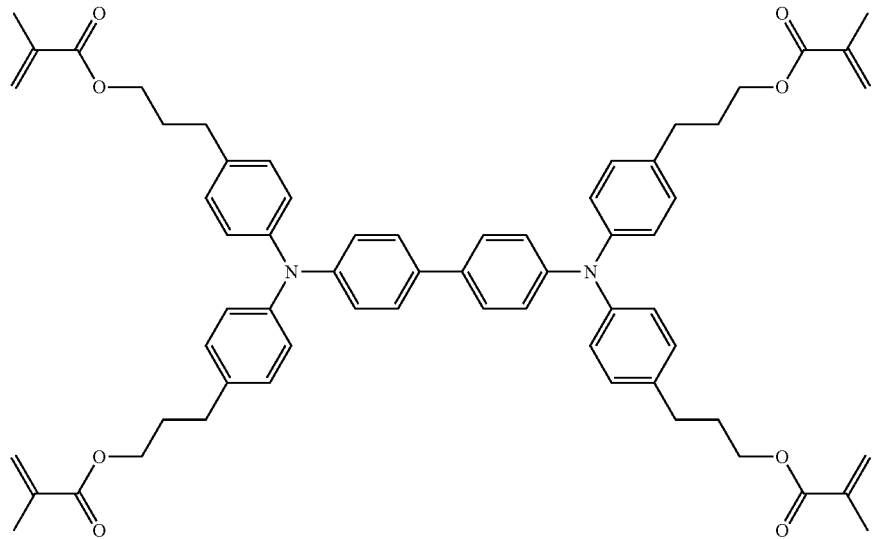
iv-16
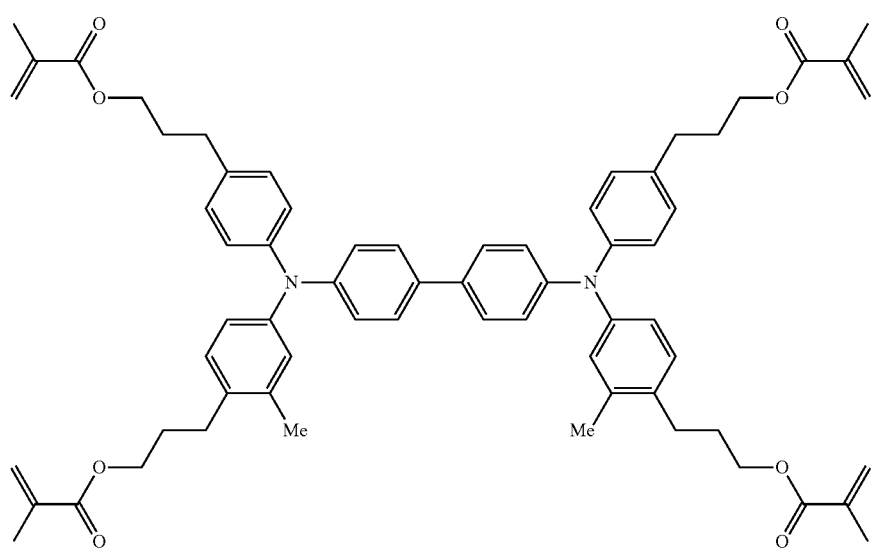
iv-17
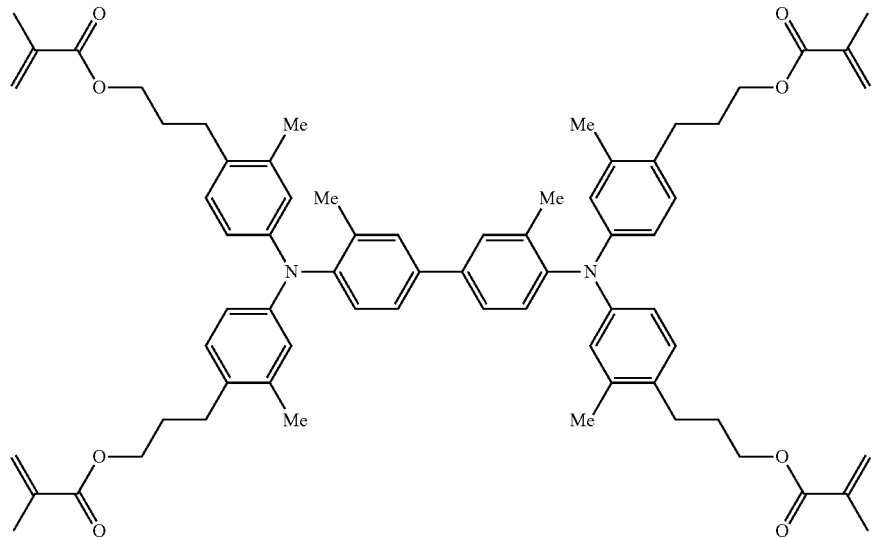
iv-18

-continued
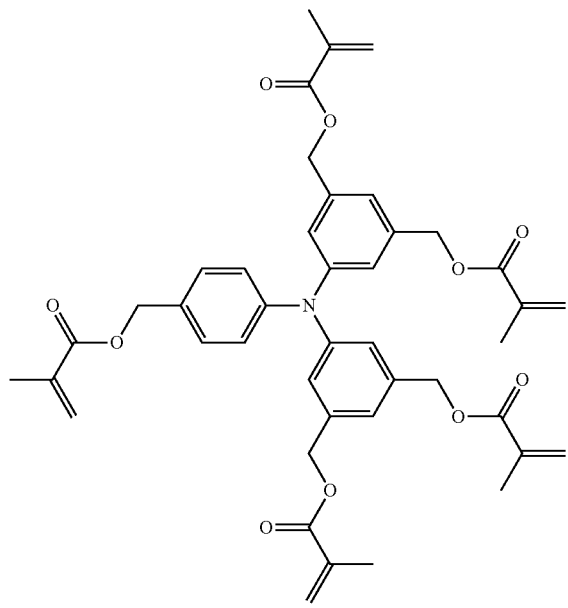
iv-19
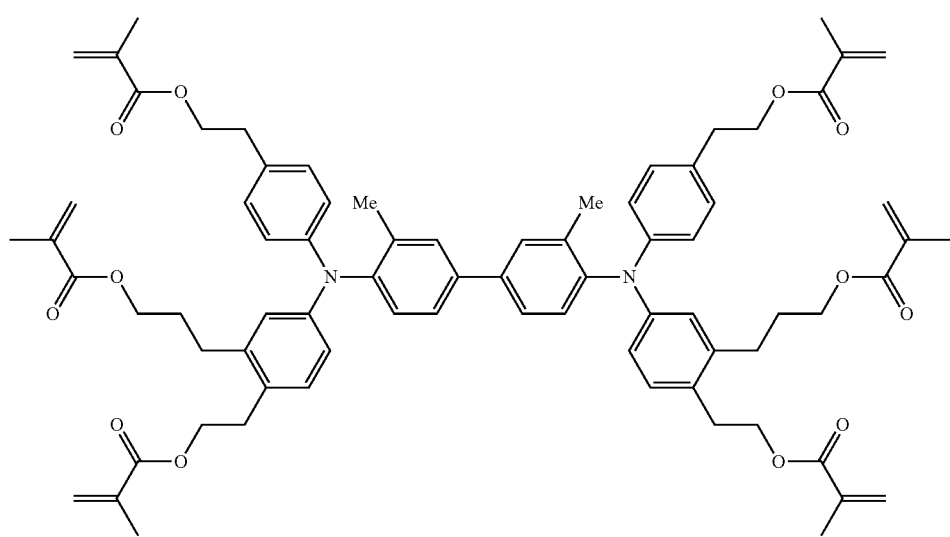
iv-20

-continued
iv-21
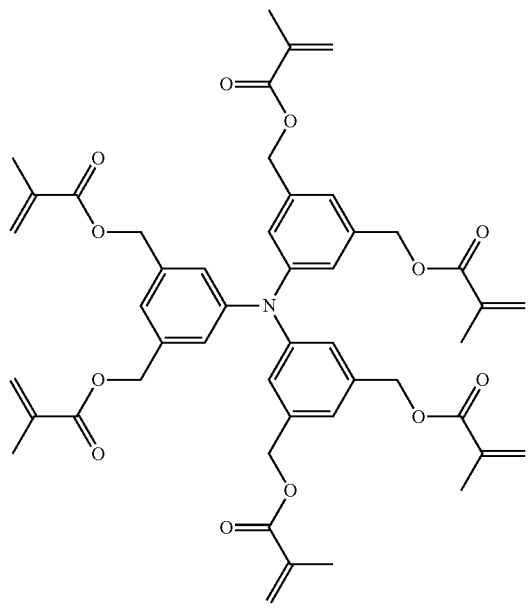
iv-22
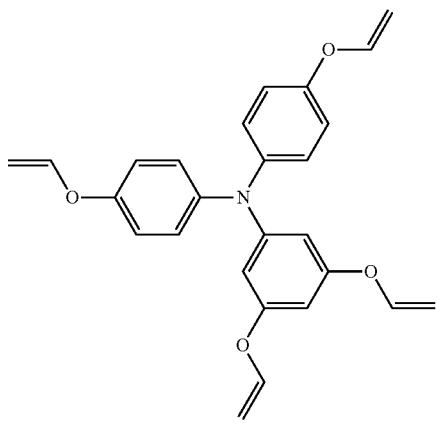
iv-23
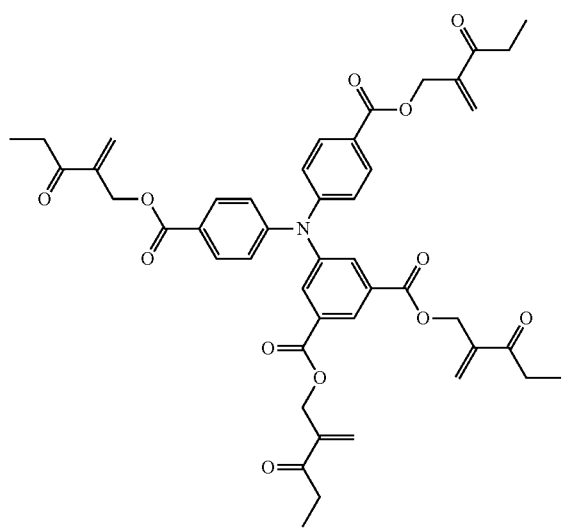
iv-24
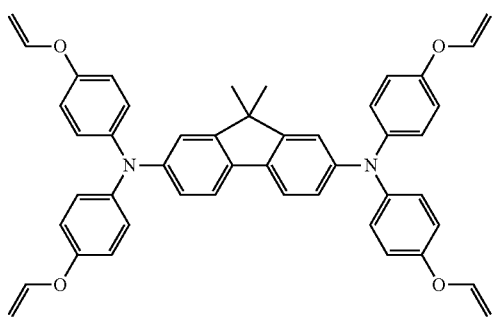

-continued
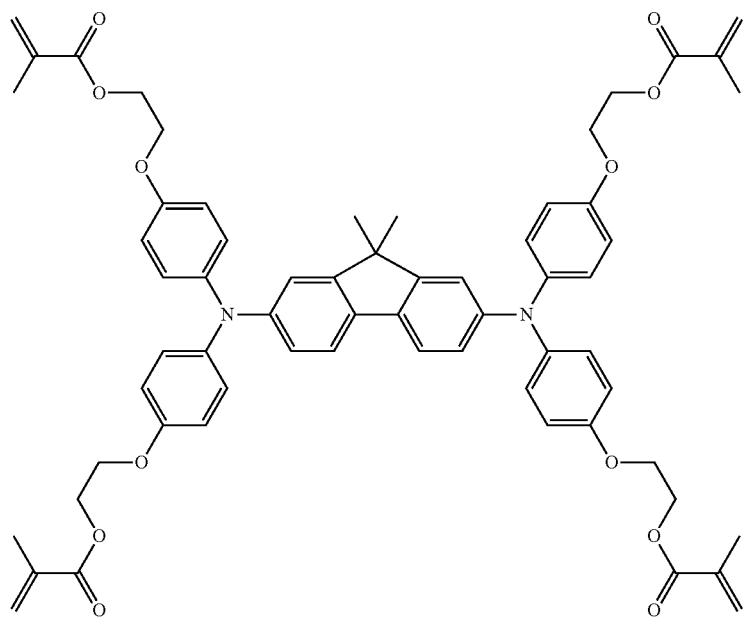
iv-25
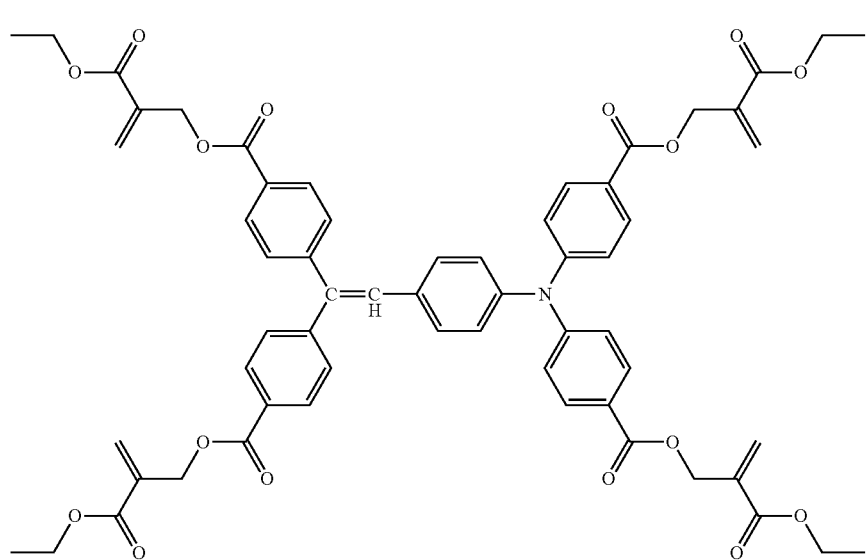
iv-26 iv-27
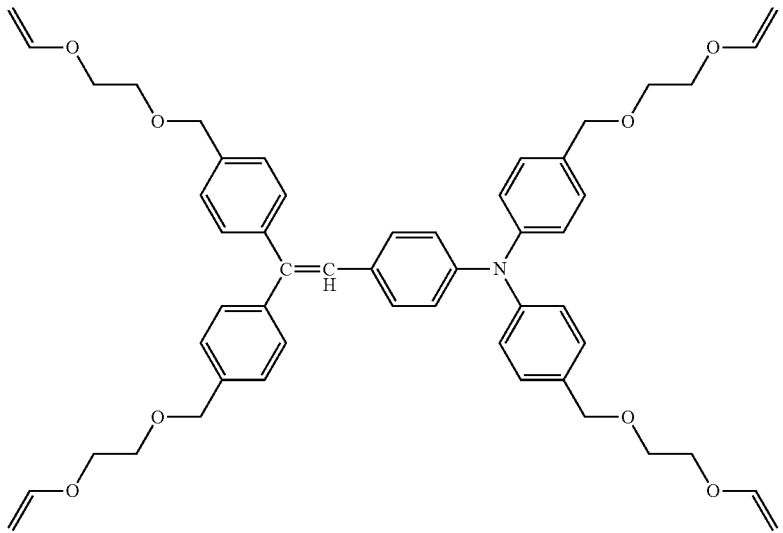
iv-28
iv-29
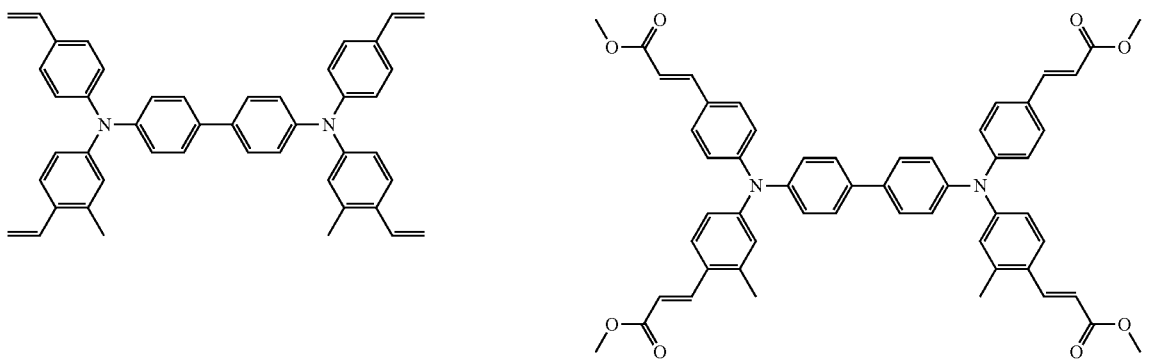
iv-30
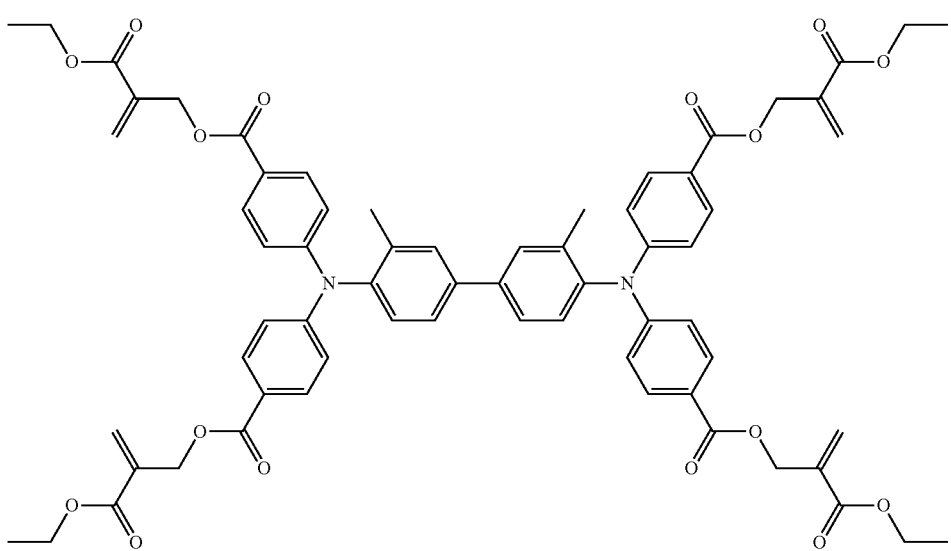

-continued
iv-31
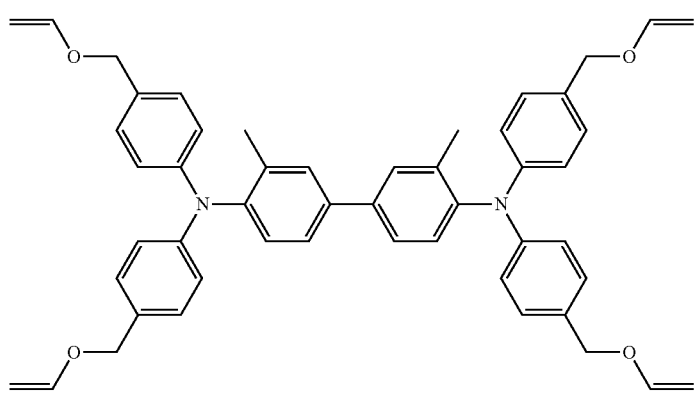
iv-32
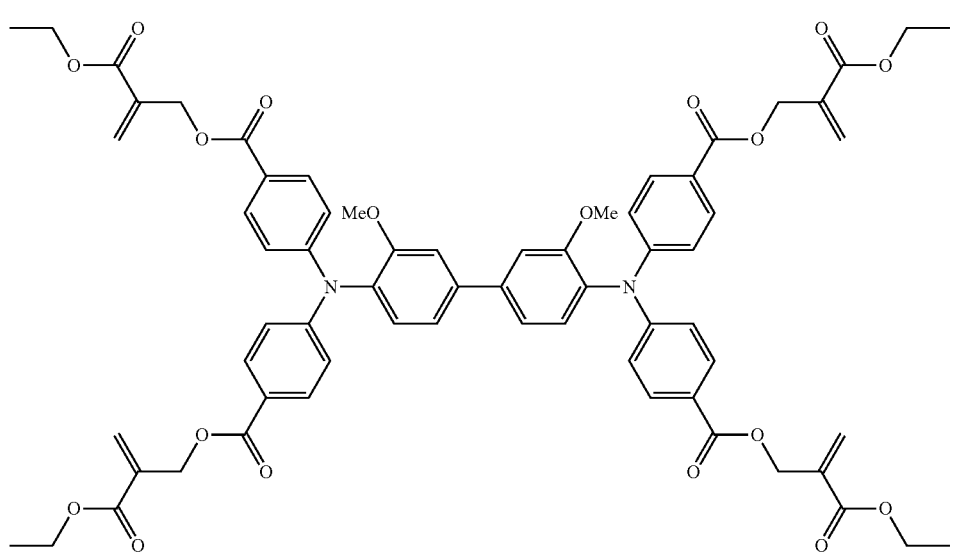
iv-33
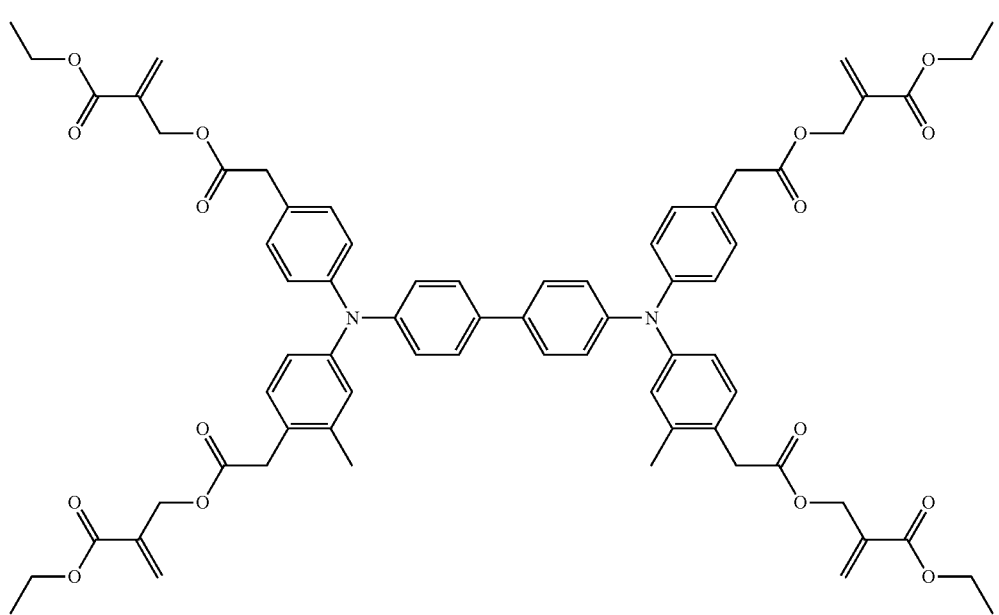

iv-34
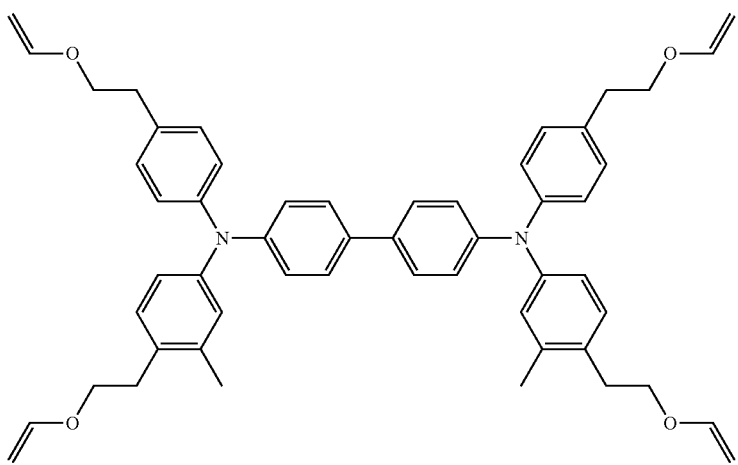
iv-35
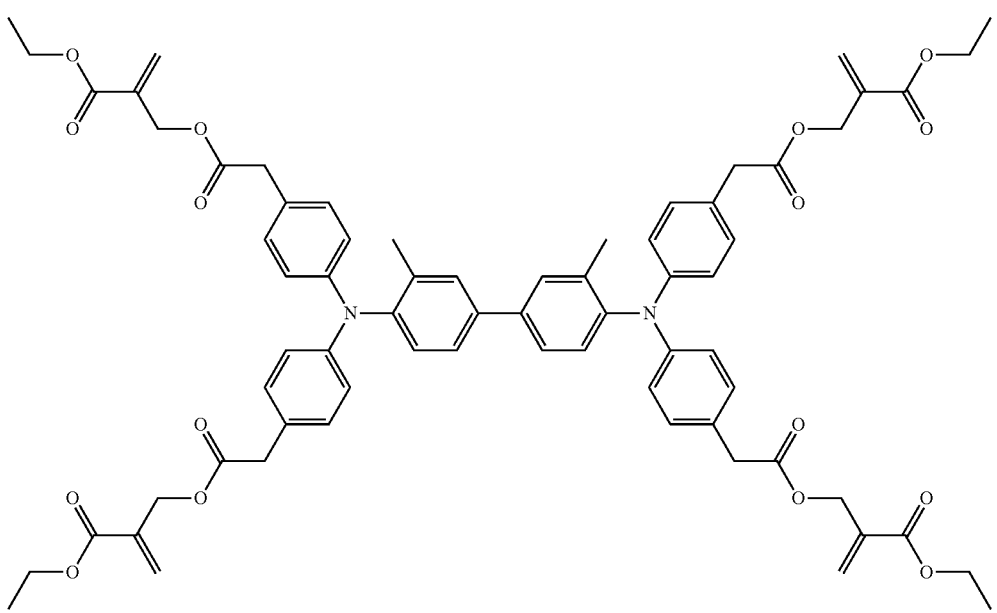
iv-36
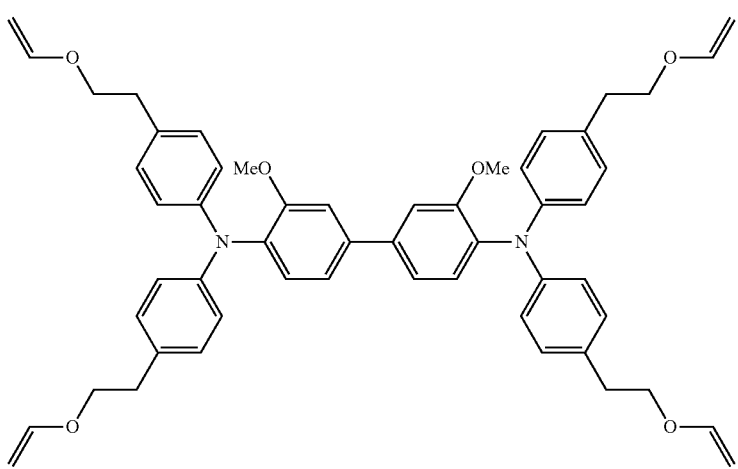

-continued
iv-37
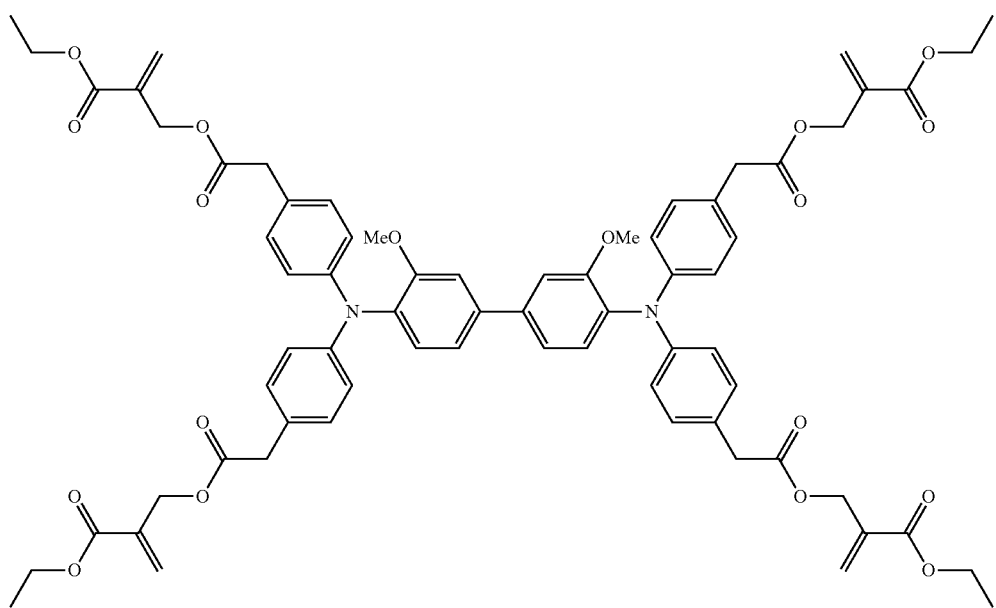
iv-38
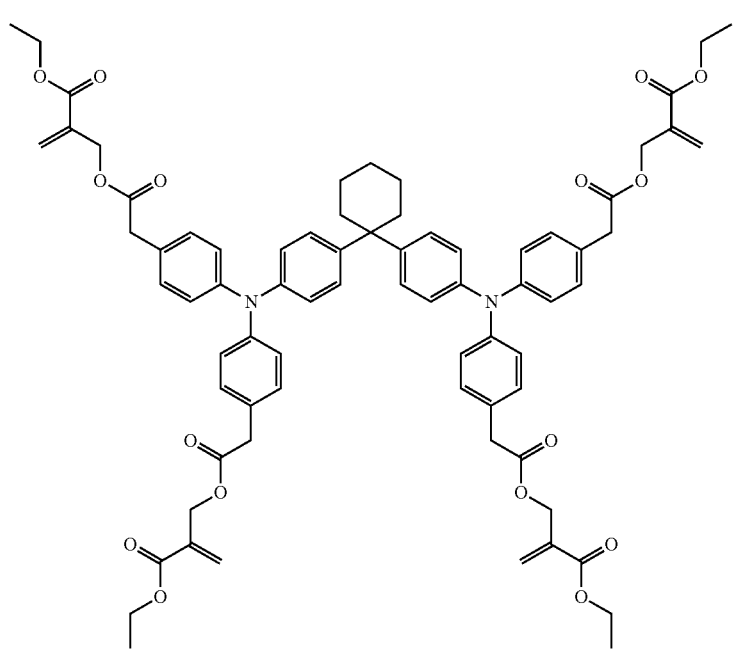

-continued
iv-39
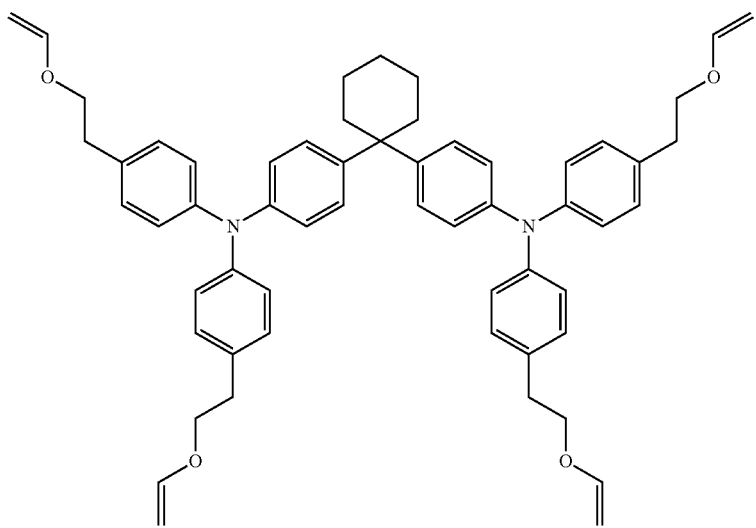
iv-40
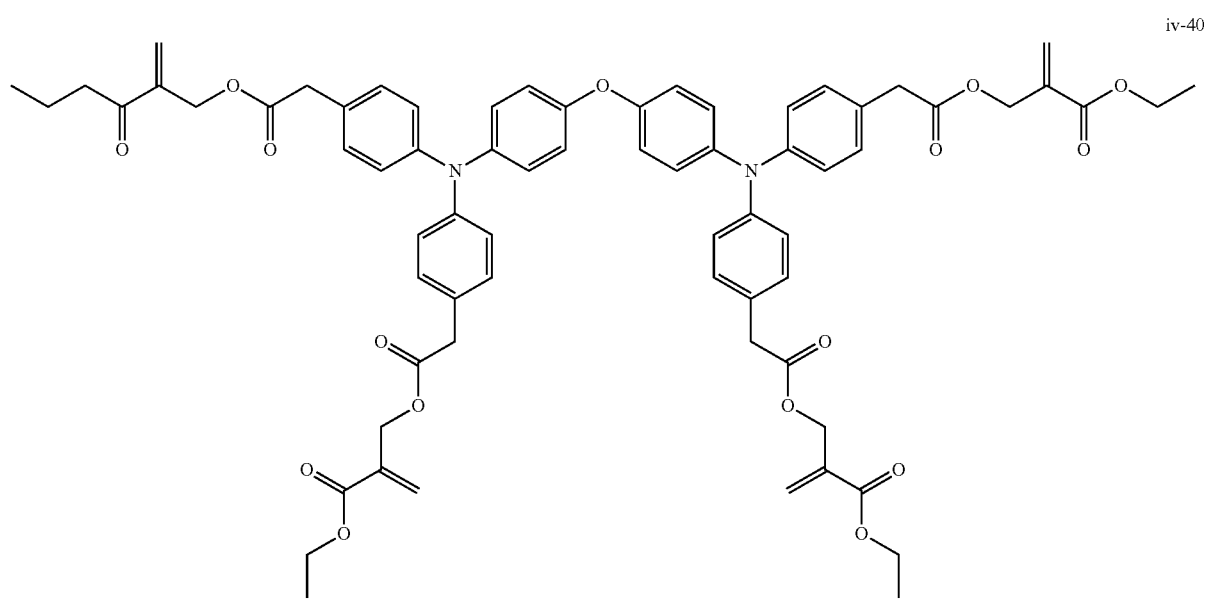

iv-41
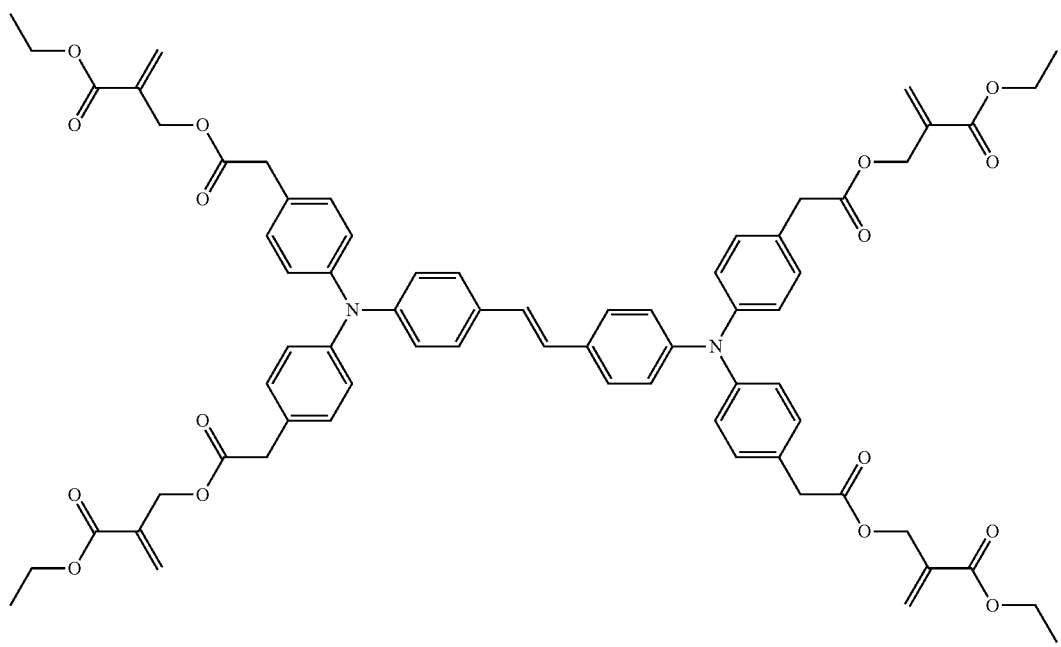
iv-42
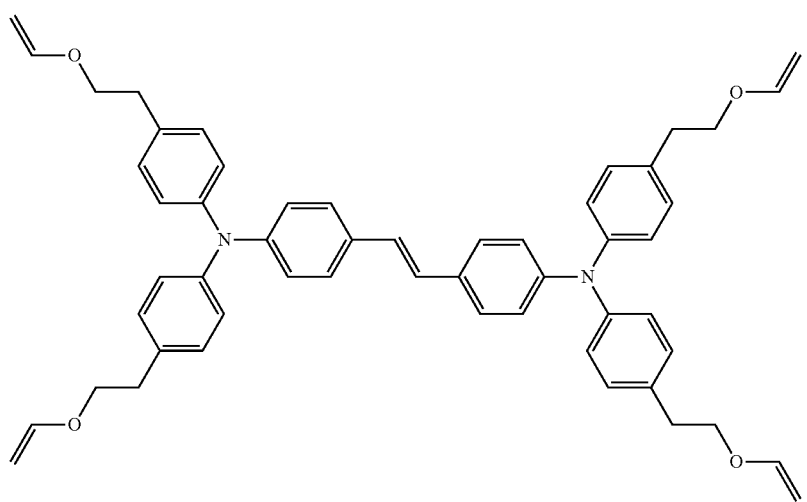

iv-43
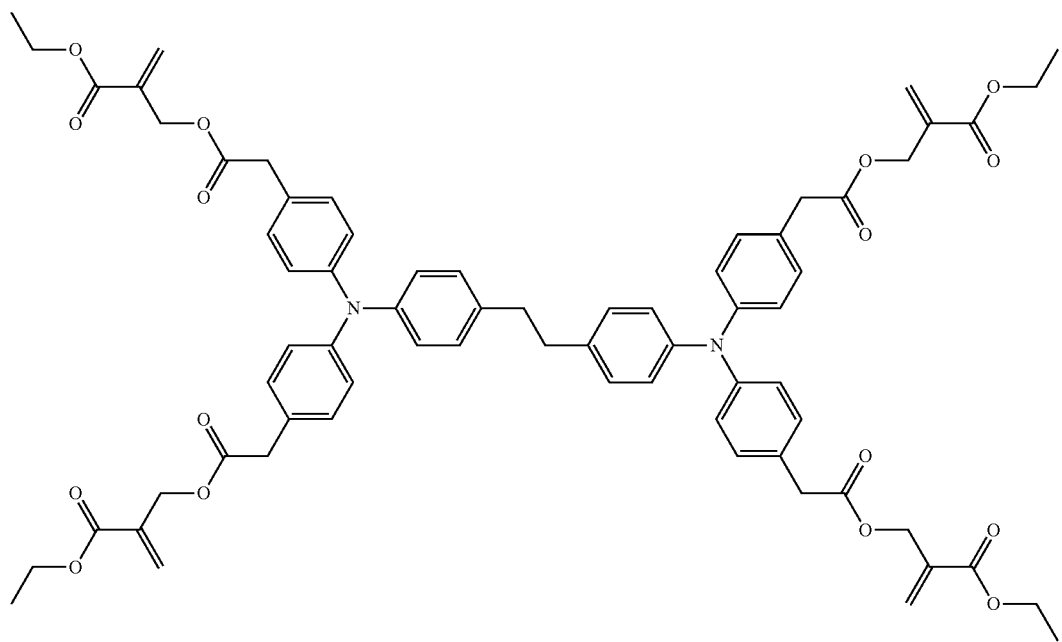
iv-44
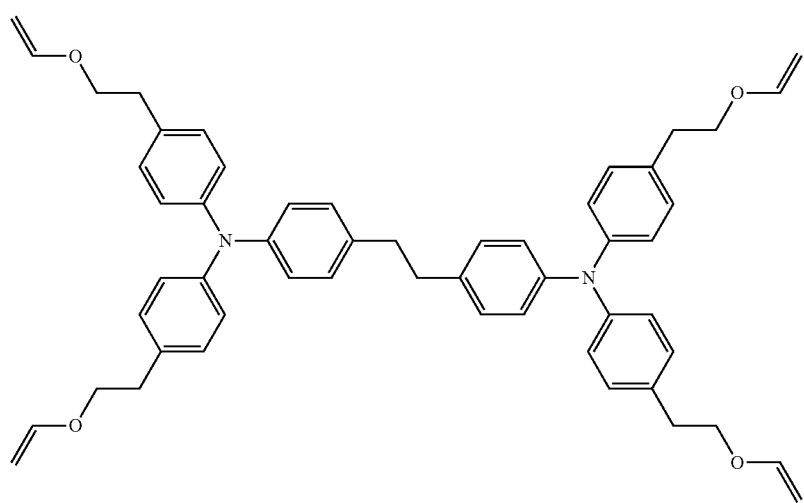

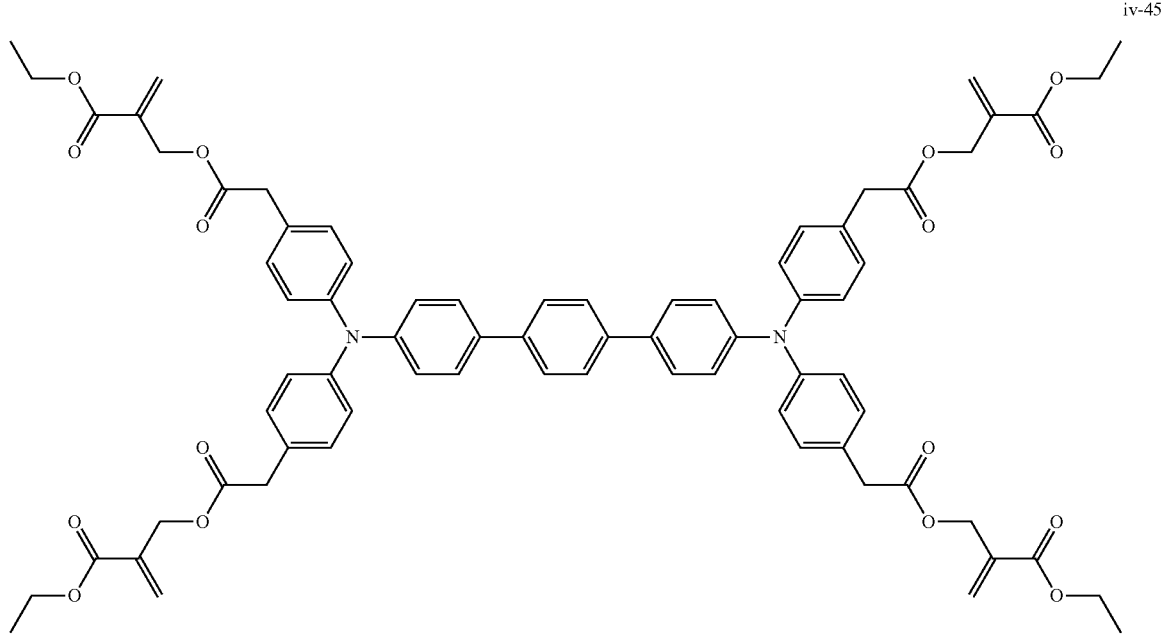
iv-45
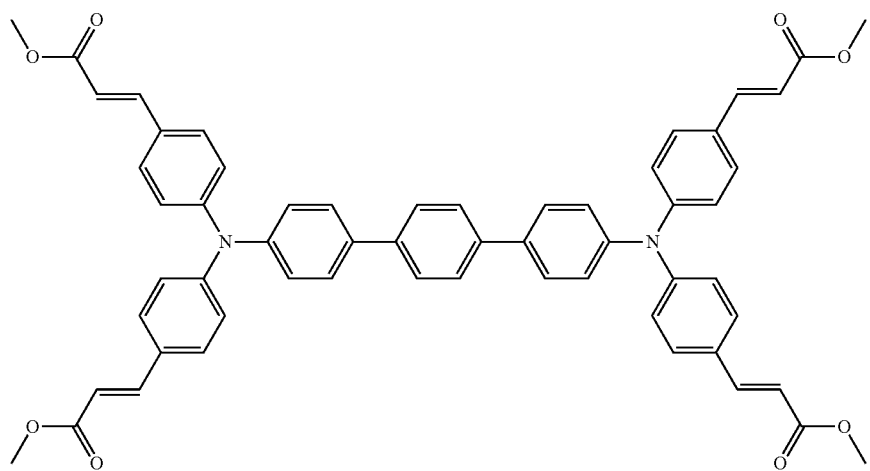
iv-46
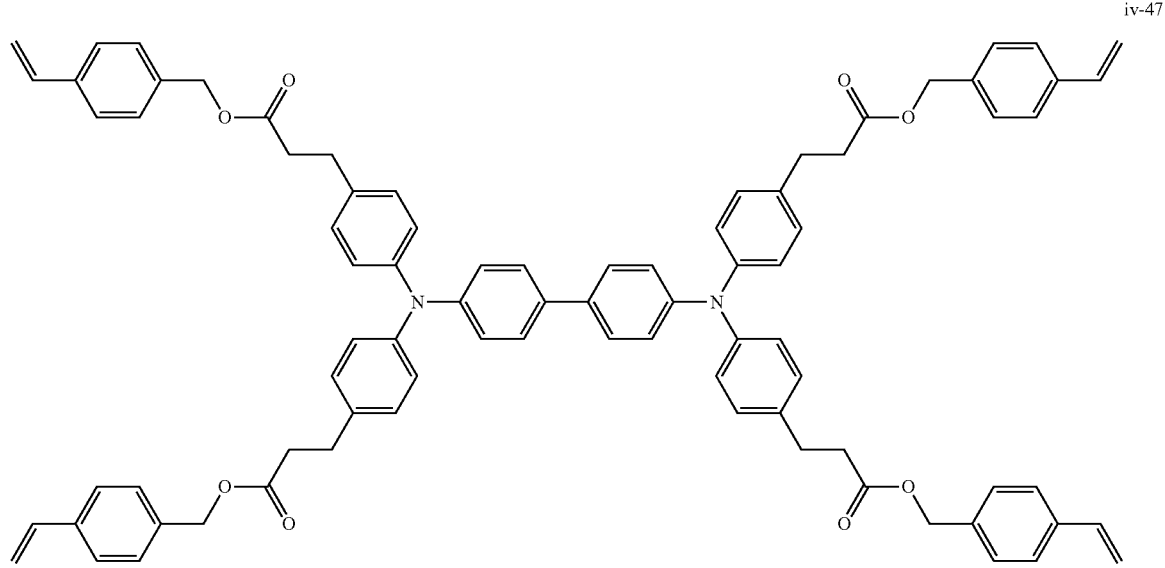
iv-47

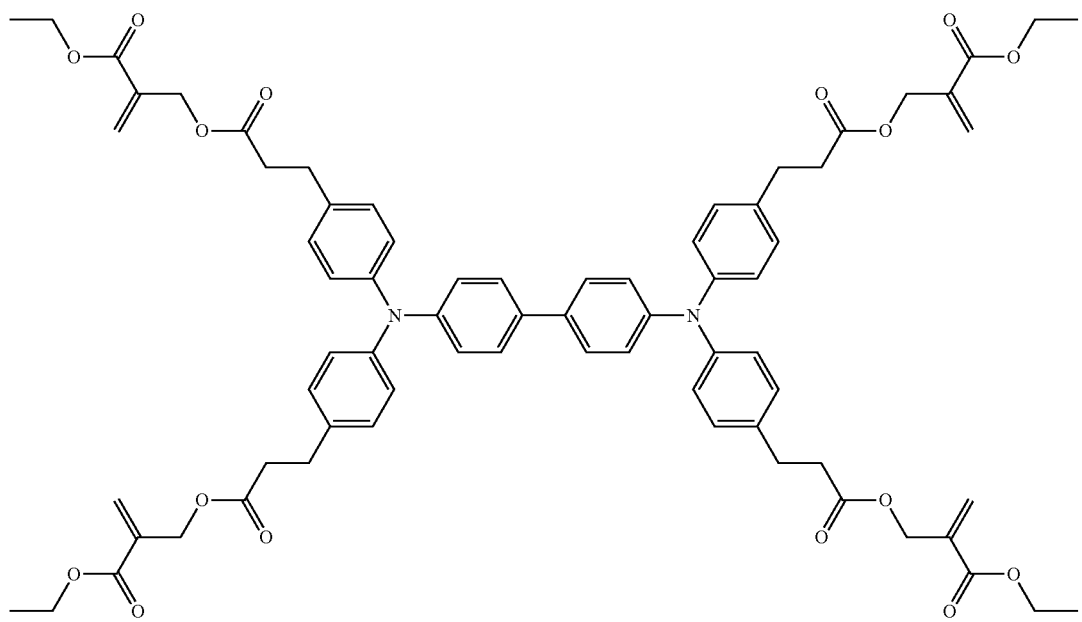
iv-48
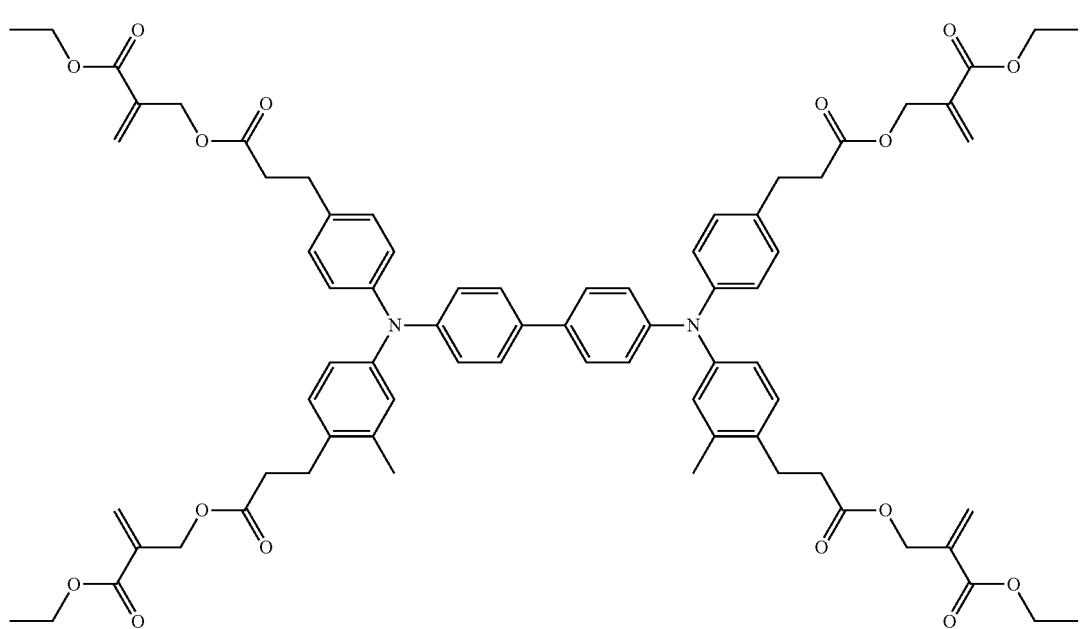
iv-49 iv-50
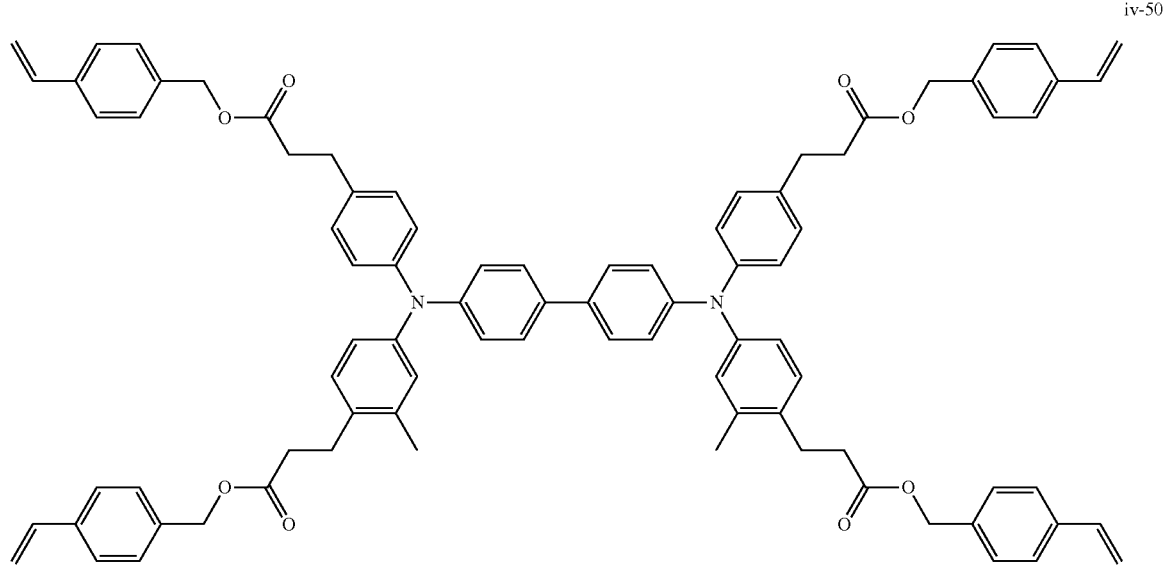
iv-51
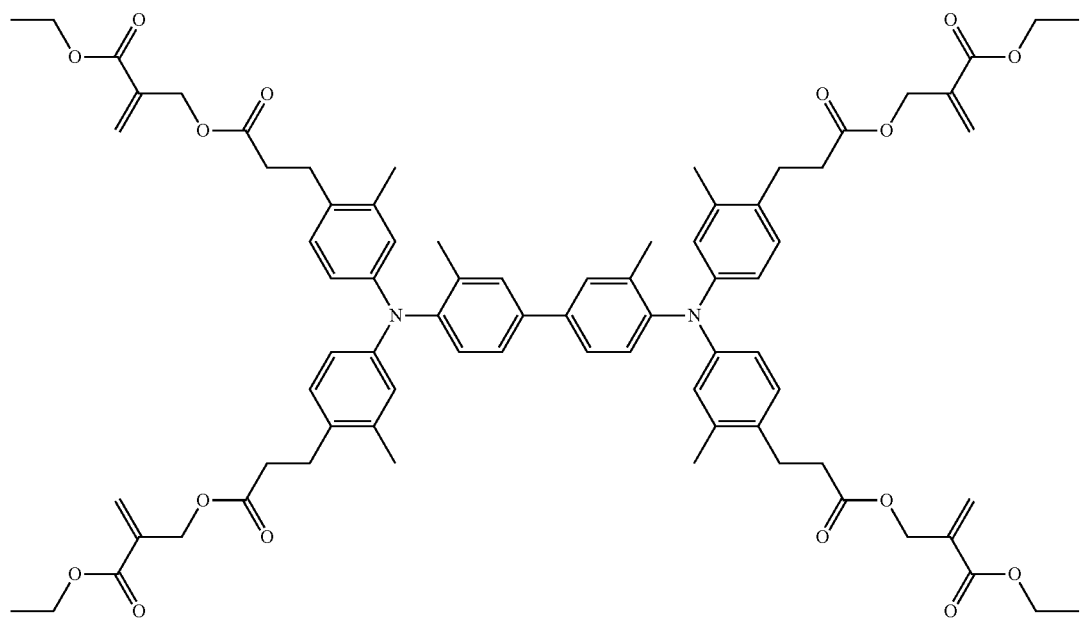

-continued
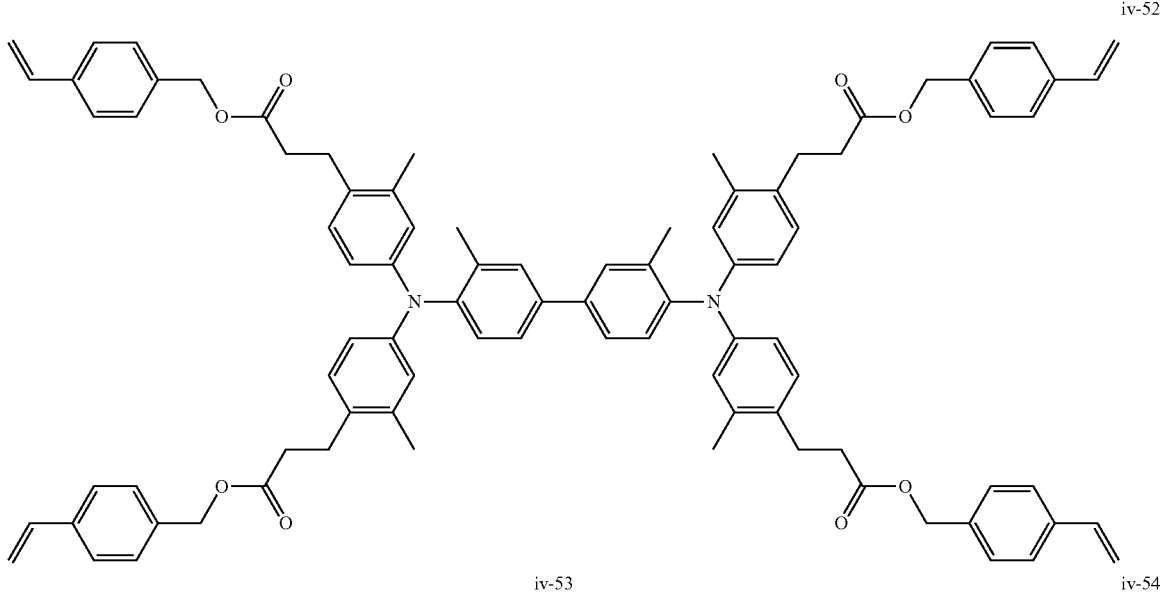
iv-52
iv-53
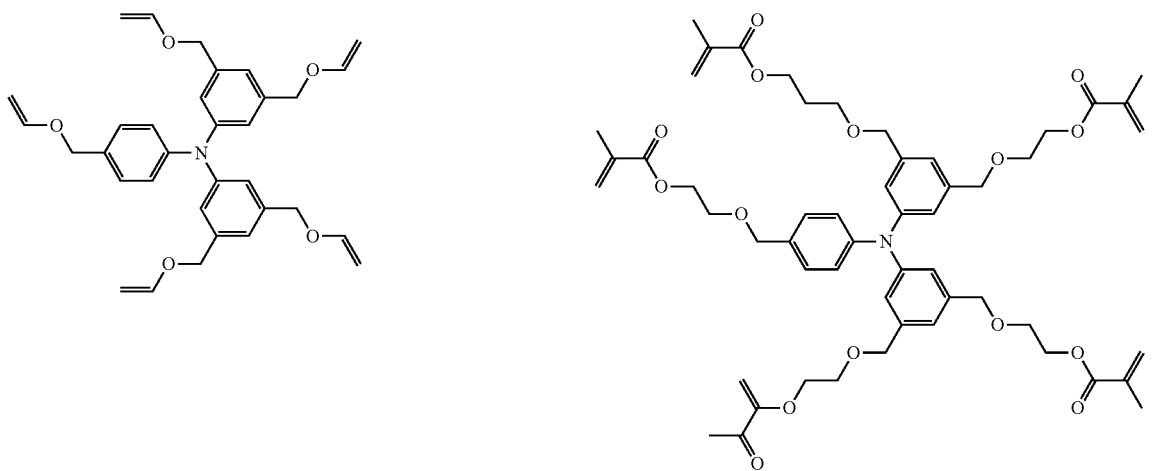
iv-54
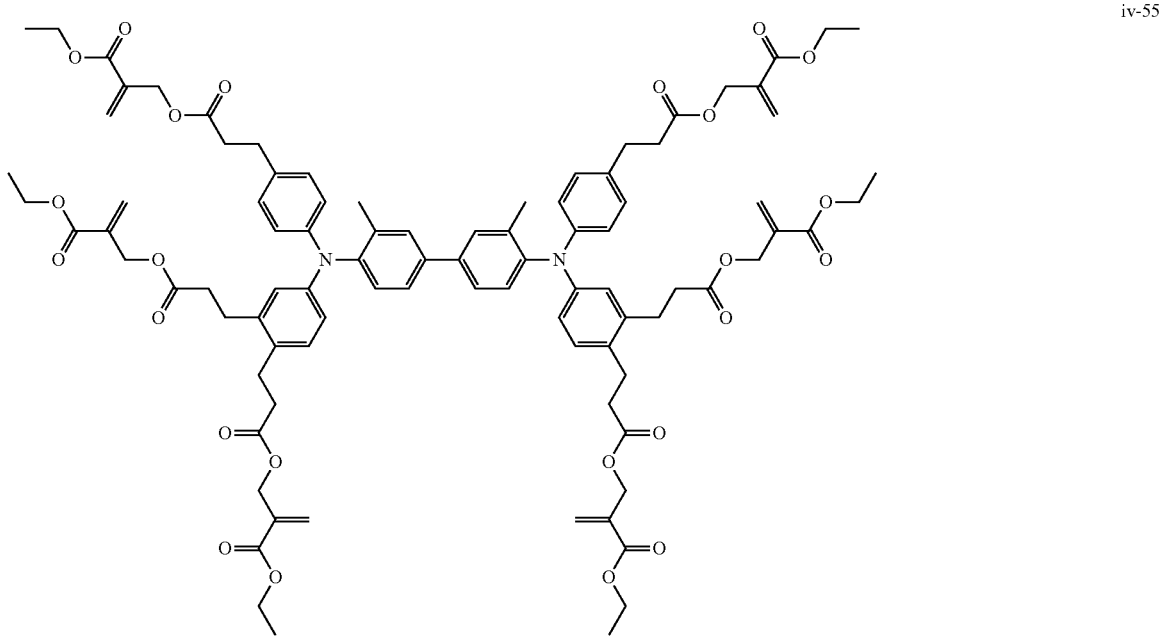
iv-55 iv-56
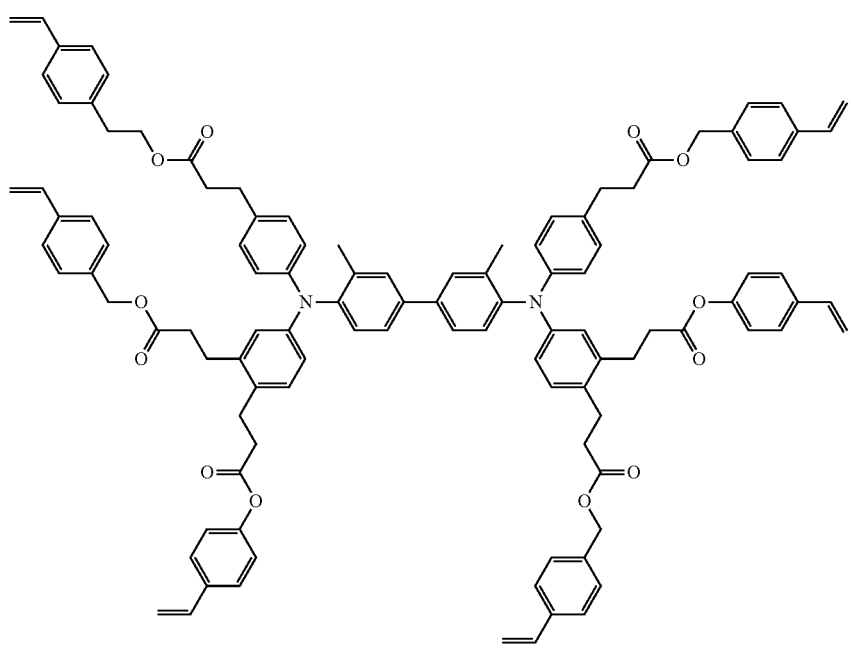
iv-57
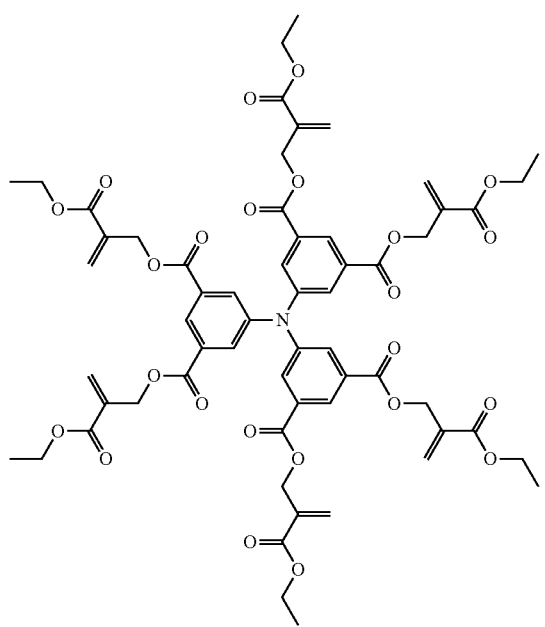
iv-58
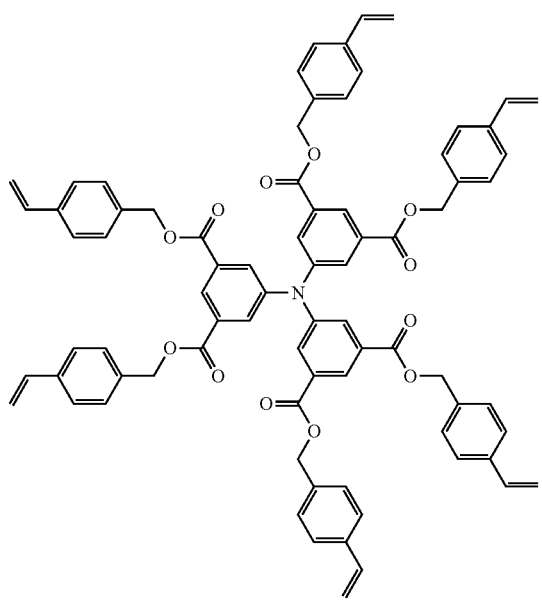

The compound of (I) is synthesized, for example, in the following manner.

That is, the compound of (I) is synthesized, for example, by condensing an alcohol which is a precursor with a corresponding methacrylic acid or methacrylic halide. A specific charge transporting material may be synthesized by dehydration/etherification or the like with an alcohol and a methacrylic acid having a hydroxyl group, such as hydroxyethyl methacrylate and the like, for example, in the case where the alcohol as a precursor has a benzyl alcohol structure.

The synthesis routes of the exemplary compound iv-4 and the exemplary compound iv-17 are shown below as examples.

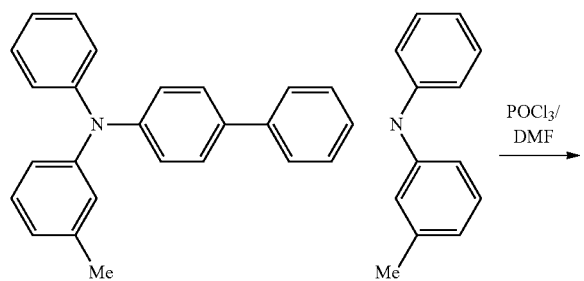

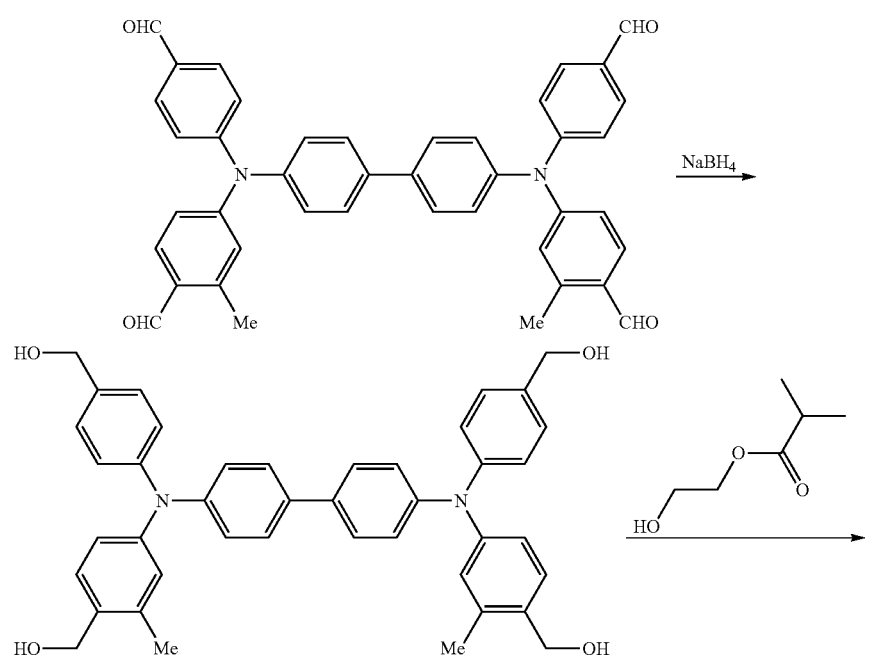

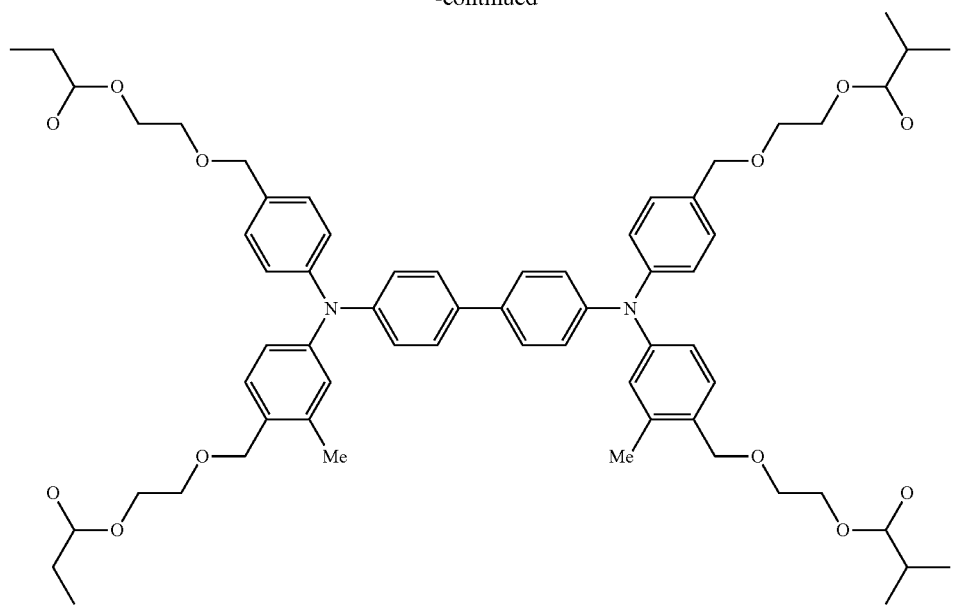
Compound iv-4
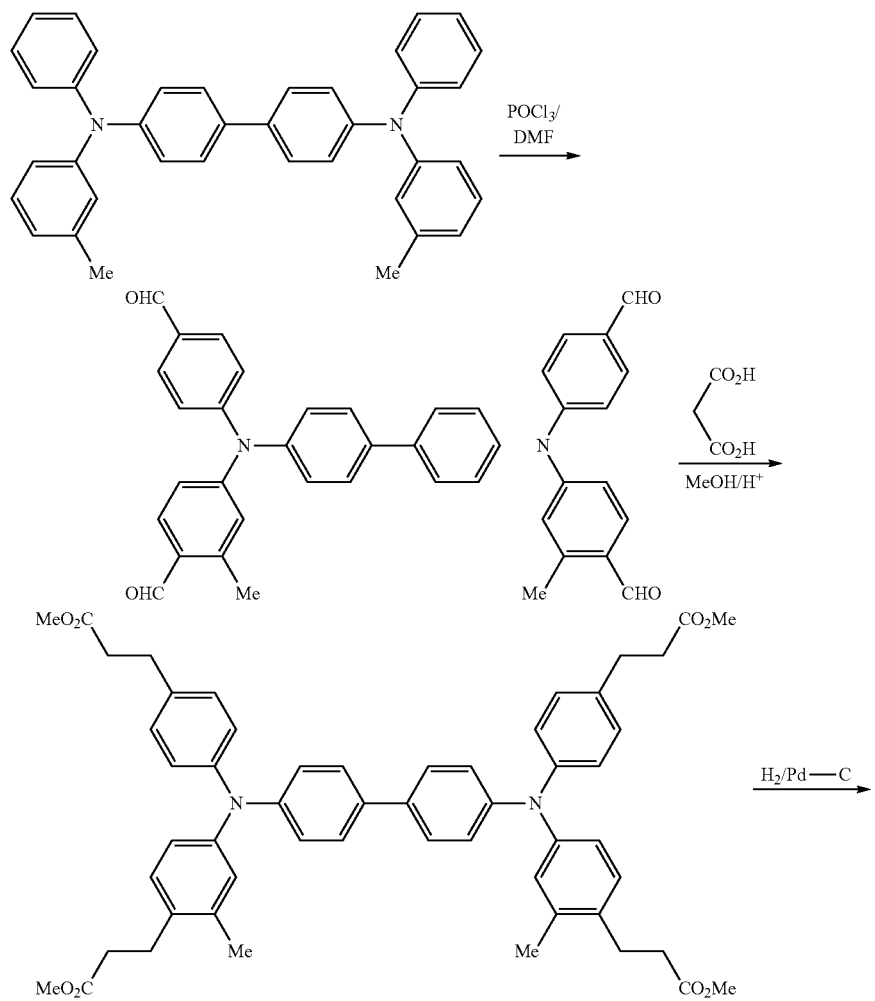

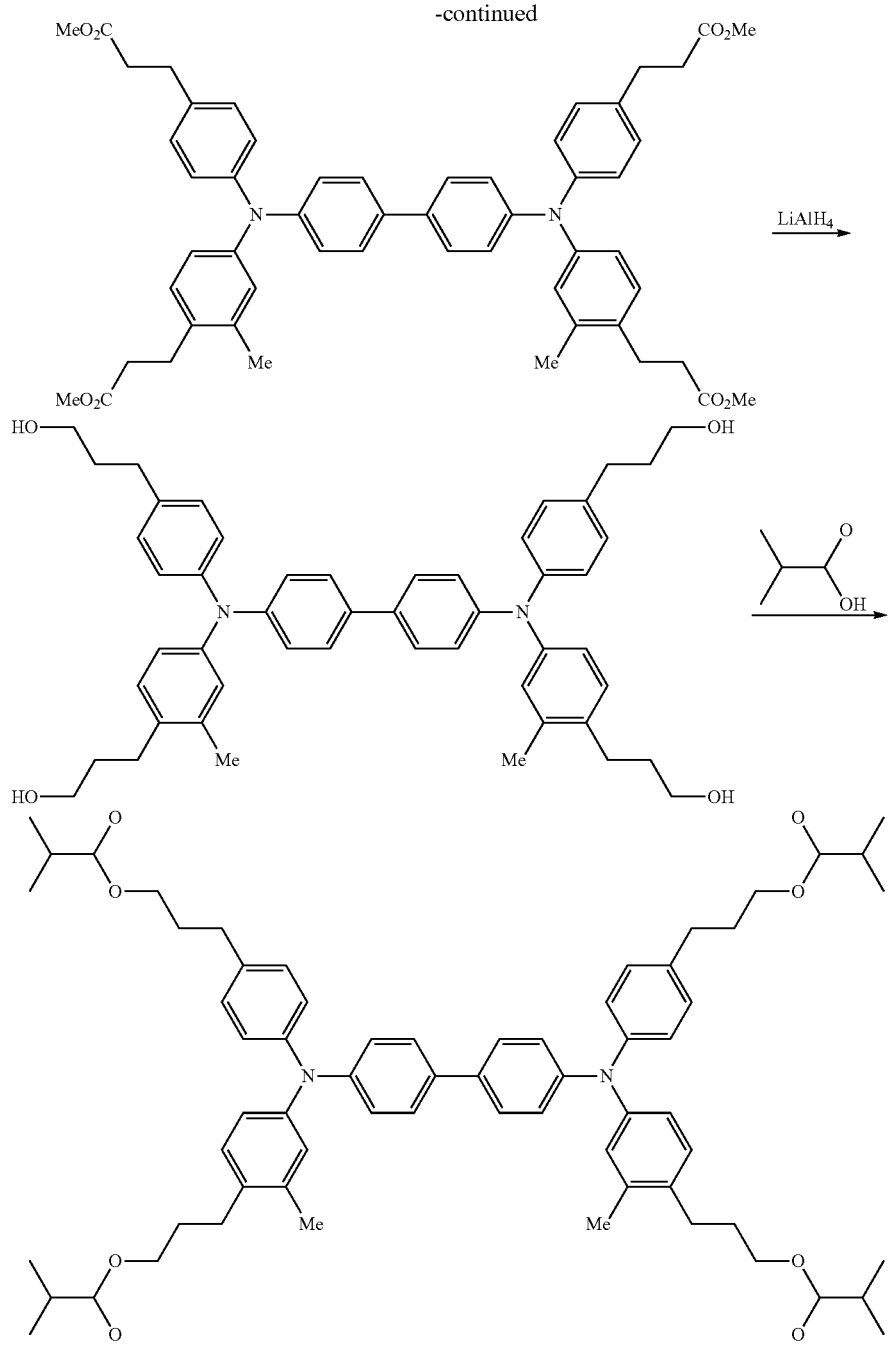

COMPOUND iv-17

Other compounds of (I) are synthesized, for example, according to the synthesis route of the compound iv-4 and the synthesis route of the compound iv-17.

As the compound of (I), a compound having four or more reactive functional groups having a carbon double bond may be used from the viewpoint of improvement of the mechanical strength of the obtained film as described above.

Furthermore, as the compound of (I), the compound having four or more reactive functional groups having a carbon double bond and the compound having one to three reactive functional groups having a carbon double bond may be used in combination. By such a use in combination, while deterioration of the charge transporting performance is inhibited, the strength of the film is adjusted.

In the case where the compound having four or more reactive functional groups having a carbon double bond and the compound having 1 to 3 reactive functional groups having a carbon double bond are used in combination as the compound of (I), the content of the compound having four or more reactive functional groups having a carbon double bond may be 5% by weight or more, and particularly 20% by weight or more, based on the total content of the compound of (I).

Next, other compounds of (I) will be described.

The compound of (I) may be a polymer including a partial structure represented by each of the following general formulae (B) and (C).

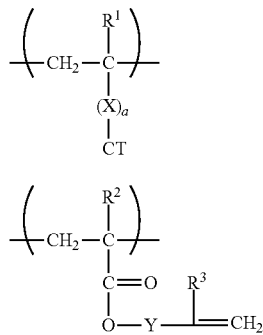

(B)

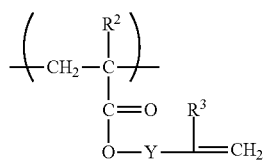

(C)

In the general formulae (B) and (C), $R^1$, $R^2$, and $R^3$ each independently represent a hydrogen atom or an alkyl group having 1 to 4 carbon atoms, X and Y each independently represent a divalent organic group having 1 to 20 carbon atoms, a represents 0 or 1, and CT represents an organic group having a charge transporting skeleton.

Here, a terminal group of the polymer including a partial structure represented by each of the following general formulae (B) and (C) has a structure formed by a termination reaction by a radical polymerization reaction.

In the general formula (B), examples of the organic group having a charge transporting skeleton represented by CT include the above-described charge transporting skeletons, but preferable examples thereof include those having a triarylamine skeleton, a bendizine skeleton, an arylalkane skeleton, an aryl-substituted ethylene skeleton, a stilbene skeleton, an anthracene skeleton, and a hydrazone skeleton. Among these, those having a triarylamine skeleton, a benzidine skeleton, and a stilbene skeleton are more preferable.

In the general formulae (B) and (C), examples of the divalent organic group represented by X and Y include divalent organic groups having one selected from an alkylene group, —C(=O)—, —O—C(=O)—, an aromatic ring, and a linking group having a combination thereof. Further, the divalent organic group represented by X and Y preferably has no hydroxyl group.

Specific examples of the divalent organic group represented by X include —C(=O)—O—(CH$_2$)$_n$— (wherein n represents 0 or an integer of 1 or more and 10 or less), and the like.

Specific examples of the divalent organic group represented by Y include —(CH)$_n$— (wherein n represents an integer of 1 or more and 10 or less), —(CH$_2$)$_n$—O—C(=O)— (wherein n represents 0 or an integer of 1 or more and 10 or less, and a part of hydrogen atoms of "(CH$_2$)$_n$" may be substituted with a hydroxyl group), —(CH$_2$)$_n$—Ar— (wherein Ar represents an arylene group having 1 to 3 aromatic rings, and n represents 0 or an integer of 1 or more and 10 or less), —Ar—O—(CH$_2$)$_n$—O—C(=O)— (wherein Ar represents an arylene group having 1 to 3 aromatic rings, and n represents 0 or an integer of 1 or more and 10 or less), and the like.

Specific examples of the partial structure represented by the general formula (B) include the following, but are not limited thereto. Further, in the section of "(X)$_a$", a case where "-" is denoted indicates a case of a=0, and a case where a group is denoted indicates a case of a=1, that is, a group represented by both CT and X.

| | $R^1$ | (X)$_a$ | CT |
|---|---|---|---|
| (B)-1 | H | — | 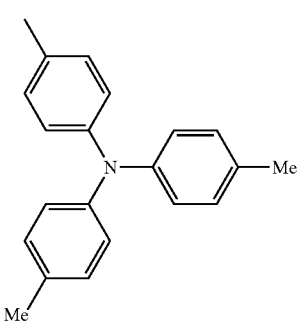 |
| (B)-2 | H | — | 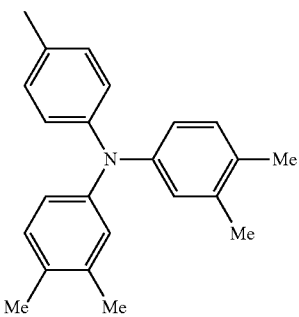 |

-continued

| | R¹ | (X)ₐ | CT |
|---|---|---|---|
| (B)-3 | H | — | |
| (B)-4 | H | — | |
| (B)-5 | H | — | |
| (B)-6 | H | — | |
| (B)-7 | H | — | |

-continued

| | R¹ | (X)ₐ | CT |
|---|---|---|---|
| (B)-8 | H | — | |
| (B)-9 | H | — | |
| (B)-10 | H | — | |
| (B)-11 | H | — | |

-continued
| | R¹ | (X)ₐ | CT |
|---|---|---|---|
| (B)-12 | H | 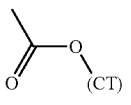 | 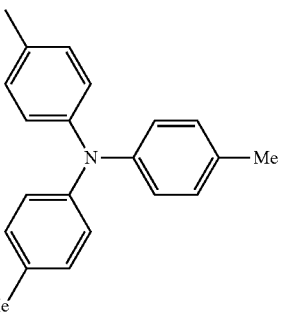 |
| (B)-13 | H | 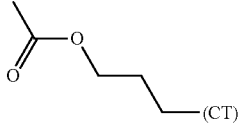 | 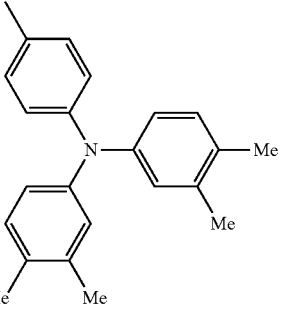 |
| (B)-14 | H | 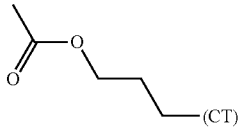 | 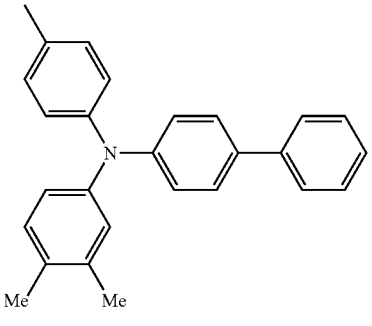 |
| (B)-15 | H | 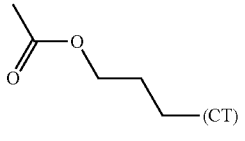 | 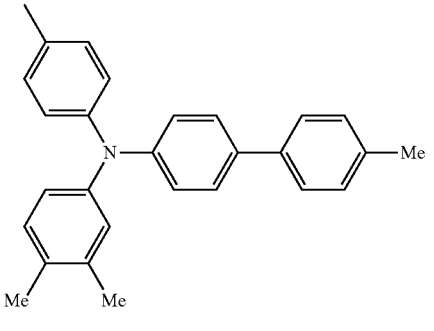 |
| (B)-16 | H | 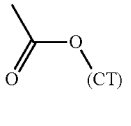 | 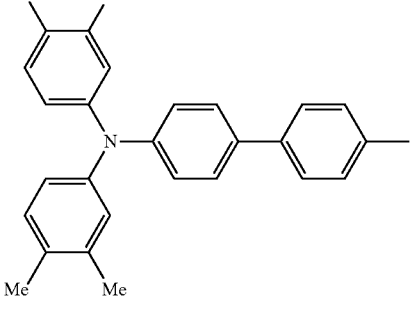 |

-continued
| | R¹ | (X)ₐ | CT |
|---|---|---|---|
| (B)-17 | H | 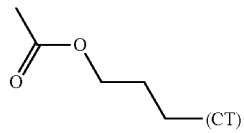 | 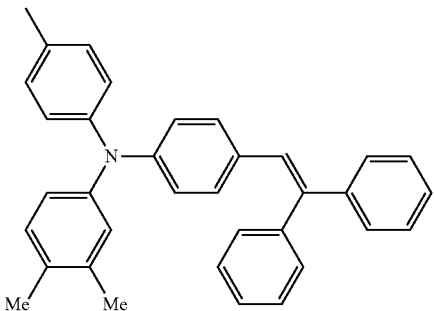 |
| (B)-18 | H | 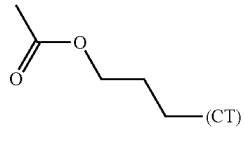 | 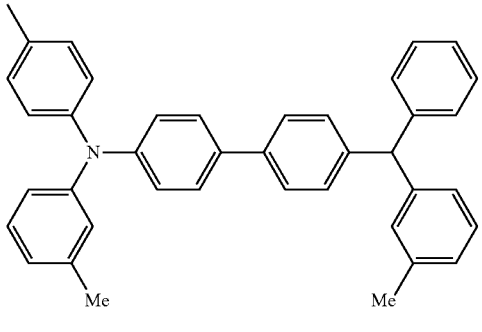 |
| (B)-19 | H | 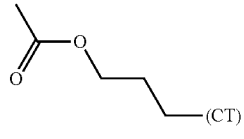 | 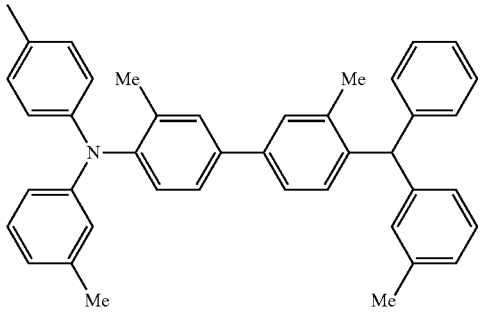 |
| (B)-20 | H | 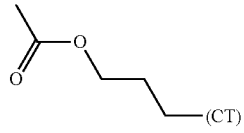 | 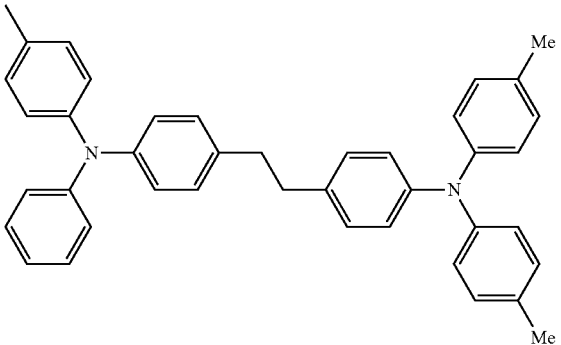 |

-continued
| | R[1] | (X)$_a$ | CT |
|---|---|---|---|
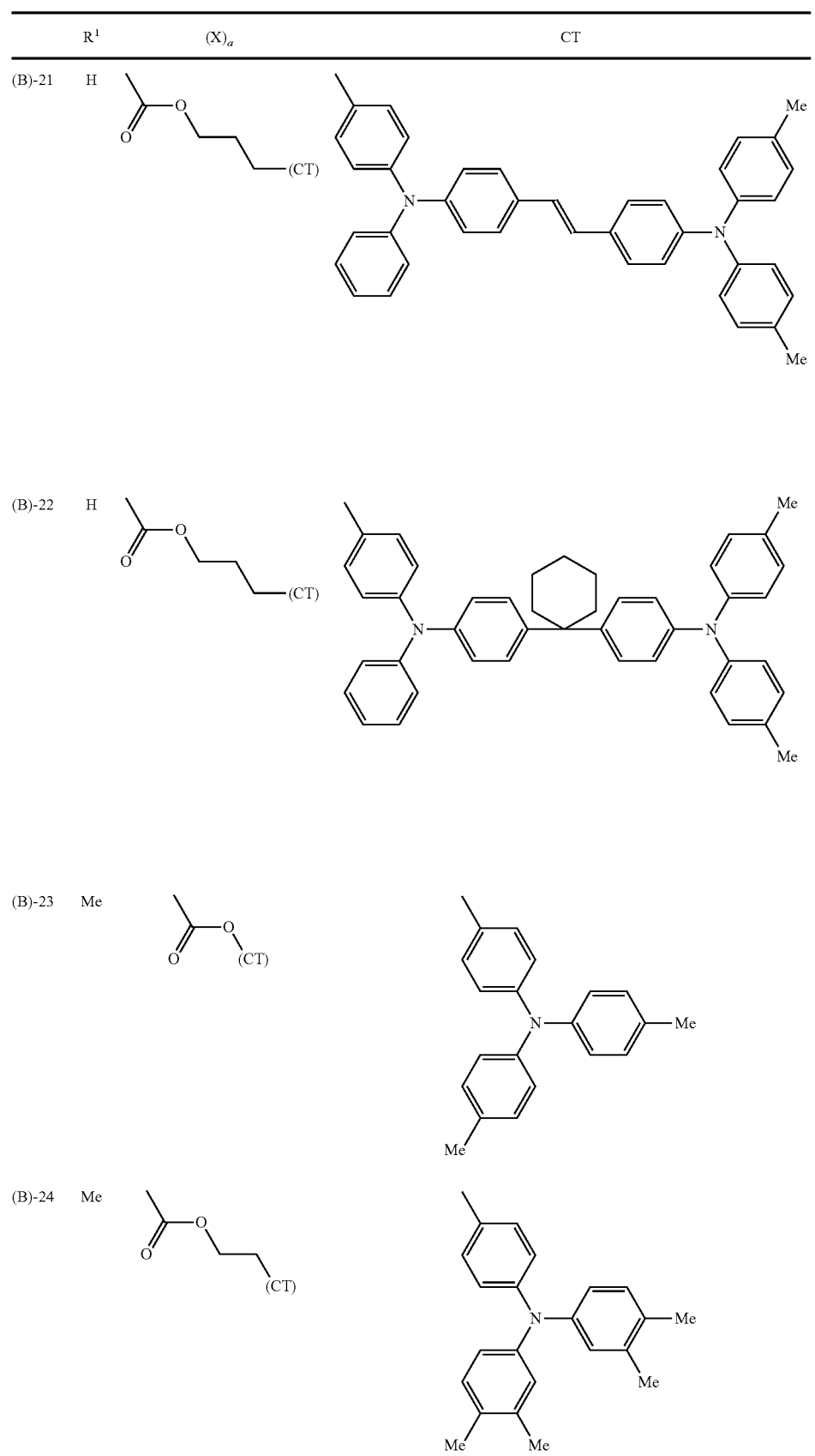
(B)-21 H
(B)-22 H
(B)-23 Me
(B)-24 Me -continued

| | R¹ | (X)ₐ | CT |
|---|---|---|---|
| (B)-25 | Me | | |
| (B)-26 | Me | | |
| (B)-27 | Me | | |
| (B)-28 | Me | | |
| (B)-29 | Me | | |

-continued
| | R¹ | (X)ₐ | CT |
|---|---|---|---|
| (B)-30 | Me | 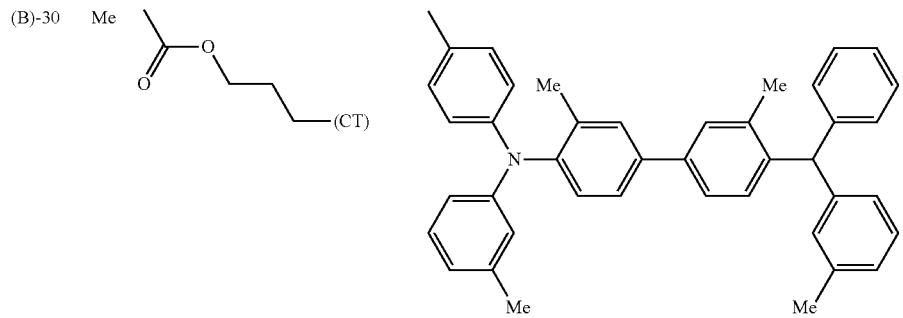 | |
| (B)-31 | Me | 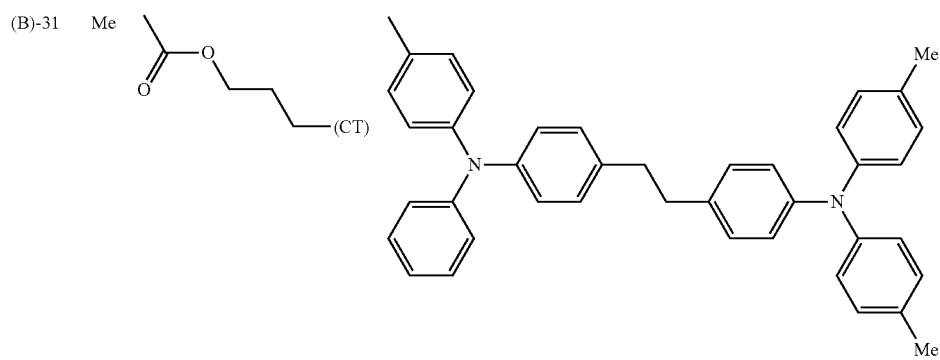 | |
| (B)-32 | Me | 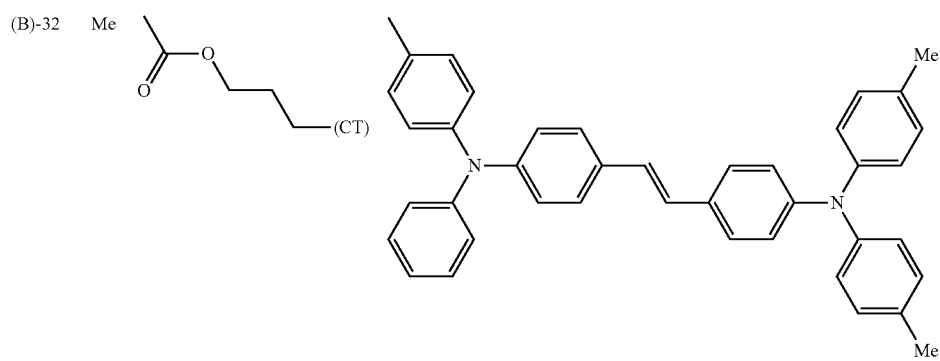 | |
| (B)-33 | Me | 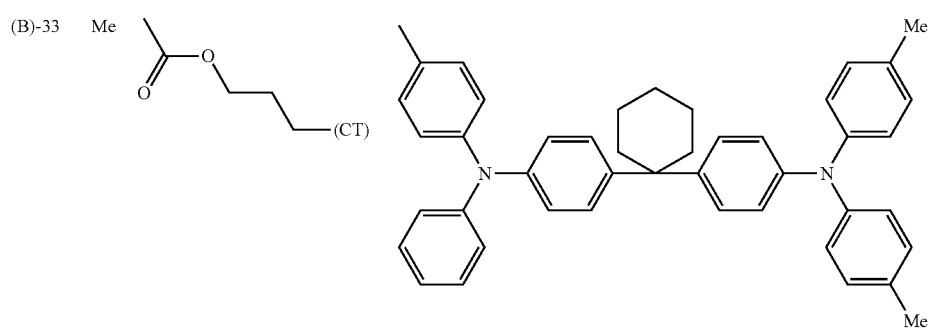 | |

Next, specific examples of the structure represented by the general formula (C) include the following, but are not limited thereto.

| | R² | Y | R³ |
|---|---|---|---|
| (C)-1 | H | —CH₂— | H |
| (C)-2 | H | propyl acetate group | H |
| (C)-3 | H | p-methylbenzyl group | H |
| (C)-4 | H | —CH₂— | Me |
| (C)-5 | H | propyl acetate group | Me |
| (C)-6 | H | p-methylbenzyl group | Bu |
| (C)-7 | H | propyl acetate group | Bu |
| (C)-8 | H | phenoxyethyl acetate group | Me |
| (C)-9 | H | 2-hydroxybutyl acetate group | H |
| (C)-10 | H | 2-hydroxybutyl acetate group | Me |
| (C)-11 | H | 2-hydroxybutyl acetate group | Bu |
| (C)-12 | Me | —CH₂— | H |
| (C)-13 | Me | propyl acetate group | H |
| (C)-14 | Me | p-methylbenzyl group | H |
| (C)-15 | Me | —CH₂— | Me |
| (C)-16 | Me | propyl acetate group | Me |
| (C)-17 | Me | p-methylbenzyl group | Bu |
| (C)-18 | Me | propyl acetate group | Bu |
| (C)-19 | Me | phenoxyethyl acetate group | Me |
| (C)-20 | Me | 2-hydroxybutyl acetate group | H |
| (C)-21 | Me | 2-hydroxybutyl acetate group | Me |
| (C)-22 | Me | 2-hydroxybutyl acetate group | Bu |

Among these, those represented by the following structural general formula (D) are excellent in solubility and a film forming property, which is thus preferable.

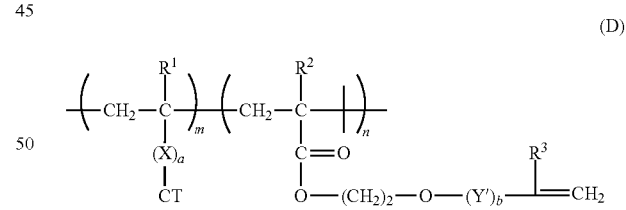

(D)

In the general formula (D), $R^1$, $R^2$, and $R^3$ each independently represent a hydrogen atom or an alkyl group having 1 to 4 carbon atoms, X represents a divalent organic group having 1 to 20 carbon atoms, Y' represents —C(=O)—, —CH₂—, or —(CH₂)₂—, a and b each independently represent 0 or 1, and CT represents an organic group having a charge transporting skeleton.

m and n each represent an integer of 5 or more, and satisfy the conditions of $10 < m+n < 2000$ and $0.2 < m/(m+n) < 0.95$, but from the viewpoint of strength, flexibility, and electrical characteristics, preferably the conditions of $15 < m+n < 2000$ and $0.3 < m/(m+n) < 0.95$, and still more preferably $20 < m+n < 2000$ and $0.4 < m/(m+n) < 0.95$.

Further, in the general formula (D), the organic group having the divalent organic group represented by X and the charge transporting skeleton represented by CT, have the same definitions as X and CT in the general formulae (B) and (C).

The polymer including a partial structure represented by each of the general formulae (B) and (C) is prepared according to, for example, a known method such as copolymerization with methacrylic acid, acrylic acid, a glycidyl compound, and derivatives thereof, and the like, using a compound represented by the general formula (A) as a monomer.

Furthermore, the polymer including a partial structure represented by each of the general formulae (B) and (C) may be copolymerized with a monovalent monomer, in addition to those represented by the general formulae (B) and (C), in order to provide solubility and flexibility.

Examples of the monofunctional monomer include acrylates or methacrylates such as isobutyl acrylate, tert-butyl acrylate, isooctyl acrylate, lauryl acrylate, stearyl acrylate, isobornyl acrylate, cyclohexyl acrylate, 2-methoxyethyl acrylate, methoxytriethylene glycol acrylate, 2-ethoxyethyl acrylate, tetrahydrofurfuryl acrylate, benzyl acrylate, ethylcarbitol acrylate, phenoxyethyl acrylate, 2-hydroxyacrylate, 2-hydroxypropyl acrylate, 4-hydroxybutyl acrylate, methoxypolyethylene glycol acrylate, methoxypolyethylene glycol methacrylate, phenoxypolyethylene glycol acrylate, phenoxypolyethylene glycol methacrylate, hydroxyethyl o-phenylphenol acrylate, o-phenylphenol glycidyl ether acrylate, and the like, and styrene derivatives such as styrene, α-methyl styrene, 4-methyl styrene, and the like.

The amount (1) used during the copolymerization of these monomers is preferably one satisfying the condition, regarding m in the general formula (D), of l/m<0.3, and more preferably l/m<0.2, from the viewpoint of providing solubility and flexibility.

Furthermore, these compounds of (I) may be used singly or in combination of two or more kinds thereof.

[Electrophotographic Photoreceptor]

The electrophotographic photoreceptor according to the present exemplary embodiment has a photosensitive layer containing a polymer formed by polymerization of at least one kind of the thiol group-containing charge transporting material represented by the general formula (I) and at least one kind of the compound having an unsaturated bond, on a conductive substrate.

Furthermore, by using the crosslinkable monomer itself as a polyfunctional charge transporting monomer, strength may be provided without lowering the concentration of the charge transporting component.

In the electrophotographic photoreceptor according to the present exemplary embodiment, a layer containing the thiol group-containing charge transporting material represented by the general formula (I) is preferably included as an outermost surface layer, and the outermost surface layer may be any one that forms an uppermost layer of the electrophotographic photoreceptor itself, and provided as a layer functioning as a protective layer or a layer functioning as a charge transporting layer.

Further, in the case where the outermost surface layer is a layer functioning as a protective layer, the undercoat layer of the protective layer may have a photosensitive layer including a charge transporting layer and a charge generating layer, or a single layer-type photosensitive layer.

In the case where the outermost surface layer is a layer functioning as a protective layer, a photosensitive layer and a protective layer as an outermost surface layer are included on the conductive substrate, in which the protective layer may have any configuration with a layer including a composition containing a polymer formed by using the thiol group-containing charge transporting material represented by the general formula (I), or a cured product thereof.

Further, in the case where the outermost surface layer is a layer functioning as a charge transporting layer, a charge generating layer and a charge transporting layer as an outermost surface layer are included on a conductive substrate, in which the charge transporting layer may have any configuration with a layer including a composition containing a polymer formed by using the thiol group-containing charge transporting material represented by the general formula (I) and at least one kind of the compound having an unsaturated bond or a cured product thereof.

Furthermore, a charge transporting material having no reactivity such as a thiol group, an unsaturated bond, and the like may be mixed.

Hereinafter, the electrophotographic photoreceptor according to the present exemplary embodiment in the case where the outermost surface layer functions as a protective layer will be described in detail with reference to the drawings. Further, in the drawings, the same or equivalent portions are referenced by the same marks, and repeated explanations are abbreviated.

FIG. 1 is a schematic cross-sectional view showing a preferable example of the electrophotographic photoreceptor according to the present exemplary embodiment.

Figure 2:
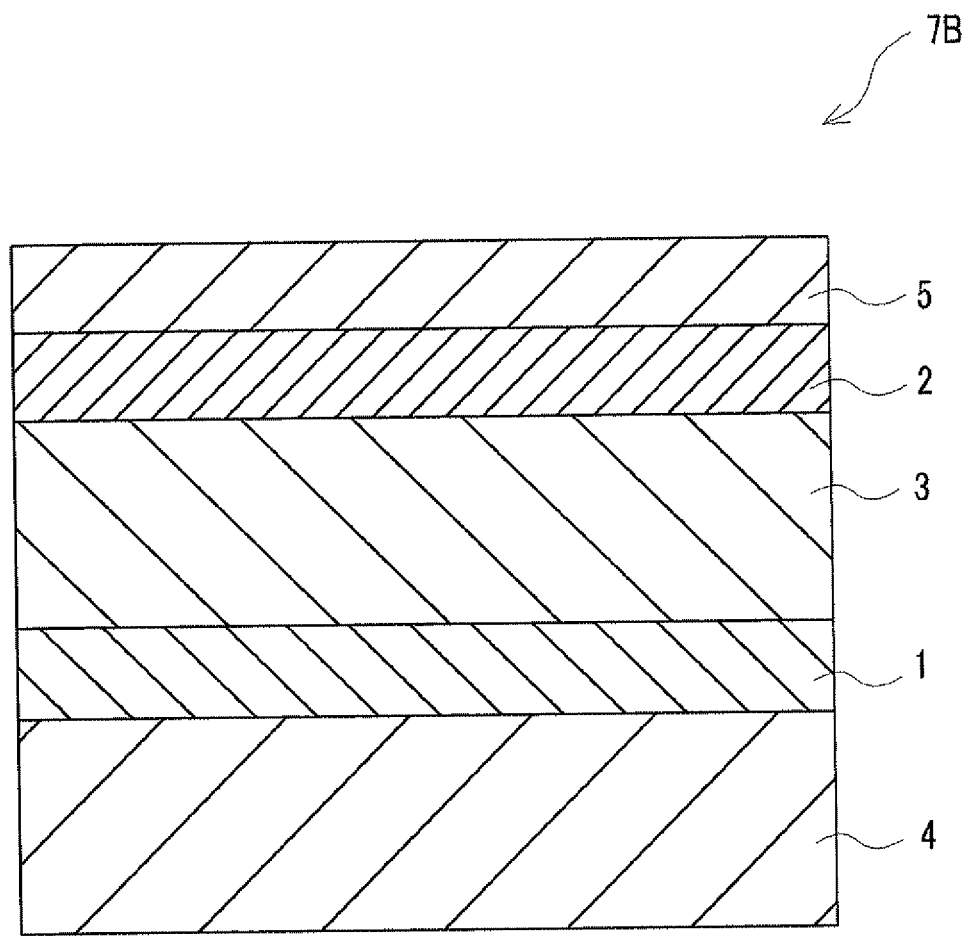
FIG. 2 is a schematic partial cross-sectional view showing another example of the layer configuration of the electrophotographic photoreceptor according to the present exemplary embodiment.
Figure 3:
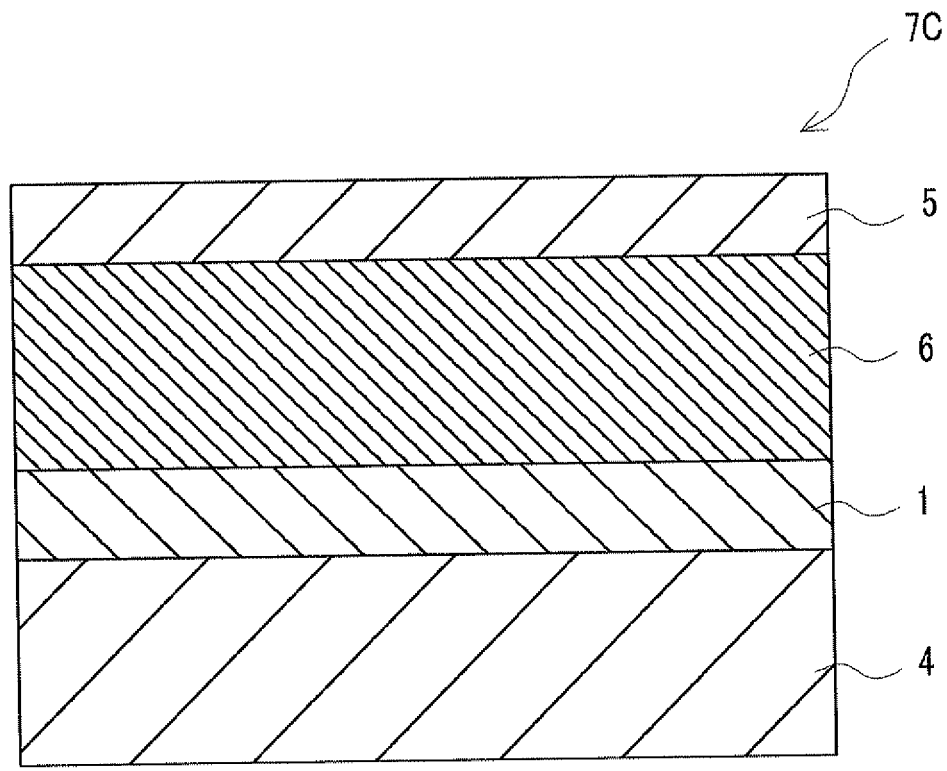
FIG. 3 is a schematic partial cross-sectional view showing a further example of the layer configuration of the electrophotographic photoreceptor according to the present exemplary embodiment.

FIGS. 2 to 3 are schematic cross-sectional views showing the electrophotographic photoreceptor according to other present exemplary embodiments.

The electrophotographic photoreceptor 7A shown in FIG. 1 is a so-called function-separate type photoreceptor (or layered photoreceptor), and has a structure in which an undercoat layer 1 is provided on a conductive substrate 4, and a charge generating layer 2, a charge transporting layer 3, and a protective layer 5 are formed in this order thereon. In the electrophotographic photoreceptor 7A, the photosensitive layer is constituted with the charge generating layer 2 and the charge transporting layer 3.

The electrophotographic photoreceptor 7B shown in FIG. 2 is a function-separate type photoreceptor having separate functions of the charge generating layer 2 and the charge transporting layer 3, similar to the electrophotographic photoreceptor 7A shown in FIG. 1.

The electrophotographic photoreceptor 7B shown in FIG. 2 has a structure in which an undercoat layer 1 is provided on a conductive substrate 4, and a charge transporting layer 3, a charge generating layer 2, and a protective layer 5 are formed in this order thereon. In the electrophotographic photoreceptor 7B, the photosensitive layer is constituted with the charge transporting layer 3 and the charge generating layer 2.

The electrophotographic photoreceptor 7C shown in FIG. 3 contains the charge generating material and the charge transporting material in the same layer (single layer-type photosensitive layer 6). The electrophotographic photoreceptor 7C shown in FIG. 3 has a structure in which an undercoat layer 1 is provided on a conductive substrate 4, and a single layer-type photosensitive layer 6 and a protective layer 5 are formed in this order thereon.

Moreover, in the electrophotographic photoreceptor 7A, 7B, and 7C shown in FIGS. 1, 2, and 3, the protective layer 5 is provided as an outermost surface layer that is formed on the farthest side from the conductive substrate 2, and the outermost surface layer is configured as described above.

Furthermore, in the electrophotographic photoreceptors shown in FIGS. 1, 2, and 3, the undercoat layer 1 may be formed or not formed.

Hereinafter, as representative examples, each of the elements will be explained, based on the electrophotographic photoreceptor 7A shown in FIG. 1.

—Protective Layer—

First, the protective layer 5 which is an outermost surface layer in the electrophotographic photoreceptor 7A will be described. The protective layer 5 is an outermost surface layer in the electrophotographic photoreceptor 7A, and is preferably formed with a polymer formed by polymerization of at least one kind of the thiol group-containing charge transporting material represented by the general formula (I) and at least one kind of the compound having an unsaturated bond.

As a curing method, radical polymerization is carried out by heat, light, radiation, or the like. If the reaction is adjusted not to advance too rapidly, unevenness of a film or generation of wrinkles are inhibited, and thus, it is preferable to carry out polymerization under a condition where the radical generation slowly occurs. From this point of view, thermal polymerization is preferable, which allows the polymerization rate to be easily adjusted.

Non-Reactive Charge Transporting Material

For the film constituting the protective layer (outermost surface layer) 5, a non-reactive charge transporting material may be used in combination. The non-reactive charge transporting material has no reactive group in charge of charge transportation, and accordingly, in the case where the non-reactive charge transporting material is used in the protective layer (outermost surface layer) 5, the concentration of the charge transporting component substantially increases, which is thus effective for further improvement of electrical characteristics. In addition, the non-reactive charge transporting material may be added to reduce the crosslinking density, and thus adjust the strength.

As the non-reactive charge transporting material, a known charge transporting material may be used, and specifically, a triarylamine-based compound, a bendizine-based compound, an arylalkane-based compound, an aryl-substituted ethylene-based compound, a stilbene-based compound, an anthracene-based compound, a hydrazone-based compound, or the like is used.

Among these, from the viewpoint of flowability, compatibility, or the like, it is preferable to have a triphenylamine skeleton.

The amount of the non-reactive charge transporting material is preferably 0% by weight or more and 30% by weight or less, more preferably 1% by weight or more and 25% by weight or less, and still more preferably 5% by weight or more and 25% by weight or less, based on the total solid content in a coating liquid for forming a layer.

Other Additives

The cured film constituting the protective layer (outermost surface layer) 5 may have other coupling agents added, particularly, a fluorine-containing coupling agent, for the purpose of, for example, adjusting film formability, flexibility, lubrication, and adhesiveness, and then used. As these compounds, various silane coupling agents and commercially available silicone-based hard coat agents are used. In addition, a radical polymerizable group-containing silicone compound or a fluorine-containing compound may be used.

Examples of the silane coupling agent include vinyltrichlorosilane, vinyltrimethoxysilane, vinyltriethoxysilane, γ-glycidoxypropylmethyldiethoxysilane, γ-glycidoxypropyltrimethoxysilane, γ-glycidoxypropyltrimethoxysilane, γ-aminopropyltriethoxysilane, γ-aminopropyltrimethoxysilane, γ-aminopropylmethyldimethoxysilane, N-β(aminoethyl) γ-aminopropyltriethoxysilane, tetramethoxysilane, methyltrimethoxysilane, dimethyldimethoxysilane, and the like.

Examples of the commercially available hard coating agent include KP-85, X-40-9740, and X-8239 (all manufactured by Shin-Etsu Silicones Co., Ltd.), AY42-440, AY42-441, and AY49-208 (all manufactured by Dow Corning Toray Co., Ltd.), and the like.

In addition, in order to provide water-repellency or the like, a fluorine-containing compound may be added, examples of which include (tridecafluoro-1,1,2,2-tetrahydrooctyl)triethoxysilane, (3,3,3-trifluoropropyl)trimethoxysilane, 3-(heptafluoroisopropoxy)propyltriethoxysilane, 1H,1H,2H,2H-perfluoroalkyltriethoxysilane, 1H,1H,2H,2H-perfluorodecyltriethoxysilane, 1H, H,2H,2H-perfluorooctyltriethoxysilane, and the like.

The silane coupling agent is used in an arbitrary amount, but the amount of the fluorine-containing compound is preferably 0.25 time or less of the weight of the compounds free of fluorine. Further, the reactive fluorine compound and the like disclosed in JP-A-2001-166510 or the like may be added therewith.

Examples of the radical polymerizable group-containing silicone compound and the fluorine-containing compound include the compounds described in JP-A-2007-11005, and the like.

A deterioration inhibitor is preferably added to the cured film constituting the protective layer (outermost surface layer) 5.

As the deterioration inhibitor, hindered phenols and hindered amines are preferable, and any of known antioxidants such as an organic sulfur antioxidant, a phosphite antioxidant, a dithiocarbamate antioxidant, a thiourea antioxidant, a benzoimidazole antioxidant, and the like may be used.

The amount of the deterioration inhibitor to be added is preferably 20% by weight or less, and more preferably 10% by weight or less.

Examples of the hindered phenol antioxidants include IRGANOX 1076, IRGANOX 1010, IRGANOX 1098, IRGANOX 245, IRGANOX 1330, IRGANOX 3114, IRGANOX 1076, 3,5-di-tert-butyl-4-hydroxybiphenyl, and the like.

Examples of the hindered amine antioxidants include SANOL LS2626, SANOL LS765, SANOL LS770, SANOL LS744, TINUVIN 144, TINUVIN 622LD, and MARK LA57, MARK LA67, MARK LA62, MARK LA68, and MARK LA63, examples of the thioether antioxidants include SUMILIZER TPS and SUMILIZER TP-D, and examples of the phosphate antioxidants include MARK 2112, MARK PEP-8, MARK PEP-24G, MARK PEP-36, MARK 329K, MARK HP-10, and the like.

Furthermore, the cured film constituting the protective layer (outermost surface layer) 5 may have conductive particles added, or organic or inorganic particles.

Examples of the particles include silicon-containing particles. The silicon-containing particles refer to particles which include silicon as a constitutional element, and specific examples thereof include colloidal silica and silicone particles. The colloidal silica used as the silicon-containing particles is selected from silica having an average particle size of 1 nm or more and 100 nm or less, and preferably 10 nm or more and 30 nm or less, and is used after being dispersed in an acidic or alkaline aqueous dispersion liquid or in an organic solvent such as an alcohol, a ketone, an ester, and the like. The colloidal silica may be a commercially available product.

The solid content of the colloidal silica in the protective layer is not particularly limited, but is preferably 0.1% by weight or more and 50% by weight or less, and more preferably 0.1% by weight or more and 30% by weight or less, with respect to the total solid content of the protective layer 5.

The silicone particles used as the silicon-containing particles are selected from silicone resin particles, silicone rubber particles, and treated silica particles whose surfaces have been treated with silicone, and commercially available silicone particles may be used.

These silicone particles are spherical, and the average particle size is preferably from 1 nm to 500 nm, and more preferably from 10 nm to 100 nm.

The amount of the silicone particles is preferably from 0.1% by weight to 30% by weight, more preferably from 0.5% by weight to 10% by weight, with respect to the total solid content of the protective layer 5.

Moreover, other examples of the particles include fluorine particles such as ethylene tetrafluoride, ethylene trifluoride, propylene hexafluoride, vinyl fluoride, vinylidene fluoride, and the like, particles of resin obtained by copolymerizing a fluorine resin and a monomer having a hydroxyl group, such as those described on page 89 of "The Proceedings of the 8th Polymer Material Forum Lecture", and particles of semiconductive metal oxides such as $ZnO—Al_2O_3$, $SnO_2—Sb_2O_3$, $In_2O_3—SnO_2$, $ZnO_2—TiO_2$, $ZnO—TiO_2$, $MgO—Al_2O_3$, $FeO—TiO_2$, $TiO_2$, $SnO_2$, $In_2O_3$, $ZnO$, $MgO$, and the like. In addition, in order to disperse the particles, various known dispersants may be used.

In addition, oils such as silicone oil and the like may be added.

Examples of the silicone oil include silicone oils such as dimethylpolysiloxane, diphenylpolysiloxane, phenylmethylsiloxane, and the like; reactive silicone oils such as amino-modified polysiloxane, epoxy-modified polysiloxane, carboxy-modified polysiloxane, carbinol-modified polysiloxane, methacryl-modified polysiloxane, mercapto-modified polysiloxane, phenol-modified polysiloxane, and the like; cyclic dimethylcyclosiloxanes such as hexamethylcyclotrisiloxane, octamethylcyclotetrasiloxane, decamethylcyclopentasiloxane, dodecamethylcyclohexasiloxane, and the like; cyclic methylphenylcyclosiloxanes such as 1,3,5-trimethyl-1,3,5-triphenylcyclotrisiloxane, 1,3,5,7-tetramethyl-1,3,5,7-tetraphenylcyclotetrasiloxane, 1,3,5,7,9-pentamethyl-1,3,5,7,9-pentaphenylcyclopentasiloxane, and the like; cyclic phenylcyclosiloxanes such as hexaphenylcyclotrisiloxane and the like; fluorine-containing cyclosiloxanes such as 3-(3,3,3-trifluoropropyl)methylcyclotrisiloxane and the like; hydrosilyl group-containing cyclosiloxanes such as a methylhydrosiloxane mixture, pentamethylcyclopentasiloxane, phenylhydrocyclosiloxane, and the like; and vinyl group-containing cyclosiloxanes such as pentavinylpentamethylcyclopentasiloxane and the like.

Furthermore, a metal, a metal oxide, carbon black, or the like may added. Examples of the metal include aluminum, zinc, copper, chromium, nickel, silver, stainless steel, and the like, and plastic particles onto which a metal such as those above is deposited. Examples of the metal oxide include zinc oxide, titanium oxide, tin oxide, antimony oxide, indium oxide, bismuth oxide, tin-doped indium oxide, antimony-doped or tantalum-doped tin oxide, antimony-doped zirconium oxide, and the like.

These may be used singly or in a combination of 2 or more kinds thereof. When 2 or more kinds thereof are used in combination, these may be simply mixed or made into a solid solution or a fused product. The average particle diameter of the conductive particles is preferably 0.3 μm or less, particularly preferably 0.1 μm or less.

(Composition)

The composition used for forming the protective layer 5 is preferably prepared with a dissolving solution in which at least one kind of the thiol group-containing charge transporting material represented by the general formula (I) and at least one kind of the compound having an unsaturated bond are dissolved in a solvent (coating liquid for forming a protective layer).

The coating liquid for forming a protective layer may be free of a solvent, or if necessary, may contain a solvent such as aromatic solvent such as toluene, xylene, and the like, ketone-based solvents such as methyl ethyl ketone, methyl isobutyl ketone, cyclohexanone, and the like, ester-based solvents such as ethyl acetate, butyl acetate, and the like, ether-based solvents such as tetrahydrofuran, dioxane, and the like, cellosolve-based solvents such as ethylene glycol monomethyl ether and the like, and alcohol-based solvents such as isopropylalcohol, butanol, and the like, singly or as a mixed solvent.

Furthermore, when a coating liquid is prepared by the reaction of the above components, they may be merely mixed and dissolved, but preferably they are heated under the conditions of room temperature (20° C.) or higher and 100° C. or lower, more preferably 30° C. or higher and 80° C. or lower for 10 minutes or more and 100 hours or less, and still more preferably for 1 hour or more and 50 hours or less. At this time, it is also preferred to use ultrasonic wave irradiation.

(Preparation of Protective Layer 5)

The coating liquid for forming a protective layer is coated on a coating surface (in the case of FIG. 1, the charge transporting layer 3), by an ordinary method such as a blade coating method, a wire bar coating method, a spray coating method, a dip coating method, a bead coating method, an air knife coating method, a curtain coating method, an inkjet coating method, and the like.

Thereafter, light, an electron beam, or heat is applied to the obtained film to polymerize and cure the film.

When the film is polymerized and cured by heat, the heating condition is preferably 50° C. or higher. Particularly, the heating temperature is preferably 100° C. or higher and 180° C. or lower.

When the film is polymerized and cured by light, light is irradiated by a known method with, for example, a mercury lamp, a metal halide lamp, and the like to obtain a cured film.

In the polymerization and curing reaction as above, the reaction is carried out in a vacuum or under an inert gas atmosphere of a low oxygen concentration of preferably 10% or less, more preferably 5% or less, still more preferably 2% or less, and most preferably 500 ppm or less so that a chain reaction may be carried out without deactivation of radicals generated by light, an electron beam, or heat.

In the present exemplary embodiment, a curing method by heat to cause radical generation relatively slowly is particularly preferable.

The film thickness of the protective layer 5 is preferably 3 μm or more and 40 nm or less, and more preferably 5 μm or more and 35 μm or less.

As above, the configuration of each of the layers in the function-separate type photosensitive layer is described with reference to the electrophotographic photoreceptor 7A shown in FIG. 1, but this configuration may also be employed in the function-separate type electrophotographic photoreceptor 7B shown in FIG. 2. Further, in the case of the single layer-type photosensitive layer 6 of the electrophotographic photoreceptor 7C shown in FIG. 3, the following embodiments are preferable.

That is, the content of the charge generating material in the single layer-type photosensitive layer 6 is preferably 5% by weight or more and 50% by weight or less, preferably 10% by weight or more and 40% by weight or less, and particularly preferably 15% by weight or more and 35% by weight or less, based on the total solid content of the composition used for forming the protective layer (outermost surface layer) 5.

As a method for forming the single layer-type photosensitive layer 6, a method for forming the charge generating layer 2 or the charge transporting layer 3 may be employed. The film thickness of the single layer-type photosensitive layer 6 is preferably 5 μm or more and 50 μm or less, and more preferably 10 μm or more and 40 μm or less.

Furthermore, an embodiment in which the outermost surface layer is the protective layer 5 is described in the above exemplary embodiment, but in the case of the layer configuration in which there is no protective layer 5, the charge transporting layer positioned at the outermost surface in the layer configuration may be the outermost surface layer. In the case of the outermost surface layer is a charge transporting layer, the thickness of the layer is preferably 7 μm or more and 70 μm or less, and more preferably 10 μm or more and 60 μm or less.

Non-Reactive Binder Resin

In the case where the thiol group-containing charge transporting material is also used in the resin, known non-reactive binder resins such as a polyester resin, a polyacrylate resin, a methacrylic resin, an acrylic resin, a polyvinyl chloride resin, a polyvinylidene chloride resin, a polystyrene resin, and the like may be used.

The total content of the non-reactive binder resin is preferably 0% by weight or more and 60% by weight or less, more preferably 0% by weight or more and 55% by weight, and still more preferably 0% by weight or more and 50% by weight or less, based on the total solid content of the composition used for forming a film.

Reactive Compound

In the case of curing, a reactive compound may be further included in the thiol group-containing charge transporting material represented by the general formula (I), and particularly, it is preferable to mix monomers, oligomers, or polymers having two or more double bonds in the same molecule and cure them in terms of improvement of strength.

Examples of the monofunctional monomer as a reactive compound include isobutyl acrylate, tert-butyl acrylate, isooctyl acrylate, lauryl acrylate, stearyl acrylate, isobornyl acrylate, cyclohexyl acrylate, 2-methoxyethyl acrylate, methoxytriethylene glycol acrylate, 2-ethoxyethyl acrylate, tetrahydrofurfuryl acrylate, benzyl acrylate, ethylcarbitolacrylate, phenoxyethyl acrylate, 2-hydroxyacrylate, 2-hydroxypropyl acrylate, 4-hydroxybutyl acrylate, methoxypolyethylene glycol acrylate, methoxypolyethylene glycol methacrylate, phenoxypolyethylene glycol acrylate, phenoxypolyethylene glycol methacrylate, hydroxyethyl o-phenylphenol acrylate, o-phenylphenol glycidyl ether acrylate, styrene, and the like.

Examples of the difunctional monomer as a reactive compound include diethylene glycol di(meth)acrylate, polyethylene glycol di(meth)acrylate, polypropylene glycol di(meth) acrylate, neopentyl glycol di(meth)acrylate, 1,6-hexanediol di(meth)acrylate, divinylbenzene, diallyl phthalate, and the like.

Examples of the trifunctional monomer as a reactive compound include trimethylolpropane tri(meth)acrylate, pentaerythritol tri(meth)acrylate, aliphatic tri(meth)acrylate, trivinyl cyclohexane, and the like.

Examples of the tetrafunctional monomer as a reactive compound include pentaerythritol tetra(meth)acrylate, ditrimethylolpropane tetra(meth)acrylate, aliphatic tetra(meth) acrylate, and the like.

Examples of the penta- or higher functional monomer as a reactive compound include dipentaerythritol penta(meth) acrylate and dipentaerythritol hexa(meth)acrylate, as well as (meth)acrylates having a polyester skeleton, a urethane skeleton or a phosphazene skeleton, and the like.

Furthermore, examples of the reactive polymer as a reactive compound include those disclosed in JP-A-5-216249, JP-A-5-323630, JP-A-11-52603, JP-A-2000-264961, JP-A-2005-2291, and the like.

In the case where the reactive compound is used, it is used singly or in a mixture of two or more kinds thereof. The reactive compound is used in an amount of preferably 60% by weight or less, more preferably 55% by weight or less, and still more preferably 50% by weight or less, based on the total solid content of the composition used for forming a film.

Polymerization and Curing

In the case where the dissolving solution in which the thiol group-containing charge transporting material is dissolved is used, and the components in the dissolving solution are polymerized to obtain a cured film, heat, light, radiation, or the like is used during the polymerization.

In the case where polymerization and curing are carried out using heat and light, a polymerization initiator is not necessarily needed, but a photocuring catalyst or a thermal polymerization initiator may be used. As the photocuring catalyst and the thermal polymerization initiator, a known photocuring catalyst or a thermal polymerization initiator is used. As the radiation, an electron beam is preferable.

—Electron Beam Curing—

In the case of using an electron beam, the acceleration voltage is preferably 300 kV or less, and optimally 150 kV or less. Further, the radiation dose is preferably in the range of 1 Mrad or more and 100 Mrad or less, and more preferably in the range of 3 Mrad or more and 50 Mrad or less. When the acceleration voltage is set to 300 kV or less, the damage of the electron beam irradiation on the photoreceptor characteristics is inhibited. Further, when the radiation dose is set to 1 Mrad or more, the crosslinking is sufficiently carried out, whereas when the radiation dose is set to 100 Mrad or less, the deterioration of the photoreceptor is inhibited.

Irradiation is carried out under an inert gas atmosphere of nitrogen, argon, or the like, at an oxygen concentration of 1000 ppm or less, and preferably 500 ppm or less, and heating may be carried out at 50° C. or higher and 150° C. or lower during irradiation or after irradiation.

—Photocuring—

As a light source, a high pressure mercury lamp, a low pressure mercury lamp, a metal halide lamp, or the like may be used and a filter such as a band-pass filter and the like may be used to select a preferable wavelength. The irradiation time and light intensity may be freely selected, but, for example, the illumination (365 nm) is preferably 300 mW/cm$^2$ or more and 100 mW/cm$^2$ or less, and for example, in the case of irradiation with UV light at 600 mW/cm$^2$, irradiation may be performed for 5 seconds or more and 360 seconds or less.

Irradiation is carried out under an inert gas atmosphere of nitrogen, argon, or the like, at an oxygen concentration of 1000 ppm or less, and preferably 500 ppm or less, and heating may be carried out at 50° C. or higher and 150° C. or lower during irradiation or after irradiation.

Examples of the intramolecular cleavage type photocuring catalysts include a benzyl ketal-based photocuring catalyst, an alkylphenone-based photocuring catalyst, an aminoalkylphenone-based photocuring catalyst, a phosphine oxide-based photocuring catalyst, a titanocene-based photocuring catalyst, an oxime-based photocuring catalyst, and the like.

More specifically, examples of the benzyl ketal-based photocuring catalyst include 2,2-dimethoxy-1,2-diphenylethan-1-one.

Furthermore, examples of the alkylphenone-based photocuring catalyst include 1-hydroxycyclohexyl phenyl ketone, 2-hydroxy-2-methyl-1-phenylpropan-1-one, 1-[4-(2-hydroxyethoxy)phenyl]-2-hydroxy-2-methyl-1-propan-1-one, 2-hydroxy-1-{4-[4-(2-hydroxy-2-methylpropionyl)benzyl]phenyl}-2-methylpropan-1-one, acetophenone, and 2-phenyl-2-(p-toluenesulfonyloxy)-acetophenone.

Examples of the aminoalkylphenone-based photocuring catalyst include p-dimethylaminoacetophenone, p-dimethylaminopropiophenone, 2-methyl-1-(4-methylthiophenyl)-2-morpholinopropan-1-one, 2-benzyl-2-dimethylamino-1-(4-morpholinophenyl)-butanone-1,2-(dimethylamino)-2-[(4-methylphenyl)methyl]-1-[4-(4-morpholinyl)phenyl]-1-butanone, and the like.

Examples of the phosphine oxide-based photocuring catalyst include 2,4,6-trimethylbenzoyl-diphenyl phosphine oxide, bis(2,4,6-trimethylbenzoyl)phenyl phosphine oxide, and the like.

Examples of the titanocene-based photocuring catalyst include bis(η5-2,4-cyclopentadien-1-yl)-bis[2,6-difluoro-3-(1H-pyrrol-1-yl)-phenyl]titanium, and the like.

Examples of the oxime-based photocuring catalyst include 1,2-octanedione, 1-[4-(phenylthio)-2-(O-benzoyloxime)]ethanone, 1-[9-ethyl-6-(2-methylbenzoyl)-9H-carbazol-3-yl]-1-(-O-acetyloxime), and the like.

Examples of the hydrogen drawing type photocuring catalyst include a benzophenone-based photocuring catalyst, a thioxanthone-based photocuring catalyst, a benzyl-based photocuring catalyst, a Michler's ketone-based photocuring catalyst, and the like.

More specifically, examples of the benzophenone-based photocuring catalyst include 2-benzoyl benzoic acid, 2-chlorobenzophenone, 4,4'-dichlorobenzophenone, 4-benzoyl-4'-methyldiphenylsulfide, p,p'-bisdiethylaminobenzophenone, and the like.

Examples of the thioxanthone-based photocuring catalyst include 2,4-diethylthioxanthen-9-one, 2-chlorothioxanthone, 2-isopropylthioxanthone, and the like.

Examples of the benzyl-based photocuring catalyst include benzyl, (±)-camphor-quinone, p-anisyl, and the like.

These photopolymerization initiators may be used singly or in combination of two or more kinds thereof.

—Thermal Curing—

Examples of the thermal polymerization initiator include V-30, V-40, V-59, V-601, V-65, V-70, VF-096, VE-73, Vam-10, and Vam-111 (manufactured by Wako Pure Chemical Industries Ltd.), and azo-based initiators such as OTazo-15, OTazo-30, AIBN, AMBN, ADVN, and ACVA (manufactured by Otsuka Chemical Co., Ltd.), as well as PERTETRA A, PERHEXA HC, PERHEXA C, PERHEXA V, PERHEXA 22, PERHEXA MC, PERBUTYL H, PERCUMYL H, PERCUMYL P, PERMENTA H, PEROCTA H, PERBUTYL C, PERBUTYL D, PERHEXYL D, PEROYL IB, PEROYL 355, PEROYL L, PEROYL SA, NYPER BW, NYPER BMT-K40/M, PEROYL IPP, PEROYL NPP, PEROYL TCP, PEROYL OPP, PEROYL SBP, PERCUMYL ND, PEROCTAND, PERHEXYL ND, PERBUTYL ND, PERBUTYL NHP, PERHEXYL PV, PERBUTYL PV, PERHEXA 250, PEROCTA O, PERHEXYL O, PERBUTYL O, PERBUTYL L, PERBUTYL 355, PERHEXYL I, PERBUTYL I, PERBUTYL E, PERHEXA 25Z, PERBUTYL A, PERHEXYL Z, PERBUTYL ZT, and PERBUTYL Z (manufactured by NOF Corporation), KAYAKETAL AM-C55, TRIGONOX 36-C75, LAUROX, PERCADOX L-W75, PERCADOX CH-50L, TRIGONOX TMBH, KAYACUMENE H, KAYABUTYL H-70, PERCADOX BC-FF, KAYAHEXA AD, PERCADOX 14, KAYABUTYL C, KAYABUTYL D, KAYAHEXA YD-E85, PERCADOX 12-XL25, PERCADOX 12-EB20, TRIGONOX 22-N70, TRIGONOX 22-70E, TRIGONOX D-T50, TRIGONOX 423-C70, KAYAESTER CND-C70, KAYAESTER CND-W50, TRIGONOX 23-C70, TRIGONOX 23-W50N, TRIGONOX 257-C70, KAYAESTER P-70, KAYAESTER TMPO-70, TRIGONOX 121, KAYAESTER O, KAYAESTER HTP-65W, KAYAESTER AN, TRIGONOX 42, TRIGONOX F-C50, KAYABUTYL B, KAYACARBON EH-C70, KAYACARBON EH-W60, KAYACARBON I-20, KAYACARBON BIC-75, TRIGONOX 117, and KAYALENE 6-70 (manufactured by Kayaku Akzo Co., Ltd.), and LUPEROX 610, LUPEROX 188, LUPEROX 844, LUPEROX 259, LUPEROX 10, LUPEROX 701, LUPEROX 11, LUPEROX 26, LUPEROX 80, LUPEROX 7, LUPEROX 270, LUPEROX P, LUPEROX 546, LUPEROX 554, LUPEROX 575, LUPEROX TANPO, LUPEROX 555, LUPEROX 570, LUPEROX TAP, LUPEROX TBIC, LUPEROX TBEC, LUPEROX JW, LUPEROX TAIC, LUPEROX TAEC, LUPEROX DC, LUPEROX 101, LUPEROX F, LUPEROX DI, LUPEROX 130, LUPEROX 220, LUPEROX 230, LUPEROX 233, and LUPEROX 531.

Among these, if the azo-based polymerization initiator has a molecular weight of 250 or more, the reaction advances without unevenness at a low temperature, and as a result, forming a film having a high strength having inhibited unevenness is promoted. The molecular weight of the azo-based polymerization initiator is preferably 250 or more, and more preferably 300 or more.

Heating is carried out under an inert gas atmosphere of nitrogen, argon, or the like at a low oxygen concentration of preferably 1000 ppm or less, more preferably 500 ppm or less, still more preferably 50° C. or higher and 170° C. or lower, even still more preferably 70° C. or higher and 150° C. or lower, and preferably for 10 minutes or more and 120 minutes or less, and more preferably 15 minutes or more and 100 minutes or less.

The total content of the photocuring catalyst or the thermal polymerization initiator is preferably 0.1% by weight or more and 10% by weight or less, more preferably 0.1% by weight or more and 8% by weight or less, and particularly preferably 0.1% by weight or more and 5% by weight or less, based on the total solid content in the dissolving solution for forming a layer.

—Conductive Substrate—

Examples of the conductive substrate 4 include metal plates, metal drums, and metal belts using metals such as aluminum, copper, zinc, stainless steel, chromium, nickel, molybdenum, vanadium, indium, gold, platinum or alloys thereof. Examples of the conductive substrate 4 also include papers, plastic films, belts, and the like which are coated, deposited, or laminated with a conductive compound such as a conductive polymer and indium oxide, a metal such as aluminum, palladium and gold, or alloys thereof.

Here, the term "conductive" means that the volume resistivity is less than $10^{13}$ Ωcm.

When the electrophotographic photoreceptor 7A is used in a laser printer, the surface of the conductive substrate 4 is preferably roughened so as to have a centerline average roughness Ra of 0.04 μm or more and 0.5 μm or less in order to prevent interference fringes which are formed when irradiated by laser light. When an incoherent light is used as a light source, surface roughening for preventing interference fringes is not particularly necessary.

Preferred examples of the method for surface roughening include wet honing in which an abrasive suspended in water is blown onto a support, centerless grinding in which a support is continuously ground by pressing the support onto a rotating grind stone, anodic oxidation treatment, and the like.

Furthermore, as another method for surface roughening, a method of surface roughening by forming on the substrate surface a layer of resin in which conductive or semiconductive particles are dispersed in the resin so that the surface roughening is achieved by the particles dispersed in the layer, without roughing the surface of the conductive substrate 4, is also preferably used.

Here, in the surface roughening treatment by anodic oxidation, an oxide film is formed on an aluminum surface by anodic oxidation in which the aluminum as an anode is anodized in an electrolyte solution. Examples of the electrolyte solution include a sulfuric acid solution, an oxalic acid solution, and the like. However, the porous anodic oxide film formed by anodic oxidation without modification is chemically active, easily contaminated and has a large resistance variation depending on the environment. Therefore, it is preferable to conduct a sealing treatment in which fine pores of the anodic oxide film are sealed by volume expansion caused by a hydration in pressurized water vapor or boiled water (to which a metallic salt such as a nickel salt may be added) to transform the anodic oxide into a more stable hydrated oxide.

The thickness of the anodic oxide film is preferably 0.3 µm or more and 15 µm or less.

Furthermore, the conductive substrate 4 may be subjected to a treatment with an acidic aqueous solution or a boehmite treatment. The treatment with an acidic treatment solution comprising phosphoric acid, chromic acid and hydrofluoric acid is carried out as follows:

First, phosphoric acid, chromic acid, and hydrofluoric acid are mixed to prepare an acidic treatment solution preferably in a mixing ratio of 10% by weight or more and 11% by weight or less of phosphoric acid, 3% by weight or more and 5% by weight or less of chromic acid, and 0.5% by weight or more and 2% by weight or less of hydrofluoric acid. The concentration of the total acid components is preferably in the range of 13.5% by weight or more and 18% by weight or less. The treatment temperature is preferably 42° C. or higher and 48° C. or lower, and by keeping the treatment temperature high, a thicker film can be obtained more speedily. The thickness of the film is preferably 0.3 µm or more and 15 µm or less.

The boehmite treatment is preferably carried out by immersing the substrate in pure water at a temperature of 90° C. or higher and 100° C. or lower for 5 minutes or more and 60 minutes or less, or by bringing it into contact with heated water vapor at a temperature of 90° C. or higher and 120° C. or lower for 5 minutes or more and 60 minutes or less. The film thickness is preferably 0.1 µm or more and 5 µm or less. The film may further be subjected to an anodic oxidation treatment using an electrolyte solution which sparingly dissolves the film, of adipic acid, boric acid, borate salt, phosphate, phthalate, maleate, benzoate, tartrate, citrate, or the like.

—Undercoat Layer—

The undercoat layer 1 is constituted with, for example, a binder resin containing inorganic particles.

The inorganic particles preferably have powder resistance (volume resistivity) of about $10^2$ Ω·cm or more and $10^{11}$ Ω·cm or less.

Preferred examples of the inorganic particles having the above resistance value include inorganic particles of tin oxide, titanium oxide, zinc oxide, zirconium oxide, or the like, and zinc oxide is preferably used.

Furthermore, the inorganic particles may be ones which are subjected to a surface treatment. Particles which are subjected to different surface treatments, or those having different particle diameters, may be used in combination of two or more kinds.

The specific surface area of the inorganic particles as measured by a BET analysis is preferably 10 $m^2$/g or more.

The volume average particle size of inorganic particles is desirably in the range of 50 nm or more and 2000 nm or less (preferably 60 nm or more and 1000 nm or less).

Furthermore, the acceptor compound is preferably included together with the inorganic particles.

The acceptor compound is not particularly limited as long as it provides desired characteristics, and preferred examples thereof include electron transporting substances such as quinone-based compounds such as chloranil, bromanil, and the like, tetracyanoquinodimethane-based compounds, fluorenone compounds such as 2,4,7-trinitrofluorenone, 2,4,5,7-tetranitro-9-fluorenone, and the like, oxadiazole-based compounds such as 2-(4-biphenyl)-5-(4-tert-butylphenyl)-1,3,4-oxadiazole, 2,5-bis(4-naphthyl)-1,3,4-oxadiazole, 2,5-bis(4-diethylaminophenyl)-1,3,4-oxadiazole, and the like, xanthone-based compounds, and thiophene compounds and diphenoquinone compounds such as 3,3',5,5'-tetra-tert-butyl-diphenoquinone and the like, and particularly preferable examples thereof include compounds having an anthraquinone structure. Still more preferred examples thereof include acceptor compounds having an anthraquinone structure such as hydroxyanthraquinone-based compounds, aminoanthraquinone-based compounds, aminohydroxyanthraquinone-based compounds, and the like, and specific examples thereof include anthraquinone, alizarin, quinizarin, antharufin, purpurin, and the like.

The content of the acceptor compound is not limited as long as it is within a range in which desired characteristics are obtained, but is preferably in the range of 0.01% by weight or more and 20% by weight or less, and more preferably in the range of 0.05% by weight or more and 10% by weight or less, based on the inorganic particles.

The acceptor compound may simply be added to a coating liquid for forming an undercoat layer, or may be previously attached to the surface of the inorganic particles.

Examples of the method of attaching the acceptor compound to the surface of the inorganic particles include a dry method and a wet method.

When a surface treatment is conducted according to the dry method, the acceptor compound is added dropwise to the inorganic particles or sprayed thereto together with dry air or nitrogen gas, either directly or in the form of a solution in which the acceptor compound is dissolved in an organic solvent, while the inorganic particles are stirred with a mixer or the like having a high shear force. The addition or spraying is preferably carried out at a temperature of the boiling point of the solvent or lower. After the addition or spraying of the acceptor compound, the inorganic particles may further be baked at a temperature of 100° C. or higher. The baking is carried out at any temperature and timing in any range.

Furthermore, in the wet method, the inorganic particles are dispersed in a solvent by means of stirring, ultrasonic waves, a sand mill, an attritor, a ball mill or the like, then the acceptor compound is added and the mixture is further stirred or dispersed, followed by removal of the solvent, whereby the particles are uniformly treated. The solvent is removed by filtration or distillation. After removal of the solvent, the particles may be baked at a temperature of 100° C. or higher.

The baking may be carried out at any temperature and timing as long as desired electrophotographic characteristics are obtained. In the wet method, the moisture contained in the inorganic particles may be removed prior to the addition of the surface treatment agent. The moisture may be removed by, for example, stirring and heating the particles in the solvent used for the surface treatment, or by azeotropic removal with the solvent.

Moreover, the inorganic particles may be subjected to a surface treatment prior to the addition of the acceptor compound. The surface treatment agent may be any agent by which desired characteristics are obtained, and may be selected from known materials. Examples thereof include a silane coupling agent, a titanate-based coupling agent, an aluminum-based coupling agent, a surfactant, and the like. Among these, a silane coupling agent is preferably used by which favorable electrophotographic characteristics are provided. Further, a silane coupling agent having an amino group is desirably used.

The silane coupling agent having an amino group may be any compound as long as desired electrophotographic photoreceptor characteristics are obtained, and specific examples thereof include, but are not limited to, γ-aminopropyltriethoxysilane, N-β-(aminoethyl)-γ-aminopropyltrimethoxysilane, N-β-(aminoethyl)-γ-aminopropylmethyldimethoxysilane, N,N-bis(β-hydroxyethyl)-γ-aminopropyltriethoxysilane, and the like.

Furthermore, the silane coupling agents may be used in a mixture of two or more kinds thereof. Examples of the silane coupling agent which may be used in combination with the silane coupling agents having an amino group include, but are not limited to, vinyltrimethoxysilane, γ-methacryloxypropyl-tris-(β-methoxyethoxy)silane, β-(3,4-epoxycyclohexyl)ethyltrimethoxysilane, γ-glycidoxypropyltrimethoxysilane, vinyltriacetoxysilane, γ-mercaptopropyltrimethoxysilane, γ-aminopropyltriethoxysilane, N-β-(aminoethyl)-γ-aminopropyltrimethoxysilane, N-β-(aminoethyl)-γ-aminopropylmethyldimethoxysilane, N,N-bis(β-hydroxyethyl)-γ-aminopropyltriethoxysilane, γ-chloropropyltrimethoxysilane, and the like.

Moreover, the surface treatment method using such a surface treatment agent may be any known method, and a dry or wet method may be used. Further, addition of an acceptor and a surface treatment using a coupling agent or the like may be carried out at the same time.

The amount of the silane coupling agent relative to the inorganic particles contained in the undercoat layer 1 is not limited as long as it is an amount at which the desired electrophotographic characteristics are obtained, but is preferably 0.5% by weight or more and 10% by weight or less relative to the inorganic particles.

Furthermore, a binder resin may be included in the undercoat layer 1.

As the binder resin included in the undercoat layer 1, any known resin that may form a favorable film and achieve desired characteristics may be used, and examples thereof include known polymer resin compounds, for example, acetal resins such as a polyvinyl butyral resin, a polyvinyl alcohol resin, casein, a polyamide resin, a cellulose resin, gelatin, a polyurethane resin, a polyester resin, a methacrylic resin, an acrylic resin, a polyvinyl chloride resin, a polyvinyl acetate resin, a vinyl chloride-vinyl acetate-maleic anhydride resin, a silicone resin, a silicone-alkyd resin, a phenolic resin, a phenol-formaldehyde resin, a melamine resin, a urethane resin, and the like, zirconium chelate compounds, titanium chelate compounds, aluminum chelate compounds, titanium alkoxide compounds, organic titanium compounds, silane coupling compounds, and the like.

In addition, as the binder resin included in the undercoat layer 1, charge transporting resins having charge transporting groups; and conductive resins such as polyaniline and the like may be used. Among these, resins which are insoluble in the coating solvent for the upper layer are preferably used, and phenolic resins, phenol-formaldehyde resins, melamine resins, urethane resins, epoxy resins, or the like are particularly preferably used. In the case of using them in combination, the mixing ratio is determined as desired.

The ratio of the inorganic particles having the acceptor-compound added to the surface (metal oxides imparted with acceptor ability) to the binder resin in the coating liquid for forming an undercoat layer or the ratio of the inorganic particles to the binder resin is set within a range in which the desired electrophotographic photoreceptor characteristics are obtained.

Furthermore, various additives may be used in the undercoat layer 1.

Examples of the additives include known materials including electron transporting pigments such as a polycyclic condensed electron transporting pigment, an azo-based electron transporting pigment, and the like, zirconium chelate compounds, titanium chelate compounds, aluminum chelate compounds, titanium alkoxide compounds, organic titanium compounds, silane coupling agents, and the like. The silane coupling agent is used for the surface treatment of the inorganic particles as described above, but may be further added as an additive to a coating liquid for forming an undercoat layer.

Specific examples of the silane coupling agent as an additive include vinyltrimethoxysilane, γ-methacryloxypropyl-tris(β-methoxyethoxy)silane, β-(3,4-epoxycyclohexyl)ethyltrimethoxysilane, γ-glycidoxypropyltrimethoxysilane, vinyltriacetoxysilane, γ-mercaptopropyltrimethoxysilane, γ-aminopropyltriethoxysilane, N-β-(aminoethyl)-γ-aminopropyltrimethoxysilane, N-β-(aminoethyl)-γ-aminopropylmethyldimethoxysilane, N,N-bis(β-hydroxyethyl)-γ-aminopropyltriethoxysilane, γ-chloropropyltrimethoxysilane, and the like.

In addition, examples of the zirconium chelate compound include zirconium butoxide, zirconium ethyl acetoacetate, zirconium triethanolamine, acetylacetonate zirconium butoxide, ethyl acetoacetate zirconium butoxide, zirconium acetate, zirconium oxalate, zirconium lactate, zirconium phosphonate, zirconium octanoate, zirconium naphthenate, zirconium laurate, zirconium stearate, zirconium isostearate, methacrylate zirconium butoxide, stearate zirconium butoxide, isostearate zirconium butoxide, and the like.

Examples of the titanium chelate compound include tetraisopropyl titanate, tetra-normal-butyl titanate, butyl titanate dimer, tetra(2-ethylhexyl)titanate, titanium acetyl acetonate, polytitanium acetylacetonate, titanium octylene glycolate, titanium lactate ammonium salt, titanium lactate, titanium lactate ethyl ester, titanium triethanolaminate, polyhydroxytitanium stearate, and the like.

Examples of the aluminum chelate compound include aluminum isopropylate, monobutoxy aluminum diisopropylate, aluminum butylate, diethylacetoacetate aluminum diisopropylate, aluminum tris(ethylacetoacetate), and the like.

These compounds may be used singly or as a mixture or a polycondensate of plural compounds.

The solvent for preparing the coating liquid for forming an undercoat layer may appropriately be selected from known organic solvents, for example, an alcohol-based solvent, an aromatic-based solvent, a hydrocarbon halide-based solvent, a ketone-based solvent, a ketone alcohol-based solvent, an ether-based solvent, an ester-based solvent, and the like.

As the solvent, specifically, for example, common organic solvents such as methanol, ethanol, n-propanol, iso-propanol, n-butanol, benzyl alcohol, methyl cellosolve, ethyl cellosolve, acetone, methyl ethyl ketone, cyclohexanone, methyl acetate, ethyl acetate, n-butyl acetate, dioxane, tetrahydrofuran, methylene chloride, chloroform, chlorobenzene, toluene, and the like, are used.

Furthermore, these solvents may be used singly or in a mixture of two or more kinds thereof. When they are mixed, any mixed solvents which can dissolve a binder resin may be used as the solvent to be used.

As a method for dispersing the inorganic particles in the preparation of the coating liquid for forming an undercoat layer, any of known methods such as a roll mill, a ball mill, a vibration ball mill, an attritor, a sand mill, a colloid mill, a paint shaker, and the like is used.

In addition, as the coating method used in the preparation of the undercoat layer 1, any of ordinary methods such as a blade coating method, a wire bar coating method, a spray coating method, a dip coating method, a bead coating method, an air knife coating method, a curtain coating method, and the like is used.

Then, the undercoat layer 1 is formed on the conductive substrate using the coating liquid for forming an undercoat layer thus obtained.

Moreover, the Vickers hardness of the undercoat layer 1 is preferably 35 or more.

In addition, the thickness of the undercoat layer 1 may be set to any thickness as long as desired characteristics are obtained, but the thickness is preferably 15 μm or more, and more preferably 15 μm or more and 50 μm or less.

Furthermore, the surface roughness (ten point average roughness) of the undercoat layer 1 is preferably adjusted within a range of from ¼n (wherein n represents a refractive index of the upper layer) of the laser wavelength λ to ½λ.

Particles of a resin or the like may also be added to the undercoat layer in order to adjust the surface roughness thereof. As the resin particles include silicone resin particles, crosslinking polymethylmethacrylate resin particles, or the like are used.

In addition, the surface of the undercoat layer may be subjected to grinding for adjusting the surface roughness thereof. As the grinding method, buffing grinding, a sandblast treatment, wet honing, a grinding treatment, or the like is used. In the case of using an incoherent light source such as an LED, an organic EL image array, and the like, a smooth surface may be used.

The undercoat layer 1 is obtained by drying the coating liquid for forming an undercoat layer applied on the conductive substrate 4, but drying is usually carried out by evaporating the solvent at a temperature at which a film may be formed.

—Charge Generating Layer—

The charge generating layer 2 is a layer containing a charge generating material and a binder resin. Further, it may be formed as a deposited film which does not contain a binder resin. Particularly, it is preferable in a case where an incoherent light source such as an LED, an organic EL image array, and the like is used.

Examples of the charge generating material include an azo pigment such as a bisazo pigment or a trisazo pigment, a condensed aromatic pigment such as dibromoanthoanthrone, a perylene pigment, a pyrrolopyrrole pigment, a phthalocyanine pigment, zinc oxide, and trigonal selenium. Among these, in order to respond to near-infrared laser exposure, a metal phthalocyanine pigment and a metal-free phthalocyanine pigment are preferably used as a charge generating material. In particular, hydroxygallium phthalocyanine disclosed in JP-A-5-263007, JP-A-5-279591, or the like, chlorogallium phthalocyanine disclosed in JP-A-5-98181 or the like, dichlorotin phthalocyanine disclosed in JP-A-5-140472, JP-A-5-140473, or the like, and titanyl phthalocyanine disclosed in JP-A-4-189873, or the like are preferred. Further, for laser exposure in the near-ultraviolet region, condense aromatic pigments such as dibromoantanthrone and the like, thioindigo pigments, porphyrazine compounds, zinc oxides, trigonal selenium, bisazo pigments disclosed in JP-A-2004-78147 and JP-A-2005-181992, and the like are more preferably used. Further, in the case where an incoherent light source such as an LED, an organic EL image array, and the like, having a light-emitting center wavelength of 450 nm or more and 780 nm or less, is used, the charge generating material may be used, but from the viewpoint of the resolution, in the case where the photosensitive layer is used as a thin film having a thickness of 20 μm or less, the field strength in the photosensitive layer is high and decrease in charge due to charge injection from a substrate, that is, image defects, called black spots, easily occurs. This becomes noticeable when a charge generating material easily generating dark currents with a p-type semiconductor such as trigonal selenium, a phthalocyanine pigment, and the like is used. In contrast, in the case where an n-type semiconductor such as a condensed aromatic pigment, a perylene pigment, an azo pigment, and the like is used, dark currents are hardly generated, and image defects called black spots even with a thin film can be inhibited. It has been found that by forming a smooth substrate and an undercoat layer formed using an incoherent light source such as an LED, an organic EL image array, and the like, having a light-emitting center wavelength of 450 nm or more and 780 nm or less, and further using an n-type charge generating material, an image is obtained, which does not cause image defects even when the photosensitive layer is made into a thin film having a thickness of 20 μm or less and has a high resolution over a long period of time. Specific examples of the n-type charge generating material include the following, but are not limited thereto. In addition, determination of the n-type is conducted by the polarity of the flowing photocurrent using a time-of-flight method that is generally used, and a type in which electrons flow more easily than holes as a carrier is taken as an n-type.

| | Structural Formula |
|---|---|
| CG-1 | 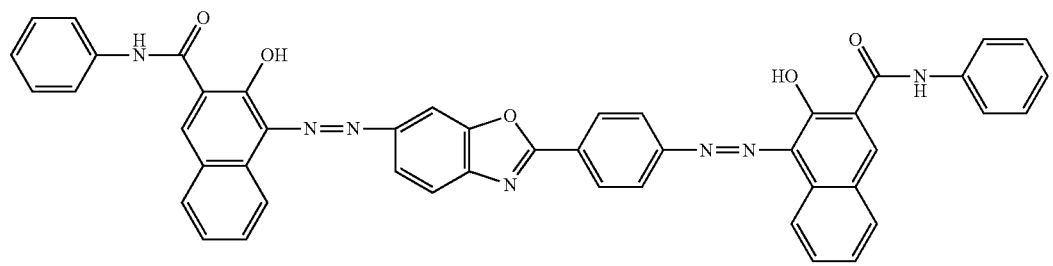 [SMILES: O=C(Nc1ccccc1)c1cc2ccccc2c(N=Nc2ccc(-c3nc4ccc(N=Nc5c(O)c(C(=O)Nc6ccccc6)cc6ccccc56)cc4o3)cc2)c1O] |
| CG-2 | 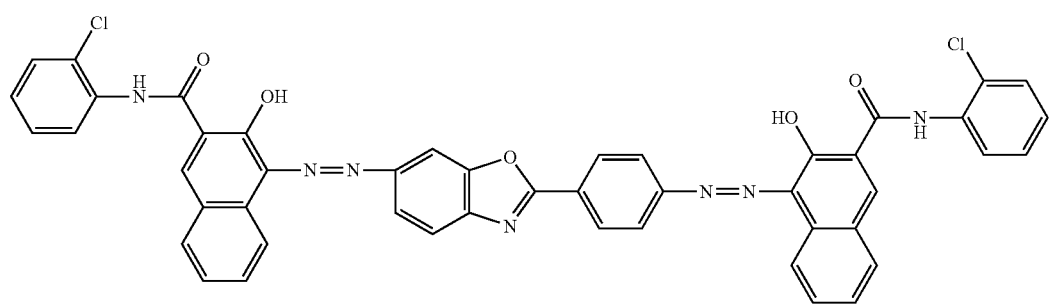 [SMILES: O=C(Nc1ccccc1Cl)c1cc2ccccc2c(N=Nc2ccc(-c3nc4ccc(N=Nc5c(O)c(C(=O)Nc6ccccc6Cl)cc6ccccc56)cc4o3)cc2)c1O] |
| CG-3 | 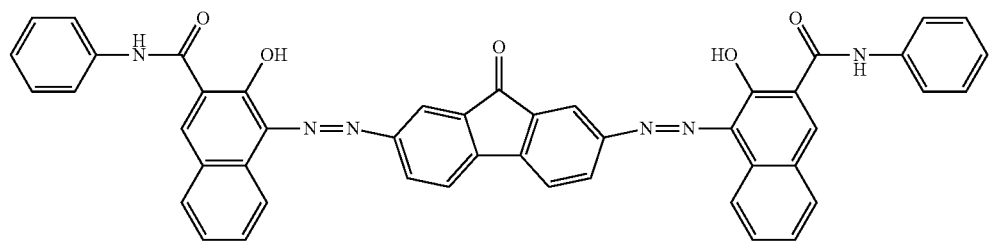 [SMILES: O=C1c2cc(N=Nc3c(O)c(C(=O)Nc4ccccc4)cc4ccccc34)ccc2-c2ccc(N=Nc3c(O)c(C(=O)Nc4ccccc4)cc4ccccc34)cc21] |
| CG-4 | 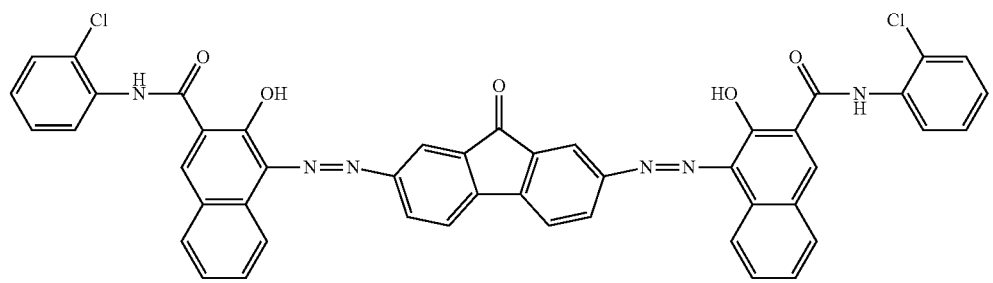 [SMILES: O=C1c2cc(N=Nc3c(O)c(C(=O)Nc4ccccc4Cl)cc4ccccc34)ccc2-c2ccc(N=Nc3c(O)c(C(=O)Nc4ccccc4Cl)cc4ccccc34)cc21] |
| CG-5 | 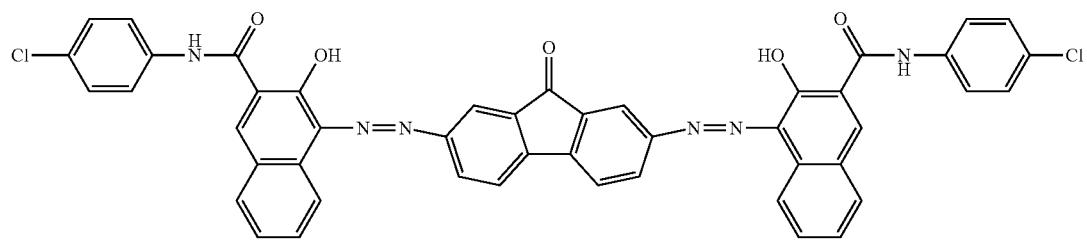 [SMILES: O=C1c2cc(N=Nc3c(O)c(C(=O)Nc4ccc(Cl)cc4)cc4ccccc34)ccc2-c2ccc(N=Nc3c(O)c(C(=O)Nc4ccc(Cl)cc4)cc4ccccc34)cc21] |

-continued
| | Structural Formula |
|---|---|
| CG-6 | 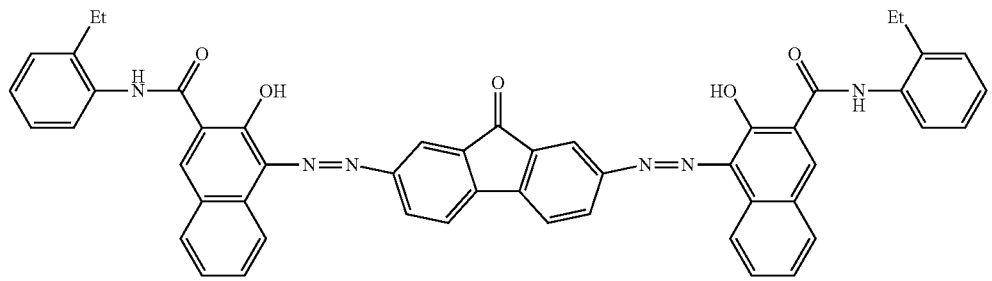 [SMILES: CCc1ccccc1NC(=O)c1cc2ccccc2c(N=Nc2ccc3c(c2)C(=O)c2cc(N=Nc4c(O)c(C(=O)Nc5ccccc5CC)cc5ccccc45)ccc2-3)c1O] |
| CG-7 | 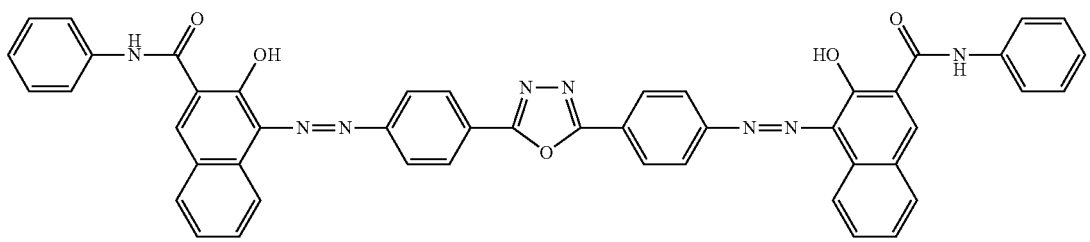 [SMILES: O=C(Nc1ccccc1)c1cc2ccccc2c(N=Nc2ccc(-c3nnc(-c4ccc(N=Nc5c(O)c(C(=O)Nc6ccccc6)cc6ccccc56)cc4)o3)cc2)c1O] |
| CG-8 | 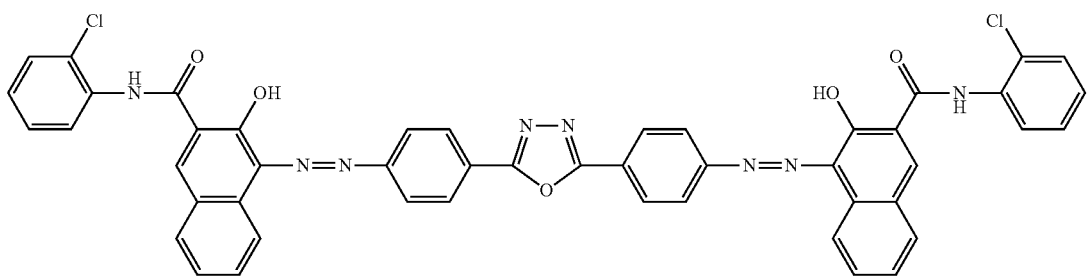 [SMILES: O=C(Nc1ccccc1Cl)c1cc2ccccc2c(N=Nc2ccc(-c3nnc(-c4ccc(N=Nc5c(O)c(C(=O)Nc6ccccc6Cl)cc6ccccc56)cc4)o3)cc2)c1O] |
| CG-9 | 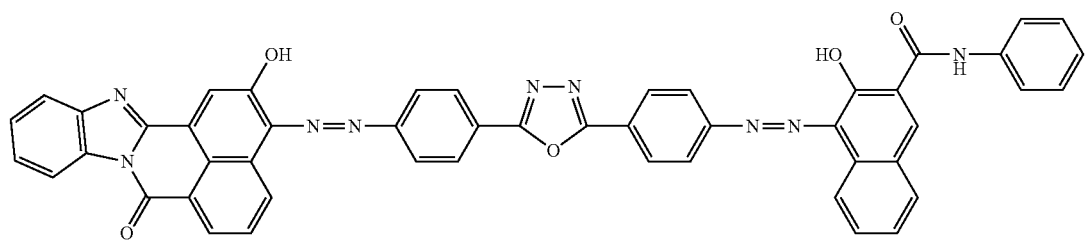 [SMILES: O=C(Nc1ccccc1)c1cc2ccccc2c(N=Nc2ccc(-c3nnc(-c4ccc(N=Nc5c(O)cc6c7c5cccc7c(=O)n5c7ccccc7nc65)cc4)o3)cc2)c1O] |
| CG-10 | 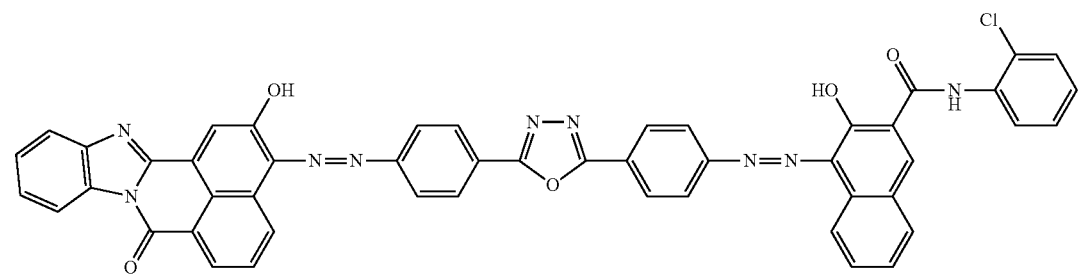 [SMILES: O=C(Nc1ccccc1Cl)c1cc2ccccc2c(N=Nc2ccc(-c3nnc(-c4ccc(N=Nc5c(O)cc6c7c5cccc7c(=O)n5c7ccccc7nc65)cc4)o3)cc2)c1O] |
| CG-11 | 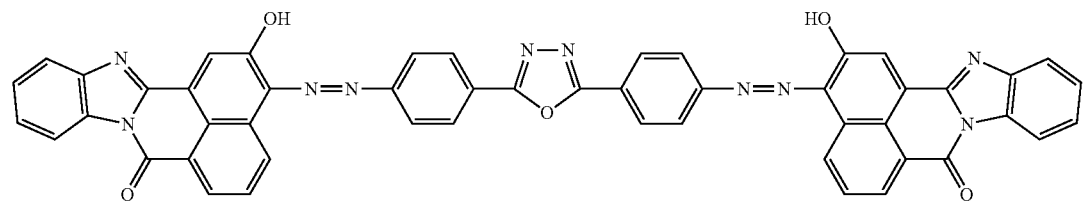 [SMILES: O=c1c2cccc3c(N=Nc4ccc(-c5nnc(-c6ccc(N=Nc7c(O)cc8c9c7cccc9c(=O)n7c9ccccc9nc87)cc6)o5)cc4)c(O)cc(c32)c2nc3ccccc3n12] |

-continued
Structural Formula
CG-12 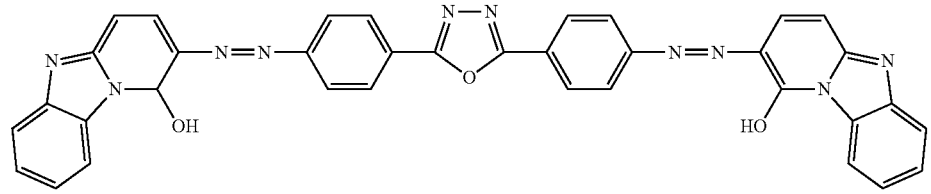
CG-13 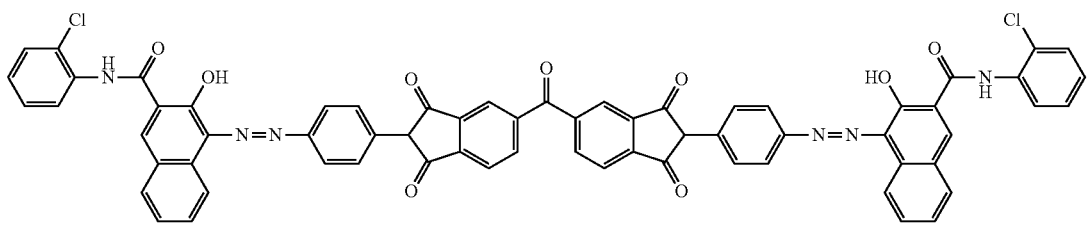 [SMILES: O=C(c1ccc2c(c1)C(=O)C(c1ccc(N=Nc3c(O)c(C(=O)Nc4ccccc4Cl)cc4ccccc34)cc1)C2=O)c1ccc2c(c1)C(=O)C(c1ccc(N=Nc3c(O)c(C(=O)Nc4ccccc4Cl)cc4ccccc34)cc1)C2=O]
CG-14 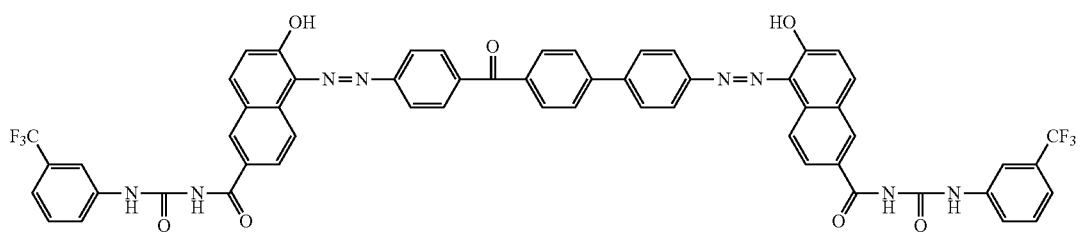 [SMILES: O=C(NC(=O)c1ccc2c(N=Nc3ccc(C(=O)c4ccc(-c5ccc(N=Nc6c(O)ccc7cc(C(=O)NC(=O)Nc8cccc(C(F)(F)F)c8)ccc67)cc5)cc4)cc3)c(O)ccc2c1)Nc1cccc(C(F)(F)F)c1]
CG-15 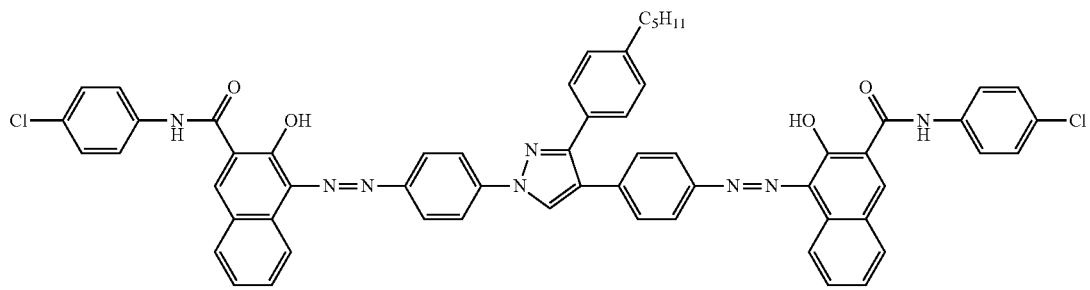
CG-16 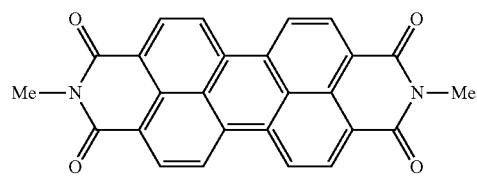
CG-17 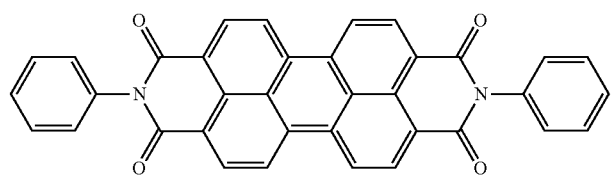
CG-18 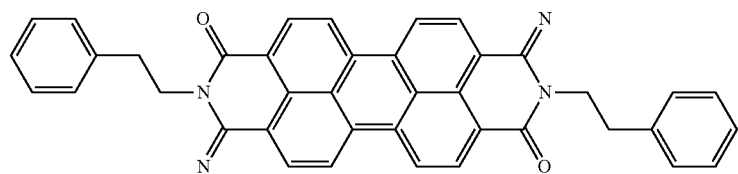

-continued
| | Structural Formula |
|---|---|
| CG-19 | 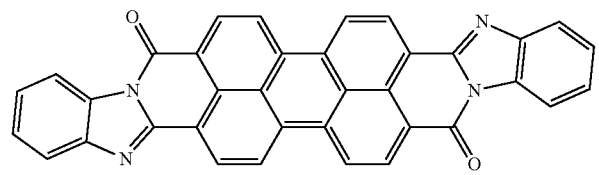 |
| CG-20 | 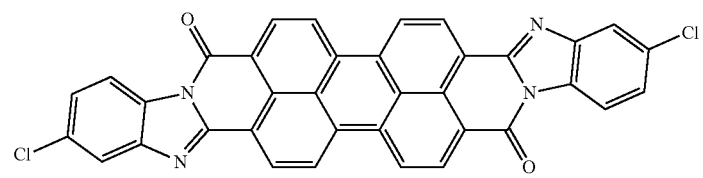 |
| CG-21 | 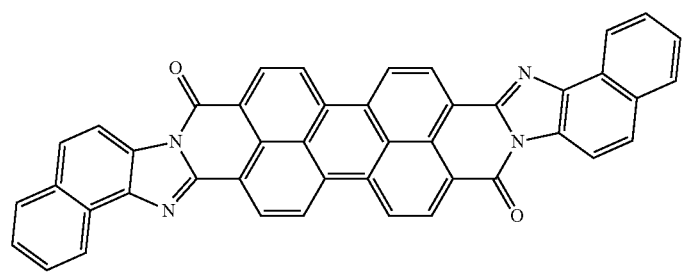 |
| CG-22 | 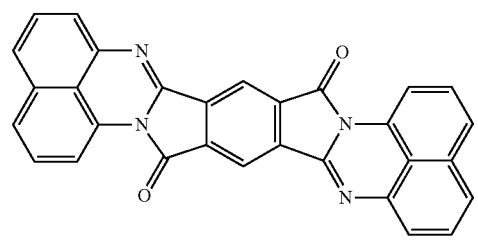 |
| CG-23 | 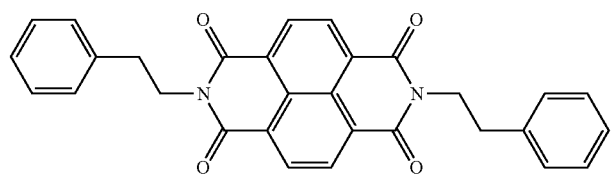 [SMILES: O=C1c2ccc3c4c(ccc(c24)C(=O)N1CCc1ccccc1)C(=O)N(CCc1ccccc1)C3=O] |
| CG-24 | 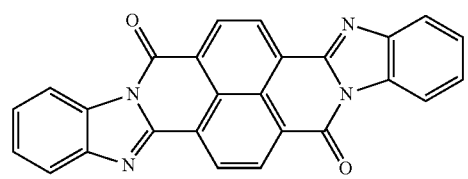 [SMILES: O=c1c2ccc3c4c(ccc(c24)c2nc4ccccc4n12)c(=O)n1c2ccccc2nc31] |
| CG-25 | 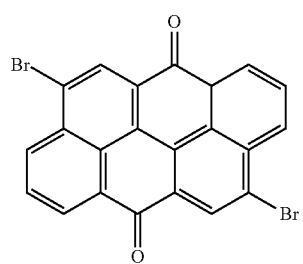 |

-continued

Structural Formula

CG-26

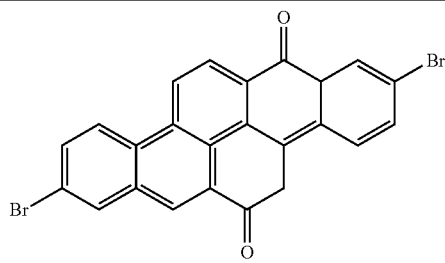

CG-27

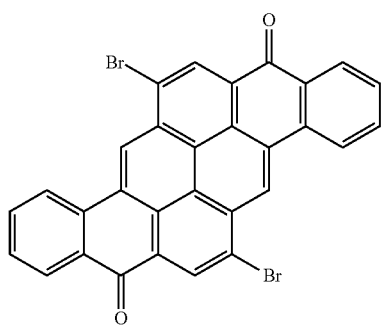 [SMILES: O=c1c2ccccc2c2cc3c(Br)cc4c(=O)c5ccccc5c5cc6c(Br)cc1c2c6c3c45]

The binder resin used in the charge generating layer 2 may be selected from a wide range of insulating resins, or from the organic light conductive polymers such as poly-N-vinylcarbazole, polyvinylanthracene, polyvinylpyrene, polysilane, and the like. Preferable examples of the binder resin include polyvinyl butyral resins, polyarylate resins (polycondensates of a bisphenol and an aromatic divalent carboxylic acid, or the like), polycarbonate resins, polyester resins, phenoxy resins, vinyl chloride-vinyl acetate copolymers, polyamide resins, acrylic resins, polyacrylamide resins, polyvinyl pyridine resins, cellulose resins, urethane resins, epoxy resins, casein, polyvinyl alcohol resins, polyvinyl pyrrolidone resins, and the like. These binder resins may be used singly or in combination of two or more kinds thereof. The blending ratio of the charge generating material and binder resin is preferably in the range of 10:1 to 1:10. The term "insulating" means that the volume resistivity is $10^{13}$ Ωcm or more.

The charge generating layer 2 is formed using a coating liquid for forming a charge generating layer, in which the charge generating material and the binder resin are dispersed in a given solvent. Further, it may be formed as a deposited film containing no binder resin, and particularly, condensed aromatic pigment and a perylene pigment may be preferably used for the deposited film.

Examples of the solvent used for dispersion include methanol, ethanol, n-propanol, n-butanol, benzyl alcohol, methyl cellosolve, ethyl cellosolve, acetone, methyl ethyl ketone, cyclohexanone, methyl acetate, n-butyl acetate, dioxane, tetrahydrofuran, methylene chloride, chloroform, chlorobenzene, toluene, and the like, and these may be used singly or in combination of two or more kinds thereof.

Furthermore, as a method for dispersing the charge generating material and the binder resin in a solvent, ordinary methods such as ball mill dispersion method, an attritor dispersion method, a sand mill dispersion method, and the like are used. By these dispersion methods, deformation of crystals of the charge generating material caused by dispersion is prevented.

In addition, it is effective that the average particle diameter of the charge generating materials to be dispersed is 0.5 µm or less, preferably 0.3 µm or less, and more preferably 0.15 µm or less.

Furthermore, for forming the charge generating layer 2, ordinary methods such as a blade coating method, a Meyer bar coating method, a spray coating method, a dip coating method, a bead coating method, an air knife coating method, a curtain coating method, and the like is used.

The film thickness of the charge generating layer 2 thus obtained is preferably 0.1 µm or more and 5.0 µm or less, and more preferably 0.2 µm or more and 2.0 µm or less.

—Charge Transporting Layer—

The charge transporting layer 3 shown in FIG. 1 is formed by including a charge transporting material and a binder resin, or including a charge transporting polymer material.

Examples of the charge transporting material include electron transporting compounds such as quinone-based compounds such as p-benzoquinone, chloranil, bromanil, anthraquinone, and the like, tetracyanoquinodimethane-based compounds, fluorenone compounds such as 2,4,7-trinitrofluorenone, xanthone-based compounds, benzophenone-based compounds, cyanovinyl-based compounds, ethylene-based compounds, and the like; and hole transporting compounds such as triarylamine-based compounds, benzidine-based compounds, arylalkane-based compounds, aryl-substituted ethylene-based compounds, stilbene-based compounds, anthracene-based compounds, hydrazone-based compounds, and the like. These charge transporting materials may be used singly or in combination of two or more kinds thereof, but are not limited thereto.

The charge transporting material is preferably a triarylamine derivative represented by the following Formula (a-1) and a benzidine derivative represented by the following Formula (a-2) from the viewpoint of charge mobility.

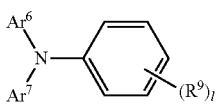
(a-1)

In the structural formula (a-1), $R^9$ represents a hydrogen atom, a methyl group, —C($R^{10}$)=C($R^{11}$)($R^{12}$), or —CH=CH—CH=C($R^{13}$)($R^{14}$). l represents 1 or 2. $Ar^6$ and $Ar^7$ each independently represent a substituted or unsubstituted aryl group, —$C_6H_4$—C($R^{10}$)=C($R^{11}$)($R^{12}$), or —$C_6H_4$—CH=CH—CH=C($R^{13}$)($R^{14}$), and $R^{10}$, $R^{11}$, $R^{12}$, $R^{13}$, and $R^{14}$ each independently represent a hydrogen atom, a substituted or unsubstituted alkyl group, or a substituted or unsubstituted aryl group.

Here, examples of the substituents of each of the above groups include a halogen atom, an alkyl group having 1 to 5 carbon atoms, an alkoxy group having 1 to 5 carbon atoms, and a substituted amino group substituted with an alkyl group having 1 to 3 carbon atoms.

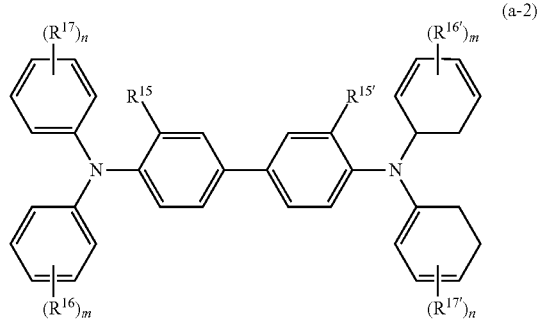
(a-2)

In the structural formula (a-2), $R^{15}$ and $R^{15'}$ each independently represent a hydrogen atom, a halogen atom, an alkyl group having 1 to 5 carbon atoms, or an alkoxy group having 1 to 5 carbon atoms. $R^{16}$, $R^{16'}$, $R^{17}$, and $R^{17'}$ each independently represent a hydrogen atom, a halogen atom, an alkyl group having 1 to 5 carbon atoms, an alkoxy group having 1 to 5 carbon atoms, an amino group substituted with an alkyl group having 1 to 2 carbon atoms, a substituted or unsubstituted aryl group, —C($R^{18}$)=C($R^{19}$)($R^{20}$), or —CH=CH—CH=C($R^{21}$)($R^{22}$), and $R^{18}$, $R^{19}$, $R^{20}$, $R^{21}$, and $R^{22}$ each independently represent a hydrogen atom, a substituted or unsubstituted alkyl group, or a substituted or unsubstituted aryl group. m and n each independently represent an integer of 0 or more and 2 or less.

Among the triarylamine derivatives represented by the formula (a-1) and the benzidine derivatives represented by the formula (a-2), triarylamine derivatives having "—$C_6H_4$—CH=CH—CH=C($R^{13}$)($R^{14}$)" and benzidine derivatives having "—CH=CH—CH=C($R^{21}$)($R^{22}$)" are preferable because they are excellent in charge mobility, adhesiveness to the protective layer, and prevention of the latent image caused by the residue of the preceding image (which may be sometimes hereinafter referred to as a "ghost").

Examples of the binder resin used in the charge transporting layer 3 include polycarbonate resins, polyester resins, polyarylate resins, methacrylic resins, acrylic resins, polyvinyl chloride resins, polyvinylidene chloride resins, polystyrene resins, polyvinyl acetate resins, styrene-butadiene copolymers, vinylidene chloride-acrylonitrile copolymers, vinyl chloride-vinyl acetate copolymers, vinyl chloride-vinyl acetate-maleic anhydride copolymers, silicone resins, silicone alkyd resins, phenol-formaldehyde resins, styrene-alkyd resins, poly-N-vinylcarbazole, polysilane, and the like. The polyester-based charge transporting polymer material disclosed in JP-A-8-176293 and JP-A-8-208820, and the like may be used. Among these, polycarbonate resins and polyarylate resins are preferable.

These binder resins are used singly or in combination of two or more kinds thereof. The blending ratio between the charge transporting material and the binder resin is preferably 10:1 to 1:5 ratio.

Particularly, for providing a protective layer (outermost surface layer) including a cured film of a composition containing a reactive charge transporting material and a polycarbonate resin on the charge transporting layer 3, it is preferred for the binder resin used in the charge transporting layer 3 to have a viscosity average molecular weight of 50000 or more, and more preferably 55000 or more.

Further, the upper limit of the viscosity average molecular weight of the binder resin used in the charge transporting layer 3 is preferably 100000 or less.

Here, the viscosity average molecular weight of the binder resin in the present exemplary embodiment is a value measured with a capillary viscometer.

Further, in the case where the outermost surface layer is a charge transporting layer, the viscosity average molecular weight of the binder resin contained in the underocat layer is preferably in the above range.

Furthermore, as the charge transporting material, a polymer charge transporting material may also be used. As the charge transporting polymer material, known materials having charge transporting properties such as poly-N-vinylcarbazole, polysilane, and the like are used. The polyester-based charge transporting polymer materials disclosed in JP-A-8-176293, JP-A-8-208820, or the like are particularly preferred. The charge transporting polymer materials can form a film independently, but may also be mixed with the above-described binder resin to form a film.

The charge transporting layer 3 can be formed using the coating liquid containing the above-described constituents.

Examples of the solvent used for the coating liquid for forming the charge transporting layer include ordinary organic solvents such as aromatic hydrocarbons such as benzene, toluene, xylene, chlorobenzene, and the like, ketones such as acetone, 2-butanone, and the like, aliphatic hydrocarbon halides such as methylene chloride, chloroform, ethylene chloride, and the like, cyclic or straight-chained ethers such as tetrahydrofuran, ethyl ether, and the like. These solvents may be used singly or in combination of two or more kinds thereof. Known methods can be used for dissolving the above-described constituents.

For coating the coating liquid for forming a charge transporting layer onto the charge generating layer 2, ordinary methods such as a blade coating method, a Meyer bar coating method, a spray coating method, a dip coating method, a bead coating method, an air knife coating method, a curtain coating method, and the like are used.

The film thickness of the charge transporting layer 3 is preferably 5 μm or more and 50 μm or less, and more preferably 10 μm or more and 30 μm or less.

As the charge transporting layer, the surface layer material of the present exemplary embodiment may be used.

<Process Cartridge and Image Forming Apparatus>

Next, a process cartridge and an image forming apparatus, in which the electrophotographic photoreceptor of the present exemplary embodiment is used, will be described.

The process cartridge of the present exemplary embodiment is configured to be detached from an image forming apparatus that transfers a toner image obtained by developing an electrostatic latent image on the surface of the latent image holding member to a recording medium to form an image on the recording medium, and includes, as the latent image holding member, at least the above-described electrophotographic photoreceptor according to the present exemplary embodiment, which.

Furthermore, the image forming apparatus of the present exemplary embodiment is configured to include the electrophotographic photoreceptor according to the present exemplary embodiment, a charging device that charges the electrophotographic photoreceptor, an exposure device that exposes the surface of the charged electrophotographic photoreceptor to form an electrostatic latent image on the surface, a developing device that develops the electrostatic latent image with a developer to form a toner image, and a transfer device that transfers the toner image to a recording medium. Further, the image forming apparatus of the present exemplary embodiment may be of a tandem type having plural photoreceptors corresponding to the toner of each color, and in this case, it is preferable that all the photoreceptors be the electrophotographic photoreceptor of the present exemplary embodiment. In addition, the transfer of the toner image may be in an intermediate transfer manner using an intermediate transfer medium.

Figure 4:
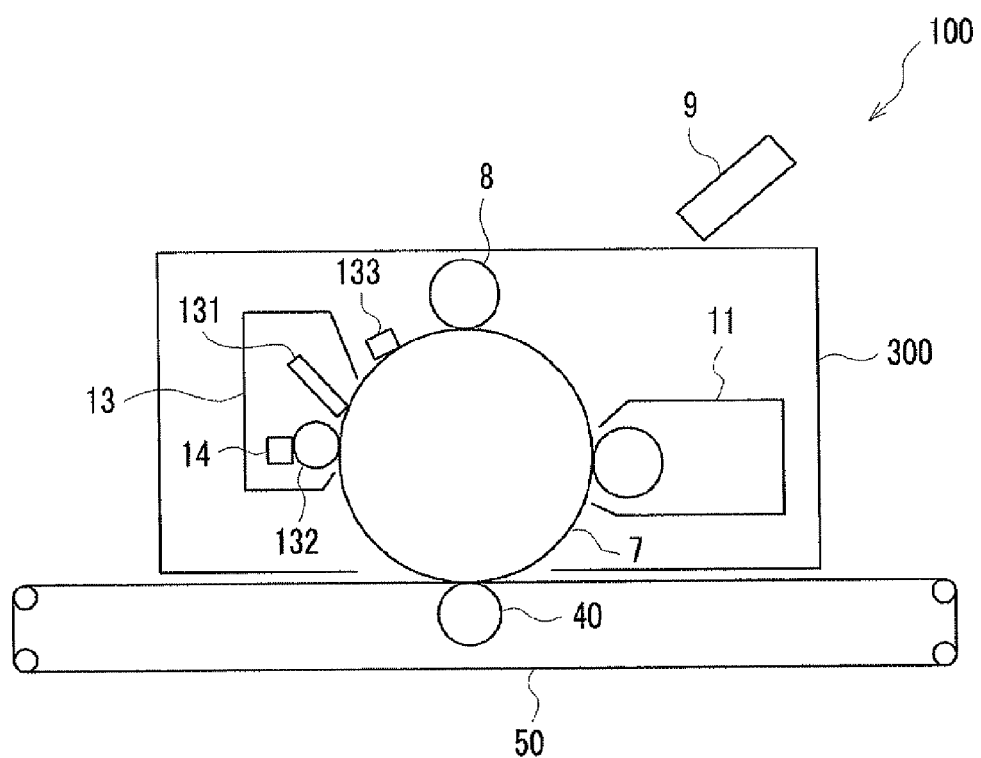
FIG. 4 is a schematic partial cross-sectional view showing an image forming apparatus having a process cartridge according to the present exemplary embodiment.

FIG. 4 is a schematic structural view showing an image forming apparatus according to the present exemplary embodiment. As shown in FIG. 4, the image forming apparatus 100 includes a process cartridge 300 equipped with electrophotographic photoreceptor 7, an exposure device 9, a transfer device 40, and an intermediate transfer medium 50. Further, in the image forming apparatus 100, the exposure device 9 is disposed so as to irradiate the electrophotographic photoreceptor 7 through the opening of the process cartridge 300, the transfer device 40 is disposed so as to oppose the electrophotographic photoreceptor 7 via the intermediate transfer medium 50, and the intermediate transfer medium 50 is disposed so as to be in partial that is in contact with the electrophotographic photoreceptor 7.

The process cartridge 300 in FIG. 4 integrally supports the electrophotographic photoreceptor 7, the charging device 8, a developing device 11 and a cleaning device 13, in a housing. The cleaning device 13 has a cleaning blade (member to be cleaned). The cleaning blade 131 is disposed so as to be in contact with the surface of the electrophotographic photoreceptor 7.

Furthermore, an example for the cleaning device 13 is shown, which is equipped with fibrous member 132 (in the form of a roll) feeding a lubricant 14 to the surface of photoreceptor 7, and using fibrous member 133 (in the form of a flat brush) as a cleaning assist, but these members may be used or may not be used.

As the charging device 8, for example, a contact-type charging device employing a conductive or semiconductive charging roller, a charging brush, a charging film, a charging rubber blade, a charging tube, or the like may be used. Known non-contact-type charging devices such as a non-contact-type roller charging device, a scorotron or corotron charging device utilizing corona discharge, and the like, may also be used.

Further, in order to improve stability of the image, a photoreceptor heating member, although not shown, may be provided around the electrophotographic photoreceptor 7 thereby increasing the temperature of the electrophotographic photoreceptor 7 and reducing the relative temperature.

Examples of the exposure device 9 include optical instruments which can expose the surface of the photoreceptor 7 so that a desired image is formed by using light of semiconductor laser light, LED light, a liquid-crystal shutter light, or the like. The wavelength of light sources to be used is in the range of the spectral sensitivity region of the photoreceptor. As the semiconductor laser light, near-infrared light having an oscillation wavelength in the vicinity of 780 nm is predominantly used. However, the wavelength of the light source is not limited to the above-described wavelength, and lasers having an oscillation wavelength on the order of 600 nm and blue lasers having an oscillation wavelength in the vicinity of 400 nm or more and 450 nm or less may also be used. Further, a surface-emitting type laser light source which is capable of multi-beam output is effective to form a color image. In particular, an incoherent exposure light source having a light-emitting center wavelength of 450 nm or more and 780 nm or less is preferable in terms of high image quality.

Furthermore, the total film thickness of the photosensitive layer in the electrophotographic photoreceptor is 20 μm or less, and the exposure device 9 preferably has an incoherent exposure light source. In addition, in a more preferable exemplary embodiment, the area of the exposures spot of the surface of the electrophotographic photoreceptor exposed by the incoherent exposure light source is 1000 μm$^2$ or less, and the light-emitting center wavelength of the incoherent exposure light source is 450 nm or more and 780 nm or less.

Next, the exposure head will be described.

Figure 10:
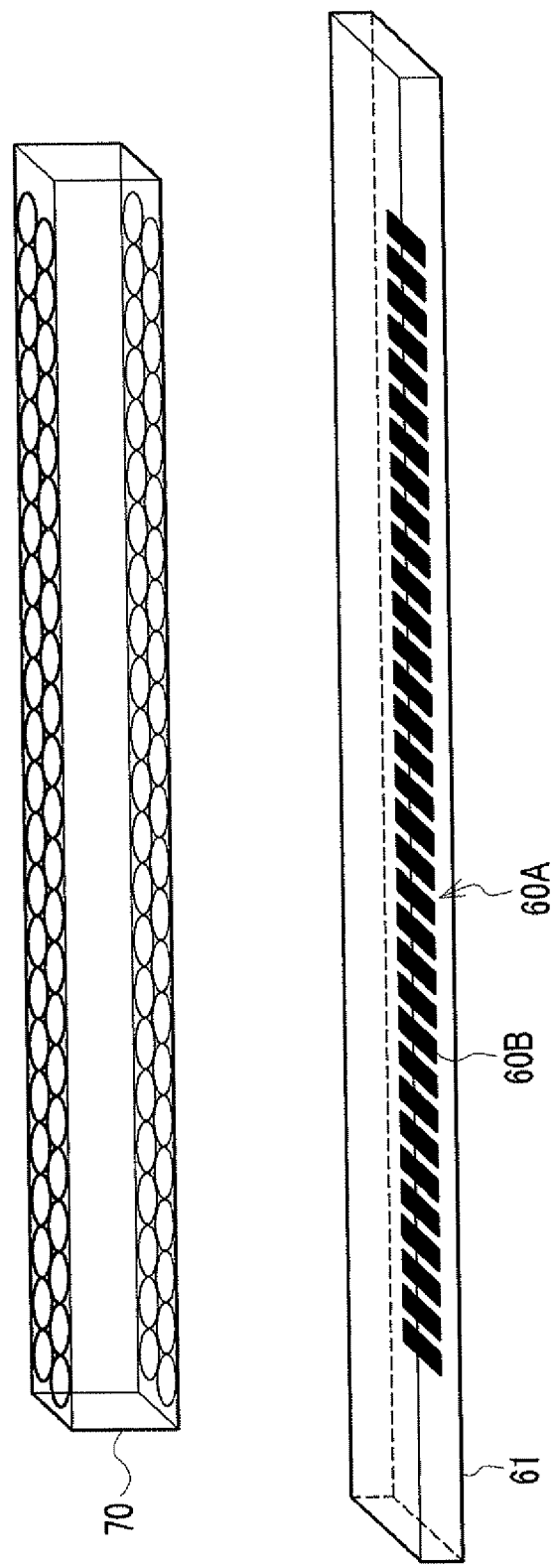
FIG. 10 is a diagram showing an exposure head.
Figure 11:
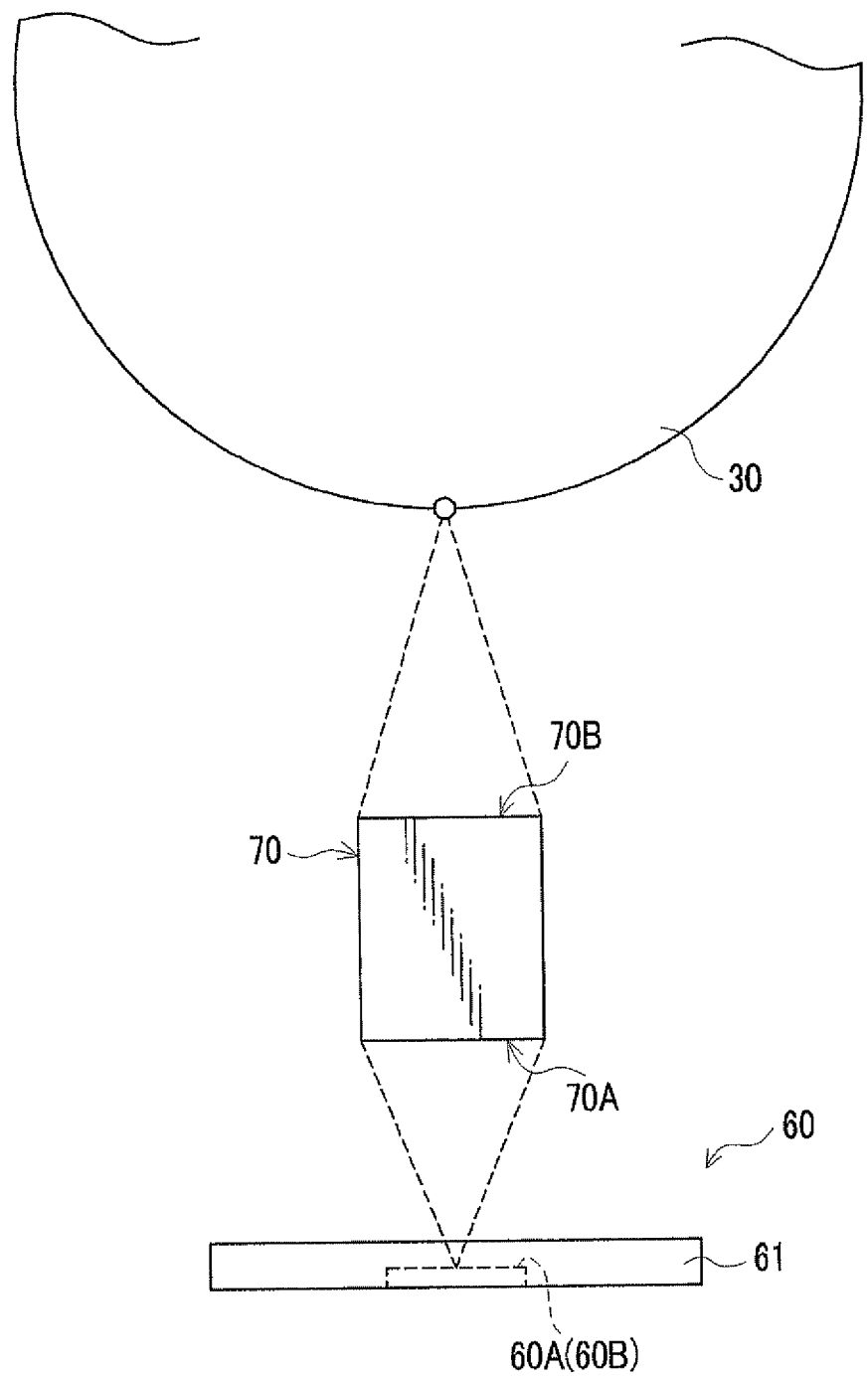
FIG. 11 is a diagram showing a state in which exposure is performed on a photoreceptor by an exposure head.

FIG. 10 is a view showing the exposure head, and FIG. 11 is a view showing a state in which the photoreceptor is subjected to exposure by the exposure head. Each of the exposure heads includes, as shown in FIGS. 10 and 11, for example, an organic EL device array (light-emitting element array 60B) and an image pickup unit (lens 70).

The light emitting element array 60B includes, for example, a light emitting unit constituted with an organic EL element (light-emitting element 60A), and a mounting substrate on which the organic EL element is mounted (corresponding to the light-emitting element array substrate 61 in FIG. 10).

The organic EL element array (light-emitting element array 60B) and the image pickup unit (lens 70) are held apart by a holding member such that the optical distance between the light-emitting unit (light-emitting element 60A) and the light incidence surface 70A of the image pickup unit is a working distance of the image pickup unit.

Here, the working distance of the image pickup unit refers to a distance between a focal point of the lens 70 used in the image pickup unit to the incident surface 70A of the image pickup unit.

Further, in the image pickup unit, the light emitted from the light-emitting unit is incident from the light incidence surface 70A and simultaneously, output from the light emitting surface 70B to pickup an image at a predetermined position.

That is, by pickup of the image emitted from the light-emitting element 60A on the photoreceptor 30, the photoreceptor 30 is exposed to form a latent image (FIG. 11).

Here, the organic EL element array (light-emitting element array 60B) will be described.

The organic EL element array may be, for example, a so-called bottom-emission type that extracts light irradiated from a light-emitting unit to the side of a mounting substrate (light-emitting element array substrate 61), but a top-emission type is also available.

The light-emitting unit is constituted with, for example, a group of singular light-emitting elements 60A. The light-emitting elements 60A are arranged linearly (in series) or in a zigzag form along the longitudinal direction of the mounting substrate (light-emitting element array substrate 61) to constitute the light-emitting unit. The light-emitting unit constituted with the group of the light-emitting elements 60A is at least as long as the image forming area of the photoreceptor 30.

Next, the image pickup unit (lens 70) will be described.

The image pickup unit is constituted with, for example, an array of multiple lens, in which plural rod lens are arranged. As the lens array, specifically, for example, a distributed refractive index lens array called an SELFOC lens array (SLA: SELFOC is a registered trademark of Nippon Sheet Glass Co., Ltd.) is most preferably used, but a combination of cylindrical lenses may be used. In addition, a microlens may be bonded to an individual organic EL element for a light source.

As the developing device 11, for example, a common developing device, in which a magnetic or non-magnetic one-component or two-component developer is contacted or not contacted for forming an image, can be used. Such a developing device is not particularly limited as long as it has the above-described functions, and can be appropriately selected according to the preferred use. Examples thereof include a known developing device in which the one-component or two-component developer is applied to the photoreceptor 7 using a brush or a roller. Among these, the developing device using developing roller retaining developer on the surface thereof is preferable.

Hereinafter, a toner used in the developing device 11 will be described.

The toner used in the image forming apparatus of the present exemplary embodiment preferably has an average shape factor $(ML^2/A) \times (\pi/4) \times 100$, wherein ML represents the maximum length of a particle and A represents the projection area of the particle) of 100 or more and 150 or less, preferably 105 or more and 145 or less, and more preferably 110 or more and 140 or less. Furthermore, the volume average particle diameter of the toner is preferably 3 μm or more and 12 μm or less, and more preferably 3.5 μm or more and 9 μm or less.

The method of preparing the toner is not particularly limited, but a toner prepared by, for example, a kneading and grinding method in which a binder resin, a coloring agent, a releasing agent, and optionally a charge control agent or the like are mixed and kneaded, ground, and classified; a method of altering the shape of the particles obtained by the kneading and grinding method using mechanical shock or heat energy; an emulsion polymerization aggregation method in which a dispersion solution obtained by emulsifying and polymerizing polymerizable monomers of a binder resin is mixed with a dispersion solution containing a coloring agent, a releasing agent, and optionally a charge control agent and other agents, then aggregated, heated, and fused to obtain toner particles; a suspension polymerization method in which monomers are polymerized to obtain a binder resin and a solution containing a coloring agent, a releasing agent, and optionally a charge control agent and other agents, are suspended in an aqueous solvent and polymerized therein; a dissolution-suspension method in which a binder resin and a solution containing a coloring agent, a releasing agent, and optionally a charge control agent and other agents, is suspended in an aqueous solvent to form particles; or the like is used.

Moreover, known methods such as a method of preparing toner particles having a core-shell structure in which aggregated particles are further attached to the toner particles obtained by the above-described method, as the core, then heated and fused are used. Further, as the method of preparing toner particles, a suspension-polymerization method, an emulsion polymerization aggregation method, and a dissolution suspension method carried out in an aqueous solvent are preferred, and an emulsion polymerization aggregation method is particularly preferable from the viewpoint of controlling the shape and the particle size distribution.

The toner mother particles preferably contain a binder resin, a coloring agent and a releasing agent, and as appropriate, further contain silica and a charge control agent.

Examples of the binder resins used in the toner mother particles include monopolymers and copolymers of styrenes such as styrene, chlorostyrene, and the like, monoolefins such as ethylene, propylene, butylene, isoprene, and the like, vinyl esters such as vinyl acetate, vinyl propionate, vinyl benzoate, vinyl butyrate, α-methylene aliphatic monocarboxylic acid esters such as methyl acrylate, ethyl acrylate, butyl acrylate, dodecyl acrylate, octyl acrylate, phenyl acrylate, methyl methacrylate, ethyl methacrylate, butyl methacrylate, dodecyl methacrylate, and the like, vinyl ethers such as vinyl methyl ether, vinyl ethyl ether, vinyl butyl ether, and the like, and vinyl ketones such as vinyl methyl ketone, vinyl hexyl ketone, vinyl isopropenyl ketone, and the like, polyester resins synthesized by copolymerization of dicarboxylic acids and diols, and the like.

Examples of the typical binder resins include a polystyrene, a styrene-alkyl acrylate copolymer, a styrene-alkyl methacrylate copolymer, a styrene-acrylonitrile copolymer, a styrene-butadiene copolymer, a styrene-maleic anhydride copolymer, a polyethylene, a polypropylene, a polyester resin, and the like. Other examples include a polyurethane, an epoxy resin, a silicone resin, a polyamide, a modified rosin, a paraffin wax and the like.

As the crystalline resin used in the toner mother particle, a crystalline polyester resin is particularly preferable, and in view of the melting point thereof, an aliphatic crystalline resin is preferable. Since the aliphatic crystalline resin has a small aggregation force between the molecules, a releasing effect using a releasing agent is further required, which shall apply to a case where the viscosity of a binder resin included in a core layer is lowered in order to further provide a high gloss image.

—Binder Resin: (Crystalline) Polyester Resin—

The crystalline polyester resin and all the other polyester resins used in the toner are synthesized from polyvalent carboxylic acid components and polyol components. Further, in the present exemplary embodiment, as a polyester resin, commercially available products may be used or synthesized products may also be used.

Examples of the polyvalent aliphatic carboxylic acid components include aliphatic dicarboxylic acids such as oxalic acid, succinic acid, glutaric acid, adipic acid, suberic acid, azelaic acid, sebacic acid, 1,9-nonanedicarboxylic acid, 1,10-decanedicarboxylic acid, 1,12-dodecanedicarboxylic acid, 1,14-tetradecanedicarboxylic acid, 1,18-octadecanedicarboxylic acid, and the like, and aromatic dicarboxylic acid of dibasic acids such as phthalic acid, isophthalic acid, terephthalic acid, naphthalene-2,6-dicarboxylic acid, malonic acid, mesaconic acid, and the like, and anhydrides or lower alkyl esters thereof, but are not limited thereto.

Examples of trivalent or higher-valent carboxylic acids include 1,2,4-benzene tricarboxylic acid, 1,2,5-benzene tricarboxylic acid, 1,2,4-naphthalene tricarboxylic acid, and anhydrides and lower alkyl esters thereof. These may be used singly or in combination of two or more kinds thereof.

Furthermore, as the acid component, a dicarboxylic acid component having a sulfonic acid group is preferably included, in addition to the above-described aliphatic dicarboxylic acid or aromatic dicarboxylic acid. The dicarboxylic acid component having a sulfonic acid group is effective in terms of good dispersion of color materials such as a pigment and the like. Further, when the whole resin is emulsified or suspended in water to prepare particles, the presence of the sulfonic acid group enables the emulsification or suspension without using a surfactant as described later.

Examples of the dicarboxylic acid having a sulfonic acid group include a sodium 2-sulfoterepthalate salt, a sodium 5-sulfoisophthalate salt, a sodium sulfosuccinate salt, and the like, but are not limited thereto. Additional examples thereof include lower alkyl esters and acid anhydrides thereof, and the like. The divalent or higher-valent carboxylic acid component having a sulfonic acid group is contained in an amount of 1% by mole or more and 15% by mole or less, and preferably 2% by mole or more and 10% by mole or less, based on all the carboxylic acid components constituting the polyester. If the content is 1% by mole or more, the stability over time of the emulsified particles is obtained, whereas if the content is 15% by mole or less, decrease in the crystallinity of the polyester resin is inhibited as well as in the process of fusion of particles after aggregation, and the diameter of the toner is easily adjusted.

Further, it is more preferable that dicarboxylic acid components having a double bond be included, in addition to the above-described aliphatic dicarboxylic acids or aromatic dicarboxylic acids. The dicarboxylic acid having a double bond is preferably used for preventing hot offset at a fixing step because it is capable of crosslinking radically by utilizing its double bond. Examples of the dicarboxylic acid include fumaric acid, maleic acid, 3-hexenedioic acid, 3-octenedioic acid, and the like, but are not limited thereto. Additional examples thereof include lower alkyl esters and acid anhydrides thereof, and the like. Among them, fumaric acid, maleic acid, and the like are mentioned from the viewpoint of cost.

As a polyol component, an aliphatic diol is preferable, and a straight-chain type aliphatic diol containing a chain having 7 to 20 carbon atoms is more preferable. When the aliphatic diol is straight-chained, decrease in the crystallinity of a polyester resin is inhibited and decrease in the melting point is also inhibited, whereby toner blocking resistance, image storability, and lower temperature fixability are further improved. Further, when the carbon number is more than 7, the melting point does not become too higher upon polycondensation with an aromatic dicarboxylic acid, thus obtaining low-temperature fixability, whereas when the chain carbon number is 20 or less, the material may be easily obtained. It is more preferable that the carbon number be 14 or less.

Examples of the aliphatic diol that is preferably used in the synthesis of the crystalline polyester used in the toner include, but is not limited to, ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,18-octadecanediol, 1,14-eicosdecanediol, and the like. Among these, 1,8-octanediol, 1,9-nonanediol, and 1,10-decanediol are preferable in consideration of easy availability.

Examples of the trihydric or higher-hydric alcohol include glycerin, trimethylolethane, trimethylolpropane, pentaerythritol, and the like. These may be used singly or in combination of two or more kinds thereof.

The content of the aliphatic diol components is preferably 80% by mole or more, and more preferably 90% or more in the polyol component. If the content of the aliphatic diol is 80% by mole or more, decrease in the crystallinity of the polyester resin is inhibited and decrease in the melting point is inhibited. Thus, toner blocking resistance, image storability, and low temperature fixability are further improved.

In addition, if necessary, for the purpose of adjustment of an acid value, a hydroxyl value, or the like, monovalent acids such as acetic acid, benzoic acid, and the like, or monohydric alcohols such as cyclohexanol, benzyl alcohol, and the like may also be used.

Furthermore, the crystalline polyester used in the toner preferably has an ester concentration as determined by the formula (7) in the range of 0.01 or more and 0.12 or less:

$$M=K/A \quad (7)$$

In the formula (7), M represents an ester concentration, K represents the number of ester groups in the crystalline polyester, and A represents the number of atoms constituting a polymer chain of the crystalline polyester.

By suppressing the ester concentration of the crystalline polyester to 0.01 or more and 0.12 or less, toner blocking resistance, image storability, and low temperature fixability are further improved, as well as the charging property is also improved.

If the ester concentration of the crystalline polyester is 0.01 or more, the charging property is good, as well as the melting point of the crystalline polyester not becoming too high, and the lower limit of the ester concentration with inhibition of decrease in the low temperature fixability is more preferably 0.04 or more.

Further, if the ester concentration is 0.12 or less, decrease in the charging property is inhibited, and thus, the melting point of the crystalline polyester does not become too low and decrease in the stability of the fixing image and powder blocking resistance is inhibited. The upper limit of the ester concentration is preferably 0.10 or less.

Furthermore, the "ester concentration" is one index indicative of the content ratio of the ester groups in a polymer of a crystalline polyester resin. The "number of the ester groups in a polymer" represented by K in the above formula refers to, in other words, the number of the ester bonds included in the whole polymer.

The "number of atoms constituting a polymer chain of a polymer" represented by A in the formula (7) is a sum of the atoms constituting a polymer chain of a polymer, which includes all the atom number involved in the ester bond, but does not include the number of atoms in other branches of the constituent area.

That is, carbon atoms and oxygen atoms derived from a carboxyl group and an alcohol group involved in the ester bond (the number of oxygen atoms in one ester bond is 2) and 6 carbon atoms in, for example, an aromatic ring, constituting a polymer chain are counted for calculation of the atom number, but hydrogen atoms in, for example, an aromatic ring or an alkyl group, constituting a polymer chain, or an atom or atom group of the substituent thereof are not counted for the calculation.

—Binder Resin: Amorphous Polymer—

Examples of the amorphous polymer resin used in the toner include conventionally known thermoplastic binder resins and the like, and specific examples thereof include homopolymers or copolymers (styrenic resins) of styrene or derivatives thereof such as parachlorostyrene, α-methylstyrene, and the like; homopolymers or copolymers (vinyl-based resins) of esters having a vinyl group, such as methyl acrylate, ethyl acrylate, n-propyl acrylate, n-butyl acrylate, lauryl acrylate, 2-ethylhexyl acrylate, methyl methacrylate, ethyl methacrylate, n-propyl methacrylate, lauryl methacrylate, 2-ethylhexyl methacrylate, and the like; homopolymers or copolymers (vinyl-based resins) of vinyl nitriles such as acrylonitrile, methacrylonitile, and the like; homopolymers or copolymers (vinyl-based resins) of vinyl ethers such as vinyl methyl ether, vinyl isobutyl ether, and the like; homopolymers or copolymers (vinyl-based resins) of vinyl ketones such as vinyl methyl ketone, vinyl ethyl ketone, vinyl isopropenyl ketone, and the like; homopolymers or copolymers (olefin-based resin) of olefins such as ethylene, propylene, butadiene, isoprene, and the like; and non-vinyl condensed resins such as epoxy resin, polyester resin, polyurethane resin, polyamide resin, cellulose resin and polyether resin, graft polymers of these non-vinyl condensed resins with vinyl monomers, and the like. These resins may be used singly or in combination of two or more kinds thereof. Among these resins, vinyl-based resins and polyester resins are particularly preferable.

In the case of the vinyl-based resins, an ionic surfactant or the like is used to perform emulsification polymerization or seed polymerization, thereby easily preparing a resin particle dispersion, which is thus advantageous. Examples of the vinyl-based monomer include vinyl-based polymer acids such as acrylic acid, methacrylic acid, maleic acid, cinnamic acid, fumaric acid, vinylsulfonic acid, ethylene imine, vinyl pyridine and vinyl amine, and monomers functioning as starting materials of vinyl-based polymer bases.

Furthermore, the vinyl-based monomers are preferably contained as monomer components in the above resin particles. Among these vinyl-based monomers, the vinyl-based polymer acids are preferable for easier reaction to form vinyl-based resins, and specifically, dissociable vinyl-based monomers having a carboxyl group as a dissociable group, such as acrylic acid, methacrylic acid, maleic acid, cinnamic acid and fumaric acid, are particularly preferable for regulation of the degree of polymerization and glass transition point.

Moreover, examples of the typical coloring agent include magnetic powder such as magnetite and ferrite, carbon black, aniline blue, calcoil blue, chrome yellow, ultramarine blue, Du Pont oil red, quinoline yellow, methylene blue chloride, phthalocyanine blue, malachite green oxalate, lamp black, Rose Bengal, C. I. Pigment Red 48:1, C. I. Pigment Red 122, C. I. Pigment Red 57:1, C. I. Pigment Yellow 97, C. I. Pigment Yellow 17, C. I. Pigment Blue 15:1, C. I. Pigment Blue 15:3, and the like.

Examples of the typical releasing agent include low-molecular-weight polyethylene, low-molecular-weight polypropylene, Fischer-Tropsch wax, montan wax, carnauba wax, rice wax, candelilla wax, and the like.

Furthermore, as the charge control agent, any of known agents such as azo-based metal-complex compounds, metal-complex compounds of salicylic acid, and resin-type charge control agents having polar groups may be used. When a toner is prepared by a wet preparation method, materials hardly soluble in water may be used in view of controlling ion strength and reducing contamination by waste water. Further, the toner may be either a magnetic toner which contains a magnetic material or a non-magnetic toner which contains no magnetic material.

The toner used in developing device 11 is prepared by mixing the above-mentioned toner mother particles and external additives using a Henschel mixer, a V blender, or the like. When the toner mother particles are prepared by a wet process, external additives may be added by a wet method.

Particles having a fluorine element may be included in the toner used in developing device 11.

Examples of the particles having a fluorine element include carbon fluoride in which fluorine is bound to graphite, polytetrafluoroethylene (PTFE) resin, perfluoroalkoxy-fluorine (PFA) resin, ethylene tetrafluoride-propylene hexafluoride (FEP) copolymer, ethylene-ethylene tetrafluoride (ETFE) copolymer, polychloroethylene trifluoride (PCTFE), polyvinylidene fluoride (PVDF) and polyvinyl fluoride (PVF), and the average particle diameter is preferably in the range of 0.1 μm or more and 4 μm or less. Further, those having the above chemical structures may be ground into particles having the same particle diameter. The amount of the toner to be added is in the range of preferably 0.05% by weight or more and 2.0% by weight or less, and more preferably 0.1% by weight or more and 1.5% by weight or less. If the amount is 0.05% by weight or more, the coefficient of friction is not too high, generation of ghost is inhibited, whereas if the amount is 2.0% by weight or less, generation of a reversely polar toner is inhibited.

In addition, lubricant particles may be added. Examples of the lubricant particles include solid lubricants including graphite, molybdenum disulfide, talc, fatty acids, metal salts of fatty acids or the like, low molecular-weight polyolefins such as polypropylene, polyethylene and polybutene, fluorine-containing particles such as PTEF and PFA, silicones having a softening point when heated, fatty-acid amides such as oleic acid amide, erucic acid amide, ricinoleic acid amide and stearic acid amide, vegetable-based waxes such as carnauba wax, rice wax, candelilla wax, Japan wax and jojoba oil, animal-based waxes such as beeswax, mineral and petroleum-based waxes such as montan wax, ozokerite, ceresine, paraffin wax, microcrystalline wax and Fischer-Tropsch wax, and modified products thereof. These may be used singly or in combination of two or more kinds thereof. The average particle diameter of the lubricant particles is preferably in the range of 0.1 μm or more and 10 μm or less, and those having the above-mentioned chemical structure may be ground into particles having the same particle diameter. The amount of the particles in the toner is in the range of preferably 0.05% by weight or more and 2.0% by weight or less, and more preferably 0.1% by weight or more and 1.5% by weight or less.

Inorganic particles, organic particles, composite particles in which inorganic particles have been attached to the organic particles, or the like may be added to the toner used in developing device 11 for the purpose of removing a deposition or a deterioration-inducing substance from the surface of the electrophotographic photoreceptor.

As the inorganic particles, various inorganic oxides, nitrides, borides, and the like such as silica, alumina, titania, zirconia, barium titanate, aluminum titanate, strontium titanate, magnesium titanate, zinc oxide, chromium oxide, cerium oxide, antimony oxide, tungsten oxide, tin oxide, tellurium oxide, manganese oxide, boron oxide, silicon carbide, boron carbide, titanium carbide, silicon nitride, titanium nitride, boron nitride, and the like are preferably used.

Furthermore, the inorganic particles may be treated with a titanium coupling agent such as tetrabutyl titanate, tetraethyl titanate, isopropyltriisostearoyl titanate, isopropyltridecylbenzenesulfonyl titanate, bis(dioctylpyrophosphate)oxyacetate titanate, and the like; and a silane coupling agent such as γ-(2-aminoethyl)aminopropyltrimethoxysilane, γ-(2-aminoethyl)aminopropylmethyldimethoxysilane, γ-methacryloxypropyltrimethoxysilane, N-β-(N-vinylbenzylaminoethyl)-γ-aminopropyltrimethoxysilane hydrochloride, hexamethyldisilazane, methyltrimethoxysilane, butyltrimethoxysilane, isobutyltrimethoxysilane, hexyltrimethoxysilane, octyltrimethoxysilane, decyltrimethoxysilane, dodecyltrimethoxysilane, phenyltrimethoxysilane, o-methylphenyltrimethoxysilane, p-methylphenyltrimethoxysilane, and the like. Further, the inorganic particles that are subjected to a hydrophilization treatment with silicone oil, or metal salts of higher fatty acids such as aluminum stearate, zinc stearate, calcium stearate, and the like are also preferably used.

Examples of the organic particles include styrene resin particles, styrene acrylic resin particles, polyester resin particles, urethane resin particles, and the like.

The particle diameter is preferably 5 nm or more and 1000 nm or less, more preferably 5 nm or more and 800 nm or less, and still more preferably 5 nm or more and 700 nm or less in terms of a number average particle diameter. When the average particle diameter is no less than the lower limit, the particles tend to have excellent abrasive properties. On the other hand, when the average particle diameter is no more than the upper limit, the particles tend to inhibit the surface of the electrophotographic photoreceptor from being scratched. The total amount of the above-mentioned particles and the lubricant particles to be added is preferably 0.6% by weight or more.

As the other inorganic oxides added to the toner articles, small inorganic oxide particles having a primary diameter of 40 nm or less are preferably used in view of powder mobility and charge control, and inorganic oxide particles having a larger diameter than that of the small inorganic oxide particles are preferably added in view of adhesiveness reduction and charge control. Known inorganic oxide particles may be used, but combined use of silica and titanium oxide particles is preferable for precise charge control.

Furthermore, surface treatment of small inorganic particles increases dispersibility and enhances the effect of increasing powder mobility. In addition, addition of a carbonate such as calcium carbonate, magnesium carbonate, and the like, or an inorganic mineral such as hydrotalcite and cerium oxide is also preferable to remove discharge products.

Moreover, a color toner for electrophotography may be used in combination with a carrier. Examples of the carrier include iron powder, glass beads, ferrite powder, nickel powder and those carriers coated with a resin. Further, the mixing ratio of the toner and carrier may be determined as appropriate.

As a method for cleaning the toner remaining on the photoreceptor, a cleaning blade method using a rubber blade is used, since it enables a smaller device to be prepared.

For the purpose of improving the abrasion resistance of the cleaning blade, a unit that removes the discharge products is added, or a carrier collecting unit may be added so as to collect fine particle carriers which will causes edge chipping derived from attachment on the surface of the image holding member as BCO occurs. BCO refers to Bead Carry Over, which is a phenomenon in which a part of the carrier is transferred onto the surface of a photoreceptor (image holding member) owing to an electrostatic attraction force.

Furthermore, in order to improve the abrasion resistance of the cleaning blade, as a material at a part that is in contact with the image holding member, a high-hardness or high-modulus material may be employed. This high-modulus material may be used as a single layer rubber blade, but generally, the resistance is improved but the elasticity decreases in some cases. Decrease in the elasticity indicates that the rubber-like property is lost, and thus, elongation becomes difficult. Since the elongation is difficult, foreign matter such as carrier pieces and the like buried on the surface of the image holding member as BCO occurs passes through the contact portion between the edge of the cleaning blade and the surface of the image holding member, the blade edge may be easily missed in some cases so as to prevent modification of the edge tip, following the force by which the material modifies the edge.

Furthermore, since the high-modulus (high-hardness) material has a high permanent elongation, the settling (permanent deformation) may be deteriorated in some cases. Thus, if the amount of settling increases, the contact pressure is not maintained, and as a result, poor cleaning may be brought about in some cases.

In order to prevent the edge chipping of the cleaning blade above, when the foreign matter passes through the contact portion between the edge of the cleaning blade and the surface of the image holding member, the edge tip is advantageously constituted with low-hardness materials which allow modification (elongation) of the edge tip. In addition, from the viewpoint of preventing the settling above, the low-hardness materials are advantageous.

However, since the abrasion resistance is deteriorated with these low-hardness materials, a cleaning performance may not be maintained over a long period of time.

Thus, the cleaning blade is constituted with a first layer that contacts the surface of the photoreceptor and a back layer that does not contact the surface of the photoreceptor, and the material of the first layer preferably satisfies the following formulae (1) to (3):

$$3.92 \leq M \leq 29.42 \quad \text{Formula (1)}$$

$$0 < \alpha \leq 0.294 \quad \text{Formula (2)}$$

$$S \geq 250 \quad \text{Formula (3)}$$

(in the formulae (1) to (3), M represents a 100% modulus (MPa), $\alpha$ represents a ratio of a change in stress ($\Delta$ stress) to a change in a strain amount ($\Delta$ strain amount) from 100% strain to 200% strain {$\Delta$ stress/$\Delta$ strain amount=(stress at a strain amount of 200%−stress at a strain amount of 100%)/(200−100)}(MPa/%) in a stress-strain curve, and S represents a breaking elongation (%) measured according to JIS K6251 (using a dumbbell type #3 test piece)).

Here, the cleaning blade may have a bilayer configuration in which two layers as a back layer are provided on the back side of the first layer that is in contact with the surface of the member to be cleaned, or a configuration in which back layers including plural layers including a second layer, a third layer, and the like are provided on the back side of the first layer. Further, hereinafter, a cleaning blade having a bilayer configuration including a first layer and a second layer as a back layer will be adopted and described in detail.

—First Layer—

The cleaning blade exerts a good cleaning property and has excellent abrasion resistance since the material of the first layer that is in contact with the surface of the member to be cleaned satisfies the formula (1).

If the 100% modulus M is 3.92 MPa (40 kgf/cm$^2$) or more, abrasion resistance is obtained, and a good cleaning property over a long period of time. On the other hand, if the 100% modulus M is 29.42 MPa (300 kgf/cm$^2$) or less, the first layer material is not too hard, the cleaning blade has a property of following the member to be cleaned, and a good cleaning property is exerted. In addition, damage to the surface of member to be cleaned is inhibited.

Furthermore, the 100% modulus M is preferably in the range of 5 MPa or more and 20 MPa or less, and more preferably in the range of 6.5 MPa or more and 15 MPa or less.

Furthermore, since the first layer material satisfies the formulae (2) and (3), the chipping resistance is excellent.

If α shown in formula (2) is 0.294 or less, the flexibility of the first layer material can be obtained. Thus, as BCO occurs, foreign matter present on the surface of the member to be cleaned such as foreign matter buried and fixed on the surface of the image holding member, in particular, foreign matter buried and fixed on the surface repeatedly passes through the contact portion between the member to be cleaned and the cleaning blade, and thus, even when a high strain is repeatedly applied on the edge tip of the first layer of the cleaning blade, the strain is modified to be dispersed efficiently and accordingly, the edge chipping is inhibited in a relatively short period of time. Therefore, since early chipping is inhibited, a good cleaning property is maintained over a long period of time.

In addition, α is preferably 0.2 or less, and more preferably 0.1 or less. α is preferably closer to zero, which is the physical lower limit value.

When the breaking elongation S shown in formula (3) is 250% or more, the edge chipping in a relatively short period of time is inhibited even when the foreign matter on the surface of the member to be cleaned collides with the edge tip of the first layer with a strong force. Thus, since the edge chipping in a short period of time is inhibited, a good cleaning property is maintained over a long period of time.

In addition, the breaking elongation S is preferably 300% or more, and more preferably 350% or more. A larger breaking elongation S is preferred from the viewpoint of the edge chipping. However, when the breaking elongation S is 500% or less, the tracking property (adhesiveness) to the surface of the member to be cleaned is not excessive and increase in the friction force with the surface of the member to be cleaned is inhibited, resulting in inhibition of edge tip abrasion (edge abrasion) of the first layer. Therefore, from the viewpoints of the edge abrasion, the breaking elongation S is preferably 500% or less, more preferably 450% or less, and still more preferably 400% or less.

Furthermore, the ambient temperature, that is, the environmental temperature during use, around the cleaning blade of the image forming apparatus may be approximately in the range of 10° C. or higher and 60° C. or lower. Accordingly, when the glass transition temperature Tg of the material of the first layer that contacts the surface of the member to be cleaned is no higher than the environmental temperature during use, the cleaning blade keeps its rubber-like property, and the contact pressure of the cleaning blade is thereby maintained. Therefore, the glass transition temperature Tg of the material of the first layer is preferably no higher than the lower limit value (10° C.) of the environmental temperature at use.

Furthermore, when the glass transition temperature Tg of the material of the first layer that contacts the surface of the member to be cleaned is 10° C. or lower, the rebound resilience R of the material is decreased as the glass transition temperature Tg is lower. Thus, if the rebound resilience R is 10% or more, the sticking-and-slipping behavior at the edge tip of the first layer is not too slow, and occurrence of a portion that rubs against the surface of the member to be cleaned while maintaining a certain deformed shape that is in contact with the surface is inhibited.

When the deformed shape is canceled by the sticking-and-slipping behavior, the edge tip does not rub against the surface while maintaining the shape of the edge tip of the first layer, whereby occurrence of the localized plastic deformation is inhibited. When generation of such localized plastic deformation is inhibited, decrease in the adhesiveness between the edge tip of the first layer and the surface of the member to be cleaned is inhibited, and thus, occurrence of cleaning failure is inhibited. In order to inhibit such localized plastic deformation, it is preferable that the sticking-and-slipping behavior always occurs at the edge tip of the first layer. In order that the sticking-and-slipping behavior always occurs at the edge tip, the rebound resilience R is preferably 10% or more, more preferably 15% or more, and still more preferably 20% or more in an environment of a temperature of 10° C. or higher, which is substantially the lower limit value of the environmental temperature at use.

Moreover, the rebound resilience R is measured in accordance with JIS K6255 (1996) as described above.

Furthermore, the 100% modulus M shown in the formula (1) is measured in accordance with JIS K6251 (1993) with a dumbbell #3 test piece at a tensile speed of 500 mm/min and obtained from the stress at 100% strain. As a measurement device, a STROGRAPH AE ELASTOMER manufactured by Toyo Seiki Seisakusho, Ltd. is used.

In addition, the value α shown in the formula (2) is obtained from a stress-strain curve. The stress and the amount of strain are obtained by a procedure and method described below. That is, in accordance with JIS K6251 (1993), a measurement is carried out with a dumbbell #3 test piece at a tensile speed of 500 mm/min, and α is obtained from stresses at 100% strain and 200% strain. As a measurement device, a STROGRAPH AE ELASTOMER manufactured by Toyo Seiki Seisakusho, Ltd. is used.

Furthermore, in an aspect of the invention, the glass transition temperature of the material of the first layer that contacts the surface of the member to be cleaned, and the glass transition temperatures of the soft segment material and the hard segment material described below, are determined as a peak temperature of tan δ (loss tangent) after the temperature dispersion is measured with a viscoelastometer.

Here, the tan δ value is derived from the storage and loss elastic moduli as described below. When a sine-wave strain as a stationary vibration is applied to a linear elastic body, the stress is represented by the formula (4).

|E*| is called a complex elastic modulus. Further, from a rheological theory, the elastic component and the viscous component are represented by the formulae (5) and (6), respectively. In the formulae, E' represents a storage elastic modulus and E" represents a loss elastic modulus. S represents a phase difference angle between the stress and the strain, and is called "a mechanical loss angle".

The tan δ value is represented by E"/E' as shown in formula (7), and is called a "loss tangent". As the loss tangent is higher, the linear elastic member has a property closer to rubber elasticity.

$$\sigma = |E^*| \gamma \cos(\omega t) \qquad \text{Formula (4)}$$

$$E' = |E^*| \cos \delta \qquad \text{Formula (5)}$$

$$E'' = |E^*| \sin \delta \qquad \text{Formula (6)}$$

$$\tan \delta = E''/E' \qquad \text{Formula (7)}$$

The tan δ value is measured with a RHEOPECTROLER DVE-V4 (manufactured by Rheology Co., Ltd.) under a static strain of 5% and a 10 Hz sine-wave tensile vibration in the temperature range of −60° C. or higher and 100° C. or lower.

As described above, the material for the first layer used in the cleaning blade is excellent in both the abrasion resistance and the chipping resistance, and a good cleaning performance is maintained.

Thus, since there is no need for a separate device for improving the abrasion resistance or chipping resistance in the image forming apparatus in order to respond to foreign matter present on the surface of the member to be cleaned such as foreign matter buried and fixed on the surface of the image holding member, in particular, foreign matter buried and fixed on the surface as BCO occurs, increase in the size and cost of the device is prevented.

In addition, since the life of the cleaning blade increases, a longer life of a process cartridge or cleaning device provided with the cleaning blade or decrease in the maintenance cost is easily achieved Particularly, with a process cartridge or cleaning device provided with both an image holding member and the cleaning blade having improved abrasion resistance of the surface, the above-described merits can be further enjoyed.

The material satisfying formulae (1) to (3) is not particularly limited as long as it is an elastomer material. However, the material may be specifically an elastomer material containing a hard segment and a soft segment. When the elastomer material contains both of the hard segment and the soft segment, the elastomer material may easily satisfy the physical properties defined by formulae (1) to (3), and may achieve both of high abrasion resistance and high chipping resistance at a high level.

Further, the "hard segments" and the "soft segments" refer to the material constituting the former being relatively harder than the material constituting the latter and the material constituting the latter being relatively softer than the material constituting the former.

The elastomer material containing a hard segment and a soft segment preferably has a glass transition temperature in the range of −50° C. or higher and 30° C. or lower, and more preferably in the range of −30° C. or higher and 10° C. or lower. If the glass transition temperature is 30° C. or lower, the cleaning blade is prevented from being fragile in a temperature range for practical use of the cleaning blade in some cases. If the glass transition temperature is −50° C. or higher, sufficient hardness and stress are obtained in a temperature range for practical use.

Consequently, in order to realize the above-mentioned glass transition temperature, the glass transition temperature of the material constituting the hard segment of the elastomer material (hereinafter sometimes referred to as a "hard segment material") is preferably in the range of 30° C. or higher and 100° C. or lower, and more preferably in the range of 35° C. or higher and 60° C. or lower, and the glass transition temperature of the material constituting the soft segment of the elastomer material (hereinafter sometimes referred to as a "soft segment material") is preferably in the range of −100° C. or higher and −50° C. or lower, and more preferably in the range of −90° C. or higher and −60° C. or lower.

Furthermore, in the case where a hard segment material and a soft segment material having such a glass transition temperature is used, the weight ratio of the hard segment material to the total weight of the hard segment material and the soft segment material (hereinafter sometimes referred to as a "hard segment material ratio") is preferably in the range of 46% by weight or more and 96% by weight or less, more preferably in the range of 50% by weight or more and 90% by weight or less, and still more preferably 60% by weight or more and 85% by weight or less.

If the hard segment material ratio is 46% by weight or more, abrasion resistance of the edge tip of the first layer is secured, and occurrence of abrasion is inhibited, and therefore, a good cleaning property is maintained over a long time. If the hard segment material ratio is 96% by weight or less, the edge tip of the first layer is not too hard, and the flexibility and the tensibility are obtained, and further, occurrence of chipping is inhibited, and thus, a good cleaning property is maintained over a long period of time.

The combination of the hard segment material and the soft segment material is not particularly limited, and materials may be selected from conventionally known resin materials such that one material is relatively harder than the other, but the following combinations are preferable.

That is, as a hard segment material, a polyurethane resin is preferably used. In this case, the weight average molecular weight of the polyurethane resin is preferably in the range of 1000 or more and 4000 or less, and more preferably in the range of 1500 or more and 3500 or less.

In the case where the weight average molecular weight is 1000 or more, cleaning failure is inhibited upon use of the cleaning blade at low temperature environment, owing to decrease in the elasticity of the polyurethane resin constituting the hard segments. On the other hand, in the case where the weight average molecular weight is 4000 or less, the permanent strain of the polyurethane resin constituting the hard segments does not become too high, and the edge tip of the first layer holds the contact pressure against the surface of the member to be cleaned. As a result, cleaning failure is inhibited.

Furthermore, examples of the polyurethane resin to be used as the hard segment material include PLACCEL 205 and PLACCEL 240 manufactured by Daicel Chemical Industries, Ltd., and the like.

In addition, the pressure applied by the cleaning blade is preferably set to 1.7 gf/mm or more and 6.5 gf/mm or less, and more preferably 2.0 gf/mm or more and 6.0 gf/mm or less. If the pressure is the lower limit or more, cleaning failure of the toner is inhibited even when a high-hardness blade is used, whereas if the pressure is the upper limit or less, the friction with the photoreceptor does not becomes too severe, and increase in the torque, abrasion of the photoreceptor, occurrence of streak due to chipping of the blade edge, occurrence of ghost due to friction with the photoreceptor, and the like are inhibited.

Examples of transfer apparatus 40 include known transfer chargers such as a contact type transfer charger using a belt, a roller, a film, a rubber blade, or the like, a scorotron transfer charger, a corotron transfer charger utilizing corona discharge, and the like.

As the intermediate transfer medium 50, a belt which is imparted with the semiconductivity (intermediate transfer belt) of polyimide, polyamideimide, polycarbonate, polyarylate, polyester, rubber, or the like is used. In addition, the intermediate transfer medium 50 may also take the form of a drum, in addition to the form of a belt.

In addition to the above-described devices, the image forming apparatus 100 may further be provided with, for example, a photo-erasing device for photo-erasing the photoreceptor 7.

Figure 5:
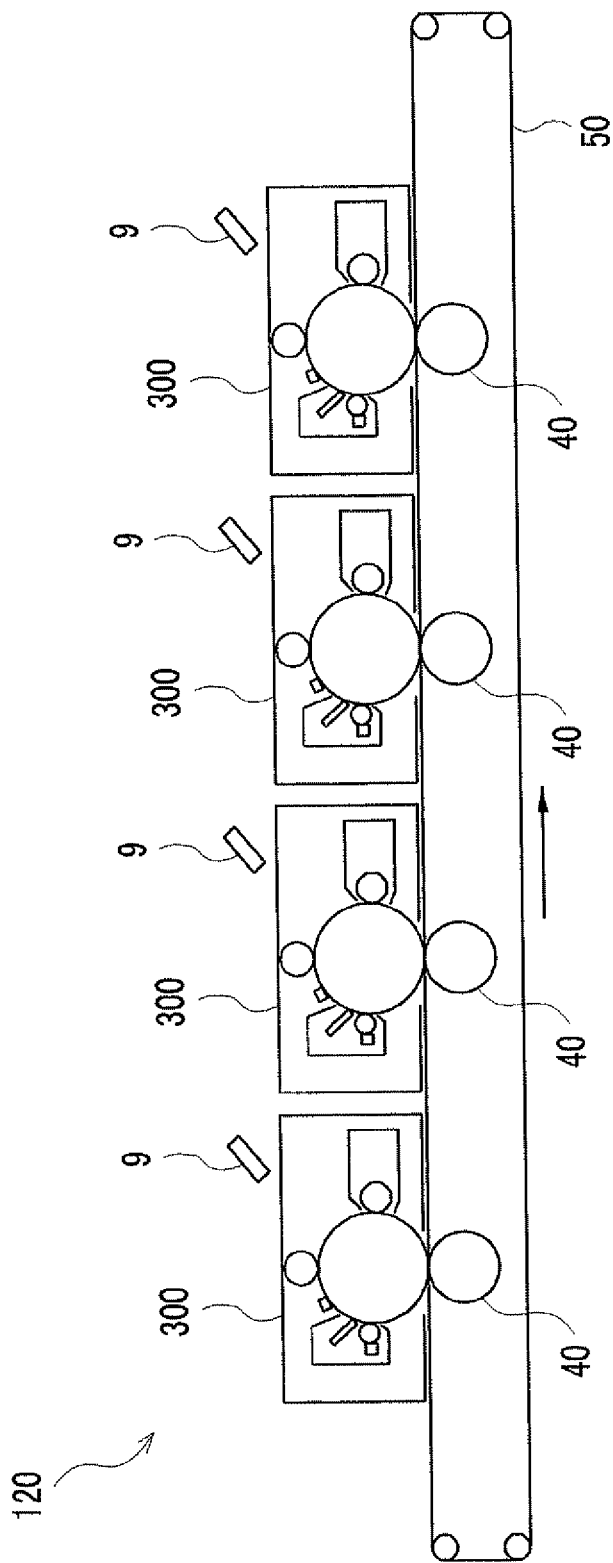
FIG. 5 is a schematic cross-sectional view showing a tandem-type image forming apparatus according to the present exemplary embodiment.

FIG. 5 is a schematic cross-sectional view showing an exemplary embodiment of a tandem type image forming apparatus 120 using a process cartridge including the electrophotographic photoreceptor of the present exemplary embodiment.

FIG. 5 is a diagram (schematic cross-sectional view) showing another exemplary embodiment of the image forming apparatus of the present exemplary embodiment. The image forming apparatus 120 is a tandem type full color image forming apparatus equipped with four process cartridges 300. In the image forming apparatus 120, four process cartridges 300 are disposed parallel with each other on the intermediate transfer medium 50, and one electrophotographic photoreceptor can be used for one color. Further, the image forming apparatus 120 has the same configuration as the image forming apparatus 100, except that it is a tandem type.

When the electrophotographic photoreceptor of the present exemplary embodiment is used in a tandem-type image forming apparatus, the electrical characteristics of the four photoreceptors are stabilized, which provides high image quality with excellent color balance over a longer period of time.

Furthermore, in the image forming apparatus (processing cartridge) according to the present exemplary embodiment, the development apparatus (development unit) preferably includes a development roller as a developer retainer which moves (rotates) in the direction opposite to the traveling direction (rotation direction) of the electrophotographic photoreceptor. For example, the development roller has a cylindrical development sleeve for retaining the developer on the surface thereof, and the development apparatus has a control member for controlling the amount of the developer fed to the development sleeve. When the development roller of the development apparatus is moved (rotated) in the direction opposite to the rotation direction of the electrophotographic photoreceptor, the surface of the electrophotographic photoreceptor is rubbed with the toner retained between the development roller and the electrophotographic photoreceptor.

In addition, in the image forming apparatus (processing cartridge) according to the present exemplary embodiment, from the viewpoint of preventing deposit of discharge products over the longer term, the space between the development sleeve and the photoreceptor is preferably 200 µm or more and 600 µm or less, and more preferably 300 µm or more and 500 µm or less. Further, the space between the development sleeve and control blade, which is a control member for controlling the amount of the developer, is preferably 300 µm or more and 1000 µm or less, and more preferably 400 µm or more and 750 µm or less.

Furthermore, the absolute moving velocity of the development roll surface (process speed) is preferably 1.5 times or more and 2.5 times or less, and more preferably 1.7 times or more and 2.0 times or less than the moving velocity of the surface of the photoreceptor.

In addition, in the image forming apparatus (processing cartridge) according to the present exemplary embodiment, the development apparatus (development unit) includes a developer retainer having a magnetic substance, and develops an electrostatic latent image with preferably a two-component developer containing a magnetic carrier and a toner.

[Organic EL Device]

Next, the organic EL device will be described.

The organic EL device according to the present exemplary embodiment has a film formed by using a dissolving solution in which the thiol group-containing charge transporting material represented by the general formula (1)' is dissolved.

In the case of use as an organic EL device or a solar cell, any of a single layer or a multilayer is available and may be used in any layer.

As an example of the organic EL device, the organic electroluminescent element will be described specifically with reference to the drawings.

Figure 7:
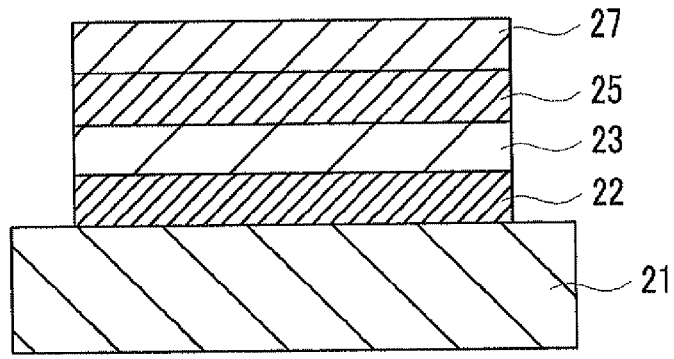
FIG. 7 is a schematic partial cross-sectional view showing an example of the layer configuration of the organic electroluminescent element according to the present exemplary embodiment.
Figure 8:
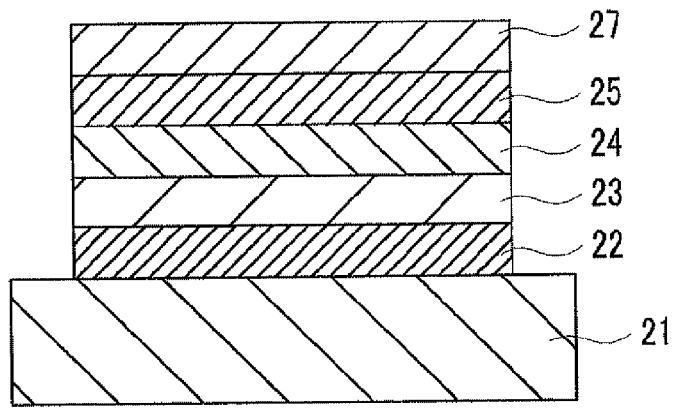
FIG. 8 is a schematic partial cross-sectional view showing another example of the layer configuration of the organic electroluminescent element according to the present exemplary embodiment.
Figure 9:
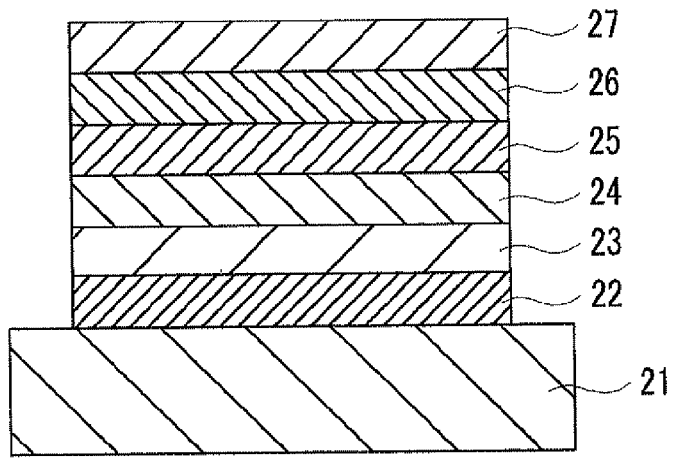
FIG. 9 is a schematic partial cross-sectional view showing a further example of the layer configuration of the organic electroluminescent element according to the present exemplary embodiment.

FIGS. 7 to 9 are schematic cross-sectional views showing the embodiments of the organic electroluminescent element of the present exemplary embodiment, in which 21 represents a substrate, 22 represents an anode, 23 represents a hole injecting layer, 24 represents a hole transporting layer, 25 represents a light-emitting layer, 26 represents an electron transporting layer, and 27 represents a cathode, but the element configuration is not limited thereto.

The substrate 21 is a support for an organic electroluminescent element, and quartz, a glass plate, a metal plate, a metal foil, a plastic film, a sheet, or the like is used. In particular, a glass plate, or a transparent plate of synthetic resins such as a polyester, a polymethacrylate, a polycarbonate, a polysulfone, and the like are preferable.

In the case of using a synthetic resin substrate, it is necessary to pay attention to a gas barrier property. For this reason, a method in which a silicon oxide film that is dense is provided on one side or both sides of the synthetic resin substrate, or the like is also one of the preferable methods.

An anode 22 is provided on the substrate 21. The anode 22 plays a role in injecting holes to a hole injecting layer 23. The anode 22 is usually constituted with metals such as aluminum, gold, silver, nickel, palladium, platinum, and the like, metal oxides such as oxides of indium and/or tin, and the like, water, metal halides such as copper iodide, carbon black, and the like. Formation of the anode 22 is usually carried out by a sputtering method, a vacuum deposition method, or the like in many cases. Further, particles of metals such as silver and the like, particles of copper iodide or the like, carbon black, particles of conductive metal oxides, or the like may be suitably dispersed in a binder resin solution, and coated on a substrate 21 to form an anode 22. The anode 22 may be formed by lamination of other materials.

The thickness of the anode 22 varies depending on the transparency as required, but generally, higher transparency is further preferable, and as a result, the visible light transmittance is usually 60% or more, and preferably 80% or more, at which the thickness is usually 10 nm or more and 1000 nm or less, and preferably 20 nm or more and 500 nm or less.

In the case where the anode may be opaque, for example, the anode may be provided with a metal deposited film or the like for the purpose of, for example, laser oscillation from one side or reflecting between the two electrodes, or the substrate 21 may be used in the anode 22. In addition, other conductive materials may be laminated on the anode 22.

In the element structures of FIGS. 7 to 9, as typically exemplified in the present exemplary embodiment, a hole injecting layer 23 is provided on the anode 22.

In the present exemplary embodiment, a layer formed by using the thiol group-containing charge transporting material represented by the general formula (1)' is formed by a vapor deposition method or a coating method, and in the case of curing, a coating method is preferable. For example, a case where the layer is formed as a hole injecting layer will be described as an example.

To a predetermined amount of the thiol group-containing charge transporting material represented by the general formula (1)', if necessary, a binder resin, a coatability improver, chain polymerizable monomers, oligomers, and the like, which do not act as a trap for a hole, may be added. A charge transporting material having an alkoxysilyl group at the end is also preferable used, and for various purposes, other silane coupling agents, aluminum coupling agents, titanate coupling agents, and the like may be added. A coating solution in which these are dissolved is prepared, coated on the anode 22 by a method such as a spin coating method, a dip coating method, and the like, and dried to form a hole injecting layer 23.

The film thickness of the hole injecting layer 23 thus formed is usually 5 nm or more and 3000 nm or less, and preferably 10 nm or more and 2000 nm or less.

A light-emitting layer 25 is provided on the hole injecting layer 23. In the light-emitting layer 25, electrons injected from the cathode 27 between the electrodes provided with electroluminescence and holes transported from the hole injecting layer 23 are recombined with high efficiency, and further, formed from the light-emitting material efficiently by the recombination. Examples of the material satisfying the condition include aluminum complexes of 8-hydroxyquinoline (JP-A-59-194393), metal complex of 10-hydroxybenzo[h]quinoline (JP-A-6-322362), bis-styrylbenzene derivatives (JP-A-1-245087 and JP-A-2-222484), bis-styrylarylene derivatives (JP-A-2-247278), metal complexes of (2-hydroxyphenyl)benzothiazole (JP-A-8-315983), silole derivatives, and the like.

These organic light-emitting layer materials are usually laminated on the hole injecting layer 23 by a vacuum deposition method or a coating method. In the case of using a coating method, it is preferable to use a solvent that does not substantially dissolve the hole injecting layer 23, but in the present exemplary embodiment, in the case where the undercoat layer is crosslinked three-dimensionally, the resistance to the solvent is high and the solvent can be selected within a wide range.

For the purpose of enhancing the light-emitting efficiency of the element and changing the color of emitted light simultaneously, the device is, for example, doped with a laser fluorescent dye such as coumarin and the like with an aluminum complex of 8-hydroxyquinolione as a host material (J. Appl. Phys., vol. 65, page 3610, 1989).

For example, the host material may be a metal complex such as an aluminum complex of 8-hydroxyquinoline, naphthacene derivatives typically such as rubrene (JP-A-4-335087), quinacridone derivatives (JP-A-5-70773), condensed polycyclic aromatic rings such as perylene and the like (JP-A-5-198377) are doped at 0.1% by weight or more and 10% by weight or less, based on the host material. Examples of the method for doping the host material of the light-emitting layer with the naphthacene derivatives, quinacridones derivatives, or fluorescent colorants such as perylene and the like include a method of co-deposition, and a method in which the deposition sources are mixed at a predetermined concentration.

Examples of the polymeric light-emitting layer material include, as aforementioned, polymer materials such as poly(p-phenylenevinylene), poly[2-methoxy-5-(2-ethylhexyloxy)-1,4-phenylenevinylene], poly(3-alkylthiophene), and the like, and a system obtained by mixing a light-emitting material and an electron transfer material with a polymer such as polyvinylcarbazole and the like.

These materials are coated on the hole injecting layer by a method such as a spin coating method, a dip coating method, and the like, as in the hole injecting layer 23, to form a thin film, and in the case of using a coating method, it is preferable to use a solvent which does not substantially dissolve the hole injecting layer 23, but in the present exemplary embodiment, in the case where the undercoat layer is crosslinked three-dimensionally, the resistance to the solvent is high and the solvent can be selected within a wide range.

The film thickness of the light-emitting layer 25 thus formed is usually 10 nm or more and 200 nm or less, and preferably 30 nm or more and 100 nm or less.

A function-separate type of operation is carried out, for example, as shown in FIG. 8, the hole transporting layer 24 is provided between the hole injecting layer 23 and the light-emitting layer 25, or as shown in FIG. 9, the electron transporting layer 26 is provided between the light-emitting layer 25 and the cathode 27. In the function-separate type elements in FIGS. 8 and 9, as a material for the hole transporting layer 24, a material having a high hole injecting efficiency from the hole injecting layer 23 as well as being capable of efficiently transporting the injected holes is preferable. Examples of the hole transporting material include an aromatic diamine compound in which tertiary aromatic amine units such as 1,1-bis(4-di-p-tolylaminophenyl)cyclohexane and the like are linked (JP-A-59-194393), an aromatic amine which contains two or more tertiary amines, has nitrogen atoms substituted for two or more fused aromatic rings and is represented by 4,4'-bis(N-(1-naphthyl)-N-phenylamino)biphenyl (JP-A-5-234681), an aromatic triamine that is a derivative of triphenylbenzene and has a starburst structure (U.S. Pat. No. 4,923,774), an aromatic diamine such as N,N'-diphenyl-N,N'-bis(3-methylphenyl)biphenyl-4,4'-diamine, and the like (U.S. Pat. No. 4,764,625), a triphenylamine derivative which is three-dimensionally asymmetric in the whole molecule (JP-4-129271), a compound having pyrenyl groups substituted for plural aromatic diamine groups (JP-A-4-175395), an aromatic diamine having tertiary aromatic amine units linked by ethylene groups (JP-A-4-264189), a compound having a plurality of aromatic diamino groups substituted on pyrenyl group such as N,N'-diphenyl-N,N'-bis(3-methylphenyl)biphenyl-4,4'-diamine, an aromatic diamine having a styryl structure (JP-A-4-290851), an aromatic diamine with a styryl structure in which aromatic tertiary amine units are linked through a thiophene group (JP-A-4-304466), starburst-type aromatic triamines (JP-A-4-308688), a benzylphenyl compound (JP-A-4-364153), a compound composed of tertiary amines linked through a fluorene group (JP-A-5-25473), a triamine compound (JP-A-5-239455), bisdipyridyl aminobiphenyl (JP-A-5-320634), an N,N,N-triphenylamine derivative (JP-A-6-1972), an aromatic diamine having a phenoxadine structure (JP-A-7-138562), a diaminophenyl phenanthridine derivative (JP-A-7-252474), silazane compounds (U.S. Pat. No. 4,950,950), a silanamine derivative (JP-A-6-49079), a phosphamine derivative (JP-A-6-25659), and the like. These compounds may be used singly and in a mixture of two or more kinds thereof, as desired. In addition to the above-mentioned compounds, examples of the materials for the hole transporting layer 24 include polyvinyl carbazole or polysilane, polyphosphozene (JP-A-5-310949), polyamide (JP-A-5-310949), polyvinyl triphenyl amine (JP-A-7-53953), a polymer having a triphenyl amine skeleton (JP-A-4-133065), and a polymer material such as polymethacrylate and the like containing aromatic amine.

The hole transporting layer 24 is formed by laminating the hole transporting material on the hole injecting layer 23 by a vapor deposition method or a coating method. In the case of a coating method, if necessary, a binder resin, and additives such as a coatability improver and the like are added to one or two or more kinds of the hole transporting materials, dissolved to prepare a coating solution, coated on the hole injecting layer 23 by a method such as a spin coating method, and dried to form the hole transporting layer 24. In the case of using a coating method, it is preferable to use a solvent which does not substantially dissolve the hole injecting layer 23, but in the present exemplary embodiment, in the case where the undercoat layer is crosslinked three-dimensionally, the resistance to the solvent is high and the solvent can be selected within a wide range.

Here, examples of the binder resin include polycarbonate, polyarylate, polyester, and the like. Thus, the amount of the binder resin to be added is usually preferably 50% by weight or less.

In the case of a vacuum deposition method, the hole transporting material is put into a crucible placed in a vacuum container. The vacuum container is evacuated to a pressure of about $10^{-4}$ Pa by a suitable pump. The crucible is then heated to evaporate the hole transporting material so that a hole transporting layer 24 is formed on the substrate 21 having the anode 22 and the hole injecting layer 23 formed thereon which is disposed opposed to the crucible.

The film thickness of the hole transporting layer 24 thus formed is usually 10 nm or more and 300 nm or less, and preferably 30 nm or more and 100 nm or less.

Generally, the vacuum deposition method is frequently used.

Furthermore, the compound used in the electron transporting layer 26 is required to easily inject electrons from the cathode 27, and thus have a higher electron transporting ability. Examples of the electron transporting material include aluminum complexes of 8-hydroxyquinoline, oxadiazole derivatives (Appl. Phys. Lett., vol. 55, p. 1489, 1989), a system in which these are dispersed in a resin such as polymethylmethacrylate (PMMA) and the like, phenanthroline derivatives (JP-A-5-331459), 2-tert-butyl-9,10-N,N'-dicyanoanthraquinonedimine, n-type hydrogenated amorphous silicon carbide, n-type zinc sulfide, n-type zinc selenide, and the like, as mentioned above for the light-emitting layer material.

The film thickness of the electron transporting layer 26 is usually 5 nm or more and 200 nm or less, and preferably 10 nm or more and 100 nm or less.

The cathode 27 plays a role in injecting electrons to the light-emitting layer 25. As a method used for the cathode 27, a material used for the anode 22 is used. However, in order to inject electrons efficiently, a metal having a small work function is preferable, and suitable metals such as tin, magnesium, indium, calcium, aluminum, silver, and the like, or alloys thereof are used. Specific examples thereof include electrodes having a low-work function of alloys such as a magnesium-silver alloy, a magnesium-indium alloy, an aluminum-lithium alloy, and the like.

The film thickness of the cathode 27 is usually in the range as mentioned above in the description of the anode 22.

For the purpose of protecting the cathode 27 formed with the low-work function metal, it is effective to laminate a metal layer having a high-work function and stable in atmospheric air. For this purpose, metals such as aluminum, silver, copper, nickel, chromium, gold, platinum, and the like are used. Further, a method in which an ultra-thin insulating film (0.1 nm or more and 5 nm or less) of LiF, $MgF_2$, $Li_2O$, or the like is injected to the interface of the light-emitting layer 25 or the electron transporting layer 26 with the cathode 27 is also effective (Appl. Phys. Lett., vol. 70, p. 152, 1997; JP-A-10-74586; and IEEE Trans. Electron. Devices, vol. 44, p. 1245, 1997).

FIGS. 7 to 9 are each one example of the element structures employed in the present exemplary embodiment, but the present exemplary embodiment is not limited to any of these illustrations. For example, a structure reverse to FIG. 7, that is, where the cathode 27, the light-emitting layer 25, the hole injecting layer 23, and the anode 22 may be sequentially laminated on the substrate 21 may be used, and as described above, the organic electroluminescent element of the present exemplary embodiment may be provided between the two substrates having one thereof being more transparent. Further, with those shown in FIGS. 8 and 9, the respective constituent layers may be laminated in the reverse structure. It is also effective to form a sealing layer that seals with materials such as a resin, a metal, and the like, and protects from atmospheric air or water, or to give a structure that enables the element itself to work in a vacuum system.

EXAMPLES

Hereinafter, Examples and Comparative Examples will be described, but the present invention is not limited to the following Examples. Further, the "parts" below are based on weight unless otherwise specified.

Example I-1

Synthesis of Compound (13)

To a 500-ml flask are put 20 g of a compound represented by the following structural formula (A), 15 g of 3-mercaptopropionic acid, 0.5 g of para-toluenesulfonic acid, and 200 ml of toluene, followed by replacing the atmosphere with nitrogen, and then heating and refluxing for 10 hours while removing water produced with a Dean-Stark trap. After the reaction, the residue is washed with an aqueous potassium carbonate solution, washed with distilled water, and then purified by silica gel column chromatography to obtain 23 g of a compound (13) as an oily matter.

Figure 12:
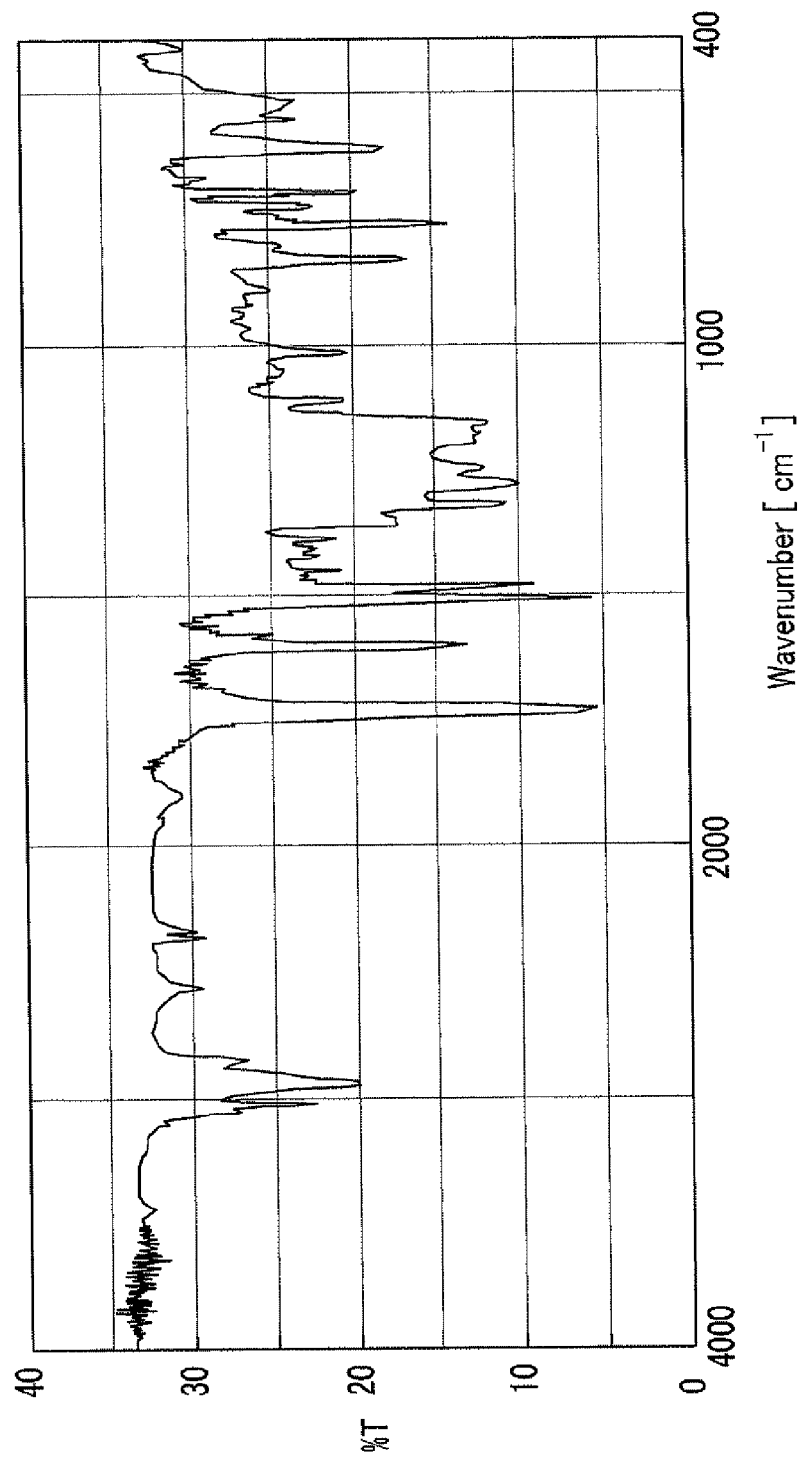
FIG. 12 is a graph showing an IR spectrum of a thiol group-containing charge transporting material synthesized in Examples.

The IR spectrum of the obtained compound (13) is shown in FIG. 12.

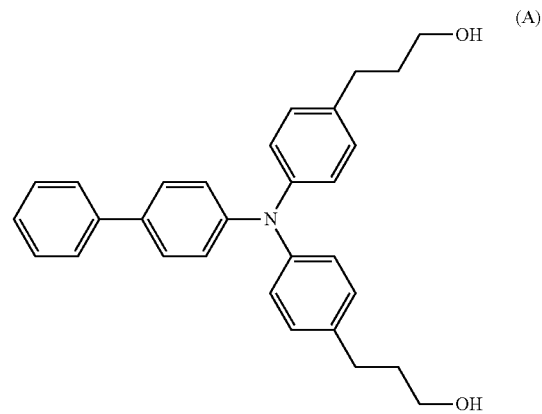 [SMILES: OCCCc1ccc(N(c2ccc(CCCO)cc2)c2ccc(-c3ccccc3)cc2)cc1]

(A)

Example I-2

Synthesis of Compound (29)

To a 500-ml flask are put 20 g of a compound represented by the following structural formula (B), 15 g of 3-mercaptopropionic acid, 0.5 g of para-toluenesulfonic acid, and 200 ml of toluene, followed by replacing the atmosphere with nitrogen, and then heating and refluxing for 10 hours while removing water produced with a Dean-Stark trap. After the reaction, the residue is washed with an aqueous potassium carbonate solution, washed with distilled water, and then purified by silica gel column chromatography to obtain 20 g of a compound (29) as an oily matter.

Figure 13:
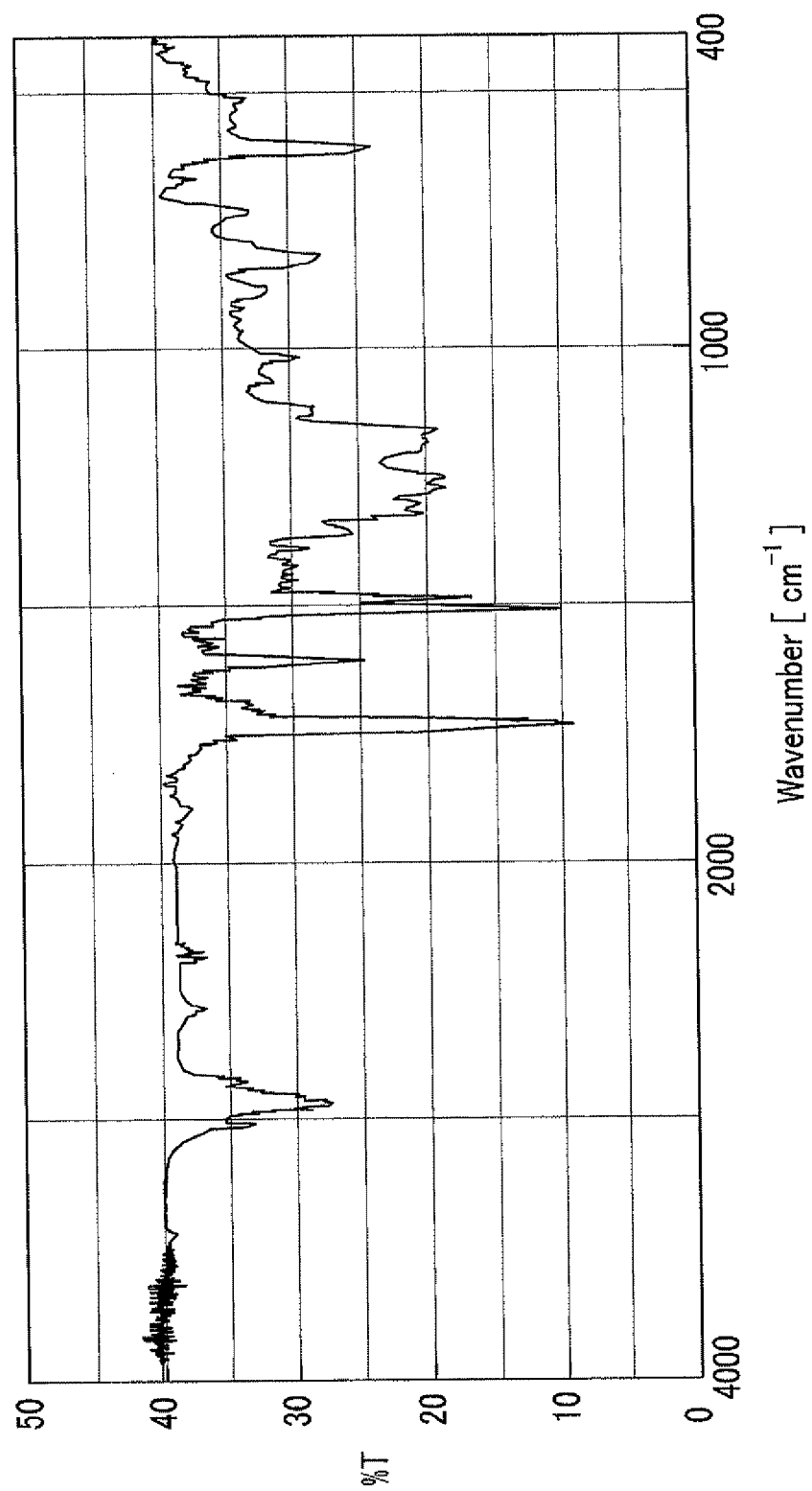
FIG. 13 is a graph showing an IR spectrum of a thiol group-containing charge transporting material synthesized in Examples.

The IR spectrum of the obtained compound (29) is shown in FIG. 13.

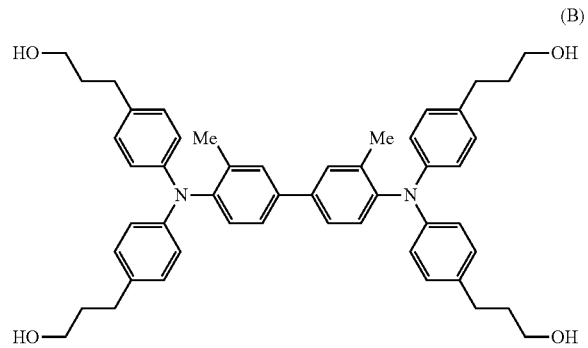 [SMILES: Cc1cc(-c2ccc(N(c3ccc(CCCO)cc3)c3ccc(CCCO)cc3)c(C)c2)ccc1N(c1ccc(CCCO)cc1)c1ccc(CCCO)cc1]

Example I-3

Synthesis of Compound (14)

To a 500-ml flask are put 20 g of a compound represented by the structural formula (A), 15 g of 2-mercaptopropionic acid, 0.5 g of para-toluenesulfonic acid, and 200 ml of toluene, followed by replacing the atmosphere with nitrogen, and then heating and refluxing for 10 hours while removing water produced with a Dean-Stark trap. After the reaction, the residue is washed with an aqueous potassium carbonate solution, washed with distilled water, and then purified by silica gel column chromatography to obtain 26 g of a compound (14) as an oily matter.

Figure 14:
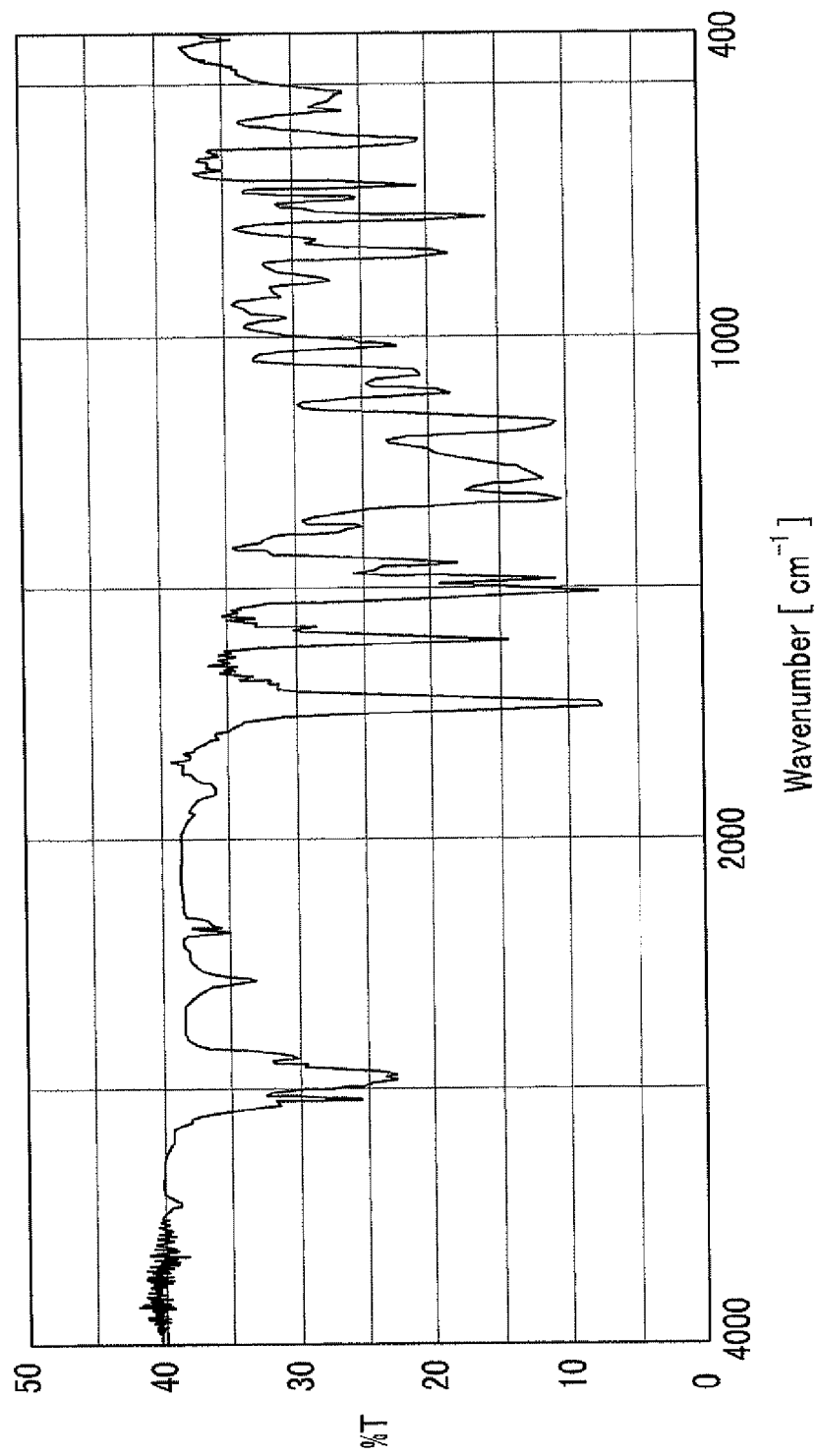
FIG. 14 is a graph showing an IR spectrum of a thiol group-containing charge transporting material synthesized in Examples.

The IR spectrum of the obtained compound (14) is shown in FIG. 14.

Example I-4

Preparation of Photoreceptor (Preparation of Undercoat Layer)

100 parts of zinc oxide (average particle diameter 70 nm: manufactured by Tayca Corporation: specific surface area value 15 m²/g) is stirred and mixed with 500 parts of tetrahydrofuran, and 1.3 parts of a silane coupling agent (KBM503: manufactured by Shin-Etsu Chemical Co., Ltd.) is added thereto, followed by stirring for 2 hours. Subsequently, toluene is evaporated by distillation under reduced pressure and baked at 120° C. for 3 hours to obtain zinc oxide having the surface treated with a silane coupling agent.

110 parts of the surface-treated zinc oxide is stirred and mixed with 500 parts of tetrahydrofuran, and a solution obtained by dissolving 1.0 part of alizarin in 50 parts of tetrahydrofuran is added thereto, followed by stirring at 50° C. for 5 hours. Thereafter, zinc oxide to which alizarin is added is separated by filtration under reduced pressure, and dried at 60° C. under reduced pressure to obtain alizarin-added zinc oxide.

38 parts of a solution obtained by dissolving 60 parts of the alizarin-added zinc oxide, 13.5 parts of a curing agent (blocked isocyanate, Sumidur 3175, manufactured by Sumitomo-Bayer Urethane Co., Ltd.), and 15 parts of a butyral resin (S-LEC BM-1, manufactured by Sekisui Chemical Co., Ltd.) in 85 parts of methyl ethyl ketone is mixed with 25 parts of methyl ethyl ketone, followed by performing dispersion with a sand mill using 1-mmϕ glass beads for 2 hours to obtain a dispersion.

To the obtained dispersion are added 0.005 part of dioctyltin dilaurate as a catalyst and 45 parts of silicon resin particles (Tospal 145, manufactured by GE Toshiba Silicone Co., Ltd.) to obtain a coating liquid for an undercoat layer. An undercoat layer having a thickness of 18 μm is obtained by applying the coating liquid on an aluminum substrate having a diameter of 30 mm, a length of 340 mm, and a thickness of 1 mm by a dip coating method, and drying to cure at a temperature of 170° C. for 40 minutes.

(Preparation of Charge Generating Layer)

A mixture comprising 15 parts of hydroxygallium phthalocyanine having diffraction peaks at least at 7.3°, 16.0°, 24.9°, and 28.0° of Bragg angles (2θ±0.2°) in an X-ray diffraction spectrum of Cukα X-rays as a charge generating substance, 10 parts of vinyl chloride-vinyl acetate copolymer resin (VMCH, manufactured by Nippon Unicar Co., Ltd.) as a binder resin, and 200 parts of n-butyl acetate is dispersed with a sand mill using 1-mmϕ glass beads for 4 hours. 175 parts of n-butyl acetate and 180 parts of methyl ethyl ketone are added to the obtained dispersion, followed by stirring, to obtain a coating liquid for a charge generating layer. The coating liquid for a charge generating layer is dip-coated to the undercoat layer, and dried at a normal temperature (20° C.) to form a charge generating layer having a film thickness of 0.2 μm.

(Preparation of Charge Transporting Layer)

40 parts of N,N'-diphenyl-N,N'-bis(3-methylphenyl)-[1,1']biphenyl-4,4'-diamine (TPD), 10 parts of N,N-bis(3,4-dimethylphenyl)biphenyl 4-amine, and 55 parts of a bisphenol Z polycarbonate resin (PC(Z): viscosity average molecular weight: 60,000) are dissolved in 800 parts of chlorobenzene to obtain a coating liquid for a charge transporting layer. The coating liquid is applied onto the charge generating layer, and dried at a temperature of 130° C. for 45 minutes to form a charge transporting layer having a film thickness of 15 μm.

(Preparation of Surface Layer)

10 parts of the compound (13), 10 parts of trimethylolpropane triacrylate (A-TMPT, manufactured by Shinnakamura Chemical Co., Ltd.), and 0.2 part of OTazo-15 (manufactured by Otsuka Chemical Co., Ltd., molecular weight 354.4) are dissolved in 30 parts of cyclopentanol and coated on the charge transporting layer by spraying coating. The coated layer is subjected to air drying at room temperature (20° C.) for 30 minutes, heating from room temperature (20° C.) to 150° C. at a rate of 10° C./minute under nitrogen with an oxygen concentration of 200 ppm, and a heating treatment at 150° C. for 1 hour to cure, thereby forming a protective layer having a film thickness of 10 μm, from which an electrophotographic photoreceptor of Example I-4 is prepared.

<Evaluation of Image Quality>

The electrophotographic photoreceptor as prepared above is mounted on an ApeosPort-III C4400 manufactured by Fuji Xerox Co., Ltd., and continuously subjected to the following evaluations under low temperature and low humidity (8° C., 20% RH), and high temperature and high humidity (30° C., 85% RH).

First, an image formation test is performed on 10000 sheets of plain paper (Paper P manufactured by Fuji Xerox Co., Ltd. (A4 size, cross-feed)) under a low temperature and low humidity environment (8° C., 20% RH), and the image quality (ghost, fog, streak, and image degradation below) of the 10000$^{th}$ sheet is evaluated. The image quality of the first sheet after standing for 24 hours under the low temperature and low humidity environment (8° C., 20% RH) for 24 hours is evaluated. The results are shown in Table I-2.

Subsequently to evaluation of the image quality under the low temperature and low humidity environment, an image formation test of 10000 sheets is performed under a high temperature and high humidity environment (30° C., 85% RH), and the image quality of the 10000$^{th}$ sheet is evaluated. Then, the image quality of the first sheet after standing for 24 hours under high temperature and high humidity (30° C., 85% RH) for 24 hours is evaluated. The results are shown in Table I-3.

(Evaluation of Ghost)

Figure 6:
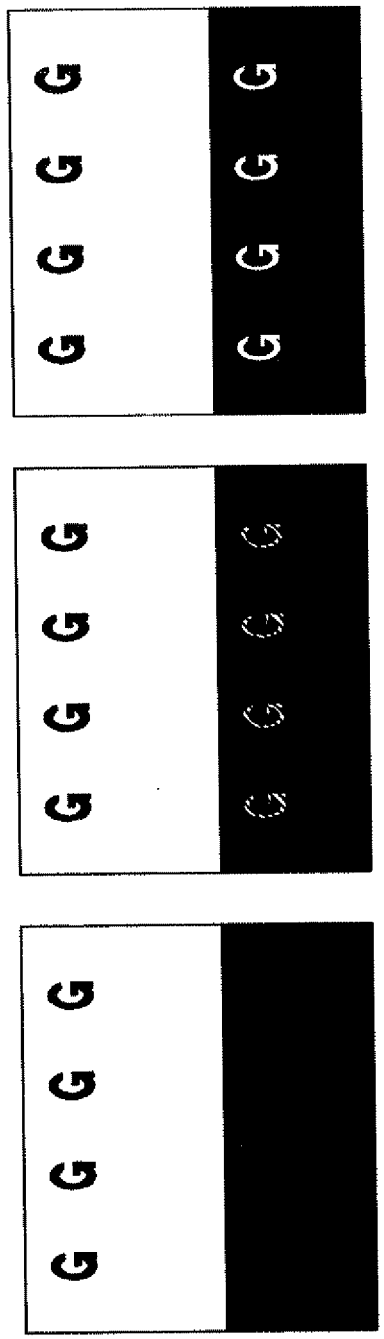
FIGS. 6A, 6B, and 6C are each an explanatory view showing the criteria for ghost evaluation.

A chart having a pattern of G's and a gray area having an image concentration of 50% shown in FIG. 6A is printed, and the state where the letters G appear in the gray area of 50% is evaluated by visual observation.

A: The degree is from good to slightly conspicuous as in FIG. 6A.
B: Slightly conspicuous as in FIG. 6B.
C: Clearly observed as in FIG. 6C.

(Evaluation of Fog)

The degree of toner adhesiveness to the white area is evaluated by visual observation using the same sample as in the evaluation of ghost.

A: Good.
B: Light fog is developed.
C: Fog having a damaging effect of image quality is developed.

(Evaluation of Streaks)

The streaks are evaluated by visual observation using the same sample as in the evaluation of ghost.

A: Good
B: Partial streaks are developed.
C: Streaks having a damaging effect on image quality are developed.

(Evaluation of Image Degradation)

The image degradation is evaluated by visual observation using the same sample as in the evaluation of ghost.

A: Good.
B: No problem occurred during the continuous printing test, but image degradation is developed after leaving the sample for one day (24 hours).
C: Image degradation is developed during the continuous printing test.

<Evaluation of Residual Potential>

By the following method, a residual potential is measured and an increment in the residual potential between before and after the print test is evaluated. A potential sensor is installed on an ApeosPort-III C4400 manufactured by Fuji Xerox Co., Ltd., and the residual potential on the surface of the electrophotographic photoreceptor before the print test under low temperature and low humidity (8° C., 20% RH) is measured. Next, immediately after the print test of 10000 sheets under low temperature and low humidity (8° C., 20% RH), the residual potential of the surface of the electrophotographic photoreceptor under low temperature and low humidity (8° C., 20% RH) is measured. The difference between the residual potential at an initial time and the residual potential after the print test of 10000 sheets (the residual potential after the print test of 10000 sheets—the residual potential at an initial time) is taken as an increment.

<Evaluation of Adhesiveness of Protective Layer>

The adhesiveness of the protective layer is evaluated by cutting the photoreceptor after the image forming test into 5×5 pieces in 2 mm-squares with a cutter knife, attaching the pieces with a 3 M mending tape, and then releasing them, and counting the number of the remaining pieces.

The results are shown in Table I-2.
A: 21 or more of the pieces remain.
B: 11 or more and 20 or less of the pieces remain.
C: 10 or less of the pieces remain.

<Evaluation of Abrasion Amount of Protective Layer>

The film thickness of the photoreceptor at an initial time and the film thickness after completion of the image forming test under a low temperature and low humidity (8° C., 20% RH) environment and under a high temperature and high humidity (30° C., 85% RH) environment are measured with an eddy current measurement device (Fischerscope MMS) and the abrasion amount is evaluated.

Example I-5

The preparation processes up to the charge transporting layer are conducted in the same manner as described in Example I-4.

(Preparation of Surface Layer)

10 parts of the compound (13), 10 parts of trimethylolpropane triacrylate (A-TMPT, manufactured by Shin Nakamura Chemical Co., Ltd.), and 0.5 part of 1-hydroxycyclohexyl phenyl ketone (Irgacure 184, manufactured by Ciba Specialty Chemicals Inc.) are dissolved in 30 parts of cyclopentanol and coated on the charge transporting layer by spraying coating. The coated layer is subjected to air drying at room temperature (20° C.) for 30 minutes, and then to light irradiation under nitrogen with an oxygen concentration of 200 ppm under the conditions of a metal halide lamp: 160 W/cm, an irradiation distance: 120 mm, an irradiation intensity: 500 mW/cm$^2$, and an irradiation time: 60 seconds to cure the coated film. The film is further dried at 130° C. for 20 minutes to form a surface layer having a film thickness of 5 μm, from which a photoreceptor of Example I-5 is prepared. Evaluation thereof is performed by the method described in Example I-4.

Example I-6

The preparation processes up to the charge transporting layer are conducted in the same manner as described in Example I-4.

(Preparation of Surface Layer)

10 parts of the compound (13) and 10 parts of trimethylolpropane triacrylate (A-TMPT, manufactured by Shin Nakamura Chemical Co., Ltd.) are dissolved in 30 parts of cyclopentanol and coated on the charge transporting layer by spraying coating. The coated layer is subjected to air drying at room temperature (20° C.) for 30 minutes, and then to electron beam irradiation while rotating the photoreceptor at a speed of 300 rpm under nitrogen with an oxygen concentration of 20 ppm under the conditions of an irradiation distance of 30 mm, an electron beam acceleration voltage of 90 kV, an electron beam current of 2 mA, and an electron beam irradiation time of 1.0 second. Immediately after the irradiation, a curing reaction is completed while performing heating at 150° C. under nitrogen with an oxygen concentration of 20 ppm and holding these conditions for 10 minutes to form a surface layer having a film thickness of 5 μm, from which a photoreceptor of Example I-6 is prepared. Evaluation thereof is performed by the method described in Example I-4.

Examples 1-7 to 1-18

By the same method as described in Example I-4 except that the compound (13) in Example I-4 is changed to those shown in Table I-1, photoreceptors are prepared, and evaluation thereof is performed.

Comparative Example I-1

The thickness of the charge transporting layer in Example I-4 is changed to 25 μm and the surface layer is not formed, thereby obtaining a photoreceptor of Comparative Example 1, and evaluation thereof is performed by the method described in Example I-4.

Comparative Example I-2

By the same method as described in Example I-4 except that the compound (13) in Example I-4 is changed to the compound (C) having the following structural formula, a photoreceptor is prepared, and evaluation thereof is performed.

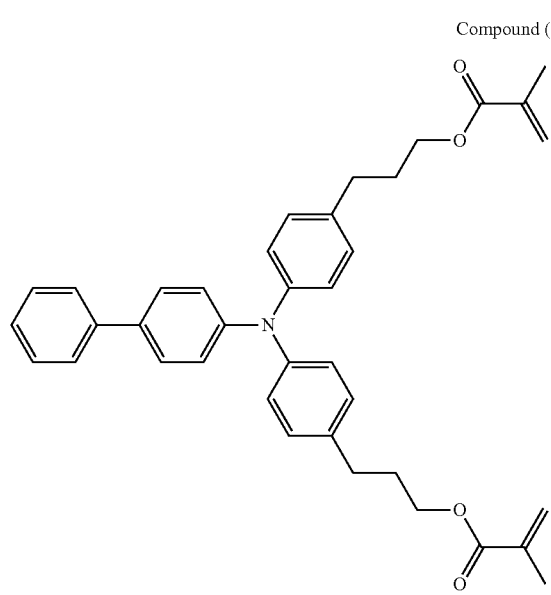

Compound (C)

TABLE I-1

| | Surface layer | | | |
|---|---|---|---|---|
| | Compound | Additive | Polymerization initiator | Film thickness [μm] |
| Example I-4 | (13) | Trimethylolpropane triacrylate | OTazo-15 | 10 |
| Example I-5 | (13) | Trimethylolpropane triacrylate | 1-Hydroxycyclohexyl phenyl ketone | 5 |
| Example I-6 | (13) | Trimethylolpropane triacrylate | — | 5 |
| Example I-7 | (14) | Trimethylolpropane triacrylate | OTazo-15 | 8 |
| Example I-8 | (29) | Trimethylolpropane triacrylate | OTazo-15 | 8 |
| Example I-9 | (4) | Trimethylolpropane triacrylate | OTazo-15 | 8 |
| Example I-10 | (6) | Trimethylolpropane triacrylate | OTazo-15 | 7 |
| Example I-11 | (9) | Trimethylolpropane triacrylate | OTazo-15 | 8 |
| Example I-12 | (10) | Trimethylolpropane triacrylate | OTazo-15 | 10 |
| Example I-13 | (17) | Trimethylolpropane triacrylate | OTazo-15 | 10 |
| Example I-14 | (31) | Trimethylolpropane triacrylate | OTazo-15 | 9 |
| Example I-15 | (36) | Trimethylolpropane triacrylate | OTazo-15 | 8 |
| Example I-16 | (46) | Trimethylolpropane triacrylate | OTazo-15 | 10 |
| Example I-17 | (53) | Trimethylolpropane triacrylate | OTazo-15 | 10 |
| Example I-18 | (51) | Trimethylolpropane triacrylate | OTazo-15 | 9 |
| Comparative Example I-1 | — | — | — | — |
| Comparative Example I-2 | (C) | Trimethylolpropane triacrylate | OTazo-15 | 10 |

TABLE I-2

| | | | Low temperature and low humidity (8° C., 20% RH) | | | | | | | |
|---|---|---|---|---|---|---|---|---|---|---|
| | | Abrasion amount [μm] | After test of 10000 sheets under low temperature and low humidity | | | | After standing under low temperature and low humidity for 24 hours | | | Increment [V] in residual potential |
| | Adhesiveness | | Ghost | Fog | Streak | Image degradation | Ghost | Fog | Streak | Image degradation | |
| Example I-4 | A | 0.60 | A | A | A | A | A | A | A | A | −13 |
| Example I-5 | A | 0.61 | A | A | A | A | A | A | A | A | −10 |
| Example I-6 | A | 0.67 | A | A | A | A | A | A | A | A | −15 |
| Example I-7 | A | 0.58 | A | A | A | A | A | A | A | A | −19 |
| Example I-8 | A | 0.34 | A | A | A | A | A | A | A | A | −13 |
| Example I-9 | A | 0.81 | A | A | A | A | A | A | A | A | −16 |
| Example I-10 | A | 0.88 | A | A | A | A | A | A | A | A | −9 |
| Example I-11 | A | 0.59 | A | A | A | A | A | A | A | A | −24 |
| Example I-12 | A | 0.68 | A | A | A | A | A | A | A | A | −23 |
| Example I-13 | A | 0.61 | A | A | A | A | A | A | A | A | −12 |
| Example I-14 | A | 0.39 | A | A | A | A | A | A | A | A | −17 |
| Example I-15 | A | 0.42 | A | A | A | A | A | A | A | A | −12 |
| Example I-16 | A | 0.67 | A | A | A | A | A | A | A | A | −17 |
| Example I-17 | A | 0.39 | A | A | A | A | A | A | A | A | −10 |
| Example I-18 | A | 0.42 | A | A | A | A | A | A | A | A | −15 |
| Comparative Example I-1 | — | 3.1 | A | A | B | A | A | B | B | A | −16 |
| Comparative Example I-2 | A | 0.41 | B | B | B | A | A | A | B | A | −56 |

TABLE I-3

| | High temperature and high humidity (30° C., 85% RH) | | | | | | | |
|---|---|---|---|---|---|---|---|---|
| | After test of 10000 sheets under high temperature and high humidity | | | | After standing under high temperature and high humidity | | | |
| | Ghost | Fog | Streak | Image degradation | Ghost | Fog | Streak | Image degradation |
| Example I-4 | A | A | A | A | A | A | A | A |
| Example I-5 | A | A | A | A | A | A | A | A |
| Example I-6 | A | A | A | A | A | A | A | A |
| Example I-7 | A | A | A | A | A | A | A | A |
| Example I-8 | A | A | A | A | A | A | A | A |
| Example I-9 | A | A | B | A | A | A | B | A |
| Example I-10 | A | A | B | A | A | A | B | A |
| Example I-11 | A | A | A | A | A | A | A | A |
| Example I-12 | A | A | A | A | A | A | A | A |
| Example I-13 | A | A | A | A | A | A | A | A |
| Example I-14 | A | A | A | A | A | A | A | A |
| Example I-15 | A | A | A | A | A | A | A | A |
| Example I-16 | A | A | A | A | A | A | A | B |
| Example I-17 | A | A | A | A | A | A | A | B |
| Example I-18 | A | A | B | A | A | A | B | A |
| Comparative Example I-1 | A | A | B | A | A | A | B | A |
| Comparative Example I-2 | B | A | B | B | A | A | B | B |

As shown in Tables I-2 and I-3, with the electrophotographic photoreceptors of Examples, decrease in the image quality after the repeated use over a long period of time is inhibited.

Example I-19

Preparation of Organic EL Element

A glass substrate provided with an ITO film having a thickness of 150 nm is washed with oxygen plasma using a plasma washer (manufactured by Samco International Lab., BP1) for 30 seconds.

A solution obtained by dissolving 10 parts of the compound (13), 5 parts of trimethylolpropane triacrylate (A-TMPT, manufactured by Shin Nakamura Chemical Co., Ltd.), and 0.2 part of OTazo-15 (manufactured by Otsuka Chemical Co., Ltd., molecular weight 354.4) in 50 parts of chloromethane is spin-coated at a rotational speed of 300 rpm and then heated under nitrogen with an oxygen concentration of 150 ppm at 160° C. for 1 hour to cure, thereby forming a hole injecting layer having a film thickness of 600 nm (measured by a stylus film thickness profiler).

Next, tris(8-hydroxyquinoline) aluminum (Alq) is vacuum-deposited as a material for a light-emitting layer on the hole injecting layer to a thickness of 50 nm, and then a magnesium/silver alloy cathode is deposited thereon to a thickness of 200 nm to prepare an organic EL element.
<Evaluation>
The ITO electrode of the organic EL element is used as an anode, the magnesium/silver alloy electrode is used as a cathode, a direct current at 7 V is applied, and the current density is determined by the following method. At the same time, the luminance is measured by the following method. In addition, the luminance after working for 1000 hours is measured by the following method and the results are shown in Table I-4.

Furthermore, the current density, the voltage, and the luminance are measured using an organic EL light-emitting efficiency measurement device (manufactured by Tokyo Instruments, Inc.) as a measurement device under the measurement condition adjusted to 25° C.

Furthermore, the organic EL element requires high current injection, when used for a display or laser, and thus, the current density and the luminance are measured at an applied voltage of 7 V, and further, the luminance after driving for 1000 hours at an applied voltage of 7 V is measured.

Examples I-20 to I-28

By the same method as described in Example I-19 except that the compound (13) is changed to the compound shown in Table I-4, an organic EL element is measured and evaluation thereof is performed. The results are shown in Table I-4.

Comparative Example I-3

By the same method as described in Example I-19 except that a hole injecting layer in which N,N'-diphenyl-N,N'-bis(3-methylphenyl)-[1,1']biphenyl-4,4'-diamine (TPD) is vacuum-deposited to a film thickness of 600 nm is applied instead of the hole injecting layer formed using the compound (13) in Example I-19, an organic EL element is measured and evaluation thereof is performed. The results are shown in Table I-4.

TABLE I-4

| | Compound | Applied voltage [V] | Current density [mA/cm$^2$] | Luminance [cd/m$^2$] | Luminance after working for 1000 hours [cd/m$^2$] |
|---|---|---|---|---|---|
| Example I-19 | (13) | 7 | 80 | 405 | 330 |
| Example I-20 | (14) | 7 | 85 | 400 | 320 |
| Example I-21 | (4) | 7 | 85 | 400 | 320 |
| Example I-22 | (9) | 7 | 90 | 405 | 320 |
| Example I-23 | (10) | 7 | 90 | 410 | 340 |
| Example I-24 | (17) | 7 | 90 | 410 | 330 |
| Example I-25 | (16) | 7 | 95 | 430 | 380 |
| Example I-26 | (28) | 7 | 90 | 420 | 340 |
| Example I-27 | (47) | 7 | 90 | 420 | 350 |
| Example I-28 | (50) | 7 | 90 | 410 | 360 |
| Comparative Example I-3 | TPD | 7 | 90 | 450 | 210 |

As shown in Table I-4, from the organic EL elements of Examples, light-emitting characteristics which have stability over a long period of time are obtained.

<Preparation of Photoreceptor>

Subsequently, the method for preparing each of the layers in the photoreceptor will be described.

(Preparation of Undercoat Layer)

[Undercoat Layer 1]

100 parts of zinc oxide (average particle diameter 70 nm: manufactured by Tayca Corporation: specific surface area value 15 m$^2$/g) is stirred and mixed with 500 parts of tetrahydrofuran, and 1.3 parts of a silane coupling agent (KBM503: manufactured by Shin-Etsu Chemical Co., Ltd.) is added thereto, followed by stirring for 2 hours. Subsequently, toluene is evaporated by distillation under reduced pressure and baked at 120° C. for 3 hours to obtain zinc oxide having the surface treated with a silane coupling agent.

110 parts of the surface-treated zinc oxide is stirred and mixed with 500 parts of tetrahydrofuran, and a solution obtained by dissolving 1.0 part of alizarin in 50 parts of tetrahydrofuran is added thereto, followed by stirring at 50° C. for 5 hours. Thereafter, zinc oxide to which alizarin is added is separated by filtration under reduced pressure, and dried at 60° C. under reduced pressure to obtain alizarin-added zinc oxide.

38 parts of a solution obtained by dissolving 60 parts of the alizarin-added zinc oxide, 13.5 parts of a curing agent (blocked isocyanate, Sumidur 3175, manufactured by Sumitomo-Bayer Urethane Co., Ltd.), and 15 parts of a butyral resin (S-Lec BM-1, manufactured by Sekisui Chemical Co., Ltd.) in 85 parts of methyl ethyl ketone is mixed with 25 parts of methyl ethyl ketone, followed by performing dispersion with a sand mill using 1-mmφ glass beads for 2 hours to obtain a dispersion.

To the obtained dispersion are added 0.005 parts of dioctyltin dilaurate as a catalyst and 45 parts of silicon resin particles (Tospal 145, manufactured by GE Toshiba Silicone Co., Ltd.) to obtain a coating liquid for an undercoat layer. An undercoat layer having a thickness of 18 μm is obtained by applying the coating liquid on an aluminum substrate having a diameter of 30 mm, a length of 340 mm, and a thickness of 1 mm by a dip coating method, and drying to cure at a temperature of 170° C. for 40 minutes. The surface roughness (centerline average roughness) Ra of the outer surface of the formed undercoat layer is 0.3 μm.

[Undercoat Layer 2]

By the same method as described for the undercoat layer 1 except that 45 parts of the silicone resin particles (Tospal 145, manufactured by GE Toshiba Silicone Co., Ltd.) are not added, an undercoat layer 2 is formed. The surface roughness (centerline average roughness) Ra of the outer surface of the formed undercoat layer is 0.1 μm.

[Undercoat Layer 3]

A coating liquid formed of 10 parts of an organozirconium compound (trade name: Organotex ZC540, manufactured by Matsumoto Fine Chemical Co., Ltd.), 2 parts of a silane coupling agent (trade name: A1110, manufactured by Nippon Unicar Co., Ltd.), 30 parts of isopropylalcohol, and 30 parts of n-butanol is coated on an aluminum substrate having a diameter of 30 mm, a length of 340 mm, and a thickness of 1 mm by a dip coating method, and heated and dried at 150° C. for 5 minutes to form an undercoat layer having a film thickness of 0.1 μm. The surface roughness (centerline average roughness) Ra of the outer surface of the formed undercoat layer is 0.05 μm.

(Preparation of Charge Generating Layer)

[Charge Generating Layer 1]

A mixture comprising 15 parts of hydroxygallium phthalocyanine having diffraction peaks at least at 7.3°, 16.0°, 24.9°, and 28.0° of Bragg angles (2θ±0.2°) in an X-ray diffraction spectrum of CuKα X-rays as a charge generating substance, 10 parts of vinyl chloride-vinyl acetate copolymer resin (VMCH, manufactured by Nippon Unicar Co., Ltd.) as a binder resin, and 200 parts of n-butyl acetate is dispersed with a sand mill using 1-mmφ glass beads for 4 hours. 175 parts of n-butyl acetate and 180 parts of methyl ethyl ketone are added to the obtained dispersion, followed by stirring, to obtain a coating liquid for a charge generating layer. The coating liquid for a charge generating layer is dip-coated to the undercoat layer, and dried at 100° C. for 5 minutes to form a charge generating layer having a film thickness of 0.2 μm.

[Charge Generating Layer 2]

45 g of a sublimation-purified dibromoanthanthrone pigment (CG-25: manufactured by Clariant GmbH, n-type organic pigment) is put into a container having a capacity of 0.25 L, made of agate, together with 12 20-mmφ agate balls, and ground with a planetary ball mill (Fritsch P-5). Grinding is performed under a grinding condition of a disc rotational speed (revolution) of 235 rpm and a pot rotational speed (rotation) of 50 rpm for 8 hours. 10 parts of a dibromoanthanthrone pigment, 5 parts of a vinyl chloride/vinyl acetate copolymer resin (VMCH, manufactured by Nippon Unicar Co., Ltd.), and 100 parts of cyclohexanone are mixed, and dispersed with a sand mill using 1-mmφ glass beads for 4 hours. 300 parts of cyclohexanone is added to the obtained dispersion, followed by stirring, to obtain a coating liquid for a charge generating layer. The coating liquid for a charge generating layer is dip-coated to the undercoat layer, and dried at 100° C. for 5 minutes to form a charge generating layer having a film thickness of 0.5 μm.

[Charge Generating Layer 3]

A sublimation-purified dibromoanthanthrone pigment (CG-25: manufactured by Clariant GmbH, n-type organic pigment) is deposited to a film thickness of 0.1 μm by a Varian Model 3117 vacuum coater to form a charge generating layer on the undercoat layer. Further, the CG-25 is heated at 350° C. in a tantalum boat, and the pressure of the vacuum coater is reduced to 10$^{-3}$ Pas. In addition, the substrate is placed at a position of 16 cm form the boat and the photoexcited layer is attached at a rate of 6 angstroms/second.

[Charge Generating Layer 4]

A bisbenzimidazole perylene pigment (CG-19: manufactured by Fuji Xerox Co., Ltd., n-type organic pigment) is sublimation-purified. 10 g of the bisbenzimidazole perylene pigment after the sublimation-purified is ground using a planetary ball mill (using forty-four 20 mmφ agate balls, and three 25-mmφ agate balls with an inner diameter of the agate pot of 10 mmφ) for 27 hours. The obtained micronized bisbenzimidazole perylene pigment shows strong peaks at 6.2°, 12.3°, and 27.0° in an X-ray diffraction spectrum, and the particle diameter is 0.04 μm×0.08 μm to 0.05 μm×0.1 μm. 10 parts of the bisbenzimidazole perylene pigment, 5 parts of a vinyl chloride/vinyl acetate copolymer resin (VMCH, manufactured by Nippon Unicar Co., Ltd.), and 100 parts of cyclohexanone are mixed, and dispersed with a sand mill using 1-mmφ glass beads for 4 hours. 300 parts of cyclohexanone is added to the obtained dispersion, followed by stirring, to obtain a coating liquid for a charge generating layer. The coating liquid for a charge generating layer is dip-coated to the undercoat layer, and dried at 1000° C. for 5 minutes to form a charge generating layer having a film thickness of 0.5 μm.

[Charge Generating Layer 5]

A sublimation-purified bisbenzimidazole perylene pigment (CG-19: manufactured by Fuji Xerox Co., Ltd., n-type organic pigment) is deposited to a film thickness of 0.1 μm by a Varian Model 3117 vacuum coater to form a charge generating layer on the undercoat layer. Further, the CG-19 is heated at 350° C. in a tantalum boat, and the pressure of the vacuum coater is reduced to $10^{-3}$ Pas. In addition, the substrate is placed at a position of 16 cm form the boat and the photoexcited layer is attached at a rate of 4 angstroms/second.

[Charge Generating Layer 6]

10 parts of a bisazo pigment (CG-4: manufactured by Fuji Xerox Co., Ltd., n-type organic pigment), 5 parts of a vinyl chloride/vinyl acetate copolymer resin (VMCH, manufactured by Nippon Unicar Co., Ltd.), and 100 parts of cyclohexanone are mixed, and dispersed with a sand mill using 1-mmϕ glass beads for 4 hours. 300 parts of cyclohexanone is added to the obtained dispersion, followed by stirring, to obtain a coating liquid for a charge generating layer. The coating liquid for a charge generating layer is dip-coated to the undercoat layer, and dried at 100° C. for 5 minutes to form a charge generating layer having a film thickness of 0.5 μm.

[Charge Generating Layer 7]

10 parts of a bisazo pigment (CG-8: manufactured by Fuji Xerox Co., Ltd., n-type organic pigment), 5 parts of a vinyl chloride/vinyl acetate copolymer resin (VMCH, manufactured by Nippon Unicar Co., Ltd.), and 100 parts of cyclohexanone are mixed, and dispersed with a sand mill using 1-mmϕ glass beads for 4 hours. 300 parts of cyclohexanone is added to the obtained dispersion, followed by stirring, to obtain a coating liquid for a charge generating layer. The coating liquid for a charge generating layer is dip-coated to the undercoat layer, and dried at 100° C. for 5 minutes to form a charge generating layer having a film thickness of 0.5 μm.

[Charge Generating Layer 8]

10 parts of a bisazo pigment (CG-11: manufactured by Fuji Xerox Co., Ltd., n-type organic pigment), 5 parts of a vinyl chloride/vinyl acetate copolymer resin (VMCH, manufactured by Nippon Unicar Co., Ltd.), and 100 parts of cyclohexanone are mixed, and dispersed with a sand mill using 1-mmϕ glass beads for 4 hours. 300 parts of cyclohexanone is added to the obtained dispersion, followed by stirring, to obtain a coating liquid for a charge generating layer. The coating liquid for a charge generating layer is dip-coated to the undercoat layer, and dried at 100° C. for 5 minutes to form a charge generating layer having a film thickness of 0.5 μm.

(Preparation of Charge Transporting Layer)

[Charge Transporting Layer 1]

40 parts of N,N'-diphenyl-N,N'-bis(3-methylphenyl)-[1,1']biphenyl-4,4'-diamine(TPD), 10 parts of N,N-bis(3,4-dimethylphenyl)biphenyl-4-amine, and 55 parts of a bisphenol Z polycarbonate resin (PC(Z): viscosity average molecular weight: 60,000) are added to 800 parts of chlorobenzene and dissolved therein to obtain a coating liquid for a charge transporting layer. This coating liquid is coated on the charge generating layer and dried at 130° C. for 45 minutes to form a charge transporting layer having a film thickness of 15 μm.

[Charge Transporting Layer 2]

By the method as described for the charge transporting layer 1 except that the amount of N,N'-diphenyl-N,N'-bis(3-methylphenyl)-[1,1']biphenyl-4,4'-diamine (TPD) is set to 25 parts and the amount of the charge transporting material of the following structural formula (C) is set to 20 parts, a charge transporting layer 2 is formed.

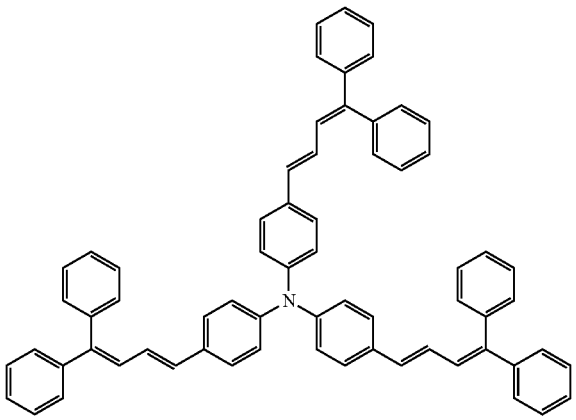

(C)

(Preparation of Surface Layer)

[Curing Method: Thermal Curing]

10 parts of the compound (13) (thiol group-containing charge transporting material), 12 parts of trimethylolpropane triacrylate (A-TMPT, manufactured by Shinnakamura Chemical Co., Ltd., compound having an unsaturated bond), and 0.2 part of OTazo-15 (manufactured by Otsuka Chemical Co., Ltd., molecular weight 354.4, polymerization initiator) are dissolved in 30 parts of cyclopentanol and coated on the charge transporting layer by spraying coating. The coated layer is subjected to air drying at room temperature (20° C.) for 30 minutes, heating from room temperature (20° C.) to 150° C. at a rate of 10° C./minute under nitrogen with an oxygen concentration of 200 ppm, and then a heating treatment at 150° C. for 1 hour to cure, thereby forming a surface layer having a film thickness of 5 μm.

In addition, in the case of thermal curing, the types and the ratios of the materials are changed to the numerical values shown in Tables II-1 to II-5, and then curing is performed under these conditions.

[Curing Method: Photocuring]

10 parts of the compound (13) (thiol group-containing charge transporting material), 12 parts of trimethylolpropane triacrylate (A-TMPT, manufactured by Shinnakamura Chemical Co., Ltd., compound having an unsaturated bond), and 0.5 part of 1-hydroxycyclohexyl phenyl ketone (Irgacure 184, manufactured by Ciba Specialty Chemicals Inc., polymerization initiator) are dissolved in 30 parts of cyclopentanol and coated on the charge transporting layer by spraying coating. The coated layer is subjected to air drying at room temperature (20° C.) for 30 minutes, and then to light irradiation under nitrogen with an oxygen concentration of 200 ppm under the conditions of a metal halide lamp: 160 W/cm, an irradiation distance: 120 mm, an irradiation intensity: 500 mW/cm$^2$, and an irradiation time: 60 seconds to cure the coated film. The film is further dried at 130° C. for 20 minutes to form a surface layer having a film thickness of 5 μm. In addition, in the case of photocuring, the types and the ratios of the materials are changed to the numerical values shown in Table II-1, and then curing is performed under these conditions.

[Curing Method: Electron Beam Curing]

10 parts of the compound (13) (thiol group-containing charge transporting material) and 12 parts of trimethylolpropane triacrylate (A-TMPT, manufactured by Shinnakamura Chemical Co., Ltd., compound having an unsaturated bond) are dissolved in 30 parts of cyclopentanol and coated on the charge transporting layer by Tsukiage coating. The coated layer is subjected to air drying at room temperature (20° C.) for 30 minutes, and then to electron beam irradiation while rotating the photoreceptor at a speed of 300 rpm under nitrogen with an oxygen concentration of 20 ppm under the conditions of an irradiation distance of 30 mm, an electron beam acceleration voltage of 90 kV, an electron beam current of 2 mA, and an electron beam irradiation time of 1.0 second. Immediately after the irradiation, a curing reaction is completed while performing heating at 150° C. under nitrogen with an oxygen concentration of 20 ppm and holding these conditions for 10 minutes to form a surface layer having a film thickness of 5 μm.

In addition, in the case of thermal curing, the types and the ratios of the materials are changed to the numerical values shown in Tables II-1 and II-2, and then curing is performed under these conditions.

[Preparation of Photoreceptors 1 to 35]

By using the undercoat layers, the charge generating layers, and the charge transporting layers to be applied as described in Tables II-1 and II-2, and further using the types and ratios of the materials used for formation of the surface layers (thiol group-containing charge transporting materials, compounds having an unsaturated bond, additives, and polymerization initiators), and the methods for curing the surface layer as described in Tables II-1 and II-2, Photoreceptors 1 to 35 are prepared.

[Preparation of Photoreceptors 36 to 57]

By using the undercoat layers and the charge generating layers to be applied as described in Table II-3 without forming the charge transporting layers, and further using the types and ratios of the materials used for formation of the surface layers (thiol group-containing charge transporting materials, compounds having an unsaturated bond, additives, and polymerization initiators), and the methods for curing the surface layer as described in Table II-3, Photoreceptors 36 to 57 are prepared.

Furthermore, the film thickness of the surface layer is 18 μm.

[Preparation of Comparative Photoreceptors 1 to 13]

By using the undercoat layers, the charge generating layers, and the charge transporting layers to be applied as described in Table II-4, and further using the types and ratios of the materials used for formation of the surface layers (compounds having an unsaturated bond, additives, and polymerization initiators), and the methods for curing the surface layer as described in Table II-4, comparative Photoreceptors 1 to 13 are prepared.

[Preparation of Comparative Photoreceptors 14 to 26]

By using the undercoat layers and the charge generating layers to be applied as described in Table II-5 without forming the charge transporting layers, and further using the types and ratios of the materials used for formation of the surface layers (compounds having an unsaturated bond, additives, and polymerization initiators), and the methods for curing the surface layer as described in Table II-5, comparative Photoreceptors 14 to 26 are prepared.

TABLE II-1

| Photoreceptor | Undercoat layer | Charge generating layer | Charge transporting layer | Protective layer |||||||
|---|---|---|---|---|---|---|---|---|---|---|
| | | | | Thiol group-containing charge transporting material || Compound having unsaturated bond || Additive || Polymerization initiator || Curing method |
| Photoreceptor 1 | 1 | 1 | 1 | Compound (13) | 10 parts | A-TMPT | 12 parts | — | | OTazo-15 | 0.2 part | Thermal curing |
| Photoreceptor 2 | 1 | 1 | 1 | Compound (13) | 10 parts | A-TMPT | 12 parts | PTFE | 1 part | OTazo-15 | 0.2 part | Thermal curing |
| Photoreceptor 3 | 1 | 1 | 1 | Compound (13) | 10 parts | A-TMPT | 12 parts | — | | Irgacure 184 | 0.5 part | Photocuring |
| Photoreceptor 4 | 1 | 1 | 1 | Compound (13) | 10 parts | A-TMPT | 12 parts | PTFE | 1 part | Irgacure 184 | 0.5 part | Photocuring |
| Photoreceptor 5 | 1 | 1 | 1 | Compound (13) | 10 parts | A-TMPT | 12 parts | — | | — | | Electron beam curing |
| Photoreceptor 6 | 1 | 1 | 1 | Compound (13) | 10 parts | A-TMPT | 12 parts | PTFE | 1 part | — | | Electron beam curing |
| Photoreceptor 7 | 2 | 1 | 1 | Compound (13) | 10 parts | A-TMPT | 12 parts | — | | OTazo-15 | 0.2 part | Thermal curing |
| Photoreceptor 8 | 2 | 1 | 1 | Compound (13) | 10 parts | A-TMPT | 12 parts | PTFE | 1 part | OTazo-15 | 0.2 part | Thermal curing |
| Photoreceptor 9 | 3 | 1 | 1 | Compound (13) | 10 parts | A-TMPT | 12 parts | — | | OTazo-15 | 0.2 part | Thermal curing |
| Photoreceptor 10 | 3 | 1 | 1 | Compound (13) | 10 parts | A-TMPT | 12 parts | PTFE | 1 part | OTazo-15 | 0.2 part | Thermal curing |
| Photoreceptor 11 | 1 | 1 | 1 | Compound (14) | 10 parts | A-TMPT | 12 parts | — | | OTazo-15 | 0.2 part | Thermal curing |
| Photoreceptor 12 | 1 | 1 | 1 | Compound (17) | 10 parts | ii-8 | 25 parts | PTFE | 2 parts | OTazo-15 | 0.2 part | Thermal curing |
| Photoreceptor 13 | 1 | 1 | 1 | Compound (29) | 10 parts | ii-29 | 25 parts | PTFE | 2 parts | OTazo-15 | 0.2 part | Thermal curing |
| Photoreceptor 14 | 1 | 1 | 1 | Compound (34) | 10 parts | iii-14 | 25 parts | PTFE | 2 parts | OTazo-15 | 0.2 part | Thermal curing |
| Photoreceptor 15 | 1 | 1 | 1 | Compound (36) | 10 parts | iv-9 | 25 parts | PTFE | 2 parts | OTazo-15 | 0.2 part | Thermal curing |
| Photoreceptor 16 | 1 | 1 | 1 | Compound (41) | 10 parts | iv-14 | 25 parts | PTFE | 2 parts | OTazo-15 | 0.2 part | Thermal curing |
| Photoreceptor 17 | 1 | 1 | 1 | Compound (43) | 10 parts | iv-28 | 25 parts | PTFE | 2 parts | OTazo-15 | 0.2 part | Thermal curing |
| Photoreceptor 18 | 1 | 1 | 1 | Compound (62) | 10 parts | iv-34 | 25 parts | PTFE | 2 parts | OTazo-15 | 0.2 part | Thermal curing |
| Photoreceptor 19 | 1 | 1 | 2 | Compound (36) | 10 parts | iv-9 | 25 parts | PTFE | 2 parts | OTazo-15 | 0.2 part | Thermal curing |

TABLE II-2

| Photoreceptor | Under-coat layer | Charge generating layer | Charge transporting layer | Protective layer |||||| Curing method |
| --- | --- | --- | --- | --- | --- | --- | --- | --- | --- | --- |
| | | | | Thiol group-containing charge transporting material || Compound having unsaturated bond || Additive || Polymerization initiator || |
| Photoreceptor 20 | 2 | 2 | 2 | Compound (13) | 10 parts | A-TMPT<br>i-7 | 12 parts<br>5 parts | — | | — | Electron beam curing |
| Photoreceptor 21 | 2 | 2 | 2 | Compound (13) | 10 parts | iv-2<br>i-7 | 12 parts<br>5 parts | PTFE | 1 part | — | Electron beam curing |
| Photoreceptor 22 | 3 | 2 | 1 | Compound (29) | 5 parts | ii-28 | 25 parts | — | | OTazo-15 0.2 part | Thermal curing |
| Photoreceptor 23 | 3 | 2 | 1 | Compound (41) | 5 parts | iv-28 | 25 parts | PTFE | 1 part | OTazo-15 0.2 part | Thermal curing |
| Photoreceptor 24 | 2 | 3 | 2 | Compound (29) | 5 parts | iv-9 | 25 parts | PTFE | 1 part | OTazo-15 0.2 part | Thermal curing |
| Photoreceptor 25 | 3 | 3 | 2 | Compound (13) | 10 parts | A-TMPT | 12 parts | PTFE | 1 part | OTazo-15 0.2 part | Thermal curing |
| Photoreceptor 26 | 2 | 4 | 2 | Compound (13) | 10 parts | A-TMPT | 10 parts | PTFE | 1 part | OTazo-15 0.2 part | Thermal curing |
| Photoreceptor 27 | 3 | 4 | 2 | Compound (34) | 5 parts | ii-28 | 25 parts | PTFE | 1 part | OTazo-15 0.2 part | Thermal curing |
| Photoreceptor 28 | 2 | 5 | 2 | Compound (29) | 5 parts | ii-6 | 25 parts | PTFE | 1 part | OTazo-15 0.2 part | Thermal curing |
| Photoreceptor 29 | 3 | 5 | 2 | Compound (29) | 5 parts | ii-15 | 25 parts | PTFE | 1 part | OTazo-15 0.2 part | Thermal curing |
| Photoreceptor 30 | 2 | 6 | 2 | Compound (13) | 10 parts | iv-34 | 25 parts | PTFE | 1 part | OTazo-15 0.2 part | Thermal curing |
| Photoreceptor 31 | 3 | 6 | 2 | Compound (13) | 10 parts | ii-59 | 25 parts | PTFE | 1 part | OTazo-15 0.2 part | Thermal curing |
| Photoreceptor 32 | 2 | 7 | 2 | Compound (34) | 5 parts | iv-14 | 25 parts | PTFE | 1 part | OTazo-15 0.2 part | Thermal curing |
| Photoreceptor 33 | 3 | 7 | 2 | Compound (34) | 5 parts | iv-14<br>i-15 | 12 parts<br>5 parts | PTFE | 1 part | OTazo-15 0.2 part | Thermal curing |
| Photoreceptor 34 | 2 | 8 | 2 | Compound (17) | 10 parts | iv-47 | 25 parts | PTFE | 1 part | OTazo-15 0.2 part | Thermal curing |
| Photoreceptor 35 | 3 | 8 | 2 | Compound (29) | 5 parts | ii-57 | 25 parts | PTFE | 1 part | OTazo-15 0.2 part | Thermal curing |

TABLE II-3

| Photoreceptor | Under-coat layer | Charge generating layer | Charge transporting layer | Protective layer |||||| Curing method |
| --- | --- | --- | --- | --- | --- | --- | --- | --- | --- | --- |
| | | | | Thiol group-containing charge transporting material || Compound having unsaturated bond || Additive || Polymerization initiator || |
| Photoreceptor 36 | 1 | 1 | — | Compound (13) | 10 parts | A-TMPT | 12 parts | — | | OTazo-15 0.2 part | Thermal curing |
| Photoreceptor 37 | 1 | 1 | — | Compound (13) | 10 parts | A-TMPT | 12 parts | PTFE | 1 part | OTazo-15 0.2 part | Thermal curing |
| Photoreceptor 38 | 1 | 1 | — | Compound (29) | 10 parts | ii-29 | 25 parts | PTFE | 2 parts | OTazo-15 0.2 part | Thermal curing |
| Photoreceptor 39 | 1 | 1 | — | Compound (36) | 10 parts | iv-9 | 25 parts | PTFE | 2 parts | OTazo-15 0.2 part | Thermal curing |
| Photoreceptor 40 | 1 | 1 | — | Compound (41) | 10 parts | iv-14 | 25 parts | PTFE | 2 parts | OTazo-15 0.2 part | Thermal curing |
| Photoreceptor 41 | 1 | 1 | — | Compound (43) | 10 parts | iv-28 | 25 parts | PTFE | 2 parts | OTazo-15 0.2 part | Thermal curing |
| Photoreceptor 42 | 1 | 1 | — | Compound (62) | 10 parts | iv-34 | 25 parts | PTFE | 2 parts | OTazo-15 0.2 part | Thermal curing |
| Photoreceptor 43 | 1 | 1 | — | Compound (36) | 10 parts | iv-9 | 25 parts | PTFE | 2 parts | OTazo-15 0.2 part | Thermal curing |
| Photoreceptor 44 | 3 | 2 | — | Compound (29) | 5 parts | ii-28 | 25 parts | — | | OTazo-15 0.2 part | Thermal curing |
| Photoreceptor 45 | 3 | 2 | — | Compound (41) | 5 parts | iv-28 | 25 parts | PTFE | 1 part | OTazo-15 0.2 part | Thermal curing |
| Photoreceptor 46 | 2 | 3 | — | Compound (29) | 5 parts | iv-9 | 25 parts | PTFE | 1 part | OTazo-15 0.2 part | Thermal curing |
| Photoreceptor 47 | 3 | 3 | — | Compound (13) | 10 parts | A-TMPT | 12 parts | PTFE | 1 part | OTazo-15 0.2 part | Thermal curing |
| Photoreceptor 48 | 2 | 4 | — | Compound (13) | 10 parts | A-TMPT | 10 parts | PTFE | 1 part | OTazo-15 0.2 part | Thermal curing |
| Photoreceptor 49 | 3 | 4 | — | Compound (34) | 5 parts | ii-28 | 25 parts | PTFE | 1 part | OTazo-15 0.2 part | Thermal curing |
| Photoreceptor 50 | 2 | 5 | — | Compound (29) | 5 parts | ii-6 | 25 parts | PTFE | 1 part | OTazo-15 0.2 part | Thermal curing |
| Photoreceptor 51 | 3 | 5 | — | Compound (29) | 5 parts | ii-15 | 25 parts | PTFE | 1 part | OTazo-15 0.2 part | Thermal curing |
| Photoreceptor 52 | 2 | 6 | — | Compound (13) | 10 parts | iv-34 | 25 parts | PTFE | 1 part | OTazo-15 0.2 part | Thermal curing |
| Photoreceptor 53 | 3 | 6 | — | Compound (13) | 10 parts | ii-59 | 25 parts | PTFE | 1 part | OTazo-15 0.2 part | Thermal curing |
| Photoreceptor 54 | 2 | 7 | — | Compound (34) | 5 parts | iv-14 | 25 parts | PTFE | 1 part | OTazo-15 0.2 part | Thermal curing |
| Photoreceptor 55 | 3 | 7 | — | Compound (34) | 5 parts | iv-14<br>i-15 | 12 parts<br>5 parts | PTFE | 1 part | OTazo-15 0.2 part | Thermal curing |
| Photoreceptor 56 | 2 | 8 | — | Compound (17) | 10 parts | iv-47 | 25 parts | PTFE | 1 part | OTazo-15 0.2 part | Thermal curing |
| Photoreceptor 57 | 3 | 8 | — | Compound (29) | 5 parts | ii-57 | 25 parts | PTFE | 1 part | OTazo-15 0.2 part | Thermal curing |

TABLE II-4

| Photoreceptor | Under-coat layer | Charge generating layer | Charge transporting layer | Thiol group-containing charge transporting material | Protective layer Compound having unsaturated bond | | Additive | | Polymerization initiator | | Curing method |
|---|---|---|---|---|---|---|---|---|---|---|---|
| Comparative photoreceptor 1 | 1 | 1 | 1 | — | ii-8 | 25 parts | PTFE | 2 parts | OTazo-15 | 0.2 part | Thermal curing |
| Comparative photoreceptor 2 | 1 | 1 | 1 | — | ii-29 | 25 parts | PTFE | 2 parts | OTazo-15 | 0.2 part | Thermal curing |
| Comparative photoreceptor 3 | 1 | 1 | 1 | — | iii-14 | 25 parts | PTFE | 2 parts | OTazo-15 | 0.2 part | Thermal curing |
| Comparative photoreceptor 4 | 1 | 1 | 1 | — | iv-9 | 25 parts | PTFE | 2 parts | OTazo-15 | 0.2 part | Thermal curing |
| Comparative photoreceptor 5 | 3 | 2 | 1 | — | ii-28 | 25 parts | — | | OTazo-15 | 0.2 part | Thermal curing |
| Comparative photoreceptor 6 | 2 | 3 | 2 | — | iv-9 | 25 parts | PTFE | 1 part | OTazo-15 | 0.2 part | Thermal curing |
| Comparative photoreceptor 7 | 3 | 4 | 2 | — | ii-28 | 25 parts | PTFE | 1 part | OTazo-15 | 0.2 part | Thermal curing |
| Comparative photoreceptor 8 | 2 | 5 | 2 | — | ii-6 | 25 parts | PTFE | 1 part | OTazo-15 | 0.2 part | Thermal curing |
| Comparative photoreceptor 9 | 3 | 5 | 2 | — | ii-15 | 25 parts | PTFE | 1 part | OTazo-15 | 0.2 part | Thermal curing |
| Comparative photoreceptor 10 | 2 | 6 | 2 | — | iv-34 | 25 parts | PTFE | 1 part | OTazo-15 | 0.2 part | Thermal curing |
| Comparative photoreceptor 11 | 2 | 7 | 2 | — | iv-14 | 25 parts | PTFE | 1 part | OTazo-15 | 0.2 part | Thermal curing |
| Comparative photoreceptor 12 | 2 | 8 | 2 | — | iv-47 | 25 parts | PTFE | 1 part | OTazo-15 | 0.2 part | Thermal curing |
| Comparative photoreceptor 13 | 3 | 8 | 2 | — | ii-57 | 25 parts | PTFE | 1 part | OTazo-15 | 0.2 part | Thermal curing |

TABLE II-5

| Photoreceptor | Under-coat layer | Charge generating layer | Charge transporting layer | Thiol group-containing charge transporting material | Protective layer Compound having unsaturated bond | | Additive | | Polymerization initiator | | Curing method |
|---|---|---|---|---|---|---|---|---|---|---|---|
| Comparative photoreceptor 14 | 1 | 1 | — | — | ii-29 | 25 parts | PTFE | 2 parts | OTazo-15 | 0.2 part | Thermal curing |
| Comparative photoreceptor 15 | 1 | 1 | — | — | iv-9 | 25 parts | PTFE | 2 parts | OTazo-15 | 0.2 part | Thermal curing |
| Comparative photoreceptor 16 | 1 | 1 | — | — | iv-14 | 25 parts | PTFE | 2 parts | OTazo-15 | 0.2 part | Thermal curing |
| Comparative photoreceptor 17 | 1 | 1 | — | — | iv-34 | 25 parts | PTFE | 2 parts | OTazo-15 | 0.2 part | Thermal curing |
| Comparative photoreceptor 18 | 3 | 2 | — | — | ii-28 | 25 parts | — | | OTazo-15 | 0.2 part | Thermal curing |
| Comparative photoreceptor 19 | 3 | 2 | — | — | iv-28 | 25 parts | PTFE | 1 part | OTazo-15 | 0.2 part | Thermal curing |
| Comparative photoreceptor 20 | 2 | 3 | — | — | iv-9 | 25 parts | PTFE | 1 part | OTazo-15 | 0.2 part | Thermal curing |
| Comparative photoreceptor 21 | 3 | 4 | — | — | ii-28 | 25 parts | PTFE | 1 part | OTazo-15 | 0.2 part | Thermal curing |
| Comparative photoreceptor 22 | 2 | 5 | — | — | ii-6 | 25 parts | PTFE | 1 part | OTazo-15 | 0.2 part | Thermal curing |
| Comparative photoreceptor 23 | 3 | 5 | — | — | ii-15 | 25 parts | PTFE | 1 part | OTazo-15 | 0.2 part | Thermal curing |
| Comparative photoreceptor 24 | 3 | 6 | — | — | ii-59 | 25 parts | PTFE | 1 part | OTazo-15 | 0.2 part | Thermal curing |
| Comparative photoreceptor 25 | 2 | 7 | — | — | iv-14 | 25 parts | PTFE | 1 part | OTazo-15 | 0.2 part | Thermal curing |
| Comparative photoreceptor 26 | 3 | 8 | — | — | ii-57 | 25 parts | PTFE | 1 part | OTazo-15 | 0.2 part | Thermal curing |

Furthermore, in Tables above, the abbreviations are as follows:

A-TMPT: Trimethylolpropane triacrylate, manufactured by Shin Nakamura Chemical Co., Ltd.

OTazo-15: manufactured by Otsuka Chemical Co., Ltd., molecular weight 354.4

Irgacure 184: 1-Hydroxycyclohexyl phenyl ketone, manufactured by Ciba Specialty Chemicals Inc.

PTFE: Lubron L2, manufactured by Daikin Industries Ltd.

<Evaluation of Image Quality>

The electrophotographic photoreceptor prepared as described above is installed in an ApeosPort-III C4400 manufactured by Fuji Xerox Co., Ltd. (original exposure device light-emitting wavelength: infrared laser at 780 nm, exposure spot: 65 μm×55 μm, area 3600 μm² (defined as a width which corresponds to 1/e² of a peak value)) modification, and continuously subjected to the following evaluations under low temperature and low humidity (8° C., 20% RH), and high temperature and high humidity (28° C., 85% RH).

[Evaluation Device-1]

The exposure device is not changed, and as a developer, a toner having an average particle diameter of 3.8 μm is used.

[Evaluation Device-2]

The exposure device is adjusted to a resolution of an imager using an LED image bar having a light-emitting wavelength: 780 nm, and an area: 30 μm×50 μm, and 1500 μm² (defined as a width which corresponds to 1/e² of a peak value) to prepare a drive circuit. As a developer, a toner having an average particle diameter of 3.8 μm is used.

[Evaluation Device-3]

The exposure device is adjusted to a resolution of an imager using an organic EL image bar having a light-emitting wavelength: 580 nm, an exposure spot: 20 μm×20 μm, and an area: 400 nm² (defined as a width which corresponds to 1/e² of a peak value) to prepare a drive circuit. As a developer, a toner having an average particle diameter of 3.8 μm is used.

The organic EL image bar is prepared as follows. As shown in FIG. 10, an anode on which ITO (Indium-Tin-Oxide) is patterned at 20-μm width and 20-μm pitch patterns is formed on a glass substrate as a substrate. Next, as a hole injecting layer, PEDOT/PSS (polyethylene dioxythiophene/polystyrene sulfonate) is coated to a thickness of 10 nm by a spin coating method. Further, on a light-emitting layer, a coating liquid obtained by dissolving MEH-PPV in monochlorobenzene at 1% by weight is coated by a spin coating method to prepare a film having a thickness of 80 nm. Finally, using a mask with openings having a width of 20 μm, Ca as a cathode and Al as a reflective layer are sequentially deposited so as to be perpendicular to an anode for an exposure light source. By this, plural organic EL elements for exposure, which are arranged along with the main scanning direction X, are formed. On the side of the glass substrate (implementation substrate) of the prepared light-emitting element array, SLA is spaced from the glass substrate (implementation substrate) and implemented by an SLA holding member such that the optical distance between the organic electroluminescent element (light-emitting unit) and the light incident surface of the SLA is a working distance of an image pickup unit.

Thus, an exposure head in which the size of a writing spot in the photoreceptor is 20 μm and the exposure center wavelength is 580 nm is prepared.

Example II-1

Using the Photoreceptor-1 and the Evaluation Device-1, the following print test is performed.

First, an image forming test of 10000 sheets under the low temperature and low humidity (8° C., 20% RH) environment is performed and the image quality (ghost, fog, adhesion to the surface of the photoreceptor, and image degradation below) of the 1000$^{th}$ sheet is evaluated. Then, the image quality of the first sheet after standing for 24 hours under the low temperature and low humidity (8° C., 20% RH) environment is evaluated.

The results are shown in Tables II-6 to II-8.

Subsequently to evaluation of the image quality under the low temperature and low humidity environment, an image formation test of 10000 sheets is performed in the high temperature and high humidity environment (30° C., 85% RH), and evaluation of the image quality of the 10000$^{th}$ sheet is performed. Then, the image quality of the first sheet after standing for 24 hours under high temperature and high humidity (30° C., 85% RH) for 24 hours is evaluated.

The results are shown in Tables II-9 to II-11.

(Evaluation of Ghost)

A chart having a pattern of G's and a gray area having an image concentration of 50% shown in FIG. 6A is printed, and the state where the letters G appear in the gray area of 50% is evaluated by visual observation.

A: The degree is from good to slight as in FIG. 6A.

B: Slightly conspicuous as in FIG. 6B.

C: Clearly observed as in FIG. 6C.

(Evaluation of Fog)

The degree of toner adhesiveness to the white area is evaluated by visual observation using the same sample as in the evaluation of ghost.

A: Good.

B: Light fog is developed.

C: Fog having a damaging effect of image quality is developed.

(Evaluation of Adhesion on Surface of Photoreceptor)

The adhesion on the surface of the photoreceptor is evaluated by visual observation using the same sample as in the evaluation of ghost.

A: good.

B: Partial streaks are developed on the image and repaired by wiping the surface of the photoreceptor softly with cloth in which isopropanol has been deeply immersed.

C: Streaks having a damaging effect on image quality are developed, and thus, are not repaired even by wiping the surface of the photoreceptor softly with cloth in which isopropanol has been deeply immersed.

(Evaluation of Image Degradation)

The image degradation is evaluated by visual observation using the same sample as in the evaluation of ghost.

A: Good.

B: No problem occurred during the continuous printing test, but image degradation is developed after leaving the sample for one day (24 hours).

C: Image degradation is developed during the continuous printing test.

<Evaluation of Development Potential Stability>

By the following method, the development potential is measured and evaluation thereof is performed.

A developing unit of ApeosPort-III C4400 is detached and an electrometer is installed therein. Then, the development potential at an initial time of the print test under low temperature and low humidity (8° C., 20% RH) is set to 250 V. Thereafter, after completion of the print test under low temperature and low humidity (8° C., 20% RH), and high temperature and high humidity (28° C., 85% RH), the developing unit is detached again and an electrometer is installed therein. Then, the development potential under low temperature and low humidity (8° C., 20% RH) is measured.

<Evaluation of Adhesiveness of Protective Layer>

The adhesiveness of the protective layer is evaluated by cutting the photoreceptor after the image forming test into 5×5 pieces of 2 mm-squares with a cut-knife, attaching the pieces with a 3 M mending tape, and then releasing them, and counting the number of the remaining pieces.

The results are shown in Tables II-6 to II-8.

A: 21 or more of the pieces remain.

B: 11 or more and 20 or less of the pieces remain.

C: 10 or less of the pieces remain.

<Evaluation of Abrasion Amount>

The film thickness of the photoreceptor at an initial time and the film thickness after completion of the image forming test under low temperature and low humidity (8° C., 20% RH) environment and in the high temperature and high humidity (30° C., 85% RH) environment are measured with an eddy current measurement device (Fischerscope MMS) and the abrasion amount is evaluated.

Examples II-2 to II-59

Using the combinations of the photoreceptors and the evaluation devices as described in Tables II-6 to II-8, evaluation is performed in the same manner as in Example II-1. The results are shown in Tables II-6 to II-11.

Particularly, with those using the Evaluation Device-3, the dot size is small and a very delicate image quality is obtained. Further, since it is not necessary to control against the interference fringes, fog does not easily occur even when the photosensitive layer is thin and a stable image is obtained over a long period of time.

Comparative Examples II-1 to II-26

Using the combinations of the comparative photoreceptors and the evaluation devices as described in Tables II-12 and II-13, evaluation is performed in the same manner as in Example II-1. The results are shown in Tables II-12 to II-15.

Reference Examples II-1 and II-2

Using the Photoreceptor 7 and the Photoreceptor 9 in combination with the Evaluation Device 1, evaluation is performed in the same manner as in Example II-1. The results are shown in Tables II-16 and II-17. Further, occurrence of the interference fringes are observed, in addition to the evaluation items shown in Tables II-16 and II-17.

TABLE II-6

| | | | | Low temperature and low humidity (8° C., 20% RH) | | | | | | | | |
|---|---|---|---|---|---|---|---|---|---|---|---|---|
| | | | | Abrasion amount [μm] | After test of 10000 sheets under low temperature and low humidity | | | | After standing for 24 hours under low temperature and low humidity | | | Development potential [V] after print test |
| | Photoreceptor | Evaluation device | Adhesiveness | | Ghost | Fog | Adhesion on surface of photoreceptor | Image degradation | Ghost | Fog | Adhesion on surface of photoreceptor | Image degradation | |
| Example II-1 | 1 | 1 | A | 0.65 | A | B | B | A | A | B | B | A | 258 |
| Example II-2 | 1 | 2 | A | 0.53 | A | B | B | A | A | B | B | A | 245 |
| Example II-3 | 1 | 3 | A | 0.66 | A | B | B | A | A | B | B | A | 253 |
| Example II-4 | 2 | 1 | A | 0.55 | A | B | A | A | A | B | A | A | 259 |
| Example II-5 | 3 | 1 | A | 0.66 | A | B | B | A | A | B | B | A | 256 |
| Example II-6 | 4 | 1 | A | 0.52 | A | B | A | A | A | B | A | A | 246 |
| Example II-7 | 5 | 1 | A | 0.63 | A | B | B | A | A | B | B | A | 245 |
| Example II-8 | 6 | 1 | A | 0.56 | A | B | A | A | A | B | A | A | 253 |
| Example II-9 | 7 | 2 | A | 0.65 | A | B | B | A | A | B | B | A | 258 |
| Example II-10 | 8 | 3 | A | 0.52 | A | B | A | A | A | B | A | A | 253 |
| Example II-11 | 9 | 2 | A | 0.69 | A | B | B | A | A | B | B | A | 245 |
| Example II-12 | 10 | 3 | A | 0.55 | A | B | A | A | A | B | A | A | 249 |
| Example II-13 | 11 | 1 | A | 0.71 | A | B | B | A | A | B | B | A | 257 |
| Example II-14 | 12 | 1 | A | 0.60 | A | B | A | A | A | B | A | A | 254 |
| Example II-15 | 13 | 1 | A | 0.43 | A | B | A | A | A | B | A | A | 256 |
| Example II-16 | 14 | 1 | A | 0.20 | A | B | A | A | A | B | A | A | 257 |
| Example II-17 | 15 | 1 | A | 0.15 | A | B | A | A | A | B | A | A | 253 |
| Example II-18 | 16 | 1 | A | 0.18 | A | B | A | A | A | B | A | A | 251 |
| Example II-19 | 17 | 1 | A | 0.20 | A | B | A | A | A | B | A | A | 253 |
| Example II-20 | 18 | 1 | A | 0.59 | A | B | A | A | A | B | A | A | 257 |

TABLE II-7

| | | | | Low temperature and low humidity (8° C., 20% RH) | | | | | | | | |
|---|---|---|---|---|---|---|---|---|---|---|---|---|
| | | | | Abrasion amount [μm] | After test of 10000 sheets under low temperature and low humidity | | | | After standing for 24 hours under low temperature and low humidity | | | Development potential [V] after print test |
| | Photoreceptor | Evaluation device | Adhesiveness | | Ghost | Fog | Adhesion on surface of photoreceptor | Image degradation | Ghost | Fog | Adhesion on surface of photoreceptor | Image degradation | |
| Example II-21 | 19 | 1 | A | 0.19 | A | B | A | A | A | B | A | A | 241 |
| Example II-22 | 20 | 3 | A | 0.75 | A | A | B | A | A | A | B | A | 259 |
| Example II-23 | 21 | 3 | A | 0.50 | A | A | A | A | A | A | A | A | 261 |
| Example II-24 | 22 | 3 | A | 0.54 | A | A | B | A | A | A | B | A | 254 |
| Example II-25 | 23 | 3 | A | 0.23 | A | A | A | A | A | A | A | A | 245 |
| Example II-26 | 24 | 3 | A | 0.19 | A | A | A | A | A | A | A | A | 253 |
| Example II-27 | 25 | 3 | A | 0.56 | A | A | A | A | A | A | A | A | 257 |
| Example II-28 | 26 | 3 | A | 0.54 | A | A | A | A | A | A | A | A | 251 |
| Example II-29 | 27 | 3 | A | 0.33 | A | A | A | A | A | A | A | A | 253 |
| Example II-30 | 28 | 3 | A | 0.35 | A | A | A | A | A | A | A | A | 256 |
| Example II-31 | 29 | 3 | A | 0.63 | A | A | A | A | A | A | A | A | 259 |
| Example II-32 | 30 | 3 | A | 0.30 | A | A | A | A | A | A | A | A | 255 |
| Example II-33 | 31 | 3 | A | 0.70 | A | A | A | A | A | A | A | A | 254 |
| Example II-34 | 32 | 3 | A | 0.20 | A | A | A | A | A | A | A | A | 243 |

TABLE II-7-continued

| | | | | Low temperature and low humidity (8° C., 20% RH) | | | | | | | | |
|---|---|---|---|---|---|---|---|---|---|---|---|---|
| | | | Abrasion amount [μm] | After test of 10000 sheets under low temperature and low humidity | | | | After standing for 24 hours under low temperature and low humidity | | | | Development potential [V] after print test |
| | Photoreceptor | Evaluation device | Adhesiveness | | Ghost | Fog | Adhesion on surface of photoreceptor | Image degradation | Ghost | Fog | Adhesion on surface of photoreceptor | Image degradation | |
| Example II-35 | 33 | 3 | A | 0.35 | A | A | A | A | A | A | A | A | 257 |
| Example II-36 | 34 | 3 | A | 0.44 | A | A | B | A | A | A | B | A | 248 |
| Example II-37 | 35 | 3 | A | 0.46 | A | A | A | A | A | A | A | A | 258 |
| Example II-38 | 36 | 1 | — | 0.62 | A | A | A | A | A | A | A | A | 247 |
| Example II-39 | 37 | 2 | — | 0.57 | A | A | A | A | A | A | A | A | 254 |
| Example II-40 | 38 | 1 | — | 0.50 | A | A | A | A | A | A | A | A | 253 |

TABLE II-8

| | | | | | Low temperature and low humidity (8° C., 20% RH) | | | | | | | | |
|---|---|---|---|---|---|---|---|---|---|---|---|---|---|
| | Comparative photoreceptor | Evaluation device | Adhesiveness | Abrasion amount [μm] | After test of 10000 sheets under low temperature and low humidity | | | | After standing for 24 hours under low temperature and low humidity | | | | Development potential [V] after print test |
| | | | | | Ghost | Fog | Adhesion on surface of photoreceptor | Image degradation | Ghost | Fog | Adhesion on surface of photoreceptor | Image degradation | |
| Example II-41 | 39 | 2 | — | 0.22 | A | A | A | A | A | A | A | A | 256 |
| Example II-42 | 40 | 1 | — | 0.19 | A | A | A | A | A | A | A | A | 254 |
| Example II-43 | 41 | 2 | — | 0.20 | A | A | A | A | A | A | A | A | 251 |
| Example II-44 | 42 | 1 | — | 0.35 | A | A | A | A | A | A | A | A | 247 |
| Example II-45 | 43 | 1 | — | 0.21 | A | A | A | A | A | A | A | A | 246 |
| Example II-46 | 44 | 3 | — | 0.40 | A | A | B | A | A | A | B | A | 254 |
| Example II-47 | 45 | 3 | — | 0.25 | A | A | A | A | A | A | A | A | 259 |
| Example II-48 | 46 | 3 | — | 0.20 | A | A | A | A | A | A | A | A | 261 |
| Example II-49 | 47 | 3 | — | 0.52 | A | A | A | A | A | A | A | A | 256 |
| Example II-50 | 48 | 3 | — | 0.54 | A | A | A | A | A | A | A | A | 252 |
| Example II-51 | 49 | 3 | — | 0.42 | A | A | A | A | A | A | A | A | 243 |
| Example II-52 | 50 | 3 | — | 0.63 | A | A | A | A | A | A | A | A | 248 |
| Example II-53 | 51 | 3 | — | 0.62 | A | A | A | A | A | A | A | A | 255 |
| Example II-54 | 52 | 3 | — | 0.24 | A | A | A | A | A | A | A | A | 251 |
| Example II-55 | 53 | 3 | — | 0.72 | A | A | A | A | A | A | A | A | 259 |
| Example II-56 | 54 | 3 | — | 0.19 | A | A | A | A | A | A | A | A | 254 |
| Example II-57 | 55 | 3 | — | 0.24 | A | A | A | A | A | A | A | A | 243 |
| Example II-58 | 56 | 3 | — | 0.25 | A | A | A | A | A | A | A | A | 260 |
| Example II-59 | 57 | 3 | — | 0.39 | A | A | A | A | A | A | A | A | 246 |

TABLE II-9

| | High temperature and high humidity (30° C., 85% RH) | | | | | | | |
|---|---|---|---|---|---|---|---|---|
| | After test of 10000 sheets under high temperature and high humidity | | | | After standing for 24 hours under high temperature and high humidity | | | |
| | Ghost | Fog | Adhesion on surface of photoreceptor | Image degradation | Ghost | Fog | Adhesion on surface of photoreceptor | Image degradation |
| Example II-1 | A | B | B | B | A | B | B | B |
| Example II-2 | A | B | B | B | A | B | B | B |
| Example II-3 | A | B | B | B | A | B | B | B |
| Example II-4 | A | B | A | A | A | B | A | A |
| Example II-5 | A | B | B | B | A | B | B | B |
| Example II-6 | A | B | A | A | A | B | A | A |
| Example II-7 | A | B | B | B | A | B | B | B |
| Example II-8 | A | B | A | A | A | B | A | A |
| Example II-9 | A | B | B | B | A | B | B | B |
| Example II-10 | A | B | A | A | A | B | A | A |
| Example II-11 | A | B | B | B | A | B | B | B |
| Example II-12 | A | B | A | A | A | B | A | A |
| Example II-13 | A | B | B | B | A | B | B | B |
| Example II-14 | A | B | A | A | A | B | A | A |
| Example II-15 | A | B | A | A | A | B | A | A |
| Example II-16 | A | B | A | A | A | B | A | A |
| Example II-17 | A | B | A | A | A | B | A | A |
| Example II-18 | A | B | A | A | A | B | A | A |

TABLE II-9-continued

| | High temperature and high humidity (30° C., 85% RH) | | | | | | | |
|---|---|---|---|---|---|---|---|---|
| | After test of 10000 sheets under high temperature and high humidity | | | | After standing for 24 hours under high temperature and high humidity | | | |
| | Ghost | Fog | Adhesion on surface of photoreceptor | Image degradation | Ghost | Fog | Adhesion on surface of photoreceptor | Image degradation |
| Example II-19 | A | B | A | A | A | B | A | A |
| Example II-20 | A | B | A | A | A | B | A | A |

TABLE II-10

| | High temperature and high humidity (30° C., 85% RH) | | | | | | | |
|---|---|---|---|---|---|---|---|---|
| | After test of 10000 sheets under high temperature and high humidity | | | | After standing for 24 hours under high temperature and high humidity | | | |
| | Ghost | Fog | Adhesion on surface of photoreceptor | Image degradation | Ghost | Fog | Adhesion on surface of photoreceptor | Image degradation |
| Example II-21 | A | B | A | A | A | B | A | A |
| Example II-22 | A | A | B | B | A | A | B | B |
| Example II-23 | A | A | A | A | A | A | A | A |
| Example II-24 | A | A | B | B | A | A | B | B |
| Example II-25 | A | A | A | A | A | A | A | A |
| Example II-26 | A | A | A | A | A | A | A | A |
| Example II-27 | A | A | A | A | A | A | A | A |
| Example II-28 | A | A | A | A | A | A | A | A |
| Example II-29 | A | A | A | A | A | A | A | A |
| Example II-30 | A | A | A | A | A | A | A | A |
| Example II-31 | A | A | A | A | A | A | A | A |
| Example II-32 | A | A | A | A | A | A | A | A |
| Example II-33 | A | A | A | A | A | A | A | A |
| Example II-34 | A | A | A | A | A | A | A | A |
| Example II-35 | A | A | A | A | A | A | A | A |
| Example II-36 | A | A | B | B | A | A | B | B |
| Example II-37 | A | A | A | A | A | A | A | A |
| Example II-38 | A | A | A | A | A | A | A | A |
| Example II-39 | A | A | A | A | A | A | A | A |
| Example II-40 | A | A | A | A | A | A | A | A |

TABLE II-11

| | High temperature and high humidity (30° C., 85% RH) | | | | | | | |
|---|---|---|---|---|---|---|---|---|
| | After test of 10000 sheets under high temperature and high humidity | | | | After standing for 24 hours under high temperature and high humidity | | | |
| | Ghost | Fog | Adhesion on surface of photoreceptor | Image degradation | Ghost | Fog | Adhesion on surface of photoreceptor | Image degradation |
| Example II-41 | A | A | A | A | A | A | A | A |
| Example II-42 | A | A | A | A | A | A | A | A |
| Example II-43 | A | A | A | A | A | A | A | A |
| Example II-44 | A | A | A | A | A | A | A | A |
| Example II-45 | A | A | A | A | A | A | A | A |
| Example II-46 | A | A | B | B | A | A | B | B |
| Example II-47 | A | A | A | A | A | A | A | A |
| Example II-48 | A | A | A | A | A | A | A | A |
| Example II-49 | A | A | A | A | A | A | A | A |
| Example II-50 | A | A | A | A | A | A | A | A |
| Example II-51 | A | A | B | B | A | A | B | B |
| Example II-52 | A | A | A | A | A | A | A | A |
| Example II-53 | A | A | A | A | A | A | A | A |
| Example II-54 | A | A | A | A | A | A | A | A |
| Example II-55 | A | A | A | A | A | A | A | A |
| Example II-56 | A | A | A | A | A | A | A | A |
| Example II-57 | A | A | A | A | A | A | A | A |
| Example II-58 | A | A | A | A | A | A | A | A |
| Example II-59 | A | A | B | B | A | A | B | B |

TABLE II-12

| | Comparative photo-receptor | Evaluation device | Adhesiveness | Abrasion amount [μm] | \multicolumn{4}{c|}{After test of 10000 sheets under low temperature and low humidity} | \multicolumn{4}{c|}{After standing for 24 hours under low temperature and low humidity} | Development potential [V] after print test |
|---|---|---|---|---|---|---|---|---|---|---|---|---|---|
| | | | | | Ghost | Fog | Adhesion on surface of photoreceptor | Image degradation | Ghost | Fog | Adhesion on surface of photoreceptor | Image degradation | |
| Comparative Example II-1 | 1 | 1 | A | 0.83 | A | B | B | A | A | B | B | A | 278 |
| Comparative Example II-2 | 2 | 2 | A | 0.88 | A | B | B | A | A | B | B | A | 280 |
| Comparative Example II-3 | 3 | 3 | B | 0.70 | A | B | B | A | A | B | B | A | 275 |
| Comparative Example II-4 | 4 | 1 | A | 0.41 | A | B | B | A | A | B | B | A | 284 |
| Comparative Example II-5 | 5 | 3 | A | 0.95 | A | A | B | A | A | A | B | A | 279 |
| Comparative Example II-6 | 6 | 3 | A | 0.50 | A | A | B | A | A | A | B | A | 275 |
| Comparative Example II-7 | 7 | 3 | B | 0.87 | A | A | B | A | A | A | B | A | 280 |
| Comparative Example II-8 | 8 | 3 | A | 0.87 | A | A | B | A | A | A | B | A | 281 |
| Comparative Example II-9 | 9 | 3 | A | 0.83 | A | A | B | A | A | A | B | A | 278 |
| Comparative Example II-10 | 10 | 3 | A | 0.40 | A | A | B | A | A | A | B | A | 271 |
| Comparative Example II-11 | 11 | 3 | B | 0.46 | A | A | B | A | A | A | B | A | 277 |
| Comparative Example II-12 | 12 | 3 | A | 0.39 | A | A | B | A | A | A | B | A | 280 |
| Comparative Example II-13 | 13 | 3 | A | 0.82 | A | A | B | A | A | A | B | A | 285 |

TABLE II-13

| | Comparative photo-receptor | Evaluation device | Adhesiveness | Abrasion amount [μm] | \multicolumn{4}{c|}{After test of 10000 sheets under low temperature and low humidity} | \multicolumn{4}{c|}{After standing for 24 hours under low temperature and low humidity} | Development potential [V] after print test |
|---|---|---|---|---|---|---|---|---|---|---|---|---|---|
| | | | | | Ghost | Fog | Adhesion on surface of photoreceptor | Image degradation | Ghost | Fog | Adhesion on surface of photoreceptor | Image degradation | |
| Comparative Example II-14 | 14 | 1 | — | 0.87 | B | A | B | A | B | A | B | A | 278 |
| Comparative Example II-15 | 15 | 2 | — | 0.46 | B | A | B | A | B | A | B | A | 282 |
| Comparative Example II-16 | 16 | 3 | — | 0.44 | B | A | B | A | B | A | B | A | 289 |
| Comparative Example II-17 | 17 | 1 | — | 0.38 | B | A | B | A | B | A | B | A | 290 |
| Comparative Example II-18 | 18 | 3 | — | 0.91 | B | A | B | A | B | A | B | A | 278 |
| Comparative Example II-19 | 19 | 3 | — | 0.46 | B | A | B | A | B | A | B | A | 277 |
| Comparative Example II-20 | 20 | 3 | — | 0.41 | B | A | B | A | B | A | B | A | 289 |
| Comparative Example II-21 | 21 | 3 | — | 0.88 | B | A | B | A | B | A | B | A | 294 |
| Comparative Example II-22 | 22 | 3 | — | 0.84 | B | A | B | A | B | A | B | A | 286 |
| Comparative Example II-23 | 23 | 3 | — | 0.86 | B | A | B | A | B | A | B | A | 277 |
| Comparative Example II-24 | 24 | 3 | — | 0.79 | B | A | B | A | B | A | B | A | 276 |
| Comparative Example II-25 | 25 | 3 | — | 0.46 | B | A | B | A | B | A | B | A | 287 |
| Comparative Example II-26 | 26 | 3 | — | 0.87 | B | A | B | A | B | A | B | A | 275 |

TABLE II-14

| | High temperature and high humidity (30° C., 85% RH) | | | | | | | |
|---|---|---|---|---|---|---|---|---|
| | After test of 10000 sheets under high temperature and high humidity | | | | After standing for 24 hours under high temperature and high humidity | | | |
| | Ghost | Fog | Adhesion on surface of photoreceptor | Image degradation | Ghost | Fog | Adhesion on surface of photoreceptor | Image degradation |
| Comparative Example II-1 | A | B | B | C | A | B | B | C |
| Comparative Example II-2 | A | B | B | C | A | B | B | C |
| Comparative Example II-3 | A | B | B | C | A | B | B | C |
| Comparative Example II-4 | A | B | B | C | A | B | B | C |
| Comparative Example II-5 | A | A | C | C | A | A | C | C |
| Comparative Example II-6 | A | A | B | C | A | A | B | C |
| Comparative Example II-7 | A | A | B | C | A | A | B | C |
| Comparative Example II-8 | A | A | B | C | A | A | B | C |
| Comparative Example II-9 | A | A | B | C | A | A | B | C |
| Comparative Example II-10 | A | A | B | C | A | A | B | C |
| Comparative Example II-11 | A | A | B | C | A | A | B | C |
| Comparative Example II-12 | A | A | C | C | A | A | C | C |
| Comparative Example II-13 | A | A | B | C | A | A | B | C |

TABLE II-15

| | High temperature and high humidity (30° C., 85% RH) | | | | | | | |
|---|---|---|---|---|---|---|---|---|
| | After test of 10000 sheets under high temperature and high humidity | | | | After standing for 24 hours under high temperature and high humidity | | | |
| | Ghost | Fog | Adhesion on surface of photoreceptor | Image degradation | Ghost | Fog | Adhesion on surface of photoreceptor | Image degradation |
| Comparative Example II-14 | B | A | B | C | B | A | B | C |
| Comparative Example II-15 | B | A | B | C | B | A | B | C |
| Comparative Example II-16 | B | A | B | C | B | A | B | C |
| Comparative Example II-17 | B | A | B | C | B | A | B | C |
| Comparative Example II-18 | B | A | C | C | B | A | C | C |
| Comparative Example II-19 | B | A | C | C | B | A | C | C |
| Comparative Example II-20 | B | A | B | C | B | A | B | C |
| Comparative Example II-21 | B | A | B | C | B | A | B | C |
| Comparative Example II-22 | B | A | B | C | B | A | B | C |
| Comparative Example II-23 | B | A | B | C | B | A | B | C |
| Comparative Example II-24 | B | A | C | C | B | A | C | C |
| Comparative Example II-25 | B | A | B | C | B | A | B | C |
| Comparative Example II-26 | B | A | B | C | B | A | B | C |

TABLE II-16

| | | | | Low temperature and low humidity (8° C., 20% RH) | | | | | | | | |
|---|---|---|---|---|---|---|---|---|---|---|---|---|
| | Comparative photoreceptor | Evaluation device | Adhesiveness | Abrasion amount [µm] | After test of 10000 sheets under low temperature and low humidity | | | | After standing for 24 hours under low temperature and low humidity | | | Development potential [V] after print test |
| | | | | | Ghost | Fog | Adhesion on surface of photoreceptor | Image degradation | Ghost | Fog | Adhesion on surface of photoreceptor | Image degradation | |
| Reference Example II-1 | 7 | 1 | A | 0.62 | A | B | B | A | A | B | B | A | 256 |
| Reference Example II-2 | 9 | 1 | A | 0.66 | A | B | B | A | A | B | B | A | 260 |

TABLE II-17

| | High temperature and high humidity (30° C., 85% RH) | | | | | | | |
|---|---|---|---|---|---|---|---|---|
| | After test of 10000 sheets under high temperature and high humidity | | | | After standing for 24 hours under high temperature and high humidity | | | |
| | Ghost | Fog | Adhesion on surface of photoreceptor | Image degradation | Ghost | Fog | Adhesion on surface of photoreceptor | Image degradation |
| Reference Example II-1 | A | B | B | B | A | B | B | B |
| Reference Example II-2 | A | B | B | B | A | B | B | B |

As shown in Tables above, with the electrophotographic photoreceptors of Examples, decrease in the image quality after the repeated use over a long period of time is inhibited.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A thiol group-containing charge transporting material represented by the following general formula (1)':

F-[(G)$_a$-X—Y—SH]$_b$ (1)' wherein F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less.

2. The thiol group-containing charge transporting material as claimed in claim 1, wherein in the general formula (1)', F is an organic group having a hole transporting ability.

3. The thiol group-containing charge transporting material as claimed in claim 1, wherein the thiol group-containing charge transporting material represented by the general formula (1) is represented by the following general formula (2)':

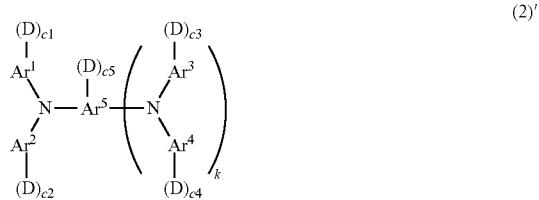

(2)' wherein D represents a binding group represented by -(G)$_a$- X—Y—SH, Ar$^1$ to Ar$^4$ each independently represent a substituted or unsubstituted aryl group, Ar$^5$ represents a substituted or unsubstituted aryl group or a substituted or unsubstituted arylene group, G represents a divalent organic group having 1 to 5 carbon atoms, X represents a —CO—O— group or an —O—CO— group, Y represents a divalent organic group having 1 to 5 carbon atoms, a represents 0 or 1, c1 to c5 each independently represent an integer of 0 or more and 2 or less, k represents 0 or 1, and one or more and four or less of Ar$^1$ to Ar$^5$ have a bond which is capable of binding to a binding group represented by -(G)$_a$-X—Y—SH.

4. A thiol group-containing charge transporting material-dissolving solution, in which the thiol group-containing charge transporting material represented by the following general formula (1)' is dissolved in a solvent:

F-[(G)$_a$-X—Y—SH]$_b$ (1)' wherein F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less.

5. A photoelectric conversion device comprising a film formed by using a dissolving solution in which the thiol group-containing charge transporting material represented by the following general formula (1)' is dissolved:

F-[(G)$a$-X—Y—SH]$_b$ (1)' wherein F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less.

6. The photoelectric conversion device as claimed in claim 5, wherein the film contains a polymer in which the thiol group-containing charge transporting material is polymerized.

7. An electrophotographic photoreceptor comprising a layer formed on a conductive substrate using a dissolving solution in which a thiol group-containing charge transporting material represented by the following general formula (1)' is dissolved:

F-[(G)$_a$-X—Y—SH]$_b$ (1)' wherein F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less.

8. An electrophotographic photoreceptor having a conductive substrate, and a photosensitive layer containing a polymer formed by polymerization of at least one kind of a thiol group-containing charge transporting material represented by the following general formula (1)' and at least one kind of a compound having an unsaturated bond, on the conductive substrate:

$$F\text{-}[(G)_a\text{-}X\text{—}Y\text{—}SH]_b \qquad (1)'$$

wherein F represents an organic group derived from a charge transporting compound, G represents a divalent organic group having 1 to 5 carbon atoms, X represents a CO—O— group or an —O—CO— group, and Y represents a divalent organic group having 1 to 5 carbon atoms, which may have an —SH group as a substituent, a represents 0 or 1, and b represents an integer of 1 or more and 6 or less.

9. The electrophotographic photoreceptor as claimed in claim 8, wherein the thiol group-containing charge transporting material represented by the general formula (1)' is a thiol group-containing charge transporting material represented by the following general formula (2)':

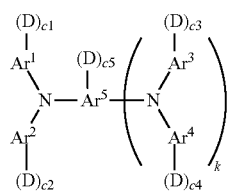

(2)' wherein D represents a binding group represented by -(G)$_a$-X—Y—SH, $Ar^1$ to $Ar^4$ each independently represent a substituted or unsubstituted aryl group, $Ar^5$ represents a substituted or unsubstituted aryl group or a substituted or unsubstituted arylene group, G represents a divalent organic group having 1 to 5 carbon atoms, X represents a CO—O— group or an —O—CO— group, Y represents a divalent organic group having 1 to 5 carbon atoms, which may have an —SH group as a substituent, a represents 0 or 1, one or more and four or less of $Ar^1$ to $Ar^5$ have a bond which is capable of binding to a binding group represented by -(G)$_a$-X—Y—SH, c1 to c5 each independently represent an integer of 0 or more and 2 or less, and k represents 0 or 1.

10. The electrophotographic photoreceptor as claimed in claim 8, wherein the compound having an unsaturated bond is a monomer, oligomer or polymer having a charge transporting skeleton.

11. The electrophotographic photoreceptor as claimed in claim 8, wherein the compound having an unsaturated bond is a monomer, oligomer or polymer having two or more unsaturated bonds in the same molecule and having no charge transporting skeleton.

12. The electrophotographic photoreceptor as claimed in claim 8, wherein the photosensitive layer contains a lubricant particle.

13. An image forming apparatus comprising:
an electrophotographic photoreceptor having a photosensitive layer containing a polymer formed by polymerization of at least one kind of a thiol group-containing charge transporting material represented by the following general formula (1)' and at least one kind of a compound having an unsaturated bond, on a conductive substrate;
a charging device that charges the surface of the electrophotographic photoreceptor;
an exposure device that exposes the surface of the charged electrophotographic photoreceptor to form an electrostatic latent image on the surface;
a developing device that develops the electrostatic latent image to form a toner image; and
a transfer device that transfers the toner image to a transfer medium:

$$F\text{-}[(G)_a\text{-}X\text{—}Y\text{—}SH]_b \qquad (1)'$$

wherein F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less.

14. A process cartridge comprising an electrophotographic photoreceptor,
wherein the electrophotographic photoreceptor comprises a photosensitive layer containing a polymer formed by polymerization of at least one kind of a thiol group-containing charge transporting material represented by the following general formula (1)' and at least one kind of a compound having an unsaturated bond, on a conductive substrate, and
wherein the process cartridge is detachable from an image forming apparatus:

$$F\text{-}[(G)_a\text{-}X\text{—}Y\text{—}SH]_b \qquad (1)'$$

wherein F represents an organic group derived from a charge transporting compound, G represents a divalent organic group having 1 to 5 carbon atoms, X represents a —CO—O— group or an —O—CO— group, Y represents a divalent organic group having 1 to 5 carbon atoms, a represents 0 or 1, and b represents an integer of 1 or more and 6 or less.

\* \* \* \* \*